United States Patent
Zou et al.

(10) Patent No.: US 7,732,155 B2
(45) Date of Patent: Jun. 8, 2010

(54) METHODS FOR IDENTIFYING LYSOPHOSPHATIDYLCHOLINE ACYLTRANSFERASES

(75) Inventors: Jitao Zou, Saskatoon (CA); Qilin Chen, Saskatoon (CA); Zhifu Zheng, Zionsville, IN (US); Jingyu Xu, Saskatoon (CA)

(73) Assignees: National Research Council of Canada, Ottawa, Ontario (CA); Dow Agrosciences LCC, Indianapolis, IN (US)

( * ) Notice: Subject to any disclaimer, the term of this patent is extended or adjusted under 35 U.S.C. 154(b) by 0 days.

(21) Appl. No.: 11/820,014

(22) Filed: Jun. 15, 2007

(65) Prior Publication Data

US 2008/0145867 A1 Jun. 19, 2008

Related U.S. Application Data

(60) Provisional application No. 60/874,497, filed on Dec. 13, 2006.

(51) Int. Cl.
  *C12Q 1/00* (2006.01)
  *G01N 33/573* (2006.01)
  *C12N 9/00* (2006.01)
  *C12N 9/10* (2006.01)
(52) U.S. Cl. ............................ 435/7.4; 435/4; 435/183; 435/193
(58) Field of Classification Search .................. None
  See application file for complete search history.

(56) References Cited

U.S. PATENT DOCUMENTS

2005/0208558 A1  9/2005  Venter et al.
2006/0046253 A1  3/2006  Nakao et al.

OTHER PUBLICATIONS

Chica et al. Curr Opin Biotechnol. Aug. 2005;16(4):378-84.*
Benghezal et al., SLC1 ad SLC4 Encode Partially Redundant Acyl-Coenzyme A 1-Acylglycerol-3-phosphate O-Acyltransferases of Budding Yeast, Journal of Biological Chemistry, Oct. 19, 2007, pp. 30845-30855, vol. 282, No. 42.
Chen et al., The yeast acylglycerol acyltransferase LCA1 is a key component of Lands cycle for phosphatidylcholine turnover, FEBS Letters, Nov. 8, 2007, pp. 5511-5516.
Hishikawa et al., Discovery of a lysophospholipid acyltransferase family essential for membrane asymmetry and diversity, PNAS, Feb. 26, 2008, pp. 2830-2835, vol. 105, No. 8.
Jain et al., Identification of a Novel Lysophospholipid Acyltransferase in *Saccharomyces cerevisiae*, Journal of Biological Chemistry, Oct. 19, 2007, pp. 30562-30569, vol. 282, No. 42.
Kazachkov et al., Substrate Preferences of a Lysophosphatidylcholine Acyltransferase Highlight Its Role in Phospholipid Remodeling, Lipids, 2008, pp. 895-902, vol. 43.
Riekhof et al., Identification and Characterization of the Major Lysophosphatidylethanolamine Acyltransferase in *Saccharomyces cerevisiae*, The Journal of Biological Chemistry, Sep. 28, 2007, pp. 28344-28352, vol. 282, No. 39.
Stahl et al., A family of eukaryotic lysophospholipid acyltransferases with broad specificity, FEB Letters, 2008, pp. 305-309, vol. 582.
Tamaki et al., LPT1 Encodes a Membrane-bound O-Acyltransferase Involved in the Acylation of Lysophospholipids in the Yeast *Saccharomyces cerevisiae*, The Journal of Biological Chemistry, Nov. 23, 2007, pp. 34288-34298, vol. 282, No. 47.
Zhao et al., Identification and Characterization of a Major liver Lysophosphatidylcholine Acyltransferase, The Journal of Biological Chemistry, Mar. 28, 2008, pp. 8258-8265, vol. 283, No. 13.
PCT International Search Report, PCT/US07/25650, dated Jan. 5, 2009.
Chen et al., Identification and characterization of a lysophosphatidylcholine acyltransferase in alveolar type II cells, PNAS, Aug. 1, 2006, pp. 11724-11729, vol. 103, No. 31.
Furukawa-Stoffer et al., Properties of Lysophosphatidylcholine Acyltransferase from *Brassica napus* Cultures, Lipids, 2003, pp. 651-656, vol. 38, No. 6.
Nakanishi et al., Cloning and Characterization of Mouse Lung-type Acyl-CoA:Lysophosphatidylcholine Acyltransferase 1 (LPCAT1), Journal of Biological Chemistry, Jul. 21, 2006, pp. 20140-20147, vol. 281, No. 29.
Neville et al., The activities of monocyte lysophosphatidylcholine acyltransferase and coenzyme A-independent transacylase are changed by the inflammatory cytokines tumor necrosis factor alpha and interferon gamma, Biochimica et Biophysica Acta, 2005, pp. 232-238, vol. 1733.
U.S. Appl. No. 11/122,943, filed May 4, 2005, Inventor: Zou et al., Title: Methods of Producing and Growing Plants Having Improved Phosphorus Utilization.
U.S. Appl. No. 12/448,061, filed Jun. 5, 2009, Inventor: Chen et al., Title: Genes Encoding a Novel Type of Lysophophatidylcholine Acyltransferases and Their Use to Increase Triacylglycerol Production and/or Modify Fatty Acid composition.
U.S. Appl. No. 61/168,532, filed Apr. 10, 2009, Inventor: Zheng et al., Title: Plant SNF1-Related Protein Kinase Gene.

* cited by examiner

*Primary Examiner*—Christian L Fronda
(74) *Attorney, Agent, or Firm*—TraskBritt

(57) ABSTRACT

Nucleic acid molecules identified in encode lyso-phosphatidylcholine (LPC) acyltransferases. Over-expression of the LPC acyltransferases in a cell may lead to enhanced production of PUFA, or other unusual fatty acids, and/or to increased oil content in the cell.

12 Claims, 12 Drawing Sheets

FIG. 2A

```
SEQ ID NO:50   (1) ------------------------------MLPYVD████ASF█LS█████LAA█LKR
SEQ ID NO:51   (1) ------------------MAYLID█PFEYFSSFL███HPDQ███FCF████████FAG█LKR
SEQ ID NO:52   (1) ------------------MYNPVDAVLTKIITNY████DSFT█████YAICL████S███LNA█LKR
SEQ ID NO:53   (1) MRLYLQFNLSINDYCHFFTVPSFVKEGVESLSAST████QDVET████EY█LGM█IC███ELGM███MLA
SEQ ID NO:54   (1) -------------------██████DMSSMAGSI█████SVA███████F█LCF████TI████VSFACRI
SEQ ID NO:55   (1) -------------------MEL██DMNSMAASI█████SVA███████F█LCF████TI██ISF█WRF
SEQ ID NO:56   (1) -------------------MG████EMEGMAAAI█████SVP██████F█LCFA████TI█████TGL██WRA
SEQ ID NO:57   (1) -------------------------------------------------------------
SEQ ID NO:58   (1) ----MLEPPKFIENDCYNGSRTFTW████ADMVGLSVDL████NFL████CQ█████SALF████SLFRSM████HPS
SEQ ID NO:59   (1) -------------------------████KCCFHHIIPR████NFV████CQ████FALLA█████I███FRTY████HSS
SEQ ID NO:60   (1) ----------MATTSTTGSTLLQP████SNAVQLPID████NFV████CQ████FALLA█████I███FRTY████HSS
SEQ ID NO:61   (1) ----------MATTSTTGSTLLQP████SNAVQLPID████NFV████CQ████FALLA█████V███FRTY████HSS
SEQ ID NO:62   (1) ----MAARPPASLSYRTTGSTCLHP████SQLLGIPLD████NFVACQ████FALSA████F███FRIY████HPG
SEQ ID NO:63   (1) ------------MAEFEEDLPHNGLMDGIASGV████PVEA██████████LTI████G████VAA████YQK
```

```
(27)  ████D███QP--WK███NA███IIA████S████YLVGL███DLWDGLRT███AYSAAGI██████AYY███DGSL██████PW██████G████
(42)  ████PS████P---W████RNL████IS████G█████YLIGVHHLYDGV█████LFDA████FT██F████AAFYRSSR███PW█II█
(42)  ████EKRI--G████CC████IIS████S████YL████GVLNLV████GFRTL████F████ST████FT████L███SRFYRSKF███PH████N████
(61)  ████HYG----K████KH██████S████FI████GA███LQ████TI████QW---████HHL████SS████IA████V████F██V█PAKFAKTAVP
(36)  ████PSR----L████GK██████AAS████A████S████LS████FS█---NLHF████VP████TIGYAS████A████YRPKCGI████T███
(39)  ████PSR----L████GK████████AAS████A████L████LS████FS█---NLHF████VP████TIGYAS████A████YRPLSGF████T████
(38)  ████G----AGR████L████AGLT████AAL████S████LS████AT█---NL████F████VP████AFGY████A████L████CRRLAGL████T████
(1)   -------------------------------------------------------------
(57)  KV████S████----K████RF████T████LS████████AFG████F████████C████GQQ█---████H████AGLPAIC████I████IRTQDPRI████QRAVL
(36)  KT████S████----F████RH████V████ATL████G████L████AL████CC█GWY█---████HFL████QSGISL████CL████MI████L████GVEN████HNYC████
(50)  KT████S████----F████RH████V████ATL████G████L████AL████CC█GWY█---████HFL████QSGISL████CL████MI████L████GVEN████HNYC████
(50)  KT████S████----F████RH████V████ATL████G████L████AF████CK█GWY█---████HFL████QSGISL████CL████MI████IAGVES████QQCC████
(57)  KA████P----E████RH████TL████ATI████L████G████FVV████CC█GWY█---████HG████F████LV████MC████G████M████SASVSN████HRYSE
(47)  FI████VIADKT████H████M████FAGC████AGC████N█N████GLDTYHSL████A████LTTYFLV████L████RKKTQIFLA████N████
```

Motif 1

```
(85)  ████LC████HVS████S████Y████R--QIIDDAHVT████I████GAQMVT████MR████S████FC████NM████DGR████S----Q████Q█
(99)  VI████G████TFSSH████I████---YI████PSENT████I████S████SQMV██LCM████S████FA████SY████DGR████P----SS████
(100) ████V████GH████A████N████H██HAQFLNEQTQTT████I████SSOM████LA████K████S████FA████SY████DGSCTSESDFK████
(115) ████FA████M████TAGH████H████-QYIN████LGWD████F████CE████MV████T████MR████YMLA████A████ADGD████LKKGK████RAA
(90)  FL████F████V████IGC████FY████SGDA████KEGG████S████A████MVLT████K████I████SC████M████YNDC████M████----████G████R
(93)  FL████F████V████IGC████FY████SGDA████KEGG████S████A████MVLT████K████I████SC████I████YNDC████M████----████G████R
(92)  ████G████F████IACL████YY████SGDA████KEGG████DA████A████MVLT████K████I████SC████I████YSDC████M████----████G████R
(1)   -------YYS████SGDA████KEGG████DA████A████MVLT████K████I████SC████I████YSDC████M████----████G████R
(111) ████V████SM████LCV████M████-QLYD████GSYA████I████G████M████TQK████SLA████S████DGF████G----████
(90)  ████FA████G████LT████CQ████TR████YIFD████GQYSA████F████G████MM████TQK████SLAC████D████GMF████K---████
(104) ████FA████G████LT████CQ████TR████YIFD████GQYSA████F████G████MM████TQK████SLAC████D████GMF████K---████
(104) ████CY████LT████SC████QT████TR████YIFD████GQYSA████F████G████MM████TQK████SLA████V████DGMF████K---████
(111) FV████G████LT████TC████SR████YIFH████GILTT████F████G████MM████TQK████SLA████V████DG████K---AE████
(107) ████H████SV████L████G████FYT----SSNDYD████LW████M████HC████V████GY████D████TDG████KE----████S████
```

```
(139) DP████KYAA████DFPG████L████G████VLF████G████AGPS████VD████RR████TTLFDVPPGTPSKVPP
(152) SY████KDRA████K████PN████G████VFF████VGPA████VD████R████TLS---------MFKPLA
(160) EH████SRA████GHPPL████K████AYFF████M████TGPS████VADD████SK████NCEMFRDLPESKKPMRRH
(174) KKCADV████SS████PG████L████VTFC████SM████AGPA████KFMADAC████SLLYDK----SGKPKG
(146) E████KNR████IQ████PSL████F████CLCCG████HFGP████MKDY████T█-G---------K████IWDT
(149) E████KNR████IQ████PSL████F████CLCCG████HFGP████MKDY████T█-E---------K████IWAV
(148) D████KKYR████K████PSL████F████CLCCG████HFGP████MKDY████T█-R---------K████LWAS
```

FIG. 2B

```
 (46) DXQKKYRLAKFPSLLEYFLYCLCCGSHFXGPXXDMXDYXEXTX-R---------KXLWAS
(167) KXQQYHXXRKXPSALEYFSXVWHFQSXLAGPXVFXKDYXEXXEGYNLLSTPPG-NXNLDS
(147) SSQXDLAVRRMPSLLEYLSXNCNXMGXLAGPXCSXKDYXTFXEGRSYHITQSGENXKEET
(161) SSQXDLAVRRMPSLDEYLSXNCNXMGXLAGPXCSXKDYXTFXEGRSYHITQSGENXKEET
(161) PXQXGLAVRRMPSLLEYXSXTCNXMGXLAGPXCSXKDYXAFXEGRASHVAQPSENXK-DE
(168) AEXHRLAXXAKPSLLEVLSXHLNXMSXXXGPCNNXKDYXALXEGRHIHMKLLEVNWTQRG
(159) KDXKETALXXPPSLXXLLAXSYFPSGFXVGBQXPXSRMKAXXGEFR-------------

(199) TRK-KRKIXRSGTPAAXXAXAXLGWXXAXXQXGSLXNQELVXXETXMQYS----------
(203) DPYEKQITXHSLEPAXGXCWRXLXWLXXXTGSSIXFXKXLXTXKXASSP----------
(220) HPGERRQIXKNGKLAXWKXXQXLAWXXLSTLGMKHXFXKXVXXKDGFPTRS---------
(230) K------IXXQVWPTXXPXFGSLXCXGXXVGTGMXPXLDPNDXQNATPIPLTPEMLAKP
(196) TEK--RKKXSXYGXTXRAXXQXXXCXALXXYXVPQXFXTRFTXXVXQEW----------
(199) SEK--GKRXSXYGXMERAXFQXXXCXALXXYXVPQXFXTRFTXXVXQEW----------
(198) P------TPSXLLPTXRALXQXXACXGXXYXSPQXXXSRFSXXLXYEW----------
 (96) P------TPSXLLPTXRALXQXXACXGXXYXSPQXXXSRFSXXLXYEW----------
(226) SKREVVLEXSXTKXVXRKXXGSLXCAFXXXKFVKIXXXKDMKXDDXMNNTS--------
(207) QYE--RTEXSXNTXVXQKLXVCXXSLXFHXXTXCTTLXXXEXNXXEHFQATXS------
(221) QYE--RTEXSXNTXVXQKLXVCXXSLXFHXXTXCTTLXXXEXNXXEHFQATXS------
(220) QHG--KADPSXNAXVTEKLXVCXXSLXFHXXTXSNMLXVXEXNXXEHFQATXS------
(228) FQS--LPEXSXTGXVXQRLXCVTLXSLXXLXXTXSKSXXXTXLXDDWXVHKXN------
(206) -----QHEGNVEXGXRXFGAXXFYLXXCQVGLRYLXDSXFXTXEXAQVS----------
                                Motif 2
                   ─────────────────────────────
(248) FXQRXWIXXXLGXTAXLKYXGVWYXTEGXCXXSGNGXNGXXPKSG-XVFWNRXENXDPWS
(253) IXLXYGXXCXXAXVARXMKYXGXWELSDGXCXXSGXGXNGLXSSK--HPXWDRXKNXDPXK
(271) XXFRXXMLXXLGXIHRXKYXMAXWXXSEGXCXXCDLGXNGXXSKT-QXIXWDRXRNXDIWT
(284) AYAXYAMSXXXLFFIXXKYXVFAMNXXGXSNXWYAXFEGXDASXN-PKGWXVSNNXDXXQ
(244) FXRXFSXQYMAGXTARXKYXVFIWXXSEAXIXXSCXGXESGXTDDXSPXPXWDXAKNXDIXG
(247) FXKRFGXQYMAGXTARXKYXVFIWXXSEAXIXXSGLGXSGXTDETQTKXWDXAKNXDIXG
(242) XWHRXFXQYNSGXTAXXKYVXFIWXXSEAXIXXSGLGXSGXSDSSPPKXWDXAKNXDXXG
(140) XWHXXFXQYMSGXTAXXKYYHIWXXSEAXIXXSGLGXSGXSDSSPPKXWDXAKNXDYXG
(277) MXYXYWXAMMXXTCIXKYXHWLXXXXAXICNNSGXGXTGXKD---NSXWDLXSNXNXXS
(256) XPTXXIMLXXXLLAXXPKYXFAWXXXAXINNAXGFCXRCXDENX--AXXWDLXSNXRXQQ
(270) XPTXXIYLYXLLAXXPKYXFAWXXXAXINNAXGFXRCXDENX--AXXWDLXSNXRXQQ
(269) XPTXATYLYXXLLAXXPKYXFAWXXXADAXINNAXGFCXRCXDKNX--VXXWDLXSNXRXQQ
(277) FXSRXXWXXLYXVMQAAXPKYXFAWXXXSXDVHNAXGFXNGMXTDX--KSXWDLXSNXNXWK
(250) FXKRXYLXGFWXKFXLXKYXISCWLXXTEXXLXCIGXXTXKGEXKNG--QPDWSGCSNXKXKL Motif 3                              Motif 4
       ─────────────────────────              ─────────
(307) XETXQNSHGYXGSXWNKXXNHWLXNYXYLRXTPKGKXPGXRAXXATXVTXAFWHGFXXGYX
(311) FEFXADNIXCAXEAWNXXXINKWLXNXVYLRXAKKXXXPGRKSXXXSXXTXSAXWHGXSAGYX
(330) XETXQNTXEMXEAWNXXXINKWLXYSMYLRXTKKGXXPGFRSXXFXXLTSAFWHGTREGYX
(343) FETXPNLXTLSAAXNKKXXNWXAKXXYIRTG--------GSLFXXTXGXXAFWHGFXXGYX
(304) XEXAKSAVQIPLVWNXXCVXTWLXNHYXXYERXVQNGKXAGXFQLCXXXQTXSAXWHGXXGYM
(307) XEXAKSAVQIPLFWNXXQVXTWLXRHXXYERXVKPGKXAXFQLDXXQTXSAXWHGXXPGYI
(302) XEXATSAVQLPLMWNXQVXTWLXRYXXYERXVQKGKXXPGXLQLXATQTXSAXWHGXXGYI
(200) XEXATSAVQLPLMWNXXQVXTWLXRYXXYERXVQKGKXXPGXLQLXATQTXSAXWHGXXGYI
(335) FEFXXNMXDAXNNWXNCGXNRWLXRTLXVYERXP------QQYGXLXTXAXGAXWHGFXXGYX
(314) XEMXTSFXMFLDNXXNIXQTXLWLXRVCYERTS-------XSPIXXQTXXIXSAXWHGXXXGYX
(328) XEMXTSFXMFLDNXXNIXQTXLWLXRVCYERTS-------XSPIXXQTXXIXSAXWHGXXXGYX
```

FIG. 2C

```
(327) EMSTSF MF DNWNTQ  LW  RVCY RAT-------SP  QT F SA WHG   GY
(335) ETATSF MY ENWNTQT TW  CVCY R S-------YP  L RL SA WHG    GY
(308) ETVN  MEHY QS N    NQW GQ  YKR KFLNN--RTISYG ALGFLA WHGY SGY
```

Motif 4

```
(371)  TF L  F QTVA NF R HV PF  TPDGSRPTAY KY D AS  V Q T S A  ----
(390)  TF SAAF QTVA YT HHV PF  KPDMETPGPF RV D  GM A N S S L  S---
(395)  TFA GA  YQTC  IY  N PI  REDGVTPLPS KI     GIYAIK AFGY  Q ---
(364)  FF SVP  AFCE IGR KLTPR G------NGKKWSP G   CI A S MTE M  ---
(367)  FF QSA  IA SIV   WQQAISPK-----MAML NIMVF N  YT V N  A G---
(362)  FF QSA  ID  SKA Y WQQAIPPK-----MAML NVLV N  YT A  NY S G---
(260)  FF QSA  MIN S V Y WQQAVS------NPVFHAILVF N SY  L V NY C G---
(389)  FF QSA  MIN G  V Y WQQAVS------NPVFHAILVF N SY  L V NY C GFQF
(367)  FA GA  VT A RTGRH  RHR QS-----TQVT MF D  TC  I R  V G ATF ---
(381)  F  GVLM TL A AG NN HY  E-----PSQL LFY D T  V Q A SY  ----
(380)  F  GVL TL A A  NN HY  E-----PSQL LFY D T  V Q A SY  ----
(388) F FF GVP TL AA A  NN HH  S-----SKAR IA D  T AV Q A SY AAE---
(366)   P  MEY  VSTE Q T F TKVV PQWG--HILNNSDIY  LF I  LKSYNVVY GWCL
```

```
(424) ----------  FL FGDS  KV HSVY Y I GNI S AFFVSPARGLLLK L ARNKPH
(428) ----------  M LN  E  HV KE   IVR YI  A A FNSPIRSKLDN I SRVNSY
(447) ----------  F LD  PS MV GSVY YV H  VAFSFF FRGPYAKVTEFF SKQP E
(446) ----------     FDW WEN SSYY A H  C  FYL VSNMPT--------PKT E
(416) ----------  M LS HE  TA GSVY I T   P G  L SY VP-----A PSRPKP K
(419) ----------  M LS HE  VA KCV Y I T P A L SY VP-----V PVRPKT K
(412) ----------   NL FKE  AS QSV    T  P   L GY IKP----A PVKPKA K
(313) VFTMLYTLRFLQ L FKE  AS QSV    T  P   L GY IKP----A PVKPKA K
(441) ----------   L EFMGS KL LRF  LCL   S  T F LPKFIRGERRL TSNGNGNV
(419) ----------   L S KPS TF SSW    CL  G   L LP KKT----Q R NTHENI
(433) ----------   L S KPS TF SSW    CL  G   L LP KKT----Q R NTHENI
(432) ----------   L S KPS TF SSW    CL  C S   LP KKS----Q RTSTQENV
(440) ----------  V LA EP  SL KSV  F L  C    FLP KPH----QPQ --QS S
(424) TA--------   FLKYERW VV G  S Y FTFL  WAAFYHTFNHFFRSSSR LAGEDQ
```

```
(474) VPRAVSSENIRQPTLGLPND IQEFDDAVQEIRAEIESRQRRGSLAHMPIGDELKAAVED
(478) KLKSYEQSMKSTSDTDMLNM VPKREDFENDE---------------------------
(497) IFIRKQKKLEKDISASSPNLGGILKAKIEHEKGKTAEEEEMNLGIPPIELEKWDNAKEDW
(487) T-----------------------------------------------------------
(461) EE----------------------------------------------------------
(464) EE----------------------------------------------------------
(458) AE----------------------------------------------------------
(369) AE----------------------------------------------------------
(491) RLSGSGNTKDAVTTSVESTA LTAGNDLNEDKEEDKHAQCKVHTPTQQQPAAGPHKTTVE
(465) QLSQSKKFDEGENSLGQNSF TTNNVCNQNQEIASRHSSLKQ-------------------
(479) QLSQSRKFDEGENSLGQNSF TTNNVCNQNQEIASRHSSLKQ-------------------
(478) HLSQAKKFDERDNPLGQNSF TMNNVCNQNRDTGSRHSSLTQ-------------------
(484) PNSVKKKAD---------------------------------------------------
(476) KLQDSNTDKLVEEKKPEDKK E------------------------------------
```

FIG. 2D

```
(534) KIGRGH--------------------------------------------------------
(510) ----------------------------------------------------------------
(557) EDFCKDYKEWRNKNGLEIEEENLSKAFERFKQEFSNAASGSGERVRKMSFSGYSPKPISK
(488) ----------------------------------------------------------------
(463) ----------------------------------------------------------------
(466) ----------------------------------------------------------------
(460) ----------------------------------------------------------------
(371) ----------------------------------------------------------------
(551) QPTEQPNNVNLRSRPQQQQPHLEKKAMPPTCARDAVSVPHDQCEMDQLSSKLKEKIEAET
(507) ----------------------------------------------------------------
(521) ----------------------------------------------------------------
(520) ----------------------------------------------------------------
(493) ----------------------------------------------------------------
(498) ----------------------------------------------------------------

(540) ----------------------------------------------------------------
(510) ----------------------------------------------------------------
(617) KEE-------------------------------------------------------------
(488) ----------------------------------------------------------------
(463) ----------------------------------------------------------------
(466) ----------------------------------------------------------------
(460) ----------------------------------------------------------------
(371) ----------------------------------------------------------------
(611) KNIEEFIDKTVTETVSGIVEFKNDLMRDIEFPKLKLPGSNGAISLDSSNGGGLRKRNISS
(507) ----------------------------------------------------------------
(521) ----------------------------------------------------------------
(520) ----------------------------------------------------------------
(493) ----------------------------------------------------------------
(498) ----------------------------------------------------------------

(540) ----------------------------------------------------------------
(510) ----------------------------------------------------------------
(620) ----------------------------------------------------------------
(488) ----------------------------------------------------------------
(463) ----------------------------------------------------------------
(466) ----------------------------------------------------------------
(460) ----------------------------------------------------------------
(371) ----------------------------------------------------------------
(671) VHDNGTDPGHATADLHPPLEENGAAFLKKEIEVINAVVQQAVPAVLSNGHAK
(507) ----------------------------------------------------------------
(521) ----------------------------------------------------------------
(520) ----------------------------------------------------------------
(493) ----------------------------------------------------------------
(498) ----------------------------------------------------------------
```

FIG. 3A

```
SEQ ID NO:64   (1) ----------------------------------------
SEQ ID NO:65   (1) ----------------------------------------
SEQ ID NO:66   (1) ----------------------------------------
SEQ ID NO:67   (1) ----------------------------------------
SEQ ID NO:68   (1) ----------------------------------------
SEQ ID NO:69   (1) ----------------------------------------
SEQ ID NO:70   (1) -MGLEMEGMAAAIGVSVPVLRFLLCFAATIPTGLMWRAVPGAAGRHLYAG
SEQ ID NO:71   (1) ----------------------------------------
SEQ ID NO:72   (1) ----------------------------------------
SEQ ID NO:73   (1) ----------------------------------------
SEQ ID NO:74   (1) ---MDMSSMAGSIGVSVAVLRFLLCFVATIPVSFACRIVPSRLGKHLYAA
SEQ ID NO:75   (1) MELLDMNSMAASIGVSVAVLRFLLCFVATIPISFLWRFIPSRLGKHIYSA
SEQ ID NO:76   (1) ----------------------------------------
SEQ ID NO:77   (1) ----------------------------------------
SEQ ID NO:78   (1) ----------------------------------------
SEQ ID NO:79   (1) ----------------------------------------
SEQ ID NO:80   (1) ----------------------------------------

(1) ----------------------------------------
               (1) ----------------------------------------
               (1) ----------------------------------------
               (1) ----------------------------------------
               (1) ----------------------------------------
               (1) ----------------------------------------
              (50) LTGAALSYLSFGATSNLLFVVPMAFGYLAMLLCRRLAGLVTFLGAFGFLI
               (1) ----------------------------------------
               (1) ------------SSNLHFLVPMLLGYAAMLLCRRRCGVITFFLGFGYLI
               (1) ----------------------------------------
              (48) ASGAFLSYLSFGFSSNLHFLVPMTIGYASMAIYRPKCGIITFFLGFAYLI
              (51) ASGAFLSYLSFGFSSNLHFLVPMTIGYASMAIYRPLSGFITFFLGFAYLI
               (1) ----------------------------------------
               (1) ----------------------------------------
               (1) ----------------------------------------
               (1) ----------------------------------------
               (1) ----------------------------------------

(1) ----------------------------------------
               (1) ----------------------------------------
               (1) ----------------------------------------
               (1) ----------------------------------------
               (1) ------------------------------ISCLINYSDGILKEEGLRDA
               (1) ----------------------------------------
             (100) ACHMYYMSGDAWKEGGIDATGALMVLTLKIISCAINYSDGMLKEEGLRDA
               (1) ---MYYMSGDAWKEGGIDATGALMVLTLKIISCAINYSDGMLKEEGLRDA
              (38) GCHVYYMSGDAWKEGGIDATGALMVLTLKVISCAMNYNDGLLKEDGLREA
               (1) ----------------------------------------
              (98) GCHVFYMSGDAWKEGGIDSTGALMVLTLKVISCSMNYNDGMLKEEGLREA
             (101) GCHVFYMSGDAWKEGGIDSTGALMVLTLKVISCSINYNDGMLKEEGLREA
               (1) ----------------------------------------
               (1) ----------------------------------------
               (1) ------------------------------INYNDGLLKKEDLREP
               (1) ----------------------------------------
               (1) ----------------------------------------

```
(296) NVDVLGVELATSAVQLPLWNIQVSTWLRYVYERLVQKGKKEGFLQLL
(194) NVDVLGVELATSAVQLPLWNIQVSTWLRSYVYERLVQKGKKEGFLQLL
(238) NVDTLGVELAKSAVTLPLVWNIQVSTWLRYVYERLENGKKEGFQLLA
 (52) NVDILRVEFAKDAQLPLAWNIQVSTWLRHYVYERLVQKGKEGFQLLA
(298) NVDTLGVELAKSAVQLPLWNIQVSTWLRHYVYERLVQNGKKAGFQLLA
(301) NVDTLGVELAKSAVQLPLFWNIQVSTWLRHYVYERVKPGKKAGFQLLA
 (55) NVDVLGVELAKSSVQLPAMWNIQVSTWLRHYVYERLQKGKEGFQLLA
 (81) NVDVLGVELAKSSVQLPLVWNIQVSTWLRHYVYEREVQKGKEGFQLLA
(167) NVDVLGVELAKSSVQLPLVWNIQVSTWLHYVYERLVQKGKKEGFQLLA
 (78) NVDTLGVEFAKSAELPLVWNIQVSTWLRHYVYERLVPGGKAGFLQLLA
(148) NVDVLGVEFAKSVELPLVWNIQVSTWLRHYVYERLVQKGKKEGFQLLA
```

Motif 8

```
(124) TQTVSAWHGLYPGYLFFVQSALMIAGSRVTYRWQQAVPPTMDVAKLL
 (88) TQTMSAWHGLYPGYLFFVQSALMIAGSRVLYRWQQAVPQNMDAKNLL
 (79) TQTVSAWHGLYPGYMFFVQSALMINGSRVLYRWQQAVKQ--FRPPHYP
(172) TQTVSAWHGLYPGYMFFVQSALMINGSRVLYRWQQAVSN--PGTLC
(217) TQTMSAWHGLYPGYLFFSALMXNGSRVLYRWQQASS--SFSGLL
(120) TQTVSAWHGLYPGYMFFVQSALMINGSRVLYRWQQAVSS--SFGTL
(346) TQTMSAWHGLYPGYLFFVQSALMINGSKVLYRWQQAVSN--PQFHALL
(244) TQTMSAWHGLYPGYLFFVQSALMINGSRVLYRWQQAVSN--PQFHALL
(288) TQTVSAWHGLYPGYLFFVQSALM-----------------------
(102) TQTVSAWHGLYPGYLFFVQSALMIAGSRVLYRWQQAVPPKMDVAKLF
(348) TQTVSAWHGLYPGYMFFVQSALMIAGSRVLYRWQQAVSPKMAMIGNTL
(351) TQTVSAWHGLYPGYLFFVQSALMIDGSLALYRWQQAVPPKMAIKNL
(105) TQTVSAWHGLYPGYLFFVQSALMIAGSRVLYRWQQAAKG--SMFEKLL
(131) TQTVSAWHGLYPGYLFFVQSALMIAGSRVLYRWQQATKG--TFEKLL
(217) TQTMSAWHGLYPGYLGFF-----------------------------
(128) TQTTSAWHGLYPGYLFFVQSALMIAGSRVLYRWQQAPSNKAKELKLL
(198) TQTVSAWHGLYPGYLFFVQSALMISCSRALYRWQQAVPP---TVKFL
```

```
(174) VFNFAYTLVLNYSCIG------------EVLSPRETIAGYGSVP-
(138) VFNFAYTLVLNYSCIG------------EVLSPRETIAGYGSVP
(127) VFTKLLIP----------------------------------------
(220) SLNCAYTLVLNYSCIG------------QVLSFQETIAYKSVY
(265) ALIILLIAGAY-YSCIG------------VQVLSF-----------
(168) AFNFAYTLVLNYSCIG------------EVLSFKETIAYQSVY
(394) VFNFSYTLVLNYSCIG------------QVLSFKETIAYQSVY
(292) VFNFSYTLVLNYSCIGFQFVFTMLYTLRFLQVLSFKETIAYQSVY
(313) -----------------------------------------------
(152) VLNFAYTLVLNISSVG------------FMVLSHETIMYGSVY
(398) VFINLVYTLVLNYSAGG------------FMVLSHETITYGSVY
(401) VLNLYTLAVLNYSSVG------------FMVLSHETEVIKSVY
(153) VANEAYTLVLNYSAGG------------FMVLSHETITYGSVY
(179) ANEAYTLVLNYSAIG------------FMVLSHETITYGSVY
(236) -----------------------------------------------
(178) VFNFAYTLVLNYSCVG------------FMVLSHETAIGYSVY
(245) LMNFAYTLVLNYSCIG------------FMVLSHETAIGYSVY
```

```
(210) -----------------------------------------
(175) GTIEPALILLSYVKPPRPARSKARKEE---------
(136) -----------------------------------------
(257) GTIEPLCILGYKPTRPVKP-------------
(288) -----------------------------------------
(205) GTIEVFLGN------------------------
(431) GTIEVVLGYKPARPVKPKARKAE---------
(342) GTIEVVLGYKPARPVKPKARKAE---------
```

FIG. 3D

```
(313)  ------------------------------------
(189)  EP F YL------------------------------
(435)  ▓▓▓▓▓▓GL▓▓▓SY▓▓PAKPSRPKPRKEE---------
(438)  ▓▓▓▓▓▓AV▓▓▓SY▓▓PVKPVRPKTRKEE---------
(190)  ▓▓▓▓▓▓AL▓▓▓SK▓▓KPPRPCTSK-------------
(216)  ▓▓▓▓▓▓LL▓▓▓SK▓▓KPPRPATSKARKAE--------
(236)  ------------------------------------
(215)  ▓▓▓▓▓▓VFF▓▓GF▓▓KPARPSRSKHGTMSEVETVFLLL
(282)  ▓▓▓▓▓▓A------------------------------
```

Figure 3 Alignment of LPCAT sequences from different plant species.
Motif 5 (SEQ ID NO:81): E A φ φ I I(L) S G φ G F S(T) G W;
Motif 6 (SEQ ID NO:82): W D R A φ N V D;
Motif 7 (SEQ ID NO:83): W N I Q V S T W L φ φ Y V Y;
Motif 8 (SEQ ID NO:84): G F φ Q L L φ T Q T φ S A φ W H G L Y P G Y

METHODS FOR IDENTIFYING LYSOPHOSPHATIDYLCHOLINE ACYLTRANSFERASES

CROSS-REFERENCE TO RELATED APPLICATION

This application claims the benefit, under 35 U.S.C. §119(e) of U.S. Provisional Patent Application 60/874,497 filed Dec. 13, 2006, the contents of the entirety of which is incorporated by this reference.

TECHNICAL FIELD

The invention relates generally to biotechnology, and, more particularly, to lyso-phosphatidylcholine (LPC) acyltransferase, polynucleotides that encode LPC acyltransferases, and associated methods.

BACKGROUND

Phosphatidylcholine (PC) serves not only as a major component of cellular membranes, but also as a major source of fatty acyl donors for triacylglycerol biosynthesis in eukaryotic organisms. At least three pathways through which PC is generated exist: (i) the CDP-choline pathway where diacylglycerol (DAG) is a direct precursor; (ii) a pathway where CDP-DAG is a direct precursor, involving phosphatidylserine formation and decarboxylation and phosphatidylethanolamine methylation (Zheng and Zou, 2001); and (iii) a pathway with LPC as substrate. The third pathway is exerted by LPC acyltransferases (LPCAT).

LPCAT enzymes catalyze the acylation of LPC molecules to form PC and play a pivotal role in membrane biogenesis. They can also exert a reversible reaction to release the fatty acyl chain esterified to the sn-2 position of PC, thereby contributing to a continuous remodeling of fatty acyl-CoA and PC pools.

The significance of LPCAT in glycerolipid metabolism of eukaryotic systems has been noted for many years. For genetic engineering of plant-based production of very long chain polyunsaturated fatty acid (PUFA), this enzyme is believed to represent a bottleneck for acyl exchange between the fatty acyl elongation and de-saturation systems. In higher plants, the function of this enzyme is largely unknown, but it has been proposed that the enzyme is involved in the selective incorporation of fatty acids into storage pool.

Although LPCAT relating to the synthesis of surfactant lipid located on the surface of (pulmonary) cells have been reported in mammalian systems (Chen X et al., PNAS 2006 103:11724-11729; Nakanishi H et al., JBC 2006 281: 20140-20147), an LPC transferase involved in membrane or storage lipid synthesis has not been reported.

Recently, a mitochondrial acyl-CoA independent LPCAT from *Saccharomyces cerevisiae* has been identified. This enzyme has been shown to function in cardiolipin metabolism (Testet et al. 2005). In addition, Shindou et al. (2007) reported that aceyl-CoA:lyso-PAF (platelet-activating factor) acetyltransferase possesses LPCAT activity.

SUMMARY OF THE INVENTION

Novel types of LPCAT enzymes whose sequences are unrelated to any known LPCAT enzymes have been identified.

Previously reported LPCAT share a substantial sequence homology to glycerol-3-phosphate acyltransferase and lyso-phosphatidic acyltransferase. In contrast, the LPCAT sequences disclosed herein are unrelated to any known LPCAT sequences, and belong to a new class of LPCAT. Four conserved motifs were identified in this novel class of LPCAT enzymes. The identified motifs are different from previously reported LPCAT, which contain motifs having a high degree of similarity to those in other known acyltransferases employing glycerol-3-phosphate and lysophosphatidic acid as substrates. In contrast, sequence information of the motifs identified herein is novel, and can lead to the identification of new class of LPCAT genes from a broad spectrum of species.

Thus, in certain embodiments, a lyso-phosphatidylcholine acyltransferase gene or class of genes is identified. The LPC acyltransferase gene may be expressed or overexpressed in a cell and used to modify glycerolipid biosynthesis in a cell. Such an LPC acyltransferase gene may be expressed or overexpressed in a cell and used to modulate or enhance production of fatty acids, especially polyunsaturated fatty acids (PUFA) or other unusual fatty acids, and/or to increased oil content in the cell. The LPC acyltransferase gene may be expressed or overexpressed in planta in order to modify glycerolipid biosynthesis in a plant. In certain embodiments, the LPC acyltransferase gene is expressed or overexpressed in planta in order to enhance the production of fatty acids in a plant.

In certain embodiments, a plant, plant seed or progeny thereof includes a recombinant cell having an LPC acyltransferase gene.

In certain embodiments, a vector is provided having an LPC acyltransferase gene. The vector may be used to transform a cell, thus producing a recombinant cell having the LPC acyltransferase gene. The cell may comprise, for example, a bacterial cell, a yeast cell, or a plant cell.

In certain embodiments, a recombinant cell expresses an LPC acyltransferase gene and produces an LPC acyltransferase polypeptide that may be isolated or purified from the cell.

In certain embodiments, nucleotide and deduced amino acid sequences associated with an LPC acyltransferase gene are disclosed. The sequence, or a portion thereof, may be used to identify genes from other species that encode polypeptides with LPC acyltransferase activity.

In certain embodiments, a process for producing fatty acids includes transforming a cell with an LPC acyltransferase gene. The transformed cell expresses the fatty acid acyltransferase gene and produces fatty acids. The fatty acids may be isolated or purified from the recombinant cell or culture media in which the cell grows, and subsequently incorporated into a composition.

In certain embodiments, knock-out mutants disrupted in LPC acyltransferase gene of yeast and plants are identified.

In certain embodiments, a peptide comprising one or more of the four motifs may be used as an LPC Acyltransferase. Similarly, a nucleotide sequence encoding a peptide comprising one or more of the four motifs may be used as an LPC Acyltransferase.

Also provided is an isolated or recombinant nucleic acid molecule encoding an LPC acyltransferase, and a cell transformed with the isolated or recombinant nucleic acid molecule as described herein. Also provided is a process for increasing fatty acid production in a cell, the process comprising: transforming a cell with a nucleic acid molecule encoding an LPC acyltransferase; and, growing the cell under conditions wherein said LPC acyltransferase is expressed. Also provided is a use of an isolated or recombinant nucleic acid molecule encoding an LPC acyltransferase for producing an LPC acyltransferase in a cell. Also provided is a purified or an isolated LPC acyltransferase.

LPCAT enzymes play a critical role in remodeling fatty acid and PC pools as well as PC synthesis. The remodeled fatty acyl chains in the form of acyl-CoA or esterified at the sn-2 position of PC can be used for triacylglycerol synthesis. Thus, this novel type of LPCAT isolated from the organisms where very-long-chain polyunsaturated fatty acids (VL-CPUFA) are present at a high level can be used to increase the production of VLCPUFA. As well, this novel type of LPCAT isolated from species containing high amount of unusual fatty acids can be used to increase the production of unusual fatty acids. For instance, LPCAT enzymes isolated from castor bean are useful in increasing the production of hydroxyl fatty acids in oil seeds.

The enzyme activity described herein provides support that the motif-based gene searching is a useful approach.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2 is an alignment of LPCAT sequences from different species that revealing, among other things, four conserved motifs unique for this type of LPCAT enzymes.

FIG. 3 is another alignment of LPCAT sequences from different plant species that revealed four conserved motifs (SEQ ID NOS: 81-84).

DESCRIPTION OF PREFERRED EMBODIMENTS

Figure 1:
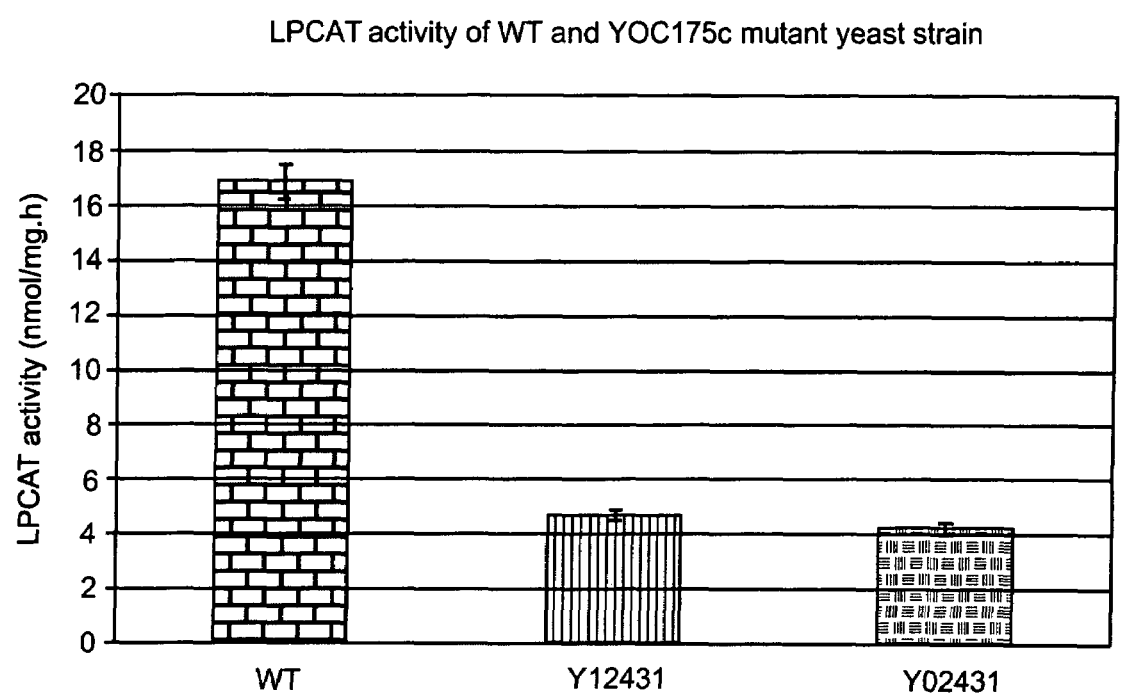
FIG. 1 is a graph of LPCAT activity (nmol/mg·h) of wild type (WT) and YOC175c mutant yeast strains.

Preferably, the nucleic acid molecule encoding the LPC acyltransferase is derived from yeast, plant and mammal species. Yeast species include, for example, species of the genus *Saccharomyces*, for example *Saccharomyces cerevisiae*. Plant species include, for example, species of the family Brassicaceae. Of the family Brassicaceae, species of genus *Brassica* and genus *Arabidopsis* are of particular note, for example *Arabidopsis thaliana*. Mammalian species include mouse and human.

In particular, provided are a nucleic acid molecule encoding an LPC acyltransferase from *S. cerevisiae* and two nucleic acid molecules encoding two different isoforms of LPC acyltransferase from *A. thaliana*. There is also provided the LPC acyltransferases encoded by the aforementioned nucleic acid molecules.

Provided herein is an isolated or recombinant nucleic acid molecule having a nucleotide sequence encoding an LPC acyltransferase such as amino acid sequence comprising SEQ ID NO: 2, SEQ ID NO: 4, SEQ ID NO: 6, SEQ ID NO: 8, SEQ ID NO:10, SEQ ID NO:11; SEQ ID NO:13, SEQ ID NO:15, SEQ ID NO:17; SEQ ID NO:19, SEQ ID NO:21, SEQ ID NO:25, SEQ ID NO:27, SEQ ID NO:29, SEQ ID NO:31, SEQ ID NO:33, and SEQ ID NO:35. In particular, there is provided an isolated or recombinant nucleic acid molecule having a nucleotide sequence comprising SEQ ID NO: 1, SEQ ID NO: 3, SEQ ID NO: 5, SEQ ID NO: 7, SEQ ID NO:9, SEQ ID NO:12, SEQ ID NO:14, SEQ ID NO:16, SEQ ID NO:18, SEQ ID NO:20, SEQ ID NO:24, SEQ ID NO:26, SEQ ID NO:28, SEQ ID NO:30, SEQ ID NO:32, or SEQ ID NO:34. Preferably, the LPC acyltransferase encoded by a nucleic acid molecule comprises an amino acid sequence comprises an amino acid sequence having at least 60% homology to the aforementioned sequences. Homology is more preferably at least 70%, 80%, 90%, or 95%. It will be appreciated that this disclosure embraces the degeneracy of codon usage as would be understood by one of ordinary skill in the art.

Homologs of the LPC acyltransferase genes described herein obtained from other organisms, for example plants, may be obtained by screening appropriate libraries that include the homologs, wherein the screening is performed with the nucleotide sequence of the specific LPC acyltransferase genes of the instant invention or portions or probes thereof, or identified by sequence homology search using sequence alignment search programs such as BLAST, FASTA.

Further included are nucleic acid molecules that hybridize to the above disclosed sequences. Hybridization conditions may be stringent in that hybridization will occur if there is at least a 90%, 95% or 97% identity with the nucleic acid molecule that encodes the LPC acyltransferase of the instant invention. The stringent conditions may include those used for known Southern hybridizations such as, for example, incubation overnight at 42° C. in a solution having 50% formamide, 5×SSC (150 mM NaCl, 15 mM trisodium citrate), 50 mM sodium phosphate (pH 7.6), 5× Denhardt's solution, 10% dextran sulfate, and 20 micrograms/milliliter denatured, sheared salmon sperm DNA, following by washing the hybridization support in 0.1×SSC at about 65° C. Other known hybridization conditions are well known and are described in Sambrook et al., Molecular Cloning: A Laboratory Manual, Third Edition, Cold Spring Harbor, N.Y. (2001), incorporated herein in its entirety by this reference.

Nucleic acid molecules that code for an LPC acyltransferase may be transformed into an organism, for example a plant. As known in the art, there are a number of ways by which genes and gene constructs can be introduced into organisms, for example plants, and a combination of transformation and tissue culture techniques have been successfully integrated into effective strategies for creating transgenic organisms, for example crop plants. These methods, which can be used in the invention, have been described elsewhere (Potrykus, 1991; Vasil, 1994; Walden and Wingender, 1995; Songstad et al., 1995), and are well known to persons skilled in the art. For example, one skilled in the art will certainly be aware that, in addition to *Agrobacterium*-mediated transformation of *Arabidopsis* by vacuum infiltration (Bechtold et at., 1993) or wound inoculation (Katavic et al., 1994), it is equally possible to transform other plant and crop species, using *Agrobacterium* Ti-plasmid-mediated transformation (e.g., hypocotyl (DeBlock et al., 1989) or cotyledonary petiole (Moloney et al., 1989) wound infection), particle bombardment/biolistic methods (Sanford et al., 1987; Nehra. et al., 1994; Becker et al., 1994) or polyethylene glycol-assisted, protoplast transformation (Rhodes et al., 1988; Shimamoto et al., 1989) methods.

As will also be apparent to persons skilled in the art, and as described elsewhere (Meyer, 1995; Dada et al., 1997), it is possible to utilize plant promoters to direct any intended up- or down-regulation of transgene expression using constitutive promoters (e.g., those based on CaMV35S), or by using promoters which can target gene expression to particular cells, tissues (e.g., napin promoter for expression of transgenes in developing seed cotyledons), organs (e.g., roots), to a particular developmental stage, or in response to a particular external stimulus (e.g., heat shock).

Promoters for use herein may be inducible, constitutive, or tissue-specific or have various combinations of such characteristics. Useftil promoters include, but are not limited to constitutive promoters such as carnation etched ring virus (CERV), cauliflower mosaic virus (CaMV) 35S promoter, or more particularly the double enhanced cauliflower mosaic virus promoter, comprising two CaMV 35S promoters in tandem (referred to as a "Double 35S"promoter).

It may be desirable to use a tissue-specific or developmentally regulated promoter instead of a constitutive promoter in certain circumstances. A tissue-specific promoter allows for overexpression in certain tissues without affecting expression in other tissues. By way of illustration, a preferred promoter used in overexpression of enzymes in seed tissue is an ACP promoter as described in PCT International Publication WO 92/18634, published Oct. 29, 1992, the disclosure of which is herein incorporated by reference.

The promoter and termination regulatory regions will be functional in the host plant cell and may be heterologous (that is, not naturally occurring) or homologous (derived from the plant host species) to the plant cell and the gene. Suitable promoters which may be used are described above.

The termination regulatory region may be derived from the 3' region of the gene from which the promoter was obtained or from another gene. Suitable termination regions which may be used are well known in the art and include *Agrobacterium tumefaciens* nopaline synthase terminator (Tnos), *A. tumefaciens* mannopine synthase terminator (Tmas) and the CaMV 35S terminator (T35S). Particularly preferred termination regions for use herein include the pea ribulose bisphosphate carboxylase small subunit termination region (TrbcS) or the Tnos termination region. Such gene constructs may suitably be screened for activity by transformation into a host plant via *Agrobacterium* and screening for increased isoprenoid levels.

Suitably, the nucleotide sequences for the genes may be extracted from the GenBank® (a registered trademark of the U.S. Department of Health and Human Services) nucleotide database and searched for restriction enzymes that do not cut. These restriction sites may be added to the genes by conventional methods such as incorporating these sites in PCR primers or by sub-cloning.

Preferably, a DNA construct for use herein is comprised within a vector, most suitably an expression vector adapted for expression in an appropriate host (plant) cell. It will be appreciated that any vector which is capable of producing a plant comprising the introduced DNA sequence will be sufficient.

Suitable vectors are well known to those skilled in the art and are described in general technical references such as Pouwels et al., Cloning Vectors. A Laboratory Manual, Elsevier, Amsterdam (1986). Particularly suitable vectors include the Ti plasmid vectors.

Transformation techniques for introducing the DNA constructs into host cells are well known in the art and include such methods as micro-injection, using polyethylene glycol, electroporation, or high velocity ballistic penetration. A preferred method relies on *Agrobacterium*-mediated transformation. After transformation of the plant cells or plant, those plant cells or plants into which the desired DNA has been incorporated may be selected by such methods as antibiotic resistance, herbicide resistance, tolerance to amino-acid analogues or using phenotypic markers.

Various assays may be used to determine whether the plant cell shows an increase in gene expression, for example, Northern blotting or quantitative reverse transcriptase PCR (RT-PCR). Whole transgenic plants may be regenerated from the transformed cell by conventional methods. Such transgenic plants having improved isoprenoid levels may be propagated and self-pollinated to produce homozygous lines. Such plants produce seeds containing the genes for the introduced trait and can be grown to produce plants that will produce the selected phenotype.

Plants that may be modified or used for fatty acid production according to the instant invention include, without limitation, borage (*Borago* spp.), Canola, castor (*Ricinus communis*); cocoa bean (*Theobroma cacao*), corn (*Zea mays*), cotton (*Gossypium* spp), *Crambe* spp., *Cuphea* spp., flax (*Linum* spp.), *Lesquerella* and *Limnanthes* spp., *Linola*, nasturtium (*Tropaeolum* spp.), *Oenanthera* spp., olive (*Olea* spp.), palm (.*Elaeis* spp.), peanut (*Arachis* spp.), rapeseed, safflower (*Carthamus* spp.), soybean (*Glycine* and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.) sorghum (*Sorghum* spp.), rye (*Secale* spp.) or other members of the Gramineae. It will further be apparent to those of ordinary skill in the art that genomic or sequence libraries of each of these plants may be screened with the nucleotide or amino acid sequences described herein (e.g., for one or more of the hereinafter identified conserved motifs (SEQ ID NO:46 through SEQ ID NO:49) for other sequences that encode or are homologous to sequences associated with the LPC acyltransferase of the instant invention.

Plants transformed with a nucleotide sequence of the instant invention that codes for an LPC acyltransferase may be grown. Seeds of the transgenic plants are harvested and fatty acids of the seeds are extracted. The extracted fatty acids are used for subsequent incorporation into a composition, for example a pharmaceutical composition, a nutraceutical composition or a food composition.

In certain embodiments, a peptide comprising one or more of the four motifs may be used as an LPC Acyltransferase. Similarly, a nucleotide sequence encoding a peptide comprising one or more of the four motifs may be used as an LPC Acyltransferase.

In certain embodiments, other methods of enhancing or altering oil production may also be used with the plant to be transformed (e.g., incorporating, for expression in the plant, a nucleic acid sequence selected from the group consisting of a nucleic acid sequence encoding a peptide having, for example, Brassica pyruvate dehydrogenase kinase activity (see, e.g., U.S. Pat. No. 7,214,859 to Marilla et al. (May 8, 2007), U.S. Pat. No. 6,500,670 to Zou et al. (December 2002), and U.S. Pat. No. 6,256,636 to Randall et al. (July 2001), the contents of the entirety of each of which is incorporated herein by this reference), a nucleic acid sequence encoding a peptide having diacylglycerol acyltransferase activity (see, e.g., U.S. Pat. No. 7,015,373 and U.S. Pat. No. 6,500,670 to Zou et al. (December 2002), the contents of the entirety of each of which is incorporated herein by this reference), a nucleic acid sequence encoding a peptide having glycerol-3-phosphate dehydrogenase activity (see, e.g., U.S. Pat. No. 7,112,724, the contents of the entirety of which is incorporated herein by this reference), and combinations thereof).

Also described is a method of transforming a cell or a plant, the method comprising introducing the isolated, purified or recombinant nucleic acid into the cell or plant. A process for producing a genetically transformed plant seed comprises introducing the nucleic acid into the plant seed.

Also described is a vector comprising SEQ ID NO: 1, SEQ ID NO: 3, SEQ ID NO: 5, SEQ ID NO: 7, SEQ ID NO:9, SEQ ID NO:12, SEQ ID NO:14, SEQ ID NO:16, SEQ ID NO:18, SEQ ID NO:20, SEQ ID NO:24, SEQ ID NO:26, SEQ ID NO:28, SEQ ID NO:30, SEQ ID NO:32, and/or SEQ ID NO:34.

Also described is a vector comprising a nucleic acid sequence encoding a polypeptide having lyso-phosphatidyl-choline acyltransferase activity, wherein the nucleic acid sequence comprises SEQ ID NO: 1, SEQ ID NO: 3, SEQ ID NO: 5, SEQ ID NO: 7, SEQ ID NO:9, SEQ ID NO:12, SEQ ID NO:14, SEQ ID NO:16, SEQ ID NO:18, SEQ ID NO:20, SEQ ID NO:24, SEQ ID NO:26, SEQ ID NO:28, SEQ ID NO:30, SEQ ID NO:32, or SEQ ID NO:34, or a fragment of SEQ ID NO: 1, SEQ ID NO: 3, SEQ ID NO: 5, SEQ ID NO: 7, SEQ ID NO:9, SEQ ID NO:12, SEQ ID NO:14, SEQ ID NO:16, SEQ ID NO:18, SEQ ID NO:20, SEQ ID NO:24, SEQ ID NO:26, SEQ ID NO:28, SEQ ID NO:30, SEQ ID NO:32, or SEQ ID NO:34, or having 90% identity with SEQ ID NO: 1, SEQ ID NO: 3, SEQ ID NO: 5, SEQ ID NO: 7, SEQ ID NO:9, SEQ ID NO:12, SEQ ID NO:14, SEQ ID NO:16, SEQ ID NO:18, SEQ ID NO:20, SEQ ID NO:24, SEQ ID NO:26, SEQ ID NO:28, SEQ ID NO:30, SEQ ID NO:32, or SEQ ID NO:34, wherein the fragment encodes the polypeptide having the lyso-phosphatidylcholine acyltransferase activity.

Also described is a method for increasing fatty acid production in a cell, the method comprising transforming a cell with a nucleic acid molecule encoding a lyso-phosphatidyl-choline acyltransferase; and growing the cell under conditions wherein the lyso-phosphatidylcholine acyltransferase is expressed. The method can further comprise isolating the fatty acid. In such a method, the lyso-phosphatidylcholine acyltransferase preferably comprises at least one motif selected from the group consisting of SEQ ID NO: 46, SEQ ID NO: 47, SEQ ID NO: 48, SEQ ID NO: 49, and any combination thereof.

Also described is a method of altering oil content in a plant comprising screening for a peptide encoded by a nucleotide sequence for at least one of four motifs selected from the group consisting of SEQ ID NO: 46, SEQ ID NO: 47, SEQ ID NO: 48, and SEQ ID NO: 49; selecting the peptide based upon the presence of at least one of the four motifs; and expressing the nucleotide sequence encoding the peptide in the plant to alter the oil content of the plant.

Also described is a method of changing the oil content of a plant or plant seed, the method comprising introducing a nucleic acid construct comprising a nucleic acid sequence encoding a polypeptide selected from the group consisting of SEQ ID NO: 2, SEQ ID NO: 4, SEQ ID NO: 6, SEQ ID NO: 8, SEQ ID NO:10, SEQ ID NO:11; SEQ ID NO:13, SEQ ID NO:15, SEQ ID NO:17; SEQ ID NO:19, SEQ ID NO:21, SEQ ID NO:25, SEQ ID NO:27, SEQ ID NO:29, SEQ ID NO:31, SEQ ID NO:33, SEQ ID NO:35, and an amino acid sequence having at least 60% homology to any thereof having lyso-phosphatidylcholine acyltransferase activity into a plant transformation vector; transforming a genome of a plant or plant seed with the plant transformation vector; expressing the nucleic acid sequence; growing the plant or plant seed; and extracting the oil from the plant seed.

The methods can further comprise incorporating, for expression in the plant, a nucleic acid sequence selected from the group consisting of a nucleic acid sequence encoding a peptide having pyruvate dehydrogenase kinase activity, a nucleic acid sequence encoding a peptide having diacylglyc-erol acyltransferase activity, a nucleic acid sequence encoding a peptide having glycerol-3-phosphate dehydrogenase activity, and any combination thereof.

The methods preferably involve a plant of the group consisting of borage (*Borago* spp.), Canola, castor (*Ricinus communis*); cocoa bean (*Theobroma cacao*), corn (*Zea mays*), cotton (*Gossypium* spp), *Crambe* spp., *Cuphea* spp., flax (*Linum* spp.), *Lesquerella* and *Limnanthes* spp., Linola, nasturtium (*Tropaeolum* spp.), *Oeanothera* spp., olive (*Olea* spp.), palm (*.Elaeis* spp.), peanut (*Arachis* spp.), rapeseed, safflower (*Carthamus* spp.), soybean (*Glycine and Soja* spp.), sunflower (*Helianthus* spp.), tobacco (*Nicotiana* spp.), *Vernonia* spp, wheat (*Triticum* spp.), barley (*Hordeum* spp.), rice (*Oryza* spp.), oat (*Avena* spp.) sorghum (*Sorghum* spp.), rye (*Secale* spp.) or other members of the Gramineae.

The invention is further described with the aid of the following illustrative Examples.

EXAMPLE 1

Identification of Yeast LPC Acyltransferase Gene

Nucleotide sequences of nucleic acid molecules of the invention were identified through yeast genetic and functional screening. Yeast (*S. cerevisiae*) LPC acyltransferase gene was identified based on enzyme assays of yeast mutant strains in which the gene, YOR175c, was knocked out. The enzyme activity was assessed using 14C-labeled acyl-CoA and lyso-phosphatidylcholine. The reaction product of the lyso-phosphatidylcholine and radio-labeled acyl-CoA was separated through TLC and measured through scintillation counting. Deletion of the YOR175c gene in yeast resulted in a 90% reduction of LPC acyltransferase activity (FIG. 1). Therefore, YOR175c encodes LPC acyltransferase. Details are given below for the In Vitro Assay protocol for LPCAT (lyso-phosphatidylcholine (LPC) acyltransferase) activity.

Yeast culture: One colony each of wild-type (strain BY4741) and LPCAT mutants (YOR175c deletion strains Y12431, Y02431) are inoculated in 10 ml YPD media and grown overnight. After 24 hr, another 20 ml YPD media is added and growth is continued for another 24 hr.

Protein extraction: Yeast cultures are spun at 2800 rpm at 4° C. for 20 min. The supernatant is discarded and the yeast pellet washed with 10 ml of ice cold IB buffer (80 mM HEPES, 320 mM sucrose, 5 mM EDTA pH8, 10 mM KCl, 2 mM DTT). The pellets are spun again and re-suspend in 500 µl of IB buffer. Yeast cells are divided and transferred into 2 tubes appropriate for a mini-bead beater. 0.5 mm cold glass beads are added to fill completely the tube. To break the yeast cell, three 60 s pulses of the mini-bead beater are used. The mixtures are spun again to remove unbroken cells and debris.

Protein assay conditions: A reaction is conducted using the recipe for fatty-CoA substrate specificity, as listed in Table 1.

TABLE 1

| Solution | Volume added |
| --- | --- |
| 450 µM lyso-PC (18:1) | 50 µl |
| 180 µM $^{14}$C 18:1-CoA (10 nCi/nmol) | 50 µl |
| Microsome | 400 µg protein |
| pH 7.4 HEPES | to make fine volume 0.5 ml |

The reaction mixture is allowed to sit in a water bath at 30° C. and stirred at 100 rpm for 30 min. The reaction is then terminated by adding 2 ml of $CH_2Cl_2$: Isopropanol (1:2). The mixture is allowed to sit at room temperature for 15-30 min with occasional vortexing. Phases are separated by adding 2 ml $CH_2Cl_2$ followed by 2 ml 1M KCl in $H_3PO_4$. The lower layer is transferred to a clean tube and the upper aqueous phase is backwashed twice with $CH_2Cl_2$ and centrifuged, saving the organic phase each time. Organic phases are combined and dried under nitrogen. Dried material is taken up in 200 µl $CH_2Cl_2$: MeOH (2:1) and protein is separated by thin layer chromatography (TLC) using silica G (250 µm) commercial plate. Plates are developed to within 2 cm of top in ethyl acetate:isooctane:acetic acid (45:15:10, V/V/V), then dried and scraped. The phosphatidyl choline region is counted in 4 ml Aquasol-2 by a scintillation counter.

The YOR175c gene from *S. cerevisiae* has been identified as encoding an LPC acyltransferase. The coding sequence of this yeast LPC acyltransferase gene is SEQ ID NO: 1:

```
ATGTACAATCCTGTGGACGCTGTTTTAACAAAGATAATTACCAACTATGGGATTGATAGT
TTTACACTGCGATATGCTATCTGCTTATTGGGATCGTTCCCACTGAATGCTATTTTGAAG
AGAATTCCCGAGAAGCGTATAGGTTTAAAATGTTGTTTTATCATTTCTATGTCGATGTTT
TACTTATTCGGTGTGCTGAATCTAGTAAGTGGATTCAGGACCCTGTTTATTAGTACCATG
TTTACTTACTTGATCTCAAGATTTTACCGTTCCAAGTTTATGCCACACTTGAATTTCATG
TTTGTTATGGGTCATTTGGCAATAAATCATATACACGCCCAATTCCTTAACGAACAGACT
CAAACTACCGTTGACATTACAAGTTCACAAATGGTTTTAGCCATGAAACTAACTTCTTTT
GCATGGTCGTACTATGATGGTTCATGCACTAGCGAAAGCGATTTCAAAGATTTGACTGAG
CATCAAAAATCTCGTGCTGTCAGAGGTCATCCACCCTTATTAAAGTTCCTGGCATATGCA
TTTTTCTATTCAACGTTGCTAACTGGCCCAAGTTTCGATTATGCCGATTTTGACAGCTGG
TTGAATTGTGAGATGTTCCGTGACTTGCCTGAAAGCAAAAAGCCTATGAAGAAGACACCAC
CCTGGTGAAAGAAGACAGATTCCAAAGAATGGTAAACTTGCATTATGGAAAGTTGTTCAA
GGTCTTGCTTGATGATTTTAAGTACACTAGGAATGAAGCACTTCCCCGTAAAATACGTT
TTGGACAAAGATGGCTTCCCAACGAGATCTTTTATATTCAGAATCCATTACTTATTCTTG
CTTGGTTTCATCCATAGATTCAAGTACTACGCTGCCTGGACTATTTCGGAAGGATCTTGT
ATTTTGTGCGGTTTGGGTTATAATGGTTATGATTCAAAGACACAAAAGATCAGATGGGAT
CGTGTCAGAAATATTGACATTTGGACCGTAGAAACGGCGCAGAATACGCGTGAAATGTTG
GAAGCATGGAATATGAATACTAACAAGTGGCTAAAATACTCTGTTTATTTACGTGTCACA
AAGAAGGGCAAAAAACCTGGTTTCCGCTCAACTTTGTTTACTTTCCTAACTTCCGCATTT
TGGCATGGTACCAGACCTGGGTACTATCTGACTTTTGCGACAGGGGCTTTGTACCAAACA
TGTGGTAAAATCTACAGACGCAATTTTAGACCAATTTTCTTGCGAGAAGATGGTGTCACT
CCTTTGCCTTCTAAAAAAATCTACGATTTAGTTGGCATATATGCAATTAAACTAGCATTT
GGTTACATGGTGCAACCATTTATTATCCTTGATTTGAAGCCATCTTTAATGGTATGGGC
TCTGTTTATTTCTATGTTCATATTATTGTTGCTTTCTCATTTTTCCTATTCAGAGGACCA
TATGCTAAACAAGTTACTGAATTTTTTAAATCCAAACAACCTAAAGAAATATTCATTAGA
AAACAAAGAAGTTGGAAAAAGATATTTCTGCAAGCTCTCCAAACTTGGGTGGTATATTG
AAGGCAAAGATTGAACATGAAAAGGGAAAGACAGCAGAAGAAGAAGAAATGAACTTAGGT
ATTCCACCAATTGAGTTAGAAAAGTGGGACAATGCTAAGGAAGATTGGGAAGATTTCTGC
AAAGATTACAAAGAATGGAGAAATAAAAATGGTCTTGAAATAGAAGAGGAAAACCTTTCT
AAAGCTTTTGAAAGATTCAAGCAGGAATTTTCTAACGCTGCAAGTGGATCAGGTGAACGT
GTGAGAAAAATGAGTTTTAGTGGTTACTCACCAAAGCCTATTTCAAAAAAGGAAGAGTAG
```

The deduced amino acid sequence of the yeast LPC acyltransferase encoded by the gene is SEQ ID NO: 2:

```
MYNPVDAVLTKIITNYGIDSFTLRYAICLLGSFPLNAILKRIPEKRIGLKCCFIISMSMF
YLFGVLNLVSGFRTLFISTMFTYLISRFYRSKFMPHLNFMFVMGHLAINHIHAQFLNEQT
QTTVDITSSQMVLAMKLTSFAWSYYDGSCTSESDFKDLTEHQKSRAVRGHPPLLKFLAYA
FFYSTLLTGPSFDYADFDSWLNCEMFRDLPESKKPMRRHHPGERRQIPKNGKLALWKVVQ
GLAWMILSTLGMKHFPVKYVLDKDGFPTRSFIFRIHYLFLLGFIHRFKYYAAWTISEGSC
ILCGLGYNGYDSKTQKIRWDRVRNIDIWTVETAQNTREMLEAWNMNTNKWLKYSVYLRVT
KKGKKPGFRSTLFTFLTSAFWHGTRPGYYLTFATGALYQTCGKIYRRNFRPIFLREDGVT
PLPSKKIYDLVGIYAIKLAFGYMVQPFIILDLKPSLMVWGSVYFYVHIIVAFSFFLFRGP
YAKQVTEFFKSKQPKEIFIRKQKKLEKDISASSPNLGGILKAKIEHEKGKTAEEEEMNLG
IPPIELEKWDNAKEDWEDFCKDYKEWRNKNGLEIEEENLSKAFERFKQEFSNAASGSGER
VRKMSFSGYSPKPISKKEE
```

EXAMPLE 2

Identification of Plant Nucleotide Sequences Encoding LPC Acyltransferase

The nucleotide sequence of the yeast LPC acyltransferase gene was used to search for homologous sequences using computer programs designed to search for homologous sequences. For instance, readily commercially available computer programs that may be used for such searches include without limitation, BLASTN, BLASTX and TBLASTX which may be used to search for nucleotide sequences, and BLASTP and TBLASTN which may be used to search for amino acid sequences. Such computer programs are readily accessible at the web-site www.ncbi.nlm.nih.gov.

Two plant (*A. thaliana*) homologs were identified through sequence alignment searching using BLAST. The two homologs are cDNA sequences that encode two different isoforms of LPC acyltransferase.

*Arabidopsis* LPC acyltransferase 1

Nucleotide sequence of *Arabidopsis* LPC acyltransferase 1 cDNA is SEQ ID NO: 3:

```
   1 ACCAACAACC ACACGACACG ACACGACCGA TCTATAGATT
     CGGCGAGATC

51 AGAAGAAAGC TTCCCGGAGC AACTCGGTCG TTGTGACTCA
     TTCCGAGTTA

101 AAAAAAACGG GTTTTCGACA CCATGGATAT GAGTTCAATG
     GCTGGTTCAA

151 TCGGAGTTTC GGTAGCCGTA CTCCGATTCC TCCTCTGTTT
     CGTTGCCACG

201 ATCCCTGTTT CATTCGCTTG TCGAATCGTC CCGAGTAGAC
     TCGGTAAACA

251 CTTGTATGCC GCTGCTTCAG GTGCTTTCCT CTCTTACCTC
     TCCTTTGGCT

301 TCTCCTCCAA CCTTCACTTC CTTGTTCCGA TGACGATCGG
     ATATGCTTCA

351 ATGGCGATTT ATAGACCCAA GTGTGGAATC ATCACTTTCT
     TCCTCGGTTT
```

-continued

```
 401 CGCTTATCTT ATTGGCTGTC ATGTGTTTTA TATGAGTGGT
     GATGCGTGGA

451 AAGAAGGAGG AATCGATTCT ACTGGAGCGT TAATGGTGTT
     GACGCTGAAA

501 GTCATCTCAT GTTCAATGAA TTACAATGAT GGGATGTTGA
     AGGAGGAAGG

551 TCTACGTGAA GCTCAGAAGA AAAACAGATT GATTCAGATG
     CCGTCTTTGA

601 TTGAGTACTT TGGTTACTGC CTTTGTTGTG GTAGCCATTT
     TGCTGGTCCT

651 GTTTATGAAA TGAAAGATTA TCTTGAATGG ACCGAAGGGA
     AAGGGATTTG

701 GGATACTACT GAGAAAAGAA AGAAGCCATC GCCTTATGGA
     GCTACAATCC

751 GAGCTATTTT GCAAGCTGCG ATTTGCATGG CTCTGTATCT
     CTATTTAGTG

801 CCTCAATATC CGTTAACTCG GTTCACAGAA CCAGTGTATC
     AAGAATGGGG

851 ATTCTTGAGA AAATTTAGTT ACCAATACAT GGCTGGATTC
     ACGGCTCGTT

901 GGAAGTATTA CTTCATCTGG TCAATTTCAG AGGCTTCTAT
     TATCATCTCT

951 GGTTTGGGTT TCAGTGGTTG GACTGATGAT GCTTCACCAA
     AGCCCAAATG

1001 GGACCGTGCC AAGAACGTAG ATATTCTCGG TGTTGAACTA
     GCTAAGAGCG

1051 CGGTTCAGAT TCCACTTGTG TGGAACATAC AAGTCAGCAC
     GTGGCTCCGT

1101 CACTATGTGT ATGAGAGACT TGTGCAGAAC GGAAAGAAAG
     CGGGTTTCTT

1151 CCAGTTACTA GCTACACAAA CCGTCAGCGC GGTTTGGCAT
     GGACTGTATC

1201 CTGGATATAT GATGTTCTTT GTTCAGTCAG CTTTGATGAT
     CGCAGGCTCA
```

```
1251 CGGGTTATTT ACCGGTGGCA ACAAGCGATC AGTCCGAAAA
     TGGCAATGCT

1301 GAGAAATATA ATGGTCTTCA TCAACTTCCT TTACACTGTT
     TTGGTTCTCA

1351 ACTACTCAGC CGTCGGTTTC ATGGTGTTAA GCTTGCACGA
     AACACTTACC

1401 GCCTACGGAA GCGTATATTA CATTGGAACA ATCATACCTG
     TTGGATTGAT

1451 TCTCCTCAGT TACGTTGTGC CTGCAAAACC TTCAAGACCA
     AAACCGCGTA

1501 AAGAAGAATA AGCAGTTATC TTCTTCTCTT AACGGTAAGT
     AAGTTTCCCG

1551 CGCTTGCCAG CTTCTTCTTC TTCTTCTGTA ACATTTGGAA
     ACAAACCGAT

1601 CCGGTTCTTG TTTCTCTCTG ATTTTTTAGC ACCGATATTT
     TTTTTGTATT

1651 TGTTGCTTAT AAATCTTATT TTTCACACTT CTTTTTTTTA
     ATTAGTATTG

1701 GATTTGCAAT TATATAGACA ATAAGTATAA ATATGTAACT
     GTAAATTGCA

1751 AATGGGAAAA AATAGTAGTG TTTATGTTTG
```

The deduced amino acid sequence of *Arabidopsis* LPC acyltransferase 1 is SEQ ID NO: 4:

```
  1 MDMSSMAGSI GVSVAVLRFL LCFVATIPVS FACRIVPSRL
    GKHLYAAASG

51 AFLSYLSFGF SSNLHFLVPM TIGYASMAIY RPKCGIITFF
    LGFAYLIGCH

101 VFYMSGDAWK EGGIDSTGAL MVLTLKVISC SMNYNDGMLK
    EEGLREAQKK

151 NRLIQMPSLI EYFGYCLCCG SHFAGPVYEM KDYLEWTEGK
    GIWDTTEKRK

201 KPSPYGATIR AILQAAICMA LYLYLVPQYP LTRFTEPVYQ
    EWGFLRKFSY

251 QYMAGFTARW KYYFIWSISE ASIIISGLGF SGWTDDASPK
    PKWDRAKNVD

301 ILGVELAKSA VQIPLVWNIQ VSTWLRHYVY ERLVQNGKKA
    GFFQLLATQT

351 VSAVWHGLYP GYMMFFVQSA LMIAGSRVIY RWQQAISPKM
    AMLRNIMVFI

401 NFLYTVLVLN YSAVGFMVLS LHETLTAYGS VYYIGTIIPV
    GLILLSYVVP

451 AKPSRPKPRK EE
```

*Arabidopsis* LPC acyltransferase 2

Nucleotide sequence of *Arabidopsis* LPC acyltransferase 2 cDNA is SEQ ID NO: 5:

```
   1 AGATGTCCGA ACTGTGAGAG TCGTCGTCGT CGTCGTAACT
     CAGTCCGAGT

51 TGACACAATC TTCCACTTCA CGCAAGATAC AACCATGGAA
     TTGCTTGACA

101 TGAACTCAAT GGCTGCCTCA ATCGGCGTCT CGGTCGCCGT
     TCTCCGTTTC

151 CTCCTCTGTT TCGTCGCAAC GATACCAATC TCATTTTTAT
     GGCGATTCAT

201 CCCGAGTCGA CTCGGTAAAC ACATATACTC AGCTGCTTCT
     GGAGCTTTCC

251 TCTCTTATCT CTCCTTTGGC TTCTCCTCAA ATCTTCACTT
     CCTTGTCCCA

301 ATGACGATTG GTTACGCTTC AATGGCGATT TATCGACCCT
     TGTCTGGATT

351 CATTACTTTC TTCCTAGGCT TCGCTTATCT CATTGGCTGT
     CATGTGTTTT

401 ATATGAGTGG TGATGCTTGG AAAGAAGGAG GAATTGATTC
     TACTGGAGCT

451 TTGATGGTAT TAACACTGAA AGTGATTTCG TGTTCGATAA
     ACTACAACGA

501 TGGAATGTTG AAAGAAGAAG GTCTACGTGA GGCTCAGAAG
     AAGAACCGTT

551 TGATTCAGAT GGCTTCTCTT ATTGAGTACT TTGGTTATTG
     CCTCTGTTGT

601 GGAAGCCATT TGGCTGGCCC GGTTTTCGAA ATGAAAGATT
     ATCTCGAATG

651 GACTGAAGAG AAAGGAATTT GGGCTGTTTC TGAAAAAGGA
     AAGAGACCAT

701 CGCCTTATGG AGCAATGATT CGAGCTGTGT TCAAGCTGC
     GATTTGTATG

751 GCTCTCTATC TCTATTTAGT ACCTCAGTTT CCGTTAACTC
     GGTTCACTGA

801 ACCAGTGTAC CAAGAATGGG GATTCTTGAA GAGATTTGGT
     TACCAATACA

851 TGGCGGGTTT CACGGCTCGT TGGAAGTATT ACTTTATATG
     GTCTATCTCA

901 GAGGCTTCTA TTATTATCTC TGGTTTGGGT TTCAGTGGTT
     GGACTGATGA

951 AACTCAGACA AAGGCTAAAT GGGACCGCGC TAAGAATGTC
     GATATTTTGG

1001 GGGTTGAGCT TGCCAAGAGT GCGGTTCAGA TTCCGCTTTT
     CTGGAACATA

1051 CAAGTCAGCA CATGGCTCCG TCACTACGTA TATGAGAGAA
     TTGTGAAGCC

1101 CGGGAAGAAA GCGGGTTTCT TCCAATTGCT AGCTACGCAA
     ACCGTCAGTG

1151 CTGTGTGGCA TGGACTGTAT CCTGGATACA TTATATTCTT
     TGTGCAATCA

1201 GCATTGATGA TCGATGGTTC GAAAGCTATT TACCGGTGGC
     AACAAGCAAT

1251 ACCTCCGAAA ATGGCAATGC TGAGAAATGT TTTGGTTCTC
     ATCAATTTCC

1301 TCTACACAGT AGTGGTTCTC AATTACTCAT CCGTCGGTTT
     CATGGTTTTA

1351 AGCTTGCACG AAACACTAGT CGCCTTCAAG AGTGTATATT
     ACATTGGAAC

1401 AGTTATACCT ATCGCTGTGC TTCTTCTCAG CTACTTAGTT
     CCTGTGAAGC

1451 CTGTTAGACC AAAGACCAGA AAAGAAGAAT AATGTTGTCT
```

```
                         -continued
      TTTTAAAAAA

1501  TCAACAACAT TTTGGTTCTT TTCTTTTTTT CCACTTGGAC
      CGTTTTATGT

1551  AAAACAAGAG AAATCAAGAT TTGAGGTTTT ATTCTTCTTC
      TCCTTCCCAA

1601  TTTTCGAAAA TGATTTTATT TTTTCTGATA TATATCTAAG
      CTAGTCCAAA

1651  GTCAACTCG
```

The deduced amino acid sequence of *Arabidopsis* LPC acyltransferase 2 is SEQ ID NO: 6:

```
  1  MELLDMNSMA ASIGVSVAVL RFLLCFVATI PISFLWRFIP
     SRLGKHIYSA

51  ASGAFLSYLS FGFSSNLHFL VPMTIGYASM AIYRPLSGFI
     TFFLGFAYLI

101  GCHVFYMSGD AWKEGGIDST GALMVLTLKV ISCSINYNDG
     MLKEEGLREA

151  QKKNRLIQMP SLIEYFGYCL CCGSHFAGPV FEMKDYLEWT
     EEKGIWAVSE

201  KGKRPSPYGA MIRAVFQAAI CMALYLYLVP QFPLTRFTEP
     VYQEWGFLKR

251  FGYQYMAGFT ARWKYYFIWS ISEASIIISG LGFSGWTDET
     QTKAKWDRAK

301  NVDILGVELA KSAVQIPLFW NIQVSTWLRH YVYERIVKPG
     KKAGFFQLLA

351  TQTVSAVWHG LYPGYIIFFV QSALMIDGSK AIYRWQQAIP
     PKMAMLRNVL

401  VLINFLYTVV VLNYSSVGFM VLSLHETLVA FKSVYYIGTV
     IPIAVLLLSY

451  LVPVKPVRPK TRKEE
```

EXAMPLE 3

Transformation of a Plant with LPC Acyltransferase Gene

Transformation protocol is adapted from that described by Bechtold et al. (1993). Plants are grown in moist soil at a density of 10-12 plants per pot, in 4-inch square pots, and are covered with a nylon screen fixed in place with an elastic band. When the plants reach the stage at which bolts emerge, plants are watered, the bolts and some of the leaves are clipped, and the plants are infiltrated in *Agrobacterium* suspension as outlined below.

*Agrobacterium* transformed with the LPC acyltransferase gene of the instant invention is grown in a 25 mL suspension in LB medium containing kanamycin at a concentration of 50 µg/mL. The *Agrobacterium* is cultured for two to three days. The day before infiltration, this "seed culture" is added to 400 mL of LB medium containing 50 µglmL kanamycin. When the absorbance at 600 nm is >2.0, the cells are harvested by centrifugation (5,000 times g, 10 min in a GSA rotor at room temperature) and are re-suspended in 3 volumes of infiltration medium (1/.times Murashige and Skoog salts, 1 times. B5 vitamins, 5.0% sucrose, 0.044 µM benzylaminopurine) to an optical density at 600 nm of 0.8. The *Agrobacterium* suspension is poured into a beaker and the potted plants are inverted into the beaker so that the bolts and entire rosettes are submerged. The beaker is placed into a large Bell jar and a vacuum is drawn using a vacuum pump, until bubbles form on the leaf and stem surfaces and the solution starts to bubble a bit, and the vacuum is rapidly released. The necessary time and pressure vanes from one lab setup to the next; but good infiltration is visibly apparent as uniformly darkened, water-soaked tissue. Pots are removed from the beaker, are laid on their side in a plastic tray and are covered with a plastic dome, to maintain humidity. The following day, the plants are uncovered, set upright and are allowed to grow for approximately four weeks in a growth chamber under continuous light conditions as described by Katavic et al., (1995). When the siliques are mature and dry, seeds are harvested and selected for positive transformants.

EXAMPLE 4

Selection of Putative Transformants (Transgenic Plants) and Growth and Analysis of Transgenic Plants Seeds are harvested from vacuum-infiltration transformation procedures, and are sterilized by treating for 1 min in ethanol and 5 min in. 50% bleach/0.05% Tween™ 20™ in sterile distilled water. The seeds are rinsed several times with sterile distilled water. Seeds are plated by re-suspending them in sterile 0.1% agarose at room temperature (about 1 mL agarose for every 500-1000 seeds), and applying a volume equivalent to about 2,000-4,000 seeds onto 150×15 mm selection plates (1/2×Murashige and Skoog salts, 0.8% agar, autoclave, cool and add 1×B5 vitamins and kanamycin at a final concentration of 50 µg/mL). The plates are dried in a laminar flow hood until seed no longer flows when the plates are tipped. The plates are vernalized for two nights at 4° C. in the dark, and are moved to a growth chamber (conditions as described by Katavic et al., 1995). After 7-10 days, transformants are clearly identifiable as dark green plants with healthy green secondary leaves and roots that extend over and into the selective medium.

Seedlings are transplanted to soil, plants are grown to maturity and mature seeds ($T_2$ generation as defined in Katavic et al., 1994) are collected and analyzed. $T_2$ seeds are propagated. The vegetative growth patterns are monitored by measuring shoot tissue dry weights, and/or by counting the number of rosette leaves present by the time plants began to enter the generative (flower initiation) stage. Floral initiation (beginning of generative phase of growth) is analyzed by recording, on a daily basis, the percentage of plants in which a flower bud first appears and/or the percentage of plants that are bolting (as described by Zhang et al. 1997). Data is reported in terms of percentage of plants flowering/bolting on a given day after planting (d.a.p.).

EXAMPLE 5

Analysis of Fatty Acids

Cells or plants transformed with the LPC acyltransferase gene of the instant invention are grown to maturity and mature seeds are harvested. Fatty acids are extracted from the cells or plants transformed with the LPC acyltransferase gene. Normal-phase HPLC analysis is used to assay for the production of fatty acids in the transformed cells or plants.

EXAMPLE 6

Analysis of LPCAT from Various Species (1) Identification of LPCAT from the alga *Thalassiosira pseudonana*

We made use of the sequence information of LPCAT from *S. cerevisiae* (SEQ ID NO: 1) and identified a sequence coding for LPCAT from the alga *T. pseudonana*. This algal LPCAT shows 27% identity at the amino acid to the yeast LPCAT which is encoded by YOR175c.

The nucleotide and amino acid sequences of LPCAT from *T. pseudonana* a. The nucleotide sequence of LPCAT from the alga *T. pseudonana*

```
                                           (SEQ ID NO: 7)
ATGCGATTGTATTTGCAATTCAACTTATCCATCAATGATTA

TTGTCACTTCTTCACAGTACCATCCTTTGTCAAAGAGGGCGTCGAGTCTC

TCTCTGCATCCACCGGACAAGACGTCGAGACTCTCGAGTACCTCCTTGGT

ATGCTCATCTGCTACCCCCTCGGAATGATCATGCTCGCTCTACCCTACGG

AAAAGTAAAACATCTCTTCTCCTTCATCCTCGGAGCCTTCCTACTTCAAT

TCACCATTGGTATCCAGTGGATTCATCACTTAATCTCCTCAATGATTGCC

TACGTCATGTTCCTCGTCCTTCCTGCCAAATTTGCCAAAACGGCAGTGCC

TGTGTTTGCCATGATCTACATCACCGCGGGACATTTGCATCGTCAATACA

TCAATTATCTTGGGTGGGATATGGACTTCACGGGGCCTCAGATGGTGCTT

ACGATGAAACTCTACATGCTTGCTTACAACCTTGCGGATGGGGACTTGCT

CAAGAAGGGAAAGGAGGATAGGGCTGCAAAGAAGTGTGCGGATGTCGCTA

TTTCGTCTGTTCCCGGAATCATTGAGTACTTGGGCTACACGTTCTGCTTT

GCCAGTGTTTTAGCAGGCCCTGCTTTTGAGTACAAATTCTACGCCGATGC

ATGCGACGGATCACTCTTGTACGACAAATCTGGCAAACCCAAAGGAAAGA

TCCCCAGTCAGGTGTGGCCTACATTGCGTCCTCTTTTTGGAAGTCTCTTG

TGTCTCGGCATCTTTGTTGTGGGAACTGGAATGTATCCTCTTTTGGATCC

CAACGATCCTCAGAATGCCACTCCTATCCCTCTCACTCCAGAGATGTTGG

CCAAACCAGCCTATGCTCGATACGCTTACTCGTGGCTTGCACTCTTTTTC

ATCCGATTTAAGTATTACTTTGCTTGGATGAACGCCGAAGGAGCAAGCAA

CATTTGGTATGCTGGATTTGAGGGATTTGATGCCAGCGGCAACCCCAAAG

GATGGGAGGTATCCAATAACATTGACGTAATTCAGTTCGAGACTGCACCC

AATCTCAAGACTTTGAGTGCTGCTTGGAATAAGAAGACTGCGAACTGGTT

GGCGAAGTATGTGTACATTCGCACGGGTGGTTCTCTCTTTGCGACGTACG

GAATGAGTGCTTTCTGGCATGGCTTCTACCCTGGATACTACCTCTTCTTC

ATGTCGGTACCCATGATGGCTTTCTGTGAGAGGATTGGAAGGAAGAAACT

TACACCTCGTTTCGGAAATGGAAAGAAGTGGAGTCCTTATGGCATTGTGT

GCATTATCGCCACATCGTTGATGACGGAATACATGATTCAGCCATTCCAA

CTACTTGCGTTTGATTGGGCCTGGGAGAACTGGAGCAGCTACTACTTTGC

TGGACACATTGTTTGTGTTGTGTTTTACCTCGTTGTGTCCAACATGCCTA

CACCAAAGACGAAGGAGACTTAA
``` b. The amino acid sequence of LPCAT from *T. pseudonana*

```
                                           (SEQ ID NO: 8)
MRLYLQFNLSINDYCHFFTVPSFVKEGVESLSASTGQDVETLEYLLGMLI

CYPLGMIMLALPYGKVKHLFSFILGAFLLQFTIGIQWIHHLISSMIAYVM

FLVLPAKFAKTAVPVFAMIYITAGHLHRQYINYLGWDMDFTGPQMVLTMK

LYMLAYNLADGDLLKKGKEDRAAKKCADVAISSVPGIIEYLGYTFCFASV

LAGPAFEYKFYADACDGSLLYDKSGKPKGKIPSQVWPTLRPLFGSLLCLG

IFVVGTGMYPLLDPNDPQNATPIPLTPEMLAKPAYARYAYSWLALFFIRF

KYYFAWMNAEGASNIWYAGFEGFDASGNPKGWEVSNNIDVIQFETAPNLK

TLSAAWNKKTANWLAKYVYIRTGGSLFATYGMSAFWHGFYPGYYLFFMSV

PMMAFCERIGRKKLTPRFGNGKKWSPYGIVCIIATSLMTEYMIQPFQLLA

FDWAWENWSSYYFAGHIVCVVFYLVVSNMPTPKTKET
```

(2) Identification of LPCAT from diverse plant species

Taking the same approach as described above, identified were the full-length or partial sequences of LPCAT from various plant species, including apple, barley, *Capsicum annuum*, castor bean, grapevine, maize, peach, rice, tomato, snapdragon, sorghum, sunflower, vaccinium corymbosum and wheat as well as *Arabidopsis*.

(1) The partial nucleotide sequence of LPCAT from apple

```
                                           (SEQ ID NO: 9)
     TCAGGAGGCCCAAATTTCCTTTGTCAAGATTTACTGAGCCCA

TATACCAAGAATGGGGGTTTTGGAAACGACTTTTCTACCAGTATATGTCT

GGATTCACAGCAAGGTGGAAATATTATTTCATTTGGTCAATATCAGAGGC

TTCTATCATTCTTTCTGGCCTCGGTTTCAGTGGCTGGACAGAGTCCTCAC

CACCAAAACCTCGATGGGATCGTGCAAAAAATGTTGATATTATAGGCGTT

GAGTTTGCAAAGAGTTCAGTTCAGTTACCACTTGTTTGGAACATACAAGT

CAGCACCTGGCTTCGCCATTATGTTTATGATAGGCTTGTTAAACCTGGAA

AGAAGCCTGGTTTCTTCCAGTTGCTGGCTACACAGACCGTCAGTGCTGTT

TGGCATGGCCTCTATCCTGGCTACATCATATTCTTTGTTCAGTCAGCGTT

GATGATTGCTGGATCAAGAGTGATTTACCGATGGCAGCAAGCTGTACCTC

CAACTATGGATGTTGTTAAGAAGATATTGGTGTTCATCAACTTTGCTTAC

ACTGTCTTGGTTCTGAACTACTCCTGTGTTGGTTTCATTGTATTAAGCCT

TCGTGAAACACTGGCCTCGTATGGAAGCGTGCATTTC
```

The partial amino acid sequence of LPCAT from apple

```
                                          (SEQ ID NO: 10)
     RRPKFPLSRFTEPIYQEWGFWKRLFYQYMSGFTARWKYYF

IWSISEASIILSGLGFSGWTESSPPKPRWDRAKNVDIIGVEFAKSSVQLP

LVWNIQVSTWLRHYVYDRLVKPGKKPGFFQLLATQTVSAVWHGLYPGYII

FFVQSALMIAGSRVIYRWQQAVPPTMDVVKKILVFINFAYTVLVLNYSCV

GFIVLSLRETLASYGSVHF
```

(2) The partial amino acid sequence of LPCAT from barley (SEQ ID NO: 11)
EAAIIISGLGFTGWSDSSPPKAKWDRAINVDILGVELAGSSAA

QLPLKWNIQVSTWLRYYVYERLIQKGKKPGFLQLLGTQTVSAIWHGLYPG

YMIFFVQSALMINGSKVIYRWQQAVKQFRPPHYPVFTKLLHTP (3) The partial nucleotide sequence of LPCAT from *Capsicum annuum*

(SEQ ID NO: 12)
GGCACGAGAAACGGTTGGGTTACCAATATATGGCTGGCTT

TACTGCCCGGTGGAAGTATTATTTTATCTGGTCAATCTCTGAAGCTGCTA

TAATCATATCTGGACTGGGTTTCAGTGGTTGGACAGACTCTTCTCCGCCA

AAACCACGTTGGGACCGTGCAAAAAATGTTGATGTATTGGGTGTTGAGTT

AGCAAAGAGCTCGGTTCAGTTGCCTGCTGTCTGGAACATTCAAGTCAGCA

CATGGCTGCGGCATTATGTATATGAAAGGCTCATACAAAAGGGAAGGAAG

CCTGGTTTCTTCCAGTTACTGGCTACCCAAACTGTCAGTGCCGTATGGCA

TGGATTATATCCTGGGTATATCATATTCTTTGTACAGTCCGCTTTGATGA

TTGCTGGATCAAGAGTCCTTTACAGATGGCAGCAAGCTGCTAAAGGTTCT

ATGTTTGAGAAGATACTGGTAGCAATGAATTTTGCATACACACTGCTGGT

TCTAAATTACTCCGCTGTTGGGTTCATGGTATTAAGCCTGCATGAAACTC

TTACTGCTTATGGAAGTGTATACTATGTTGGAACAATTATACCAATTGCT

CTCATCCTGCTCAGTAAAGTAATTAAGCCTCCAAGACCCTGCACATCTAA

AG

The partial amino acid sequence of LPCAT from *Capsicum annuum*

(SEQ ID NO: 13)
HEKRLGYQYMAGFTARWKYYFIWSISEAAIIISGLGFSGWTD

SSPPKPRWDRAKNVDVLGVELAKSSVQLPAVWNIQVSTWLRHYVYERLIQ

KGRKPGFFQLLATQTVSAVWHGLYPGYIIFFVQSALMIAGSRVLYRWQQA

AKGSMFEKILVAMNFAYTLLVLNYSAVGFMVLSLHETLTAYGSVYYVGTI

IPIALILLSKVIKPPRPCTSK (4) The partial nucleotide sequence of LPCAT from castor bean (SEQ ID NO: 14)
ATTCATTTATACTTGGTGCCCCACTATCCTTTATCCCGGTTC

ACTGATCCTGTGTACCAAGAATGGGGCTTCTGGAAACGATTAACTTATCA

GTATATGTCAGGTTAACAGCACGTTGGAAATACTACTTCATCTGGTCAA

TTTCCGAGGCCTCCATTATTATCTCTGGATTGGGTTTCAGTGGTTGGACA

GATACTTCTCCACCAAAGCCACAGTGGGATCGCGCTAGAAACGTTGACAT

TCTAGGTGTTGAGTTTGCAAAGAGTGCAGCTGAGTTGCCACTTGTGTGGA

ACATACAAGTCAGCACATGGCTTCGCCACTATGTTTATGATCGACTTGTT

CCAAAGGGAAAGAAAGCTGGTTTCGTTCAGTTGTTGGCCACTCAGACTAC

-continued
CAGTGCTGTTTGGCATGGATTATATCCTGGATACATTATATTCTTTGTCC

AGTCAGCATTAATGATTGCAGGTTCGAAAGTCATATACAGATGGCAACAA

GCTATACCTTCAAATAAGGCTCTTGAAAAGAAGATACTAGTGTTTATGAA

CTTTGCTTACACAGTTTTGGTTCTAAATTACTCCTGTGTTGGTTTCATGG

TTTTAAGCTTGCATGAAACGATTGCAGCATATGGAAGTGTATATTTTATT

GGCACCATAGTGCCCGTTGTATTTTTCCTCCTTGGCTTCATTATTAAACC

AGCAAGGCCTTCCAGGTCTAAACACGGAACGATGAGTGAGGTAGAAACTG

TTTTTCTTCTCCTT

The partial amino acid sequence of LPCAT from castor bean (SEQ ID NO: 15)
IHLYLVPHYPLSRFTDPVYQEWGFWKRLTYQYMSGLTARWKY

YFIWSISEASIIISGLGFSGWTDTSPPKPQWDRARNVDILGVEFAKSAAE

LPLVWNIQVSTWLRHYVYDRLVPKGKKAGFLQLLATQTTSAVWHGLYPGY

IIFFVQSALMIAGSKVIYRWQQAIPSNKALEKKILVFMNFAYTVLVLNYS

CVGFMVLSLHETIAAYGSVYFIGTIVPVVFFLLGFIIKPARPSRSKHGTM

SEVETVFLLL (5) The partial nucleotide sequence of LPCAT from grapevine (SEQ ID NO: 16)
CTCGTCCAATCTCCACTTCCTCGTTCCCATGCTTCTTGGCTA

CGCGGCTATGCTTCTCTGTCGCCGTCGATGCGGTGTGATCACCTTTTTCT

TGGGATTCGGCTACCTCATTGGCTGCCATGTATACTACATGAGTGGGGAT

GCATGGAAGGAAGGGGGTATTGATGCTACTGGAGCTCTAATGGTTTTAAC

ATTGAAAGTCATTTCATGTGCAATGAATTATAATGATGGATTGTTAAAAG

AAGACGGTTTGCGTGAGGCACAGAAGAAAAACCGATTGCTTAAGTTACCA

TCATTGATCGAGTACTTTGGTTATTGTCTCTGCTGTGGAAGTCACTTTGC

TGGACCAGTTTATGAAATAAAGGATTATCTTGAATGGACAGAAAGAAAAG

GGATTTGGGCCAAATCAGAGAAAGGGCCACCACCATCACCTTATGGGCA

ACGATTCGAGCTCTTATCCAAGCTGCCTTTTGCATGGGCTTGTATGTGTA

TCTAGTACCCCATTTTCCCTTGACCATATTTACTGATCCTGTATATCAAG

AATGGGGCTTCTGGAAACGGTTGGGATACCAATATATGTGTGGCTTTACA

GCACGCTGGAAATACTATTTCATCTGGTCAATCTCTGAGGCAGCTGTCAT

TATTTCTGGCCTGGGATTCAGTGGGTGGACAGAATCTTCCCCACCAAAAC

CAAAATGGGACCGTGCAAAGAATGTTGACATTTTAGGTGTTGAGTTGGCA

AAGAGTGCAGTAACACTGCCACTTGTTTGGAACATACAAGTCAGCACCTG

GCTACGTTATTATGTTTATGAGAGGCTCATTCAAAATGGGAAGAAACCTG

GTTTCTTCCAGTTGCTGGCTACACAAACTGTCAGTGCTGTTTGGCATGGA

TTATATCCTGGATACATCATATTCTTTGTTCAGTCTGCACTGATG

The partial amino acid sequence of LPCAT from grapevine (SEQ ID NO: 17)
SSNLHFLVPMLLGYAAMLLCRRRCGVITFFLGFGYLIGCHVYYMSGDAWK
EGGIDATGALMVLTLKVISCAMNYNDGLLKEDGLREAQKKNRLLKLPSLI
EYFGYCLCCGSHFAGPVYEIKDYLEWTERKGIWAKSEKGPPPSPYGATIR
ALIQAAFCMGLYVYLVPHFPLTIFTDPVYQEWGFWKRLGYQYMCGFTARW
KYYFIWSISEAAVIISGLGFSGWTESSPPKPKWDRAKNVDILGVELAKSA
VTLPLVWNIQVSTWLRYYVYERLIQNGKKPGFFQLLATQTVSAVWHGLYP
GYIIFFVQSALM (6) The partial nucleotide sequence of LPCAT from maize (SEQ ID NO: 18)
CATTTCGTGTCTCATAAACTACAGTGATGGTATCTTGAAGGAAGAGGGTT
TACGCGATGCTCAGATTAAACACCGATTGACTAAGCTTCCTTCTCTAATT
GAATATTTGGGTACTGTCTCTGTTGTGGGAGCCACTTTGCTGGACCGGT
ATATGAGATGAAAGATTATCTTGAATGGACTGAAAGGAAAGGAATATGGG
CTAGCCCAACTCCTTCGCCATTGTTACCTACTTTGCGTGCTCTAGTTCAG
GCTGGTATATGCATGGGGTTATATTTTATACCTGTCACCTAAATTTCCACT
CTCACGGTTTAGTGAGCCCCTATATTATGAATGGGGTTTTTGGCACCGAC
TCTTCTATCAGTACATGTCAGGCTTTACCGGTCGTTGGAAATATTACTTT
ATATGGTCAATTTCAGAAGCCTCAATTATCATATCTGGTCTAGGCTTTAC
TGGTTGGTCGGAATCTTCTCCCCCAAAAGCCAAATGGGATCGTGCAAAAA
ATGTTGATGTATTAGGTGTTGAATTAGCTGGAAGTTCAGTTGAATTGCCC
CTTGTGTGGAATATTCAAGTGAGCACATGGCTACGATACTATGTCTATGA
GAGGTTAATTCAGAAAGGAAAGAAACCAGGTTTCCTTCAATTGTTGGGTA
CACAGACAGTCAGTGCCATCTGGCATGGACTATATCCTGGATATATCATA
TTCTTTTTTCATCAGCATTGATGATNAATGGTTCACGAGTTATATACAG
ATGGCAGCAAGCAGCGAGCAGTTCATTCCTGAGCGGTATCCTGGCCCTTC
TAATTTTGCTATACATTGCTGGGGCTTACTACTCCTGCATCGGGGTCCAG
GTACTGAGCTTCAA The partial amino acid sequence of LPCAT from maize (SEQ ID NO: 19)
ISCLINYSDGILKEEGLRDAQIKHRLTKLPSLIEYFGYCLCCGSHFAGPV
YEMKDYLEWTERKGIWASPTPSPLLPTLRALVQAGICMGLYLYLSPKFPL
SRFSEPLYYEWGFWHRLFYQYMSGFTARWKYYFIWSISEASIIISGLGFT
GWSESSPPKAKWDRAKNVDVLGVELAGSSVQLPLVWNIQVSTWLRYYVYE
RLIQKGKKPGFLQLLGTQTVSAIWHGLYPGYIIFFFSSALMXNGSRVIYR
WQQAASSSFLSGILALLILLYIAGAYYSCIGVQVLSF (7) The partial nucleotide sequence of LPCAT from peach (SEQ ID NO: 20)
AAATATTATTTCATCTGGTCAATTTCAGAGGCTTCTATCATTCTTTCTGG
TTTGGGTTTCACTGGCTGGACAGAATCTTCACCACCAAAGCCGCGATGGG
ATCGTGCAAAAAATGTTGATATTCTAGGCGTTGAGTTTGCAAAGAGTTCA
GTTCAGTTACCACTTGTTTGGAACATACAAGTCAGCACCTGGCTACGTCA
TTATGTTTATGAAAGGCTTGTTAAACCTGGCAAGAAGGCTGGTTTCTTCC
AGTTGCTGACTACACAGACCGTCAGTGCGGTTTGGCATGGACTCTATCCT
GGGTACATCATATTCTTTGTTCAGTCAGCATTGATGATTGCTGGTTCAAG
AGTGATTTACAGATGGCAACAAGCTGTACCTCAAAACATGGATGCTGTTA
AGAACATACTGGTGTTCATAAACTTTGCTTACACTCTCTTGGTTCTGAAC
TACTCCTGCGTTGGTTTCATTGTATTAAGCCTTCGTGAAACACTTGCCTC
ATATGGGAGCGTGCATTTCATCGGAACCATTCTTCCGATAGCATTGATAC
TACTGAGTTACGTAATAAAACCTCCAAGGCCTGCAAGATCAAAGGCTCGG
AAGGAAGAGTGAGGTTGTCANCCGCAACAGCATTTTTAACG The partial amino acid sequence of LPCAT from peach (SEQ ID NO: 21)
KYYFIWSISEASIILSGLGFTGWTESSPPKPRWDRAKNVDILGVEFAKSS
VQLPLVWNIQVSTWLRHYVYERLVKPGKKAGFFQLLTTQTVSAVWHGLYP
GYIIFFVQSALMIAGSRVIYRWQQAVPQNMDAVKNILVFINFAYTLLVLN
YSCVGFIVLSLRETLASYGSVHFIGTILPIALILLSYVIKPPRPARSKAR
KEE (8) The full-length or partial amino acid sequence of LPCAT from rice Sequence 1 (accession number Os02g0676000
(SEQ ID NO: 22))
MGLEMEGMAAAIGVSVPVLRFLLCFAATIPTGLMWRAVPGAAGRHLYAGL
TGAALSYLSFGATSNLLFVVPMAFGYLAMLLCRRLAGLVTFLGAFGFLIA
CHMYYMSGDAWKEGGIDATGALMVLTLKIISCAINYSDGMLKEEGLRDAQ
KKYRLAKLPSLIEYFGYCLCCGSHFAGPVYEMKDYLEYTERKGLWASPTP
SPLLPTLRALVQAGACMGLYLYLSPQFPLSRFSEPLYYEWGFWHRLFYQY
MSGFTARWKYYFIWSLSEAAIISGLGFSGWSDSSPPKAKWDRAKNVDVL
GVELATSAVQLPLMWNIQVSTWLRYYVYERLVQKGKKPGFLQLLGTQTVS
AVWHGLYPGYIIFFVQSALMINGSKVIYRWQQAVSNPVFHAILVFVNFSY
TLMVLNYSCIGFQVLSFKETLASYQSVYYIGTIVPIVVVLLGYVIKPARP
VKPKARKAE Sequence 2 (accession number EAY87053
(SEQ ID NO: 23))
MYYMSGDAWKEGGIDATGALMVLTLKIISCAINYSDGMLKEEGLRDAQKK
YRLAKLPSLIEYFGYCLCCGSHFAGPVYEMKDYLEYTERKGLWASPTPSP
LLPTLRALVQAGACMGLYLYLSPQFPLSRFSEPLYYEWGFWHRLFYQYMS
GFTARWKYYFIWSLSEAAIISGLGFSGWSDSSPPKAKWDRAKNVDVLGV
ELATSAVQLPLMWNIQVSTWLRYYVYERLVQKGKKPGFLQLLGTQTVSAV
WHGLYPGYIIFFVQSALMINGSKVIYRWQQAVSNPVFHAILVFVNFSYTL -continued

MVLNYSCIGFQFVFTMLYTLRFLQVLSFKETLASYQSVYYIGTIVPIVVV
LLGYVIKPARPVKPKARKAE (9) The partial nucleotide sequence of LPCAT from snapdragon (SEQ ID NO: 24)
GCATTAATTACAACGATGGATTACTTAAAAAGGAAGATCTACGTGAGCCA

CAAAAGAAAAACCGCTTGCTCAAGATGCCATCATTACTTGAGTACATTGG

TTACTGTTTGTGTTGTGGAAGTCACTTTGCTGGTCCTGTGTATGAAATGA

AAGATTATCTTGAATGGACTGAGAGGAAAGGGATCTGGCAACATACAACC

AAGGGACCGAAACCTTCTCCGTATTGGGCGACTCTCAGGGCTATTTTGCA

AGCTGCCATCTGTATGGGCTTGTATCTATATCTTGTACCACATTACCCAC

TTTCCAGATTCACGGAGCCAGAATACCAAGAGTATGGGTTCTGGAAACGG

TTAAGTTACCAGTACATGTCAGGCTTCACCGCTCGTTGGAAGTACTATTT

CATTTGGTCTATCTCAGAAGCTTCCATAATTATTTCTGGCCTGGGGTTCA

GTGGCTGGACAGATTCTGATCCACCCAAAGCACTGTGGGATCGTGCAAAA

AATGTTGATGTATTAGGTGTTGAGTTGGCAAAGAGTTCTGTGCAGTTACC

ACTTGTATGGAATATTCAAGTTAGCACCTGGCTTAAACACTATGTCTATG

AGAGGCTGGTTCAGAAAGGTAAGAAACCAGGCTTCTTCCAGTTGCTGGCT

ACCCAGACCGTGAGTGCAGTGTGGCATGGATTGTACCCTGGGTACATCAT

ATTCTTT

The partial amino acid sequence of LPCAT from snapdragon (SEQ ID NO: 25)
INYNDGLLKKEDLREPQKKNRLLKMPSLLEYIGYCLCCGSHFAGPVYEMK

DYLEWTERKGIWQHTTKGPKPSPYWATLRAILQAAICMGLYLYLVPHYPL

SRFTEPEYQEYGFWKRLSYQYMSGFTARWKYYFIWSISEASIIISGLGFS

GWTDSDPPKALWDRAKNVDVLGVELAKSSVQLPLVWNIQVSTWLKHYVYE

RLVQKGKKPGFFQLLATQTVSAVWHGLYPGYIIFF

(10) The partial nucleotide sequence of LPCAT from sorghum (SEQ ID NO: 26)
GCACGAGGCTCTCACGGTTTAGTGAGCCCTTATATTATGAATGGGGTTTC

TGGCACCGACTCTTCTATCAGTACATGTCAGGCTTCACTGCTCGTTGGAA

ATATTACTTTATATGGTCAATTTCAGAAGCCTCAATTATCATATCTGGTC

TGGGCTTTACTGGTTGGTCAGAATCTTCTCCCCCGAAAGCCAAATGGGAT

CGTGCGAAAATGTTGATGTATTAGGTGTTGAATTAGCTGGAAGTGCAGT

TCAAATTCCCCTTGTGTGGAATATTCAAGTGAGCACATGGTTACGATACT

ATGTCTATGAGAGGCTAATTCAGAAAGGAAAGAAACCAGGTTTCCTTCAG

TTGTTGGGTACACAGACAGTCAGCGCCATCTGGCATGGACTGTATCCTGG

ATATATCATATTCTTTGTTCAGTCAGCATTGATGATAAATGGTTCACGAG

TTATATACAGATGGCAGCAAGCAGTGAGCAGTTCATTCCTCCGCGGTATC

CTGGCTTTTCTAAATTTTGCTTATACATTGCTGGTGCTTAACTACTCCTG

CATCGGGTTCCTGGTACTGAGCTTCAAAGAAACCTTGGCGTCCTACCAGA

GCGTATATTATGTTGGCACAATTGTTCCCATTGTGTTTCTCCTGCTGGGC

AAT

The partial amino acid sequence of LPCAT from sorghum (SEQ ID NO: 27)
TRLSRFSEPLYYEWGFWHRLFYQYMSGFTARWKYYFIWSISEASIIISGL

GFTGWSESSPPKAKWDRAKNVDVLGVELAGSAVQIPLVWNIQVSTWLRYY

VYERLIQKGKKPGFLQLLGTQTVSAIWHGLYPGYIIFFVQSALMINGSRV

IYRWQQAVSSSFLRGILAFLNFAYTLLVLNYSGIGFLVLSFKETLASYQS

VYYVGTIVPIVFLLLGN

(11) The partial nucleotide sequence of LPCAT from sunflower (SEQ ID NO: 28)
GAAAACCGCATACTTAAGTTGCCATCTTTAATCGAGTATGTGGGATATTG

CTTATGCTGCGGAAGTCACTTTGCTGGTCCGGTTTACGAAATCAAAGATT

ATTTGGATTGGACCGAAAGAAAGGGGATTTGGACAAAGTCCGAGAAGGC

ACACCATCACCATTTTTGCCAACACTACGAGCGATTCTCCAAGCGGGTTT

CTGTATGGGTTTGTATTTATATCTATCGCCTTCGTATCCGCTTTCAAGAT

TCAGTGAGCCGATATATCAAGAATGGGGATTTGTGAAACGTCTGACCGTC

CAATACATGTCGGGCTTCACCGCGCGTTGGAAATACTATTTCATTTGGTC

TATCTCAGAAGCTTCTATCATTATTTCGGGCTTCGGTTTCAGTGGCTGGA

CTGATTCTTCTCCACCAAAAGCCCGATGGGACCGTGCGAAAAACGTTGAC

GTTTTGGGTGTTGAGTTTGCAAAGAGTTCAGTTGAGTTACCACTCGTGTG

GAATATCCAAGTCAGCACATGGCTTCGTCACTATGTTTATGACAGACTTG

TTCAAAAGGGAAAGAAGCCTGGCTTTTTCCAATTGTTAGCAACACAGACT

GTTAGCGCTGTCTGGCATGGATTATATCCTGGGTACTTGATATTCTTTGT

TCAATCTGCTTTGATGATTTCCGGGTCAAGAGCCATTTACAGATGGCAGC

AGGCGGTTCCGCCAACCGTTAAGAAGTTTTTGATGCTCATGAACTTTGCT

TACACGCTTCTTGTTCTTAACTACTCCTGCATAGGTTTTATGGTATTAAG

CCTACACGAAACACTGGCTGCATACGGAAGTGTATACTACGTTGGAAACA

TCATTCCAGTGGCGT

The partial amino acid sequence of LPCAT from sunflower (SEQ ID NO: 29)
ENRILKLPSLIEYVGYCLCCGSHFAGPVYEIKDYLDWTERK

GIWTKSEKGTPSPFLPTLRAILQAGFCMGLYLYLSPSYPLSRFSEPIYQE

WGFVKRLTVQYMSGFTARWKYYFIWSISEASIIISGFGFSGWTDSSPPKA

RWDRAKNVDVLGVEFAKSSVELPLVWNIQVSTWLRHYVYDRLVQKGKKPG

FFQLLATQTVSAVWHGLYPGYLIFFVQSALMISGSRAIYRWQQAVPPTVK

KFLMLMNFAYTLLVLNYSCIGFMVLSLHETLAAYGSVYYVGNIIPVA

(12) The partial nucleotide sequence of LPCAT from tomato (SEQ ID NO: 30)
GGTATGGGGTTGTATCTCTATCTGGTGCCTCAGTTCCCACTTTCCAGGTT

CACTGAGTCAGTATACCACGAATGGGGTTTCTTCAAACGACTGGGTTACC

AATATATGGCTGGCTTTACTGCCCGGTGGAAATATTATTTTATTTGGTCA

ATCTCTGAAGCTTCTATAATCATATCTGGACTGGGTTTCAGTGGTTGGAC

AAACTCTTCTCCGCCAAAACCACGTTGGGACCGAGCAAAAAATGTTGATG

TATTGGGTGTTGAGTTAGCAAAGAGCTCGGTTCAGTTACCACTAGTATGG

AACATTCAAGTCAGCACATGGCTGCGGCATTATGTGTATGAAAGGCTCGT

ACAGAAGGGAAGGAAGCCTGGTTTCTTCCAGTTGCTGGCTACCCAAACTG

TCAGTGCCGTTTGGCATGGATTATATCCTGGATACATCATATTCTTTGTT

CAGTCCGCTTTGATGATTGCTGGATCAAGAGTCATTTACAGATGGCAGCA

AGCTACAAAAGGTACTATGTTTGAGAAGATACTGATAGCAATGAATTTTG

CATACACACTGCTGGTTCTAAACTACTCCGCTGTTGGATTCATGGTATTA

AGTCTGCATGAAACTCTTACTGCTTATGGAAGTGTATACTATATTGGAAC

AATTGTACCAATTCTTCTCATCCTGCTTAGTAAAGTGATTAAGCCTCCAA

GACCTGCGACGTCTAAAGCTAGGAAAGCAGAGTAAATCCAAGTCAGTT

The partial amino acid sequence of LPCAT from tomato (SEQ ID NO: 31)
GMGLYLYLVPQFPLSRFTESVYHEWGFFKRLGYQYMAG

FTARWKYYFIWSISEASIIISGLGFSGWTNSSPPKPRWDRAKNVDVLGVE

LAKSSVQLPLVWNIQVSTWLRHYVYERLVQKGRKPGFFQLLATQTVSAVW

HGLYPGYIIFFVQSALMIAGSRVIYRWQQATKGTMFEKILIAMNFAYTLL

VLNYSAVGFMVLSLHETLTAYGSVYYIGTIVPILLILLSKVIKPPRPATS

KARKAE

(13) The partial nucleotide sequence of LPCAT from Vaccinium corymbosum (SEQ ID NO:32)
GGGGTTGGGTTACCAGTACATGGCTGGCTTTACAGCACGGTGGAAGTATT

ATTTCATTTGGTCAATCTCAGAAGCTTCCATCATCATTTCTGGCCTGGGG

TTCAGTGGTTGGACAGATTCTTCTCCACCAAAACCAAAATGGGACCGTGC

AAAGAATGTAGATATTTTGCGGGTTGAGTTTGCAAAGACTGCAGCTCAGA

TTCCACTTGCATGGAACATTCAAGTCAGCACCTGGCTACGCCATTATGTT

TATGAGAGGCTCGTGCAGAAGGGAAAGAAACCTGGTTTCTTTCAGTTGTT

GGCTACCCAGACTGTCAGTGCTGTTTGGCATGGTTTATATCCTGGATACA

TCATATTCTTTGTGCAGTCAGCATTGATGATTGCTGGTTCAAGAGTTATT

TATAGATGGCAGCAAGCTGTTCCTCCTAAAATGGATCTGGTGAAGAAAGT

ATTCGTACTTTTAAACTTTGCTTACACAGTTCTGGTGTTGAACTACTCCT

CTGTCGGTTTCATGGTACTAAGCCTACATGAAACAATTGTTGCATACGGG

AGCGTGTATTCGTTGGAACCATTGTTCCCATACTTGTAATCCTCCTTGGT

TACGTAATT

The partial amino acid sequence of LPCAT from Vaccinium corymbosum (SEQ ID NO: 33)
GLGYQYMAGFTARWKYYFIWSISEASIIISGLGFSGWTDSSPPKPKWDRA

KNVDILRVEFAKTAAQIPLAWNIQVSTWLRHYVYERLVQKGKKPGFFQLL

ATQTVSAVWHGLYPGYIIFFVQSALMIAGSRVIYRWQQAVPPKMDLVKKV

FVLLNFAYTVLVLNYSSVGFMYLSLHETIVAYGSVYSLEPLFPYL

(14) The partial nucleotide sequence of LPCAT from wheat (SEQ ID NO: 34)
CACTTTGCTGGACCAGTATATGAGATGAAAGATTATCTTGAATGGACTGA

AAGGAAAGGAATATGGGCCGGCTCAACTCCTTCACCATTATTACCTACTC

TGCGTGCTCTAGTTCAGGCTGGAATATGCATGGGGTTATATTTGTATCTG

TCACCTATGTTTCCCCATTCATAATATAGAGGTTCACTAAATCGTGAAAG

GGGTTTCTGGCACCGGCTCTTCTTTCAATACATGTCAGGATTTACTGCTC

GATGGAAATACTACTTTATATGGTCAGTCTCAGAAGCTGCAATTATTATA

TCTGGCCTGGGTTTCACTGGTTGGTCTGATTCTTCTCCCCCAAAAGCCAA

ATGGGACCGTGCTATAAATGTTGATATTCTGGGCGTCGAGCTAGCTGGAA

GTGCAGCTCAATTGCCACTTAAGTGGAATATTCAAGTGAGCACATGGCTA

AGATACTATGTGTATGAGAGGTTAATTCAGAAAGGGAAGAAGCCTGGTTT

CCTTCAGTTGTTGGGTACACAGACAGTCAGTGCTATCTGGCATGGACTGT

ATCCAGGATATATGTTTTTCTTTGTTCAGTCAGCGTTGATGATAAATGGT

TCAAAAGTTATATACAGATGGCAACAAGCTGTGAGCAATCCAGGCCTCCG

CACTATCCTGTCTTTACTAAATTGTGCATACACCATGATGGTGCTTAACT

ACTCATGCATTGGCTTCCAGGTACTGAGCTTCCAGGAGACCTTAGCATCC

TACAAGAGCGTGTATTATGTCGGCACAATCGTTCCTATTCTATGTGTCTT

GCTGGGCTATGTCGTCAAGCCCACGAGACCTGTGAAGCCGA

The partial amino acid sequence of LPCAT from wheat (SEQ ID NO: 35)
HFAGPVYEMKDYLEWTERKGIWAGSTPSPLLPTLRALVQAGICMGLYLYL

SPMFPHS*YRGSLNRERGFWHRLFFQYMSGFTARWKYYFIWSVSEAAIII

SGLGFTGWSDSSPPKAKWDRAINVDILGVELAGSAAQLPLKWNIQVSTWL

RYYVYERLIQKGKKPGFLQLLGTQTVSAIWHGLYPGYMFFFVQSALMING

SKVIYRWQQAVSNPGLRTILSLLNCAYTMMVLNYSCIGFQVLSFQETLAS

YKSVYYVGTIVPILCVLLGYVVKPTRPVKP

(15) The amino acid sequences of LPCAT from A. thaliana

Sequence (accession number At1g12640
(SEQ ID NO: 36))
MDMSSMAGSIGVSVAVLRFLLCFVATIPVSFACRIVPSRL

GKHLYAAASGAFLSYLSFGFSSNLHFLVPMTIGYASMAIYRPKCGIITFF

LGFAYLIGCHVFYMSGDAWKEGGIDSTGALMVLTLKVISCSMNYNDGMLK

-continued

EEGLREAQKKNRLIQMPSLIEYFGYCLCCGSHFAGPVYEMKDYLEWTEGK

GIWDTTEKRKKPSPYGATIRAILQAAICMALYLYLVPQYPLTRFTEPVYQ

EWGFLRKFSYQYMAGFTARWKYYFIWSISEASIIISGLGFSGWTDDASPK

PKWDRAKNVDILGVELAKSAVQIPLVWNIQVSTWLRHYVYERLVQNGKKA

GFFQLLATQTVSAVWHGLYPGYMMFFVQSALMIAGSRVIYRWQQAISPKM

AMLRNIMVFINFLYTVLVLNYSAVGFMVLSLHETLTAYGSVYYIGTIIPV

GLILLSYVVPAKPSRPKPRKEE

```
Sequence (accession number At1g63050
(SEQ ID NO: 37))
```
MELLDMNSMAASIGVSVAVLRFLLCFVATIPISFLWRFIP

SRLGKHIYSAASGAFLSYLSFGFSSNLHFLVPMTIGYASMAIYRPLSGFI

TFFLGFAYLIGCHVFYMSGDAWKEGGIDSTGALMVLTLKVISCSINYDG

MLKEEGLREAQKKNRLIQMPSLIEYFGYCLCCGSHFAGPVFEMKDYLEWT

EEKGIWAVSEKGKRPSPYGAMIRAVFQAAICMALYLYLVPQFPLTRFTEP

VYQEWGFLKRFGYQYMAGFTARWKYYFIWSISEASIIISGLGFSGWTDET

QTKAKWDRAKNVDILGVELAKSAVQIPLFWNIQVSTWLRHYVYERIVKPG

KKAGFFQLLATQTVSAVWHGLYPGYIIFFVQSALMIDGSKAIYRWQQAIP

PKMAMLRNVLVLINFLYTVVVLNYSSVGFMVLSLHETLVAFKSVYYIGTV

IPIAVLLLSYLVPVKPVRPKTRKEE

The amino acid sequences of LCPAT from fruit fly, human, mouse, *S. pombe* and *Aspergillus oryzae*

(1) The amino acid sequences of LCPAT from fruit fly

```
Sequence 1 (accession number AAR99097
(SEQ ID NO: 38))
```
MLEPPKFIENDCYNGSRTFTWLADMVGLSVDLVNFLICQISALFLASLFR

SMLHPSKVSSKLRHTFALSIGLAFGYFCFGQQAIHIAGLPAICYIVIRTQ

DPRIVQRAVLLVAMSYLLCVHLMRQLYDYGSYALDITGPLMIITQKVTSL

AFSIHDGFVRGDEELTKAQQYHAIRKMPSALEYFSYVWHFQSILAGPLVF

YKDYIEFVEGYNLLSTPPGNGNLDSSKREVVLEPSPTKAVIRKVVGSLVC

AFIFMKFVKIYPVKDMKEDDFMNNTSMVYKYWYAMMATTCIRFKYYHAWL

LADAICNNSGLGFTGYDKDGNSKWDLISNINVLSFEFSTNMRDAINNWNC

GTNRWLRTLVYERVPQQYGTLLTFALSAVWHGFYPGYYLTFATGAVVVTA

ARTGRRLFRHRFQSTQVTRMFYDILTCLITRVVLGYATFPFVLLEFMGSI

KLYLRFYLCLHIISLVTIFILPKFIRGERRLRTSNGNGNVRLSGSGNTKD

AVTTSVESTAALTAGNDLNEDKEEDKHAQCKVHTPTQQQPAAGPHKTTVE

QPTEQPNNVNLRSRPQQQQPHLEKKAMPPTCARDAVSVPHDQCEMDQLSS

KLKEKIEAETKNIEEFIDKTVTETVSGIVEFKNDLMRDIEFPKLKLPGSN

GAISLDSSNGGGLRKRNISSVHDNGTDPGHATADLHPPLEENGAAFLKKE

IEVINAVVQQAVPAVLSNGHAK

```
Sequence 2 (accession number AAO41223
(SEQ ID NO: 39))
```
MAEFEEDLPHNGLMDGIASGVGVPVEALRLLLTILAGYPV

AALYQKFISVIADKTVHHMFFAGCGAGLCYFNYGLDTYHSLIAILTTYFL

VLLLRKKTQIFLAINFVFHMSYLLLGYFYTSSNDYDILWTMPHCILVLRM

IGYGFDITDGLKEESELSKDQKETALKKPPSLLELLAFSYFPSGFLVGPQ

FPFRRYKAFVDGEFRQHEGNVEAGVRRFGAGAFYLIVCQVGLRYLPDSYF

LTPEFAQVSFVKRIYLLGFWAKFSLYKYISCWLLTEGALICIGLTYKGED

KNGQPDWSGCSNVKLKLLETGNTMEHYVQSFNVNTNQWVGQYIYKRLKFL

NNRTISYGAALGFLAVWHGYHSGYYMTFLMEYMVVSTEKQITRFYTKVVL

PQWGHILNNSDIYKLLYFITLKSYNVVYMGWCLTAFVFLKYERWIVVYGA

VSYYGFTFLVLWAAFYHTFNHFFRSSSRKLAGEDQKLQDSNTDKLVEEKK

PEDKKSE (2) The amino acid sequences of LCPAT from human

```
Sequence 1 (accession number EAX01013
(SEQ ID NO: 40))
```
MKCCFHHIIPRVNFVVCQLFALLAAIWFRTYLHSSKTSSFIRHVVATLLG

LYLALFCFGWYALHFLVQSGISYCIMIIIGVENMHNYCFVFALGYLTVCQ

VTRVYIFDYGQYSADFSGPMMIITQKITSLACEIHDGMFRKDEELTSSQR

DLAVRRMPSLLEYLSYNCNFMGILAGPLCSYKDYITFIEGRSYHITQSGE

NGKEETQYERTEPSPNTAVVQKLLVCGLSLLFHLTICTTLPVEYNIDEHF

QATASWPTKIIYLYISLLAARPKYYFAWTLADAINNAAGFGFRGYDENGA

ARWDLISNLRIQQIEMSTSFKMFLDNWNIQTALWLKRVCYERTSFSPTIQ

TFILSAIWHGVYPGYYLTFLTGVLMTLAARAMRNNFRHYFIEPSQLKLFY

DVITWIVTQVAISYTVVPFVLLSIKPSLTFYSSWYYCLHILGILVLLLLP

VKKTQRRKNTHENIQLSQSKKFDEGENSLGQNSFSTTNNVCNQNQEIASR

HSSLKQ

```
Sequence 2 (accession number Q6ZWT7
(SEQ ID NO: 41))
```
MATTSTTGSTLLQPLSNAVQLPIDQVNFVVCQLFALLAAIWFRTYLHSSK

TSSFIRHVVATLLGLYLALFCFGWYALHFLVQSGISYCIMIIIGVENMHN

YCFVFALGYLTVCQVTRVYIFDYGQYSADFSGPMMIITQKITSLACEIHD

GMFRKDEELTSSQRDLAVRRMPSLLEYLSYNCNFMGILAGPLCSYKDYIT

FIEGRSYHITQSGENGKEETQYERTEPSPNTAVVQKLLVCGLSLLFHLTI

CTTLPVEYNIDEHFQATASWPTKIIYLYISLLAARPKYYFAWTLADAINN

AAGFGFRGYDENGAARWDLISNLRIQQIEMSTSFKMFLDNWNIQTALWLK

RVCYERTSFSPTIQTFILSAIWHGVYPGYYLTFLTGVLMTLAARAMRNNF

RHYFIEPSQLKLFYDVITWIVTQVAISYTVVPFVLLSIKPSLTFYSSWYY

CLHILGILVLLLLPVKKTQRRKNTHENIQLSQSRKFDEGENSLGQNSFST

TNNVCNQNQEIASRHSSLKQ

```
Sequence 3 (accession number Q6P1A2
(SEQ ID NO: 85))
```
MASSAEGDEGTVVALAGVLQSGFQELSLNKLATSLGASEQ

ALRLIISIFLGYPPALFYRHYLFYKETYLIHLFHTFTGLSIAYFNFGNQL

YHSLLCIVLQFLILRLMGRTITAVLTTFCFQMAYLLAGYYYTATGNYDIK

WTMPHCVLTLKLIGLAVDYFDGGKDQNSLSSEQQKYAIRGVPSLLEVAGF

-continued

SYFYGAFLVGPQFSMNHYMKLVQGELIDIPGKIPNSIIPALKRLSLGLFY

LVGYTLLSPHITEDYLLTEDYDNHPFWFRCMYMLIWGKFVLYKYVTCWLV

TEGVCILTGLGFNGFEEKGKAKWDACANMKVWLFETNPRFTGTIASFNIN

TNAWVARYIFKRLKFLGNKELSQGLSLLFLALWHGLHSGYLVCFQMEFLI

VIVERQAARLIQESPTLSKLAAITVLQPFYYLVQQTIHWLFMGYSMTAFC

LFTWDKWLKVYKSIYFLGHIFFLSLLFILPYIHKAMVPRKEKLKKME

Sequence 4 (accession number Q6ZNC8
(SEQ ID NO: 86))
      MAAEPQPSSLSYRTTGSTYLHPLSELLGIPLDQVNFVVCQ

LVALFAAFWFRIYLRPGTTSSDVRHAVATIFGIYFVIFCFGWYSVHLFVL

VLMCYAIMVTASVSNIHRYSFFVAMGYLTICHISRIYIFHYGILTTDFSG

PLMIVTQKITTLAFQVHDGLGRRAEDLSAEQHRLAIKVKPSFLEYLSYLL

NFMSVIAGPCNNFKDYIAFIEGKHIHMKLLEVNWKRKGFHSLPEPSPTGA

VIHKLGITLVSLLLFLTLTKTFPVTCLVDDWFVHKASFPARLCYLYVVMQ

ASKPKYYFAWTLADAVNNAAGFGFSGVDKNGNFCWDLLSNLNIWKIETAT

SFKMYLENWNIQTATWLKCVCYQRVPWYPTVLTFILSALWHGVYPGYYFT

FLTGILVTLAARAVRNNYRHYFLSSRALKAVYDAGTWAVTQLAVSYTVAP

FVMLAVEPTISLYKSMYFYLHIISLLIILFLPMKPQAHTQRRPQTLNSIN

KRKTD

Sequence 5 (accession number XP_001129292
(SEQ ID NO: 87))
      MVMMMMKVLLLLMKQRGAGLPAPAGVEPRPSSHHPKARV

RLQGDESVRPRGCSQLWAFTRHSPRQRGFSARSLFWFVVLPAPTFVPNFP

WRWLGGVPHIVPPAATPGPFVVCRLSQRGVGGRDIPGRRNRGVRGKDALP

CSHPRSAPHDAGQPFSGDARHPRAEREVGRALLPATAPGEGGRRMGVRVCM

RSLPFAAAALGSGGRVPEQPPVRMDRVVERVRKAALWGAWRGAACPARAS

ERPPERLMHGSGDGLLGFSFVRASLTVFGEEAGPSFLLAVLCAVVWGGRG

EDVVSDVQACPAEQGFLLAEPSVFGVNFVVCQLFALLAAIWFRTYLHSSK

TSSFIRHVVATLLGLYLALFCFGWYALHFLVQSGISYCIMIIIGVENMHN

YCFVFALGYLTVCQVTRVYIFDYGQYSADFSGPMMIITQKITSLACEIHD

GMFRKDEELTSSQRDLAVRRMPSLLEYLSYNCNFMGILAGPLCSYKDYIT

FIEGRSYHITQSGENGKEETQYERTEPSPNTAVVQKLLVCGLSLLFHLTI

CTTLPVEYNIDEHFQATASWPTKIIYLYISLLAARPKYYFAWTLADAINN

AAGFGFRGYDENGAARWDLISNLRIQQIEMSTSFKMFLDNWNIQTALWLK

RVCYERTSFSPTIQTFILSAIWHGVYPGYYLTFLTGVLMTLAARAMRNNF

RHYFIEPSQLKLFYDVITWIVTQVAISYTVVPFVLLSIKPSLTFYSSWYY

CLHILGILVLLLLPVKKTQRRKNTHENIQLSQSKKFDEGENSLGQNSFST

TNNVCNQNQEIASRHSSLKQ

Sequence 6 (accession number XP_001131044
(SEQ ID NO: 88))
      MVNFVVCQLVALFAAFWFRIYLRPGTTSSDVRHAVATIFG

IYFVIFCFGWYSVHLFVLVLMCYAIMVTASVSNIHRYSFFVAMGYLTICH

ISRIYIFHYGILTTDFSGPLMIVTQKITTLAFQVHDGLGRRAEDLSAEQH

-continued

RLAIKVKPSFLEYLSYLLNFMSVIAGPCNNFKDYIAFIEGKHIHMKLLEV

NWKRKGFHSLPEPSPTGAVIHKLGITLVSLLLPLTLTKTFPVTCLVDDWF

VHKASFPARLCYLYVVMQASKPKYYFAWTLADAVNNAAGFGFSGVDKNGN

FCWDLLSNLNIWKIETATSFKMYLENWNIQTATWLKCVCYQRVPWYPTVL

TFILSALWHGVYPGYYFTFLTGILVTLAARAVRNNYRHYFLSSRALKAVY

DAGTWAVTQLAVSYTVAPFVMLAVEPTISLYKSMYFYLHIISLLIILFLP

MKPQAHTQRRPQTLNSINKRKTD (3) The amino acid sequences of LCPAT from mouse

Sequence 1 (accession number AAH24653
(SEQ ID NO: 42))
      MAARPPASLSYRTTGSTCLHPLSQLLGIPLDQVNFVACQL

FALSAAFWFRIYLHPGKASPEVRHTLATILGIYFVVFCFGWYAVHLFVLV

LMCYGVMVSASVSNIHRYSFFVAMGYLTICHISRIYIFHYGILTTDFSGP

LMIVTQKITTLAFQVHDGLGRKAEDLSAEQHRLAVKAKPSLLEYLSYHLN

FMSVIAGPCNNFKDYVAFIEGRHIHMKLLEVNWTQRGFQSLPEPSPTGAV

IQKLCVTLMSLLLFLTLSKSFPVTFLIDDWFVHKANFLSRLWYLYVVMQA

AKPKYYFAWTLADAVHNAAGFGFNGMDTDGKSRWDLLSNLNIWKIETATS

FKMYLENWNIQTSTWLKCVCYERVSWYPTVLTFLLSALWHGVYPGYYFTF

LTGVPVTLAARAVRNNYRHHFLSSKARKIAYDVVTWAVTQLAVSYTAAPF

VMLAVEPTISLYKSVFFFLHIICLLIILFLPIKPHQPQRQSRSPNSVKKK

AD

Sequence 2 (accession number AAH25429
(SEQ ID NO: 43))
      MATTSTTGSTLLQPLSNAVQLPIDQVNFVVCQLFALLAAVWFRTYLHSSK

TSSFIRHVVATLLGLYLAFFCFGWYALHFLVQSGISYCIMIIAGVESMQQ

CCFVFALGYLSVCQITRVYIFDYGQYSADFSGPMMIITQKITSLAYEIHD

GMFRKDEELTPSQRGLAVRRMPSLLEYVSYTCNFMGILAGPLCSYKDYIA

FIEGRASHVAQPSENGKDEQHGKADPSPNAAVTEKLLVCGLSLLFHLTIS

NMLPVEYNIDEHFQATASWPTKATYLYVSLLAARPKYYFAWTLADAINNA

AGFGFRGYDKNGVARWDLISNLRIQQIEMSTSFKMFLDNWNIQTALWLKR

VCYERATFSPTIQTFFLSAIWHGVYPGYYLTFLTGVLMTLAARAVRWRFR

HYFLEPPQLKLFYDLITWVATQITISYTVVPFVLLSIKPSFTFYSSWYYC

LHVCSILVLLLLPVKKSQRRTSTQENVHLSQAKKFDERDNPLGQNSFSTM

NNVCNQNRDTGSRHSSLTQ (4) The amino acid sequences of LCPAT from S. pombe

Sequence (accession number CAA16861
(SEQ ID NO: 44))
      MAYLIDIPFEYFSSFLGVHPDQLKLLFCFLSAYPFAGILK

RLPSAPWIRNLFSISIGLFYLIGVHHLYDGVLVLLFDALFTYFVAAFYRS

SRMPWIIFWILGHTFSSHVIRYIYPSENTDITASQMVLCMKLTAFAWSVY

DGRLPSSELSSYQKDRALRKIPNILYFLGYVFFFPSLLVGPAFDYVDYER

FITLSMFKPLADPYEKQITPHSLEPALGRCWRGLLWLILFITGSSIYPLK

-continued

FLLTPKFASSPILLKYGYVCITAFVARMKYYGAWELSDGACILSGIGYNG

LDSSKHPRWDRVKNIDPIKFEFADNIKCALEAWNMNTNKWLRNYVYLRVA

KKGKRPGFKSTLSTFTVSAMWHGVSAGYYLTFVSAAFIQTVAKYTRRHVR

PFFLKPDMETPGPFKRVYDVIGMVATNLSLSYLIISFLLLNLKESIHVWK

ELYFIVHIYILIALAVFNSPIRSKLDNKIRSRVNSYKLKSYEQSMKSTSD

TDMLNMSVPKREDFENDE (5) The amino acid sequences of LCPAT from *Aspergillus oryzae*

Sequence (accession number BAE61812
(SEQ ID NO: 45))
MLPYVDLLKLIASFLLSYPLAALLKRIPDAQPWKKNAFIIAVSLFYLVGL

FDLWDGLRTLAYSAAGIYAIAYYIDGSLMPWIGFIFLMGHMSISHIYRQI

IDDAHVTDITGAQMVLVMKLSSFCWNVHDGRLSQEQLSDPQKYAAIKDFP

GILDYLGYVLFFPSLFAGPSFEYVDYRRWIDTTLFDVPPGTDPSKVPPTR

KKRKIPRSGTPAAKKALAGLGWILAFLQLGSLYNQELVLDETFMQYSFVQ

RVWILHMLGFTARLKYYGVWYLTEGACVLSGMGYNGFDPKSGKVFWNRLE

NVDPWSLETAQNSHGYLGSWNKNTNHWLRNYVYLRVTPKGKKPGFRASLA

TFVTSAFWHGFYPGYYLTFVLGSFIQTVAKNFRRHVRPFFLTPDGSRPTA

YKKYYDIASYVVTQLTLSFAVMPFIFLSFGDSIKVWHSVYFYGIVGNIVS

LAFFVSPARGLLLKKLKARNKPHVPRAVSSENIRQPTLGLPNDAIQEFDD

AVQEIRAEIESRQRRGSLAHMPIGDELKAAVEDKIGRGH

Alignment of the LPCAT sequences from different species that reveals four conserved motifs unique for this novel type of LPCAT enzymes (FIG. 2). They are not present in the previously identified glycerol-3-phosphate acyltransferases, lyso-phosphatidic acid acyltransferases, and known LPCAT enzymes. The sequences of these motifs are as follows. The letter "φ" represents a certain amino acid.

Motif 1: M V(I) L(I) φ φ K L(V,I) φ φ φ φ φ φ D G (or Met Xaa Xaa Xaa Xaa Lys Xaa Xaa Xaa Xaa Xaa Xaa Xaa Asp Gly (SEQ ID NO:46), wherein the Xaa at position 2 can be Val or Ile, the Xaa at position 3 can be Leu or Ile, the Xaa at position 7 can be Leu, Val, or Ile, while the other Xaa's in the motif may be any amino acid.

Motif 2: R φ K Y Y φ φ W φ φ φ E(D) A(G) φ φ φ φ G φ G F(Y) φ G (or Arg Xaa Lys Tyr Tyr Xaa Xaa Trp Xaa Xaa Xaa Xaa Xaa Xaa Xaa Xaa Xaa Gly Xaa Gly Xaa Xaa Gly (SEQ ID NO:47), wherein the Xaa at position 12 is Glu or Asp, wherein the Xaa at position 13 is Ala or Gly, wherein the Xaa at position 22 is Phe or Tyr, while the other Xaa's in the motif may be any amino acid.

Motif 3: E φ φ φ φ φ φ φ φ φ φ W N φ φ T(V) φ φ W (or Glu Xaa Xaa Xaa Xaa Xaa Xaa Xaa Xaa Xaa Xaa Xaa Trp Asn Xaa Xaa Xaa Xaa Xaa Trp (SEQ ID NO:48) wherein the Xaa at position 17 is Thr or Val, while the other Xaa's in the motif may be any amino acid.

Motif 4: S A φ W H G φ φ P G Y φ φ T(F) F (or Ser Ala Xaa Trp His Gly Xaa Xaa Pro Gly Tyr Xaa Xaa Xaa Phe (SEQ ID NO:49) wherein Xaa at position 14 is Thr or Phe, while the other Xaa's in the motif may be any amino acid.

FIG. 3 depicts another alignment of LPCAT sequences from different plant species that revealed the following motifs:

Motif 5 (SEQ ID NO: 81):
E A φ φ I I(L) S G φ G F S(T) G W;

Motif 6 (SEQ ID NO: 82):
W D R A φ N V D;

Motif 7 (SEQ ID NO: 83):
W N I Q V S T W L φ φ Y V Y;
and

Motif 8 (SEQ ID NO: 84):
G F φ Q L L φ T Q T φ S A φ W H G L Y P G Y.

EXAMPLE 7

Analysis of LPCAT from the Alga *Thalassiosira pseudonana*

Materials and Methods

Isolation of the LPCAT cDNA from *T. pseudonana*: PCR primers were designed for nucleotide sequence of the putative TpLPCAT obtained by a BLAST search of the sequenced *T. pseudonana* genome using the yeast LPCAT sequence. Plasmid from a cDNA library of *T. pseudonana* was used as template. A 50 µl PCR reaction contained 50 ng of plasmid DNA, 20 pM of each primer: 5'-GGTATGCTCATCTGC-TACCCCCTC-3' (SEQ ID NO:89) and 5'-TTAAGTCTCCT-TCGTCTTTGGTGTAG-3' (SEQ ID NO:90) and 1 µl of BD Advantage™ 2 Polymerase Mix (Clontech Laboratories, Inc.), and was amplified in a thermocycler during 30 cycles of the following program: 94° C for 30 sec, 58° C. for 30 sec, and 72° C. for 1 min 30 sec. The PCR product was purified, and subsequently cloned into the pYES2.1/V5-His-TOPO expression vector (Invitrogen).

Expression of TpLPCAT in yeast: The TpLPCAT in pYES2.1/V5-His-TOPO plasmid was transformed into yeast lpcat mutant By02431 using the method provided by the producer's manual (Invitrogen). Yeast cells transformed with pYES2.1/V5-His-TOPO plasmid only were used as a control. Transformants were selected by growth on synthetic complete medium lacking uracil (SC-ura), supplemented with 2% (w/v) glucose. The colonies were transferred into liquid SC-ura with 2% (w/v) glucose and grown at 28° C. overnight. The overnight cultures were diluted to an OD 0.4 in induction medium (SC-ura+2% Galactose+1% Raffinose), and were induced by incubating at 28° C. for 24 hours. The yeast cells were collected and broken using glass beads. The protein concentrations in the lysates were normalized using the Biorad assay (Bradford 1976) and then assayed for LPCAT activity.

Identification of LPCAT from the algae *Thalassiosira pseudonana*

Figure 4:
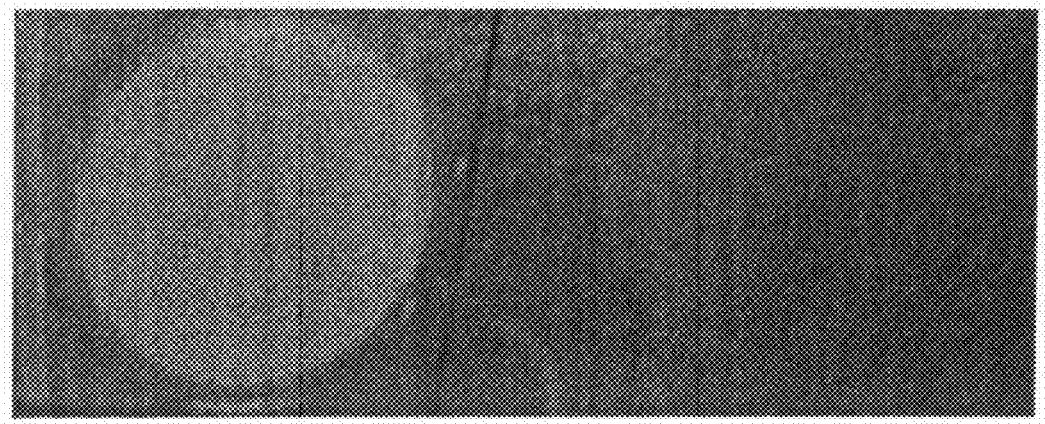
FIG. 4 is depicts the expression of the TpLCAT in lpcat mutant was able to complement the sensitivity of the lpcat mutant to Lyso-PAF.

Isolation of the LPCAT cDNA from *T. pseudonana* A full-length *T. pseudonana* LPCAT cDNA clone was amplified by PCR from an algae cDNA library. The nucleotide sequence had an open reading frame of 1,323 bp encoding a polypeptide of 440 amino acids with a calculated molecular mass of 49.75 kD Expression of TpLPCAT in Yeast: To confirm the function of the protein encoded by the TpLPCAT, the full-length coding region of TpLPCAT was cloned into a yeast expression vector pYES2.1/V5-His-TOPO under the control of the galactose-inducible GAL1 promoter, and the construct was used to transform a LPCAT-deficient yeast strain By02431(a yeast lpcat strain). Yeast cells harboring an empty pYES2.1 vector plasmid were used as a control. We also discovered that the yeast lpcat strain is hypersensitive to lyso-PAF (lyso-Platelet-activating factor, 1-O-alkyl-sn-glycero-3-phosphocholine). Expression of the TpLPCAT in yeast lpcat mutant was able to overcome lyso-PAF the sensitivity of the lpcat mutant (FIG. 4).

Figure 5:
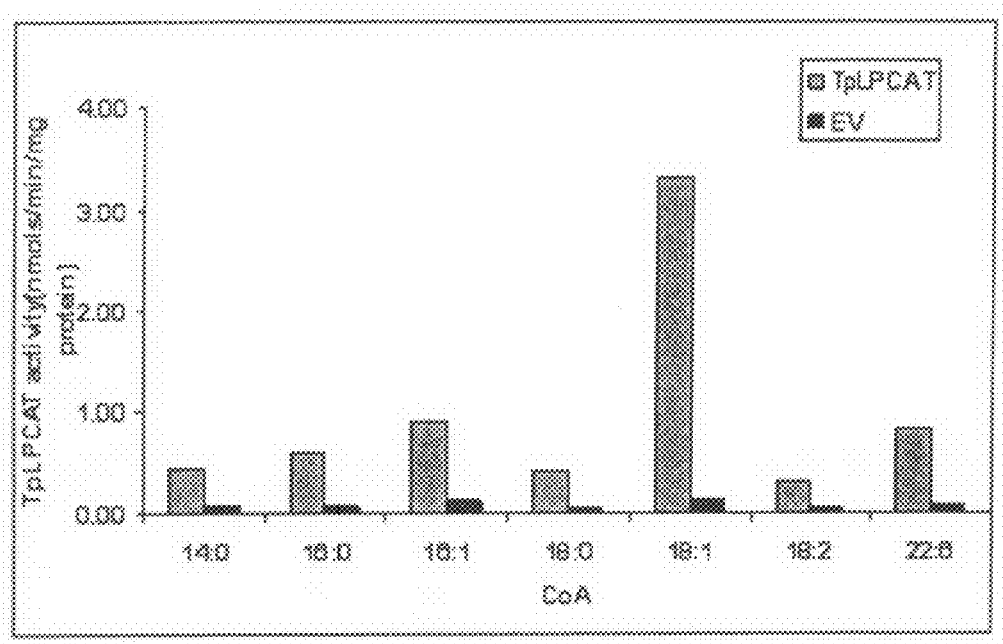
FIG. 5 is a graph showing the expression of TpLPCAT in yeast. LPCAT assays were performed on cell lysates of yeast lpcat mutant strain By02431 transformed with TpLPCAT/pYES2.1 and pYes2.1/V5-His-TOPO plasmid only (control) in the presence of $^{14}$C-Lyso-PC and different acyl-CoAs.
Figure 6:
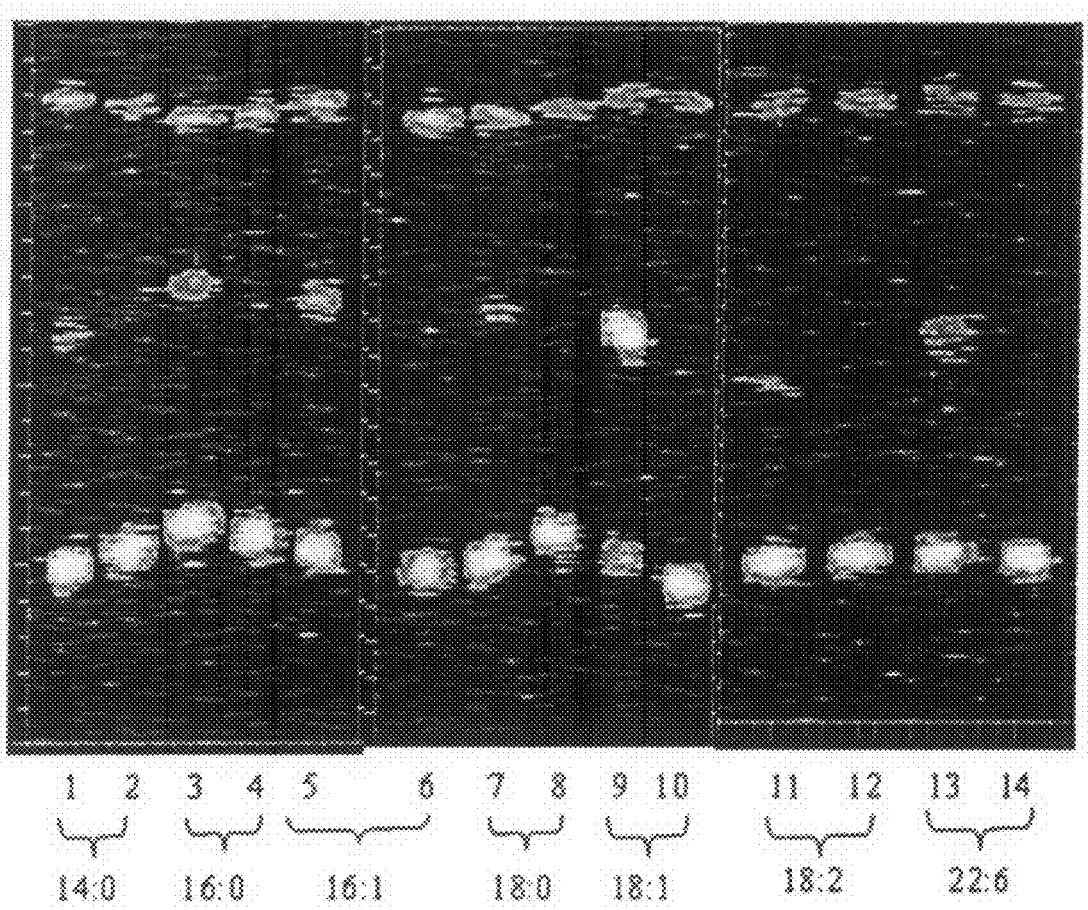
FIG. 6 comprises TLC plates of LPCAT assays on cell lysates of yeast lpcat mutant strain By02431 transformed with TpLPCAT/pYES2.1 and pYes2.1/V5-His-TOPO plasmid only (control) in the presence of $^{14}$C-Lyso-PC and different acyl-CoAs. 1, 3, 5, 7, 9, 11, and 13-TpLPCAT; 2, 4, 6, 8, 10, 12, and 14-empty vector.

The microsomal membrane fractions prepared from lysates of the induced yeast cells were assayed for LPCAT activity using 14C-labelled Lyso-PC as acceptor, and different unlabeled acyl-CoAs as acyl donors. Under our assay conditions, expression of the TpLPCAT in yeast lpcat mutant resulted in a restoration of LPCAT function and produced a recombinant LPCAT protein capable of incorporating a range of different acyl-CoAs into PC including 14:0-, 16:0-, 16:1-, 18:0-, 18:1-, 18:2-, and 22:6(DHA)-, with the most preference of 18:1-CoA, and efficiently utilization of the very long chain polyunsaturated fatty acid—22:6-CoA(DHA) (FIGS. 5 & 6).

EXAMPLE 8

Arabidopsis Gene Assays

Experimental procedure:

TA-cloning and yeast complementation: Total RNA was prepared from *Arabidopsis* seedlings using RNeasy Plant Mini Kit (Qiagen). RT-PCR of the ORFs of *Arabidopsis* At1g12460, At1g63050 was performed with primer pairs designed based on sequences of gene annotation available at TAIR (The *Arabidopsis* Information Resources). The cDNA was cloned into vector pYES2.1 using pYES2.1 TOPO TA Cloning Kit according to the manufacturer's protocol (Invitrogen). Correctly-oriented positive colonies were identified through double digestion with restriction enzyme, followed by verification through DNA sequencing. The construct was introduced into yeast strain YOR175c, BY02431. Yeast extract, Yeast Nitrogen Base, Bacto-peptone, and Bacto-agar were purchased from Difco™, D-glucose, D-galactose and D-raffinose were from Sigma. SC minimal medium and plates was prepared according to Invitrogen's recipe described for the pYES2.1 TOPO TA Cloning Kit.

Lyso-PAF sensitivity: Yeast strains BY02431 carrying pYES 2.1-AtLPCATs or the empty vector were first grown in 15 ml of SC-Leu-His-ura medium containing 2% glucose. Yeast transformant strains of AtLPCATs were first grown in YPD overnight. Protein expression induction were carried out by protocol described in Invitrogen manufacturer manual for yeast expression vector pYES2.1. After 12 hr induction, 5 µl cultures were inoculated onto YPD plate with 10 µg/ml LysoPAF. The plates were incubated at 28° C. for 2 days. The final lysoPAF is 10 µg/ml.

In vitro assay: Yeast strains BY02431 carrying pYES 2.1-AtLPCATs or the empty vector were first grown in 15 ml of SC-Leu-His-ura medium containing 2% glucose. Yeast transformant strains of AtLPCATs were first grown in YPD overnight. Protein expression induction were carried out by protocol described in Invitrogen manufacturer manual for yeast expression vector pYES2.1. After 24 hr of growth in the galactose induction conditions, the cells were washed first with distilled water and then with wall-breaking buffer (50 mM sodium phosphate, pH7.4; 1 mM EDTA; 1 mM PMSF; 5% glycerol) and spun down at 4,000 rpm (Eppendorf Centrifuge 5145C) to re-pellet cells. The cells, resuspended in 1 ml cell wall-breaking buffer, were shaken vigorously in the presence of acid-washed glass beads (diameter 0.5 mm) in a mini-bead beater at 5,000 rpm for 3' 1-min intervals. The resultant homogenate was centrifuged at 1,500' g for 5 min at 4° C. The supernatant was decanted for in vitro assay. Protein concentration was measured using Bio-Rad Protein Assay Kit for final AtSAT1 activity calculation.

AtLPCAT substrate specificity was determined by counting incorporation of 14C-labeled lysophosphatidylcholine or 14C-labled palmityl-CoA into phosphatidylcholine. All assays were performed at least twice. 200 ml reaction mixture contained 50 mg microsomal protein, 50 mM acyl-CoA and 45 mM palmitoyl-PC, pH7.4. 14C-lysophosphatidylcholine (1.4 nCi/nmol) or 14C-palmityl-CoA (5.5 nCi/nmol) was used to assess fatty-CoA or lyso-lipid substrate specificity. Reaction was allowed for 10 min at 30° C. All radiolabel chemicals for these assays were purchased from ARC, Inc.

Figure 7:
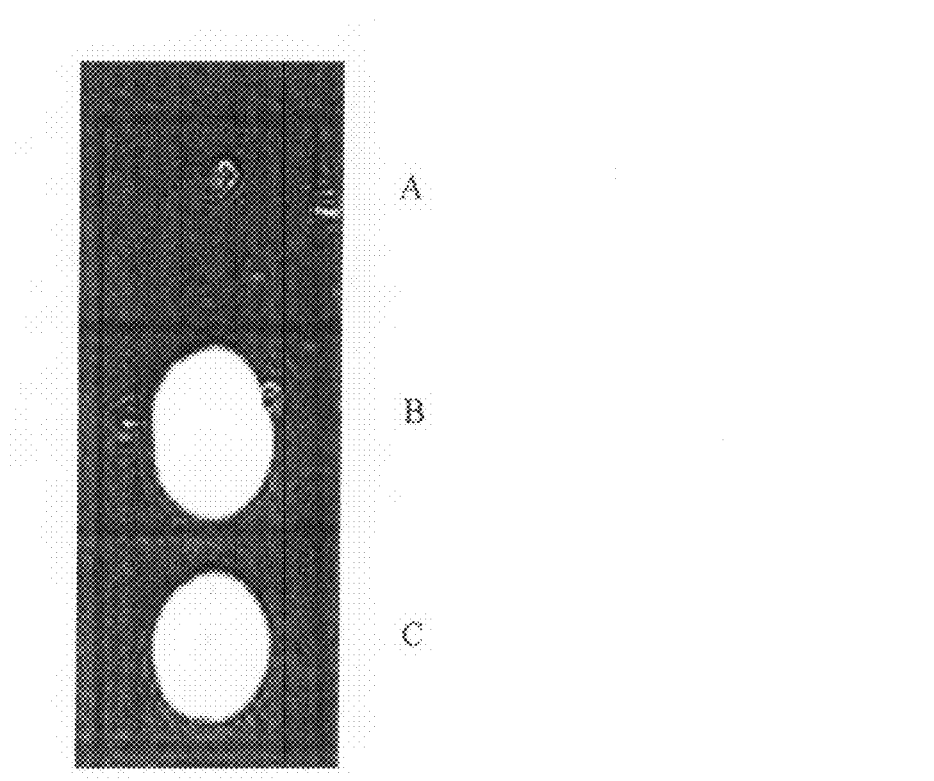
FIG. 7 shows a LysoPAF sensitivity test of YOR175c mutant, AtLPCATs transformant, wherein A is VO/BY02431, B is AtLPCAT1/BY02431, and C is AtLPCAT2/BY02431.

Lyso-PAF sensitivity test (FIG. 7): The yeast lpcat strain is deficient in its endogenous LPCAT and hypersensitive to lyso-PAF (lyso-Platelet-activating factor, 1-O-alkyl-sn-glycero-3-phosphocholine). The lpcat yeast mutant is incapable of growth in the presence of 10 ug/ml lyso-PAF (lyso-Platelet-activating factor, 1-O-alkyl-sn-glycero-3-phosphocholine). However, when the *Arabidopsis* LPCAT genes, At1g12640 and At1g63050, were introduced into the yeast mutant, the transformants could survive on lyso-PAF-containing YPD plate. These results indicated that the *Arabidopsis* genes encode for LPCAT.

In vitro enzyme characterization with the yeast cell free lysate expressing the *Arabidopsis* LPCATs was further conducted.

Figure 8:
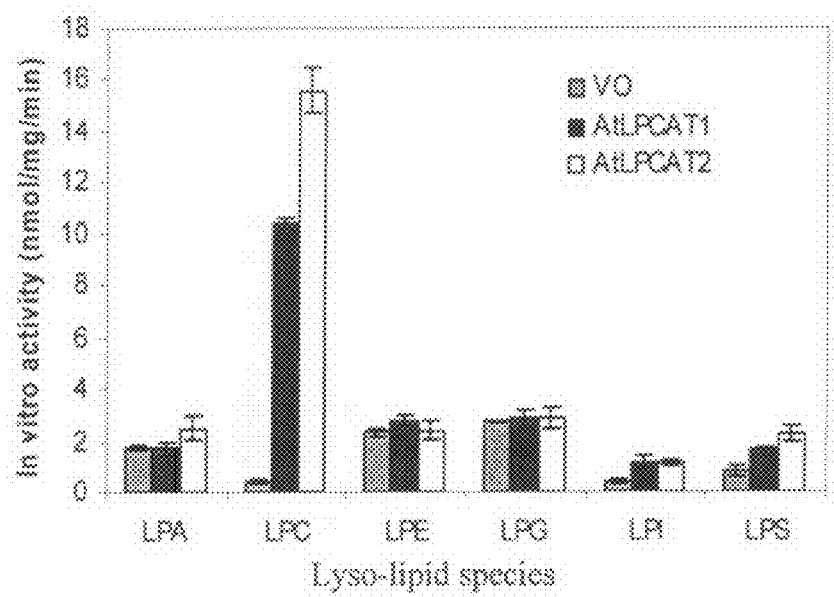
FIG. 8 is a graph showing the Lyso-lipid substrate specificity of Arabidopsis LPCATs.

Lyso-lipid substrate specificity (FIG. 8): LPA (lysophosphatidic acid), LPC (lysophosphatidic choline), LPE (lysophosphatidylethanolamine), LPG (lysophosphatidylglycerol), LPI (lysophosphatidyl inositol) and LPS (lysophosphatidyl serine) were first tested as substrates to compare their acyltransferase activity. The results clearly showed that At1g12640 and At1g63050 both exhibited high activity towards LPC (FIG. 8).

References: The contents of the following references are incorporated herein in their entirety.

Abbadi A, Domergue F, Bauer J, Napier J A, Welti R, Zähinger U, Cirpus P, Heinz E (2004). Biosynthesis of very-long-chain polyunsaturated fatty acids in transgenic oilseeds: constraints on their accumulation. Plat Cell 16: 2734-2748.

Bechtold, N., Ellis, J. and Pellefer, G. (1993) In planta *Agrobacterium*-mediated gene transfer by infiltration of adult *Arabidopsis thaliana* plants. C.R. Acad. Sci. Ser. Ill Sci. Vie, 316: 1194-1199.

Becker, D., Brettschneider, R. and. Lorz, H. (1994) Fertile transgenic wheat from microprojectile bombardment of scutellar tissue. Plant J. 5: 299-307.

Chen X, Hyatt B A, Mucenski M L, Mason R J, Shannon J M (2006). Identification and characterization of a lysophosphatidylcholine acyltransferase in alveolar type II cells. Proc. Natl. Acad. Sci. USA 103: 11724-11729.

Datla, R, Anderson, J. W. and Selvaraj, G. (1997) Plant promoters for transgene expression. Biotechnology Annual Review 3: 269-296.

DeBlock, M., DeBrouwer, D. and Tenning, P. (1989) Transformation of *Brassica napus* and *Brassica oleracea* using *Agrobacterium tumefaciens* and the expression of the bar and neo genes in the transgenic plants. Plant Physiol. 91: 694-701.

Domergue F, Abbadi A, Heinz E (2005). Relief for fish stocks: oceanic fatty acids in transgenic oilseeds. Trend Plant Sci 10: 112-116.

Huang Y S, Pereira S L, Leonard A E (2004). Enzymes for transgenic biosynthesis of long-chain polyunsaturated fatty acids. Biochimie 86: 793-798.

Katavic, Y., Haughn, G. W., Reed, D., Martin, M. and Kunst, L. (1994) In *planta* transformation of *Arabidopsis thaliana*. Mol. Gen. Genet. 245: 363-370.

Meyer, P. (1995) Understanding and controlling transgene expression. *Trends in Biotechnology:* 13: 332-337.

Moloney, M. M., Walker, J. M. and Sharma, K. K. (1989) High efficiency transformation of *Brassica napus* using *Agrobacterium* vectors. Plant Cell Rep. 8: 238-242.

Napier J A, Beaudoin F, Michaelson L V, Sayanova O (2004). The production of long chain polyunsaturated fatty acids in transgenic plants by reverse-engineering. Biochimic 86: 785-793.

Nehra, N. S., Chibbar, R. N., Leung, N., Caswell, K., Mallard, C., Steinhauer, L. Baga, M. and Kartha, K. K. (1994) Self-fertile transgenic wheat plants regenerated from isolated. scutellar tissues following microprojectile bombardment with two distinct gene constructs. *Plant J.* 5: 285-297.

Potrykus, L. (1991) Gene transfer to plants: Assessment of publish approaches and results. *Annu. Rev. Plant Physiol. Plant Mol. Biol.* 42: 205-225.

Pouwels et al., Cloning Vectors. A laboratory manual, Elsevier, Amsterdam (1986).

Qi B, Fraser T, Mugford S, Dobson G, Sayanova O, Butler J, Napier J A, Stobart A K, Lazarus C M (2004). Production of very long chain polyunsaturated omega-3 and omega-6 fatty acids in plants. Nat Biotechnol 22: 739-745.

Rhodes, C. A., Pierce, D. A., Mettler, I. J., Mascarenhas, D. and Detmer, J. J. (1988) Genetically transformed maize plants from protoplasts. *Science* 240: 204-207.

Sanford, J. C., Klein, T. M., Wolf, E. D. and Allen, N. (1987) Delivery of substances into cells and tissues using a particle bombardment process. *J. Part. Sci. Technol.* 5: 27-37.

Shimamoto, K., Terada, R., Izawa, T. and Fujimoto, H. (1989) Fertile transgenic rice plants regenerated from transformed protoplasts. *Nature* 335: 274-276.

Shindou H, Hishikawa D, Nakanishi H, Harayama T, Ishii S, Taguchi R, Shimizu T (2007). A single enzyme catalyzes both platelet-activating factor production and membrane biogenesis of inflammatory cells: Cloning and characterization of acetyl-CoA: lyso-PAF acetyltransferase. J Biol Chem. 282: 6532-6539.

Songstad D. D., Somers, D. A. and Griesbach, R. J. (1995) Advances in alternative DNA delivery techniques. *Plant Cell, Tissue and Organ Culture* 40: 1-15.

Testet E, Laroche-Traineau J, Noubhani A, Coulon D, Bunoust O, Camougrand N, Manon S, Lessire R, Bessoule J J (2005). Ypr140wp, 'the yeast tafazzin', displays a mitochondrial lysophosphatidylcholine (lyso-PC) acyltransferase activity related to triacylglycerol and mitochondrial lipid synthesis. Biochem J 387: 617-626.

Vasil, I. K. (1994) Molecular improvement of cereals. *Plant Mol. Biol.* 5: 925-937.

Walden, R. and Wingender, R. (1995) Gene-transfer and plant regeneration techniques. *Trends in Biotechnology* 13: 324-331.

Wu G, Truksa M, Datla N, Vrinten P, Bauer J, Zank T, Cirpus P, Heinz E, Qiu X (2005). Stepwise engineering to produce high yields of very long-chain polyunsaturated fatty acids in plants. Nat Biotechnol 23: 1013-1017.

---

SEQUENCE LISTING

<160> NUMBER OF SEQ ID NOS: 90

<210> SEQ ID NO 1
<211> LENGTH: 1860
<212> TYPE: DNA
<213> ORGANISM: Saccharomyces cerevisiae

<400> SEQUENCE: 1

```
atgtacaatc ctgtggacgc tgttttaaca aagataatta ccaactatgg gattgatagt      60
tttacactgc gatatgctat ctgcttattg ggatcgttcc cactgaatgc tattttgaag     120
agaattcccg agaagcgtat aggtttaaaa tgttgtttta tcatttctat gtcgatgttt     180
tacttattcg gtgtgctgaa tctagtaagt ggattcagga ccctgtttat tagtaccatg     240
tttacttact tgatctcaag attttaccgt tccaagttta tgccacactt gaatttcatg     300
tttgttatgg gtcatttggc aataaatcat atacacgccc aattccttaa cgaacagact     360
caaactaccg ttgacattac aagttcacaa atggttttag ccatgaaact aacttctttt     420
gcatggtcgt actatgatgg ttcatgcact agcgaaagcg atttcaaaga tttgactgag     480
catcaaaaat ctcgtgctgt cagaggtcat ccacccttat taaagttcct ggcatatgca     540
tttttctatt caacgttgct aactggccca agtttcgatt atgccgattt tgacagctgg     600
ttgaattgtg agatgttccg tgacttgcct gaaagcaaaa agcctatgag aagacaccac     660
cctggtgaaa gaagacagat tccaaagaat ggtaaacttg cattatggaa agttgttcaa     720
ggtcttgctt ggatgatttt aagtacacta ggaatgaagc acttccccgt aaaatacgtt     780
```

-continued

```
ttggacaaag atggcttccc aacgagatct tttatattca gaatccatta cttattcttg    840
cttggtttca tccatagatt caagtactac gctgcctgga ctatttcgga aggatcttgt    900
attttgtgcg gtttgggtta taatggttat gattcaaaga cacaaaagat cagatgggat    960
cgtgtcagaa atattgacat ttggaccgta gaaacggcgc agaatacgcg tgaaatgttg   1020
gaagcatgga atatgaatac taacaagtgg ctaaaatact ctgtttattt acgtgtcaca   1080
aagaagggca aaaacctggt ttccgctca actttgttta ctttcctaac ttccgcattt   1140
tggcatggta ccagacctgg gtactatctg acttttgcga caggggcttt gtaccaaaca   1200
tgtggtaaaa tctacagacg caattttaga ccaattttct gcgagaaga tggtgtcact   1260 cctttgcctt ctaaaaaaat ctacgattta gttggcatat atgcaattaa actagcattt   1320
ggttacatgg tgcaaccatt tattatcctt gatttgaagc catctttaat ggtatggggc   1380
tctgtttatt tctatgttca tattattgtt gctttctcat ttttcctatt cagaggacca   1440
tatgctaaac aagttactga atttttaaa tccaaacaac ctaaagaaat attcattaga   1500
aaacaaaaga agttggaaaa agatatttct gcaagctctc caaacttggg tggtatattg   1560
aaggcaaaga ttgaacatga aagggaaag acagcagaag aagaagaaat gaacttaggt   1620
attccaccaa ttgagttaga aaagtgggac aatgctaagg aagattggga agatttctgc   1680
aaagattaca agaatggag aaataaaaat ggtcttgaaa tagaagagga aaacctttct   1740
aaagcttttg aaagattcaa gcaggaattt tctaacgctg caagtggatc aggtgaacgt   1800
gtgagaaaaa tgagttttag tggttactca ccaaagccta tttcaaaaaa ggaagagtag   1860
```

<210> SEQ ID NO 2
<211> LENGTH: 619
<212> TYPE: PRT
<213> ORGANISM: Saccharomyces cerevisiae

<400> SEQUENCE: 2

```
Met Tyr Asn Pro Val Asp Ala Val Leu Thr Lys Ile Ile Thr Asn Tyr
  1               5                  10                  15

Gly Ile Asp Ser Phe Thr Leu Arg Tyr Ala Ile Cys Leu Leu Gly Ser
             20                  25                  30

Phe Pro Leu Asn Ala Ile Leu Lys Arg Ile Pro Glu Lys Arg Ile Gly
         35                  40                  45

Leu Lys Cys Cys Phe Ile Ile Ser Met Ser Met Phe Tyr Leu Phe Gly
     50                  55                  60

Val Leu Asn Leu Val Ser Gly Phe Arg Thr Leu Phe Ile Ser Thr Met
 65                  70                  75                  80

Phe Thr Tyr Leu Ile Ser Arg Phe Tyr Arg Ser Lys Phe Met Pro His
                 85                  90                  95

Leu Asn Phe Met Phe Val Met Gly His Leu Ala Ile Asn His Ile His
            100                 105                 110

Ala Gln Phe Leu Asn Glu Gln Thr Gln Thr Thr Val Asp Ile Thr Ser
        115                 120                 125

Ser Gln Met Val Leu Ala Met Lys Leu Thr Ser Phe Ala Trp Ser Tyr
    130                 135                 140

Tyr Asp Gly Ser Cys Thr Ser Glu Ser Asp Phe Lys Asp Leu Thr Glu
145                 150                 155                 160

His Gln Lys Ser Arg Ala Val Arg Gly His Pro Leu Leu Lys Phe
                165                 170                 175

Leu Ala Tyr Ala Phe Phe Tyr Ser Thr Leu Leu Thr Gly Pro Ser Phe
            180                 185                 190
```

-continued

```
Asp Tyr Ala Asp Phe Asp Ser Trp Leu Asn Cys Glu Met Phe Arg Asp
            195                 200                 205

Leu Pro Glu Ser Lys Lys Pro Met Arg Arg His His Pro Gly Glu Arg
    210                 215                 220

Arg Gln Ile Pro Lys Asn Gly Lys Leu Ala Leu Trp Lys Val Val Gln
225                 230                 235                 240

Gly Leu Ala Trp Met Ile Leu Ser Thr Leu Gly Met Lys His Phe Pro
                245                 250                 255

Val Lys Tyr Val Leu Asp Lys Asp Gly Phe Pro Thr Arg Ser Phe Ile
            260                 265                 270

Phe Arg Ile His Tyr Leu Phe Leu Leu Gly Phe Ile His Arg Phe Lys
        275                 280                 285

Tyr Tyr Ala Ala Trp Thr Ile Ser Glu Gly Ser Cys Ile Leu Cys Gly
    290                 295                 300

Leu Gly Tyr Asn Gly Tyr Asp Ser Lys Thr Gln Lys Ile Arg Trp Asp
305                 310                 315                 320

Arg Val Arg Asn Ile Asp Ile Trp Thr Val Glu Thr Ala Gln Asn Thr
                325                 330                 335

Arg Glu Met Leu Glu Ala Trp Asn Met Asn Thr Asn Lys Trp Leu Lys
            340                 345                 350

Tyr Ser Val Tyr Leu Arg Val Thr Lys Gly Lys Lys Pro Gly Phe
        355                 360                 365

Arg Ser Thr Leu Phe Thr Phe Leu Thr Ser Ala Phe Trp His Gly Thr
    370                 375                 380

Arg Pro Gly Tyr Tyr Leu Thr Phe Ala Thr Gly Ala Leu Tyr Gln Thr
385                 390                 395                 400

Cys Gly Lys Ile Tyr Arg Arg Asn Phe Arg Pro Ile Phe Leu Arg Glu
                405                 410                 415

Asp Gly Val Thr Pro Leu Pro Ser Lys Lys Ile Tyr Asp Leu Val Gly
            420                 425                 430

Ile Tyr Ala Ile Lys Leu Ala Phe Gly Tyr Met Val Gln Pro Phe Ile
        435                 440                 445

Ile Leu Asp Leu Lys Pro Ser Leu Met Val Trp Gly Ser Val Tyr Phe
    450                 455                 460

Tyr Val His Ile Ile Val Ala Phe Ser Phe Leu Phe Arg Gly Pro
465                 470                 475                 480

Tyr Ala Lys Gln Val Thr Glu Phe Phe Lys Ser Lys Gln Pro Lys Glu
                485                 490                 495

Ile Phe Ile Arg Lys Gln Lys Lys Leu Glu Lys Asp Ile Ser Ala Ser
            500                 505                 510

Ser Pro Asn Leu Gly Gly Ile Leu Lys Ala Lys Ile Glu His Glu Lys
        515                 520                 525

Gly Lys Thr Ala Glu Glu Glu Met Asn Leu Gly Ile Pro Pro Ile
    530                 535                 540

Glu Leu Glu Lys Trp Asp Asn Ala Lys Glu Asp Trp Glu Asp Phe Cys
545                 550                 555                 560

Lys Asp Tyr Lys Glu Trp Arg Asn Lys Asn Gly Leu Glu Ile Glu Glu
                565                 570                 575

Glu Asn Leu Ser Lys Ala Phe Glu Arg Phe Lys Gln Glu Phe Ser Asn
            580                 585                 590

Ala Ala Ser Gly Ser Gly Glu Arg Val Arg Lys Met Ser Phe Ser Gly
        595                 600                 605
```

Tyr Ser Pro Lys Pro Ile Ser Lys Lys Glu Glu
    610             615

<210> SEQ ID NO 3
<211> LENGTH: 1780
<212> TYPE: DNA
<213> ORGANISM: Arabidopsis thaliana

<400> SEQUENCE: 3

| accaacaacc | acacgacacg | acacgaccga | tctatagatt | cggcgagatc | agaagaaagc | 60 |
| ttcccggagc | aactcggtcg | ttgtgactca | ttccgagtta | aaaaaaacgg | gttttcgaca | 120 |
| ccatggatat | gagttcaatg | gctggttcaa | tcggagtttc | ggtagccgta | ctccgattcc | 180 |
| tcctctgttt | cgttgccacg | atccctgttt | cattcgcttg | tcgaatcgtc | ccgagtagac | 240 |
| tcggtaaaca | cttgtatgcc | gctgcttcag | gtgctttcct | ctcttacctc | tcctttggct | 300 |
| tctcctccaa | ccttcacttc | cttgttccga | tgacgatcgg | atatgcttca | atggcgattt | 360 |
| atagacccaa | gtgtggaatc | atcactttct | tcctcggttt | cgcttatctt | attggctgtc | 420 |
| atgtgtttta | tatgagtggt | gatgcgtgga | agaaggagg  | aatcgattct | actggagcgt | 480 |
| taatggtgtt | gacgctgaaa | gtcatctcat | gttcaatgaa | ttacaatgat | gggatgttga | 540 |
| aggaggaagg | tctacgtgaa | gctcagaaga | aaaacagatt | gattcagatg | ccgtctttga | 600 |
| ttgagtactt | tggttactgc | cttgttgtg  | gtagccattt | tgctggtcct | gtttatgaaa | 660 |
| tgaaagatta | tcttgaatgg | accgaaggga | aagggatttg | gatactact  | gagaaaagaa | 720 |
| agaagccatc | gccttatgga | gctacaatcc | gagctatttt | gcaagctgcg | atttgcatgg | 780 |
| ctctgtatct | ctatttagtg | cctcaatatc | cgttaactcg | gttcacagaa | ccagtgtatc | 840 |
| aagaatgggg | attcttgaga | aaatttagtt | accaatacat | ggctggattc | acggctcgtt | 900 |
| ggaagtatta | cttcatctgg | tcaatttcag | aggcttctat | tatcatctct | ggtttgggtt | 960 |
| tcagtggttg | gactgatgat | gcttcaccaa | agcccaaatg | ggaccgtgcc | aagaacgtag | 1020 |
| atattctcgg | tgttgaacta | gctaagagcg | cggttcagat | tccacttgtg | tggaacatac | 1080 |
| aagtcagcac | gtggctccgt | cactatgtgt | atgagagact | tgtgcagaac | ggaaagaaag | 1140 |
| cgggtttctt | ccagttacta | gctacacaaa | ccgtcagcgc | ggtttggcat | ggactgtatc | 1200 |
| ctggatatat | gatgttcttt | gttcagtcag | ctttgatgat | cgcaggctca | cgggttattt | 1260 |
| accggtggca | caagcgatc  | agtccgaaaa | tggcaatgct | gagaaatata | atggtcttca | 1320 |
| tcaacttcct | ttacactgtt | ttggttctca | actactcagc | cgtcggtttc | atggtgttaa | 1380 |
| gcttgcacga | aacacttacc | gcctacggaa | gcgtatatta | cattggaaca | atcatacctg | 1440 |
| ttggattgat | tctcctcagt | tacgttgtgc | ctgcaaaacc | ttcaagacca | aaaccgcgta | 1500 |
| aagaagaata | agcagttatc | ttcttctctt | aacggtaagt | aagtttcccg | cgcttgccag | 1560 |
| cttcttcttc | ttcttctgta | acatttggaa | acaaaccgat | ccggttcttg | tttctctctg | 1620 |
| attttttagc | accgatattt | ttttttgtatt | tgttgcttat | aaatcttatt | tttcacactt | 1680 |
| ctttttttta | attagtattg | gatttgcaat | tatatagaca | ataagtataa | atatgtaact | 1740 |
| gtaaattgca | aatgggaaaa | aatagtagtg | tttatgtttg |            |            | 1780 |

<210> SEQ ID NO 4
<211> LENGTH: 462
<212> TYPE: PRT
<213> ORGANISM: Arabidopsis thaliana

<400> SEQUENCE: 4

-continued

```
Met Asp Met Ser Ser Met Ala Gly Ser Ile Gly Val Ser Val Ala Val
1               5                   10                  15

Leu Arg Phe Leu Leu Cys Phe Val Ala Thr Ile Pro Val Ser Phe Ala
            20                  25                  30

Cys Arg Ile Val Pro Ser Arg Leu Gly Lys His Leu Tyr Ala Ala Ala
        35                  40                  45

Ser Gly Ala Phe Leu Ser Tyr Leu Ser Phe Gly Phe Ser Ser Asn Leu
    50                  55                  60

His Phe Leu Val Pro Met Thr Ile Gly Tyr Ala Ser Met Ala Ile Tyr
65                  70                  75                  80

Arg Pro Lys Cys Gly Ile Ile Thr Phe Phe Leu Gly Phe Ala Tyr Leu
                85                  90                  95

Ile Gly Cys His Val Phe Tyr Met Ser Gly Asp Ala Trp Lys Glu Gly
            100                 105                 110

Gly Ile Asp Ser Thr Gly Ala Leu Met Val Leu Thr Leu Lys Val Ile
        115                 120                 125

Ser Cys Ser Met Asn Tyr Asn Asp Gly Met Leu Lys Glu Glu Gly Leu
    130                 135                 140

Arg Glu Ala Gln Lys Lys Asn Arg Leu Ile Gln Met Pro Ser Leu Ile
145                 150                 155                 160

Glu Tyr Phe Gly Tyr Cys Leu Cys Cys Gly Ser His Phe Ala Gly Pro
                165                 170                 175

Val Tyr Glu Met Lys Asp Tyr Leu Glu Trp Thr Glu Gly Lys Gly Ile
            180                 185                 190

Trp Asp Thr Thr Glu Lys Arg Lys Lys Pro Ser Pro Tyr Gly Ala Thr
        195                 200                 205

Ile Arg Ala Ile Leu Gln Ala Ala Ile Cys Met Ala Leu Tyr Leu Tyr
    210                 215                 220

Leu Val Pro Gln Tyr Pro Leu Thr Arg Phe Thr Glu Pro Val Tyr Gln
225                 230                 235                 240

Glu Trp Gly Phe Leu Arg Lys Phe Ser Tyr Gln Tyr Met Ala Gly Phe
                245                 250                 255

Thr Ala Arg Trp Lys Tyr Tyr Phe Ile Trp Ser Ile Ser Glu Ala Ser
            260                 265                 270

Ile Ile Ile Ser Gly Leu Gly Phe Ser Gly Trp Thr Asp Asp Ala Ser
        275                 280                 285

Pro Lys Pro Lys Trp Asp Arg Ala Lys Asn Val Asp Ile Leu Gly Val
    290                 295                 300

Glu Leu Ala Lys Ser Ala Val Gln Ile Pro Leu Val Trp Asn Ile Gln
305                 310                 315                 320

Val Ser Thr Trp Leu Arg His Tyr Val Tyr Glu Arg Leu Val Gln Asn
                325                 330                 335

Gly Lys Lys Ala Gly Phe Phe Gln Leu Leu Ala Thr Gln Thr Val Ser
            340                 345                 350

Ala Val Trp His Gly Leu Tyr Pro Gly Tyr Met Met Phe Phe Val Gln
        355                 360                 365

Ser Ala Leu Met Ile Ala Gly Ser Arg Val Ile Tyr Arg Trp Gln Gln
    370                 375                 380

Ala Ile Ser Pro Lys Met Ala Met Leu Arg Asn Ile Met Val Phe Ile
385                 390                 395                 400

Asn Phe Leu Tyr Thr Val Leu Val Leu Asn Tyr Ser Ala Val Gly Phe
                405                 410                 415

Met Val Leu Ser Leu His Glu Thr Leu Thr Ala Tyr Gly Ser Val Tyr
```

```
                420              425              430
Tyr Ile Gly Thr Ile Ile Pro Val Gly Leu Ile Leu Leu Ser Tyr Val
         435              440              445
Val Pro Ala Lys Pro Ser Arg Pro Lys Pro Arg Lys Glu Glu
         450              455              460

<210> SEQ ID NO 5
<211> LENGTH: 1659
<212> TYPE: DNA
<213> ORGANISM: Arabidopsis thaliana

<400> SEQUENCE: 5
agatgtccga actgtgagag tcgtcgtcgt cgtcgtaact cagtccgagt tgacacaatc      60
ttccacttca cgcaagatac aaccatggaa ttgcttgaca tgaactcaat ggctgcctca     120
atcggcgtct ccgtcgccgt tctccgtttc ctcctctgtt tcgtcgcaac gataccaatc     180 tcattttat ggcgattcat cccgagtcga ctcggtaaac acatatactc agctgcttct     240
ggagctttcc tctcttatct ctcctttggc ttctcctcaa atcttcactt ccttgtccca     300
atgacgattg gttacgcttc aatggcgatt tatcgaccct tgtctggatt cattactttc     360
ttcctaggct cgcttatct cattggctgt catgtgtttt atatgagtgg tgatgcttgg      420
aaagaaggag gaattgattc tactggagct ttgatggtat taacactgaa agtgatttcg     480
tgttcgataa actacaacga tggaatgttg aaagaagaag gtctacgtga ggctcagaag     540
aagaaccgtt tgattcagat gccttctctt attgagtact tggttattg cctctgttgt     600 ggaagccatt tcgctggccc ggttttcgaa atgaaagatt atctcgaatg gactgaagag     660
aaaggaattt gggctgtttc tgaaaaagga aagagaccat cgccttatgg agcaatgatt     720
cgagctgtgt ttcaagctgc gatttgtatg gctctctatc tctatttagt acctcagttt     780
ccgttaactc ggttcactga accagtgtac caagaatggg gattcttgaa gagatttggt     840
taccaataca tggcgggttt cacggctcgt tggaagtatt actttatatg gtctatctca     900
gaggcttcta ttattatctc tggtttgggt tcagtggtt ggactgatga aactcagaca      960
aaggctaaat gggaccgcgc taagaatgtc gatatttgg gggttgagct tgccaagagt     1020
gcggttcaga ttccgctttt ctggaacata caagtcagca catggctccg tcactacgta     1080
tatgagagaa ttgtgaagcc cgggaagaaa gcgggtttct tccaattgct agctacgcaa     1140
accgtcagtg ctgtctggca tggactgtat cctggataca ttatattctt tgtgcaatca     1200
gcattgatga tcgatggttc gaaagctatt taccggtggc aacaagcaat acctccgaaa     1260
atggcaatgc tgagaaatgt tttggttctc atcaatttcc tctacacagt agtggttctc     1320
aattactcat ccgtcggttt catggtttta agcttgcacg aaacactagt cgccttcaag     1380
agtgtatatt acattggaac agttataccr atcgctgtgc ttcttctcag ctacttagtt     1440
cctgtgaagc ctgttagacc aaagaccaga aagaagaat aatgttgtct ttttaaaaaa     1500
tcaacaacat tttggttctt ttcttttttt ccacttggac cgttttatgt aaaacaagag     1560
aaatcaagat ttgaggtttt attcttcttc tccttcccaa ttttcgaaaa tgattttatt     1620
ttttctgata tatatctaag ctagtccaaa gtcaactcg                           1659

<210> SEQ ID NO 6
<211> LENGTH: 465
<212> TYPE: PRT
<213> ORGANISM: Arabidopsis thaliana

<400> SEQUENCE: 6
```

```
Met Glu Leu Leu Asp Met Asn Ser Met Ala Ala Ser Ile Gly Val Ser
 1               5                  10                  15

Val Ala Val Leu Arg Phe Leu Leu Cys Phe Val Ala Thr Ile Pro Ile
            20                  25                  30

Ser Phe Leu Trp Arg Phe Ile Pro Ser Arg Leu Gly Lys His Ile Tyr
        35                  40                  45

Ser Ala Ala Ser Gly Ala Phe Leu Ser Tyr Leu Ser Phe Gly Phe Ser
    50                  55                  60

Ser Asn Leu His Phe Leu Val Pro Met Thr Ile Gly Tyr Ala Ser Met
65                  70                  75                  80

Ala Ile Tyr Arg Pro Leu Ser Gly Phe Ile Thr Phe Phe Leu Gly Phe
                85                  90                  95

Ala Tyr Leu Ile Gly Cys His Val Phe Tyr Met Ser Gly Asp Ala Trp
            100                 105                 110

Lys Glu Gly Gly Ile Asp Ser Thr Gly Ala Leu Met Val Leu Thr Leu
        115                 120                 125

Lys Val Ile Ser Cys Ser Ile Asn Tyr Asn Asp Gly Met Leu Lys Glu
    130                 135                 140

Glu Gly Leu Arg Glu Ala Gln Lys Lys Asn Arg Leu Ile Gln Met Pro
145                 150                 155                 160

Ser Leu Ile Glu Tyr Phe Gly Tyr Cys Leu Cys Cys Gly Ser His Phe
                165                 170                 175

Ala Gly Pro Val Phe Glu Met Lys Asp Tyr Leu Glu Trp Thr Glu Glu
            180                 185                 190

Lys Gly Ile Trp Ala Val Ser Glu Lys Gly Lys Arg Pro Ser Pro Tyr
        195                 200                 205

Gly Ala Met Ile Arg Ala Val Phe Gln Ala Ala Ile Cys Met Ala Leu
    210                 215                 220

Tyr Leu Tyr Leu Val Pro Gln Phe Pro Leu Thr Arg Phe Thr Glu Pro
225                 230                 235                 240

Val Tyr Gln Glu Trp Gly Phe Leu Lys Arg Phe Gly Tyr Gln Tyr Met
                245                 250                 255

Ala Gly Phe Thr Ala Arg Trp Lys Tyr Tyr Phe Ile Trp Ser Ile Ser
            260                 265                 270

Glu Ala Ser Ile Ile Ser Gly Leu Gly Phe Ser Gly Trp Thr Asp
        275                 280                 285

Glu Thr Gln Thr Lys Ala Lys Trp Asp Arg Ala Lys Asn Val Asp Ile
290                 295                 300

Leu Gly Val Glu Leu Ala Lys Ser Ala Val Gln Ile Pro Leu Phe Trp
305                 310                 315                 320

Asn Ile Gln Val Ser Thr Trp Leu Arg His Tyr Val Tyr Glu Arg Ile
                325                 330                 335

Val Lys Pro Gly Lys Lys Ala Gly Phe Phe Gln Leu Leu Ala Thr Gln
            340                 345                 350

Thr Val Ser Ala Val Trp His Gly Leu Tyr Pro Gly Tyr Ile Ile Phe
        355                 360                 365

Phe Val Gln Ser Ala Leu Met Ile Asp Gly Ser Lys Ala Ile Tyr Arg
    370                 375                 380

Trp Gln Gln Ala Ile Pro Pro Lys Met Ala Met Leu Arg Asn Val Leu
385                 390                 395                 400

Val Leu Ile Asn Phe Leu Tyr Thr Val Val Leu Asn Tyr Ser Ser
                405                 410                 415
```

```
Val Gly Phe Met Val Leu Ser Leu His Glu Thr Leu Val Ala Phe Lys
                420                 425                 430

Ser Val Tyr Tyr Ile Gly Thr Val Ile Pro Ile Ala Val Leu Leu Leu
        435                 440                 445

Ser Tyr Leu Val Pro Val Lys Pro Val Arg Pro Lys Thr Arg Lys Glu
    450                 455                 460

Glu
465

<210> SEQ ID NO 7
<211> LENGTH: 1464
<212> TYPE: DNA
<213> ORGANISM: Thalassiosira pseudonana

<400> SEQUENCE: 7
atgcgattgt atttgcaatt caacttatcc atcaatgatt attgtcactt cttcacagta      60
ccatcctttg tcaaagaggg cgtcgagtct ctctctgcat ccaccggaca agacgtcgag     120
actctcgagt acctccttgg tatgctcatc tgctacccccc tcggaatgat catgctcgct   180
ctaccctacg gaaaagtaaa acatctcttc tccttcatcc tcggagcctt cctacttcaa     240
ttcaccattg gtatccagtg gattcatcac ttaatctcct caatgattgc ctacgtcatg     300
ttcctcgtcc ttcctgccaa atttgccaaa acggcagtgc ctgtgtttgc catgatctac     360
atcaccgcgg acatttgca tcgtcaatac atcaattatc ttgggtggga tatggacttc     420
acggggcctc agatggtgct acgatgaaa ctctacatgc ttgcttacaa ccttgcggat     480
ggggacttgc tcaagaaggg aaaggaggat agggctgcaa agaagtgtgc ggatgtcgct     540
atttcgtctg ttcccggaat cattgagtac ttgggctaca cgttctgctt tgccagtgtt     600
ttagcaggcc ctgcttttga gtacaaattc tacgccgatg catgcgacgg atcactcttg     660
tacgacaaat ctggcaaacc caaggaaag atccccagtc aggtgtggcc tacattgcgt       720
cctctttttg gaagtctctt gtgtctcggc atctttgttg tgggaactgg aatgtatcct     780
cttttggatc ccaacgatcc tcagaatgcc actcctatcc ctctcactcc agagatgttg     840
gccaaaccag cctatgctcg atacgcttac tcgtggcttg cactcttttt catccgattt     900
aagtattact ttgcttggat gaacgccgaa ggagcaagca catttggta tgctggattt     960
gagggatttg atgccagcgg caaccccaaa ggatgggagg tatccaataa cattgacgta   1020
attcagttcg agactgcacc caatctcaag actttgagtg ctgcttggaa taagaagact   1080
gcgaactggt tggcgaagta tgtgtacatt cgcacgggtg gttctctctt tgcgacgtac   1140
ggaatgagtg cttctctggca tggcttctac cctggatact acctcttctt catgtcggta   1200
cccatgatgg ctttctgtga gaggattgga aggaagaaac ttacacctcg tttcggaaat   1260
ggaaagaagt ggagtcctta tggcattgtg tgcattatcg ccacatcgtt gatgacggaa   1320
tacatgattc agccattcca actacttgcg tttgattggg cctgggagaa ctggagcagc   1380
tactactttg ctggacacat tgtttgtgtt gtgttttacc tcgttgtgtc caacatgcct   1440
acaccaaaga cgaaggagac ttaa                                          1464

<210> SEQ ID NO 8
<211> LENGTH: 487
<212> TYPE: PRT
<213> ORGANISM: Thalassiosira pseudonana

<400> SEQUENCE: 8

Met Arg Leu Tyr Leu Gln Phe Asn Leu Ser Ile Asn Asp Tyr Cys His
```

-continued

```
1               5                   10                  15
Phe Phe Thr Val Pro Ser Phe Val Lys Glu Gly Val Glu Ser Leu Ser
                20                  25                  30
Ala Ser Thr Gly Gln Asp Val Glu Thr Leu Glu Tyr Leu Leu Gly Met
                35                  40                  45
Leu Ile Cys Tyr Pro Leu Gly Met Ile Met Leu Ala Leu Pro Tyr Gly
                50                  55                  60
Lys Val Lys His Leu Phe Ser Phe Ile Leu Gly Ala Phe Leu Leu Gln
65                  70                  75                  80
Phe Thr Ile Gly Ile Gln Trp Ile His His Leu Ile Ser Ser Met Ile
                85                  90                  95
Ala Tyr Val Met Phe Leu Val Leu Pro Ala Lys Phe Ala Lys Thr Ala
                100                 105                 110
Val Pro Val Phe Ala Met Ile Tyr Ile Thr Ala Gly His Leu His Arg
                115                 120                 125
Gln Tyr Ile Asn Tyr Leu Gly Trp Asp Met Asp Phe Thr Gly Pro Gln
                130                 135                 140
Met Val Leu Thr Met Lys Leu Tyr Met Leu Ala Tyr Asn Leu Ala Asp
145                 150                 155                 160
Gly Asp Leu Leu Lys Lys Gly Lys Glu Asp Arg Ala Ala Lys Lys Cys
                165                 170                 175
Ala Asp Val Ala Ile Ser Ser Val Pro Gly Ile Ile Glu Tyr Leu Gly
                180                 185                 190
Tyr Thr Phe Cys Phe Ala Ser Val Leu Ala Gly Pro Ala Phe Glu Tyr
                195                 200                 205
Lys Phe Tyr Ala Asp Ala Cys Asp Gly Ser Leu Leu Tyr Asp Lys Ser
                210                 215                 220
Gly Lys Pro Lys Gly Lys Ile Pro Ser Gln Val Trp Pro Thr Leu Arg
225                 230                 235                 240
Pro Leu Phe Gly Ser Leu Leu Cys Leu Gly Ile Phe Val Val Gly Thr
                245                 250                 255
Gly Met Tyr Pro Leu Leu Asp Pro Asn Asp Pro Gln Asn Ala Thr Pro
                260                 265                 270
Ile Pro Leu Thr Pro Glu Met Leu Ala Lys Pro Ala Tyr Ala Arg Tyr
                275                 280                 285
Ala Tyr Ser Trp Leu Ala Leu Phe Phe Ile Arg Phe Lys Tyr Tyr Phe
                290                 295                 300
Ala Trp Met Asn Ala Glu Gly Ala Ser Asn Ile Trp Tyr Ala Gly Phe
305                 310                 315                 320
Glu Gly Phe Asp Ala Ser Gly Asn Pro Lys Gly Trp Glu Val Ser Asn
                325                 330                 335
Asn Ile Asp Val Ile Gln Phe Glu Thr Ala Pro Asn Leu Lys Thr Leu
                340                 345                 350
Ser Ala Ala Trp Asn Lys Lys Thr Ala Asn Trp Leu Ala Lys Tyr Val
                355                 360                 365
Tyr Ile Arg Thr Gly Gly Ser Leu Phe Ala Thr Tyr Gly Met Ser Ala
                370                 375                 380
Phe Trp His Gly Phe Tyr Pro Gly Tyr Tyr Leu Phe Phe Met Ser Val
385                 390                 395                 400
Pro Met Met Ala Phe Cys Glu Arg Ile Gly Arg Lys Lys Leu Thr Pro
                405                 410                 415
Arg Phe Gly Asn Gly Lys Lys Trp Ser Pro Tyr Gly Ile Val Cys Ile
                420                 425                 430
```

```
Ile Ala Thr Ser Leu Met Thr Glu Tyr Met Ile Gln Pro Phe Gln Leu
        435                 440                 445

Leu Ala Phe Asp Trp Ala Trp Glu Asn Trp Ser Ser Tyr Tyr Phe Ala
    450                 455                 460

Gly His Ile Val Cys Val Val Phe Tyr Leu Val Val Ser Asn Met Pro
465                 470                 475                 480

Thr Pro Lys Thr Lys Glu Thr
                485

<210> SEQ ID NO 9
<211> LENGTH: 629
<212> TYPE: DNA
<213> ORGANISM: Apple

<400> SEQUENCE: 9
tcaggaggcc caaatttcct ttgtcaagat ttactgagcc catataccaa gaatgggggt      60
tttggaaacg acttttctac cagtatatgt ctggattcac agcaaggtgg aaatattatt    120
tcatttggtc aatatcagag gcttctatca ttctttctgg cctcggtttc agtggctgga    180
cagagtcctc accaccaaaa cctcgatggg atcgtgcaaa aaatgttgat attataggcg    240
ttgagtttgc aaagagttca gttcagttac cacttgtttg gaacatacaa gtcagcacct    300
ggcttcgcca ttatgtttat gataggcttg ttaaacctgg aaagaagcct ggtttcttcc    360
agttgctggc tacacagacc gtcagtgctg tttggcatgg cctctatcct ggctacatca    420
tattctttgt tcagtcagcg ttgatgattg ctggatcaag agtgatttac cgatggcagc    480
aagctgtacc tccaactatg gatgttgtta agaagatatt ggtgttcatc aactttgctt    540
acactgtctt ggttctgaac tactcctgtg ttggtttcat tgtattaagc cttcgtgaaa    600
cactggcctc gtatggaagc gtgcatttc                                     629

<210> SEQ ID NO 10
<211> LENGTH: 209
<212> TYPE: PRT
<213> ORGANISM: Apple

<400> SEQUENCE: 10

Arg Arg Pro Lys Phe Pro Leu Ser Arg Phe Thr Glu Pro Ile Tyr Gln
1               5                  10                  15

Glu Trp Gly Phe Trp Lys Arg Leu Phe Tyr Gln Tyr Met Ser Gly Phe
                20                  25                  30

Thr Ala Arg Trp Lys Tyr Tyr Phe Ile Trp Ser Ile Ser Glu Ala Ser
        35                  40                  45

Ile Ile Leu Ser Gly Leu Gly Phe Ser Gly Trp Thr Glu Ser Ser Pro
    50                  55                  60

Pro Lys Pro Arg Trp Asp Arg Ala Lys Asn Val Asp Ile Ile Gly Val
65                  70                  75                  80

Glu Phe Ala Lys Ser Ser Val Gln Leu Pro Leu Val Trp Asn Ile Gln
                85                  90                  95

Val Ser Thr Trp Leu Arg His Tyr Val Tyr Asp Arg Leu Val Lys Pro
                100                 105                 110

Gly Lys Lys Pro Gly Phe Phe Gln Leu Leu Ala Thr Gln Thr Val Ser
            115                 120                 125

Ala Val Trp His Gly Leu Tyr Pro Gly Tyr Ile Ile Phe Phe Val Gln
        130                 135                 140

Ser Ala Leu Met Ile Ala Gly Ser Arg Val Ile Tyr Arg Trp Gln Gln
```

```
145                 150                 155                 160
Ala Val Pro Pro Thr Met Asp Val Val Lys Lys Ile Leu Val Phe Ile
                165                 170                 175

Asn Phe Ala Tyr Thr Val Leu Val Leu Asn Tyr Ser Cys Val Gly Phe
            180                 185                 190

Ile Val Leu Ser Leu Arg Glu Thr Leu Ala Ser Tyr Gly Ser Val His
        195                 200                 205

Phe

<210> SEQ ID NO 11
<211> LENGTH: 135
<212> TYPE: PRT
<213> ORGANISM: Barley

<400> SEQUENCE: 11

Glu Ala Ala Ile Ile Ile Ser Gly Leu Gly Phe Thr Gly Trp Ser Asp
1               5                   10                  15

Ser Ser Pro Pro Lys Ala Lys Trp Asp Arg Ala Ile Asn Val Asp Ile
            20                  25                  30

Leu Gly Val Glu Leu Ala Gly Ser Ala Ala Gln Leu Pro Leu Lys Trp
        35                  40                  45

Asn Ile Gln Val Ser Thr Trp Leu Arg Tyr Tyr Val Tyr Glu Arg Leu
    50                  55                  60

Ile Gln Lys Gly Lys Lys Pro Gly Phe Leu Gln Leu Leu Gly Thr Gln
65                  70                  75                  80

Thr Val Ser Ala Ile Trp His Gly Leu Tyr Pro Gly Tyr Met Ile Phe
                85                  90                  95

Phe Val Gln Ser Ala Leu Met Ile Asn Gly Ser Lys Val Ile Tyr Arg
            100                 105                 110

Trp Gln Gln Ala Val Lys Gln Phe Arg Pro Pro His Tyr Pro Val Phe
        115                 120                 125

Thr Lys Leu Leu His Thr Pro
    130                 135

<210> SEQ ID NO 12
<211> LENGTH: 642
<212> TYPE: DNA
<213> ORGANISM: Capsicum annuum

<400> SEQUENCE: 12
ggcacgagaa acggttgggt taccaatata tggctggctt tactgcccgg tgaagtatt      60 attttatctg gtcaatctct gaagctgcta aatcatatc tggactgggt ttcagtggtt    120
ggacagactc ttctccgcca aaaccacgtt gggaccgtgc aaaaaatgtt gatgtattgg   180
gtgttgagtt agcaaagagc tcggttcagt tgcctgctgt ctggaacatt caagtcagca   240
catggctgcg gcattatgta tatgaaaggc tcatacaaaa gggaaggaag cctggtttct   300
tccagttact ggctacccaa actgtcagtg ccgtatggca tggattatat cctgggtata   360
tcatattctt tgtacagtcc gctttgatga ttgctggatc aagagtcctt tacagatggc   420
agcaagctgc taaaggttct atgtttgaga agatactggt agcaatgaat tttgcataca   480
cactgctggt tctaaattac tccgctgttg ggttcatggt attaagcctg catgaaactc   540
ttactgctta tggaagtgta tactatgttg gaacaattat accaattgct ctcatcctgc   600
tcagtaaagt aattaagcct ccaagaccct gcacatctaa ag                      642
```

<210> SEQ ID NO 13
<211> LENGTH: 213
<212> TYPE: PRT
<213> ORGANISM: Capsicum annuum

<400> SEQUENCE: 13

```
His Glu Lys Arg Leu Gly Tyr Gln Tyr Met Ala Gly Phe Thr Ala Arg
1               5                   10                  15

Trp Lys Tyr Tyr Phe Ile Trp Ser Ile Ser Glu Ala Ala Ile Ile Ile
            20                  25                  30

Ser Gly Leu Gly Phe Ser Gly Trp Thr Asp Ser Ser Pro Pro Lys Pro
        35                  40                  45

Arg Trp Asp Arg Ala Lys Asn Val Asp Val Leu Gly Val Glu Leu Ala
    50                  55                  60

Lys Ser Ser Val Gln Leu Pro Ala Val Trp Asn Ile Gln Val Ser Thr
65                  70                  75                  80

Trp Leu Arg His Tyr Val Tyr Glu Arg Leu Ile Gln Lys Gly Arg Lys
                85                  90                  95

Pro Gly Phe Phe Gln Leu Leu Ala Thr Gln Thr Val Ser Ala Val Trp
            100                 105                 110

His Gly Leu Tyr Pro Gly Tyr Ile Ile Phe Phe Val Gln Ser Ala Leu
        115                 120                 125

Met Ile Ala Gly Ser Arg Val Leu Tyr Arg Trp Gln Gln Ala Ala Lys
    130                 135                 140

Gly Ser Met Phe Glu Lys Ile Leu Val Ala Met Asn Phe Ala Tyr Thr
145                 150                 155                 160

Leu Leu Val Leu Asn Tyr Ser Ala Val Gly Phe Met Val Leu Ser Leu
                165                 170                 175

His Glu Thr Leu Thr Ala Tyr Gly Ser Val Tyr Val Gly Thr Ile
            180                 185                 190

Ile Pro Ile Ala Leu Ile Leu Leu Ser Lys Val Ile Lys Pro Pro Arg
        195                 200                 205

Pro Cys Thr Ser Lys
    210
```

<210> SEQ ID NO 14
<211> LENGTH: 756
<212> TYPE: DNA
<213> ORGANISM: Castor Bean

<400> SEQUENCE: 14

```
attcatttat acttggtgcc ccactatcct ttatcccggt tcactgatcc tgtgtaccaa      60
gaatggggct tctggaaacg attaacttat cagtatatgt caggtttaac agcacgttgg     120
aaatactact tcatctggtc aatttccgag gcctccatta ttatctctgg attgggtttc     180
agtggttgga cagatacttc tccaccaaag ccacagtggg atcgcgctag aaacgttgac     240
attctaggtg ttgagtttgc aaagagtgca gctgagttgc acttgtgtg gaacatacaa     300
gtcagcacat ggcttcgcca ctatgtttat gatcgacttg ttccaaaggg aagaaagct     360
ggtttccttc agttgttggc cactcagact accagtgctg tttggcatgg attatatcct     420
ggatacatta tattctttgt ccagtcagca ttaatgattg caggttcgaa agtcatatac     480
agatggcaac aagctatacc ttcaaataag gctcttgaaa agaagatact agtgtttatg     540
aactttgctt acacagtttt ggttctaaat tactcctgtg ttggtttcat ggttttaagc     600
ttgcatgaaa cgattgcagc atatggaagt gtatatttta ttggcaccat agtgcccgtt     660
```

-continued

```
gtatttttcc tccttggctt cattattaaa ccagcaaggc cttccaggtc taaacacgga    720
acgatgagtg aggtagaaac tgtttttctt ctcctt                              756


<210> SEQ ID NO 15
<211> LENGTH: 252
<212> TYPE: PRT
<213> ORGANISM: Castor Bean

<400> SEQUENCE: 15

Ile His Leu Tyr Leu Val Pro His Tyr Pro Leu Ser Arg Phe Thr Asp
1               5                   10                  15

Pro Val Tyr Gln Glu Trp Gly Phe Trp Lys Arg Leu Thr Tyr Gln Tyr
            20                  25                  30

Met Ser Gly Leu Thr Ala Arg Trp Lys Tyr Tyr Phe Ile Trp Ser Ile
        35                  40                  45

Ser Glu Ala Ser Ile Ile Ile Ser Gly Leu Gly Phe Ser Gly Trp Thr
    50                  55                  60

Asp Thr Ser Pro Pro Lys Pro Gln Trp Asp Arg Ala Arg Asn Val Asp
65                  70                  75                  80

Ile Leu Gly Val Glu Phe Ala Lys Ser Ala Ala Glu Leu Pro Leu Val
                85                  90                  95

Trp Asn Ile Gln Val Ser Thr Trp Leu Arg His Tyr Val Tyr Asp Arg
            100                 105                 110

Leu Val Pro Lys Gly Lys Lys Ala Gly Phe Leu Gln Leu Leu Ala Thr
        115                 120                 125

Gln Thr Thr Ser Ala Val Trp His Gly Leu Tyr Pro Gly Tyr Ile Ile
    130                 135                 140

Phe Phe Val Gln Ser Ala Leu Met Ile Ala Gly Ser Lys Val Ile Tyr
145                 150                 155                 160

Arg Trp Gln Gln Ala Ile Pro Ser Asn Lys Ala Leu Glu Lys Lys Ile
                165                 170                 175

Leu Val Phe Met Asn Phe Ala Tyr Thr Val Leu Val Leu Asn Tyr Ser
            180                 185                 190

Cys Val Gly Phe Met Val Leu Ser Leu His Glu Thr Ile Ala Ala Tyr
        195                 200                 205

Gly Ser Val Tyr Phe Ile Gly Thr Ile Val Pro Val Val Phe Phe Leu
    210                 215                 220

Leu Gly Phe Ile Ile Lys Pro Ala Arg Pro Ser Arg Ser Lys His Gly
225                 230                 235                 240

Thr Met Ser Glu Val Glu Thr Val Phe Leu Leu Leu
                245                 250

<210> SEQ ID NO 16
<211> LENGTH: 937
<212> TYPE: DNA
<213> ORGANISM: Grapevine

<400> SEQUENCE: 16
ctcgtccaat ctccacttcc tcgttcccat gcttcttggc tacgcggcta tgcttctctg     60
tcgccgtcga tgcggtgtga tcaccttttt cttgggattc ggctacctca ttggctgcca    120
tgtatactac atgagtgggg atgcatggaa ggaagggggt attgatgcta ctggagctct    180
aatggtttta acattgaaag tcatttcatg tgcaatgaat tataatgatg gattgttaaa    240
agaagacggt ttgcgtgagg cacagaagaa aaaccgattg cttaagttac catcattgat    300
cgagtacttt ggttattgtc tctgctgtgg aagtcacttt gctggaccag tttatgaaat    360

-continued

```
aaaggattat cttgaatgga cagaaagaaa agggatttgg gccaaatcag agaaagggcc      420
accaccatca ccttatgggg caacgattcg agctcttatc caagctgcct tttgcatggg      480
cttgtatgtg tatctagtac cccatttttcc cttgaccata tttactgatc ctgtatatca     540
agaatggggc ttctggaaac ggttgggata ccaatatatg tgtggcttta cagcacgctg      600
gaaatactat ttcatctggt caatctctga ggcagctgtc attatttctg cctgggatt       660 cagtgggtgg acagaatctt ccccaccaaa accaaaatgg gaccgtgcaa agaatgttga      720
cattttaggt gttgagttgg caaagagtgc agtaacactg ccacttgttt ggaacataca      780
agtcagcacc tggctacgtt attatgttta tgagaggctc attcaaaatg gaagaaacc      840 tggtttcttc cagttgctgg ctacacaaac tgtcagtgct gtttggcatg gattatatcc      900
tggatacatc atattctttg ttcagtctgc actgatg                              937
```

<210> SEQ ID NO 17
<211> LENGTH: 312
<212> TYPE: PRT
<213> ORGANISM: Grapevine

<400> SEQUENCE: 17

```
Ser Ser Asn Leu His Phe Leu Val Pro Met Leu Leu Gly Tyr Ala Ala
1               5                   10                  15

Met Leu Leu Cys Arg Arg Arg Cys Gly Val Ile Thr Phe Phe Leu Gly
            20                  25                  30

Phe Gly Tyr Leu Ile Gly Cys His Val Tyr Tyr Met Ser Gly Asp Ala
        35                  40                  45

Trp Lys Glu Gly Gly Ile Asp Ala Thr Gly Ala Leu Met Val Leu Thr
    50                  55                  60

Leu Lys Val Ile Ser Cys Ala Met Asn Tyr Asn Asp Gly Leu Leu Lys
65                  70                  75                  80

Glu Asp Gly Leu Arg Glu Ala Gln Lys Lys Asn Arg Leu Leu Lys Leu
                85                  90                  95

Pro Ser Leu Ile Glu Tyr Phe Gly Tyr Cys Leu Cys Cys Gly Ser His
            100                 105                 110

Phe Ala Gly Pro Val Tyr Glu Ile Lys Asp Tyr Leu Glu Trp Thr Glu
        115                 120                 125

Arg Lys Gly Ile Trp Ala Lys Ser Glu Lys Gly Pro Pro Ser Pro
    130                 135                 140

Tyr Gly Ala Thr Ile Arg Ala Leu Ile Gln Ala Phe Cys Met Gly
145                 150                 155                 160

Leu Tyr Val Tyr Leu Val Pro His Phe Pro Leu Thr Ile Phe Thr Asp
                165                 170                 175

Pro Val Tyr Gln Glu Trp Gly Phe Trp Lys Arg Leu Gly Tyr Gln Tyr
            180                 185                 190

Met Cys Gly Phe Thr Ala Arg Trp Lys Tyr Tyr Phe Ile Trp Ser Ile
        195                 200                 205

Ser Glu Ala Ala Val Ile Ile Ser Gly Leu Gly Phe Ser Gly Trp Thr
    210                 215                 220

Glu Ser Ser Pro Pro Lys Pro Lys Trp Asp Arg Ala Lys Asn Val Asp
225                 230                 235                 240

Ile Leu Gly Val Glu Leu Ala Lys Ser Ala Val Thr Leu Pro Leu Val
                245                 250                 255

Trp Asn Ile Gln Val Ser Thr Leu Arg Tyr Val Tyr Glu Arg
            260                 265                 270
```

```
Leu Ile Gln Asn Gly Lys Lys Pro Gly Phe Phe Gln Leu Leu Ala Thr
        275                 280                 285

Gln Thr Val Ser Ala Val Trp His Gly Leu Tyr Pro Gly Tyr Ile Ile
    290                 295                 300

Phe Phe Val Gln Ser Ala Leu Met
305                 310

<210> SEQ ID NO 18
<211> LENGTH: 864
<212> TYPE: DNA
<213> ORGANISM: Maize
<220> FEATURE:
<221> NAME/KEY: misc_feature
<222> LOCATION: (727)..(727)
<223> OTHER INFORMATION: n can be A,T,G,C

<400> SEQUENCE: 18
catttcgtgt ctcataaact acagtgatgg tatcttgaag gaagagggtt tacgcgatgc      60
tcagattaaa caccgattga ctaagcttcc ttctctaatt gaatattttg ggtactgtct     120
ctgttgtggg agccactttg ctggaccggt atatgagatg aaagattatc ttgaatggac     180
tgaaaggaaa ggaatatggg ctagcccaac tccttcgcca ttgttaccta ctttgcgtgc     240
tctagttcag gctggtatat gcatgggggtt atatttatac ctgtcaccta aatttccact     300
ctcacggttt agtgagcccc tatattatga atggggtttt tggcaccgac tcttctatca     360
gtacatgtca ggctttaccg ctcgttggaa atattacttt atatggtcaa tttcagaagc     420
ctcaattatc atatctggtc taggctttac tggttggtcg aatcttctc ccccaaaagc     480
caaatgggat cgtgcaaaaa atgttgatgt attaggtgtt gaattagctg aagttcagt     540
tcaattgccc cttgtgtgga atattcaagt gagcacatgg ctacgatact atgtctatga     600
gaggttaatt cagaaaggaa agaaaccagg tttccttcaa ttgttgggta cacagacagt     660
cagtgccatc tggcatggac tatatcctgg atatatcata ttcttttttt catcagcatt     720
gatgataaat ggttcacgag ttatatacag atggcagcaa gcagcgagca gttcattcct     780
gagcggtatc ctggcccttc taattttgct atacattgct ggggcttact actcctgcat     840
cggggtccag gtactgagct caa                                             864

<210> SEQ ID NO 19
<211> LENGTH: 287
<212> TYPE: PRT
<213> ORGANISM: Maize
<220> FEATURE:
<221> NAME/KEY: MISC_FEATURE
<222> LOCATION: (242)..(242)
<223> OTHER INFORMATION: X can be Met or Ile

<400> SEQUENCE: 19

Ile Ser Cys Leu Ile Asn Tyr Ser Asp Gly Ile Leu Lys Glu Glu Gly
1               5                   10                  15

Leu Arg Asp Ala Gln Ile Lys His Arg Leu Thr Lys Leu Pro Ser Leu
            20                  25                  30

Ile Glu Tyr Phe Gly Tyr Cys Leu Cys Cys Gly Ser His Phe Ala Gly
        35                  40                  45

Pro Val Tyr Glu Met Lys Asp Tyr Leu Glu Trp Thr Glu Arg Lys Gly
    50                  55                  60

Ile Trp Ala Ser Pro Thr Pro Ser Pro Leu Leu Pro Thr Leu Arg Ala
65                  70                  75                  80
```

```
Leu Val Gln Ala Gly Ile Cys Met Gly Leu Tyr Leu Tyr Leu Ser Pro
                85                  90                  95

Lys Phe Pro Leu Ser Arg Phe Ser Glu Pro Leu Tyr Tyr Glu Trp Gly
            100                 105                 110

Phe Trp His Arg Leu Phe Tyr Gln Tyr Met Ser Gly Phe Thr Ala Arg
        115                 120                 125

Trp Lys Tyr Tyr Phe Ile Trp Ser Ile Ser Glu Ala Ser Ile Ile Ile
    130                 135                 140

Ser Gly Leu Gly Phe Thr Gly Trp Ser Glu Ser Pro Pro Lys Ala
145                 150                 155                 160

Lys Trp Asp Arg Ala Lys Asn Val Asp Val Leu Gly Val Glu Leu Ala
                165                 170                 175

Gly Ser Ser Val Gln Leu Pro Leu Val Trp Asn Ile Gln Val Ser Thr
            180                 185                 190

Trp Leu Arg Tyr Tyr Val Tyr Glu Arg Leu Ile Gln Lys Gly Lys Lys
        195                 200                 205

Pro Gly Phe Leu Gln Leu Leu Gly Thr Gln Thr Val Ser Ala Ile Trp
    210                 215                 220

His Gly Leu Tyr Pro Gly Tyr Ile Ile Phe Phe Phe Ser Ser Ala Leu
225                 230                 235                 240

Met Xaa Asn Gly Ser Arg Val Ile Tyr Arg Trp Gln Gln Ala Ala Ser
                245                 250                 255

Ser Ser Phe Leu Ser Gly Ile Leu Ala Leu Leu Ile Leu Leu Tyr Ile
            260                 265                 270

Ala Gly Ala Tyr Tyr Ser Cys Ile Gly Val Gln Val Leu Ser Phe
        275                 280                 285

<210> SEQ ID NO 20
<211> LENGTH: 641
<212> TYPE: DNA
<213> ORGANISM: Peach
<220> FEATURE:
<221> NAME/KEY: misc_feature
<222> LOCATION: (621)..(621)
<223> OTHER INFORMATION: n can be A T C G

<400> SEQUENCE: 20
aaatattatt tcatctggtc aatttcagag gcttctatca ttctttctgg tttgggtttc      60
actggctgga cagaatcttc accaccaaag ccgcgatggg atcgtgcaaa aaatgttgat     120
attctaggcg ttgagtttgc aaagagttca gttcagttac acttgtttg  aacatacaa     180
gtcagcacct ggctacgtca ttatgtttat gaaaggcttg ttaaacctgg caagaaggct     240
ggtttcttcc agttgctgac tacacagacc gtcagtgcgg tttggcatgg actctatcct     300
gggtacatca tattctttgt tcagtcagca ttgatgattg ctggttcaag agtgatttac     360
agatggcaac aagctgtacc tcaaaacatg gatgctgtta agaacatact ggtgttcata     420
aactttgctt acactctctt ggttctgaac tactcctgcg ttggtttcat tgtattaagc     480
cttcgtgaaa cacttgcctc atatgggagc gtgcatttca tcggaaccat tcttccgata     540
gcattgatac tactgagtta cgtaataaaa cctccaaggc ctgcaagatc aaaggctcgg     600
aaggaagagt gaggttgtca nccgcaacag cattttaac g                         641

<210> SEQ ID NO 21
<211> LENGTH: 203
<212> TYPE: PRT
<213> ORGANISM: Peach
```

<400> SEQUENCE: 21

```
Lys Tyr Tyr Phe Ile Trp Ser Ile Ser Glu Ala Ser Ile Ile Leu Ser
1               5                   10                  15

Gly Leu Gly Phe Thr Gly Trp Thr Glu Ser Ser Pro Pro Lys Pro Arg
            20                  25                  30

Trp Asp Arg Ala Lys Asn Val Asp Ile Leu Gly Val Glu Phe Ala Lys
                35                  40                  45

Ser Ser Val Gln Leu Pro Leu Val Trp Asn Ile Gln Val Ser Thr Trp
    50                  55                  60

Leu Arg His Tyr Val Tyr Glu Arg Leu Val Lys Pro Gly Lys Lys Ala
65                  70                  75                  80

Gly Phe Phe Gln Leu Leu Thr Thr Gln Thr Val Ser Ala Val Trp His
                85                  90                  95

Gly Leu Tyr Pro Gly Tyr Ile Ile Phe Phe Val Gln Ser Ala Leu Met
            100                 105                 110

Ile Ala Gly Ser Arg Val Ile Tyr Arg Trp Gln Gln Ala Val Pro Gln
                115                 120                 125

Asn Met Asp Ala Val Lys Asn Ile Leu Val Phe Ile Asn Phe Ala Tyr
    130                 135                 140

Thr Leu Leu Val Leu Asn Tyr Ser Cys Val Gly Phe Ile Val Leu Ser
145                 150                 155                 160

Leu Arg Glu Thr Leu Ala Ser Tyr Gly Ser Val His Phe Ile Gly Thr
                165                 170                 175

Ile Leu Pro Ile Ala Leu Ile Leu Leu Ser Tyr Val Ile Lys Pro Pro
            180                 185                 190

Arg Pro Ala Arg Ser Lys Ala Arg Lys Glu Glu
        195                 200
```

<210> SEQ ID NO 22
<211> LENGTH: 459
<212> TYPE: PRT
<213> ORGANISM: Oryza sativa

<400> SEQUENCE: 22

```
Met Gly Leu Glu Met Glu Gly Met Ala Ala Ile Gly Val Ser Val
1               5                   10                  15

Pro Val Leu Arg Phe Leu Leu Cys Phe Ala Ala Thr Ile Pro Thr Gly
            20                  25                  30

Leu Met Trp Arg Ala Val Pro Gly Ala Ala Gly Arg His Leu Tyr Ala
                35                  40                  45

Gly Leu Thr Gly Ala Ala Leu Ser Tyr Leu Ser Phe Gly Ala Thr Ser
    50                  55                  60

Asn Leu Leu Phe Val Val Pro Met Ala Phe Gly Tyr Leu Ala Met Leu
65                  70                  75                  80

Leu Cys Arg Arg Leu Ala Gly Leu Val Thr Phe Leu Gly Ala Phe Gly
                85                  90                  95

Phe Leu Ile Ala Cys His Met Tyr Tyr Met Ser Gly Asp Ala Trp Lys
            100                 105                 110

Glu Gly Gly Ile Asp Ala Thr Gly Ala Leu Met Val Leu Thr Leu Lys
                115                 120                 125

Ile Ile Ser Cys Ala Ile Asn Tyr Ser Asp Gly Met Leu Lys Glu Glu
    130                 135                 140

Gly Leu Arg Asp Ala Gln Lys Lys Tyr Arg Leu Ala Lys Leu Pro Ser
145                 150                 155                 160
```

```
Leu Ile Glu Tyr Phe Gly Tyr Cys Leu Cys Cys Gly Ser His Phe Ala
            165                 170                 175

Gly Pro Val Tyr Glu Met Lys Asp Tyr Leu Glu Tyr Thr Glu Arg Lys
        180                 185                 190

Gly Leu Trp Ala Ser Pro Thr Pro Ser Pro Leu Leu Pro Thr Leu Arg
            195                 200                 205

Ala Leu Val Gln Ala Gly Ala Cys Met Gly Leu Tyr Leu Tyr Leu Ser
        210                 215                 220

Pro Gln Phe Pro Leu Ser Arg Phe Ser Glu Pro Leu Tyr Tyr Glu Trp
225                 230                 235                 240

Gly Phe Trp His Arg Leu Phe Tyr Gln Tyr Met Ser Gly Phe Thr Ala
            245                 250                 255

Arg Trp Lys Tyr Tyr Phe Ile Trp Ser Leu Ser Glu Ala Ala Ile Ile
        260                 265                 270

Ile Ser Gly Leu Gly Phe Ser Gly Trp Ser Asp Ser Ser Pro Pro Lys
    275                 280                 285

Ala Lys Trp Asp Arg Ala Lys Asn Val Asp Val Leu Gly Val Glu Leu
    290                 295                 300

Ala Thr Ser Ala Val Gln Leu Pro Leu Met Trp Asn Ile Gln Val Ser
305                 310                 315                 320

Thr Trp Leu Arg Tyr Tyr Val Tyr Glu Arg Leu Val Gln Lys Gly Lys
            325                 330                 335

Lys Pro Gly Phe Leu Gln Leu Leu Gly Thr Gln Thr Val Ser Ala Val
            340                 345                 350

Trp His Gly Leu Tyr Pro Gly Tyr Ile Ile Phe Phe Val Gln Ser Ala
            355                 360                 365

Leu Met Ile Asn Gly Ser Lys Val Ile Tyr Arg Trp Gln Gln Ala Val
        370                 375                 380

Ser Asn Pro Val Phe His Ala Ile Leu Val Phe Val Asn Phe Ser Tyr
385                 390                 395                 400

Thr Leu Met Val Leu Asn Tyr Ser Cys Ile Gly Phe Gln Val Leu Ser
            405                 410                 415

Phe Lys Glu Thr Leu Ala Ser Tyr Gln Ser Val Tyr Tyr Ile Gly Thr
        420                 425                 430

Ile Val Pro Ile Val Val Leu Leu Gly Tyr Val Ile Lys Pro Ala
    435                 440                 445

Arg Pro Val Lys Pro Lys Ala Arg Lys Ala Glu
    450                 455

<210> SEQ ID NO 23
<211> LENGTH: 370
<212> TYPE: PRT
<213> ORGANISM: Rice

<400> SEQUENCE: 23

Met Tyr Tyr Met Ser Gly Asp Ala Trp Lys Glu Gly Gly Ile Asp Ala
1               5                   10                  15

Thr Gly Ala Leu Met Val Leu Thr Leu Lys Ile Ile Ser Cys Ala Ile
            20                  25                  30

Asn Tyr Ser Asp Gly Met Leu Lys Glu Glu Gly Leu Arg Asp Ala Gln
        35                  40                  45

Lys Lys Tyr Arg Leu Ala Lys Leu Pro Ser Leu Ile Glu Tyr Phe Gly
    50                  55                  60

Tyr Cys Leu Cys Cys Gly Ser His Phe Ala Gly Pro Val Tyr Glu Met
65                  70                  75                  80
```

Lys Asp Tyr Leu Glu Tyr Thr Glu Arg Lys Gly Leu Trp Ala Ser Pro
                85                  90                  95

Thr Pro Ser Pro Leu Leu Pro Thr Leu Arg Ala Leu Val Gln Ala Gly
            100                 105                 110

Ala Cys Met Gly Leu Tyr Leu Tyr Leu Ser Pro Gln Phe Pro Leu Ser
        115                 120                 125

Arg Phe Ser Glu Pro Leu Tyr Tyr Glu Trp Gly Phe Trp His Arg Leu
    130                 135                 140

Phe Tyr Gln Tyr Met Ser Gly Phe Thr Ala Arg Trp Lys Tyr Tyr Phe
145                 150                 155                 160

Ile Trp Ser Leu Ser Glu Ala Ala Ile Ile Ile Ser Gly Leu Gly Phe
                165                 170                 175

Ser Gly Trp Ser Asp Ser Ser Pro Lys Ala Lys Trp Asp Arg Ala
            180                 185                 190

Lys Asn Val Asp Val Leu Gly Val Glu Leu Ala Thr Ser Ala Val Gln
        195                 200                 205

Leu Pro Leu Met Trp Asn Ile Gln Val Ser Thr Trp Leu Arg Tyr Tyr
    210                 215                 220

Val Tyr Glu Arg Leu Val Gln Lys Gly Lys Lys Pro Gly Phe Leu Gln
225                 230                 235                 240

Leu Leu Gly Thr Gln Thr Val Ser Ala Val Trp His Gly Leu Tyr Pro
                245                 250                 255

Gly Tyr Ile Ile Phe Phe Val Gln Ser Ala Leu Met Ile Asn Gly Ser
            260                 265                 270

Lys Val Ile Tyr Arg Trp Gln Gln Ala Val Ser Asn Pro Val Phe His
        275                 280                 285

Ala Ile Leu Val Phe Val Asn Phe Ser Tyr Thr Leu Met Val Leu Asn
    290                 295                 300

Tyr Ser Cys Ile Gly Phe Gln Phe Val Phe Thr Met Leu Tyr Thr Leu
305                 310                 315                 320

Arg Phe Leu Gln Val Leu Ser Phe Lys Glu Thr Leu Ala Ser Tyr Gln
                325                 330                 335

Ser Val Tyr Tyr Ile Gly Thr Ile Val Pro Ile Val Val Leu Leu
            340                 345                 350

Gly Tyr Val Ile Lys Pro Ala Arg Pro Val Lys Pro Lys Ala Arg Lys
        355                 360                 365

Ala Glu
    370

<210> SEQ ID NO 24
<211> LENGTH: 707
<212> TYPE: DNA
<213> ORGANISM: Snapdragon

<400> SEQUENCE: 24
gcattaatta caacgatgga ttacttaaaa aggaagatct acgtgagcca caaagaaaa       60 accgcttgct caagatgcca tcattacttg agtacattgg ttactgtttg tgttgtggaa     120
gtcactttgc tggtcctgtg tatgaaatga agattatctt gaatggact gagaggaaag     180 ggatctggca acatacaacc aagggaccga aaccttctcc gtattgggcg actctcaggg    240
ctattttgca agctgccatc tgtatgggct tgtatctata tcttgtacca cattacccac    300
tttccagatt cacggagcca gaataccaag agtatgggt ctggaaacgg ttaagttacc     360
agtacatgtc aggcttcacc gctcgttgga agtactattt catttggtct atctcagaag   420

```
cttccataat tatttctggc ctggggttca gtggctggac agattctgat ccacccaaag    480
cactgtggga tcgtgcaaaa aatgttgatg tattaggtgt tgagttggca aagagttctg    540
tgcagttacc acttgtatgg aatattcaag ttagcacctg gcttaaacac tatgtctatg    600
agaggctggt tcagaaaggt aagaaaccag gcttcttcca gttgctggct acccagaccg    660
tgagtgcagt gtggcatgga ttgtaccctg gtacatcat attcttt                   707
```

<210> SEQ ID NO 25
<211> LENGTH: 235
<212> TYPE: PRT
<213> ORGANISM: Snapdragon

<400> SEQUENCE: 25

```
Ile Asn Tyr Asn Asp Gly Leu Leu Lys Lys Glu Asp Leu Arg Glu Pro
1               5                   10                  15

Gln Lys Lys Asn Arg Leu Leu Lys Met Pro Ser Leu Leu Glu Tyr Ile
            20                  25                  30

Gly Tyr Cys Leu Cys Cys Gly Ser His Phe Ala Gly Pro Val Tyr Glu
        35                  40                  45

Met Lys Asp Tyr Leu Glu Trp Thr Glu Arg Lys Gly Ile Trp Gln His
    50                  55                  60

Thr Thr Lys Gly Pro Lys Pro Ser Pro Tyr Trp Ala Thr Leu Arg Ala
65                  70                  75                  80

Ile Leu Gln Ala Ala Ile Cys Met Gly Leu Tyr Leu Tyr Leu Val Pro
                85                  90                  95

His Tyr Pro Leu Ser Arg Phe Thr Glu Pro Glu Tyr Gln Glu Tyr Gly
            100                 105                 110

Phe Trp Lys Arg Leu Ser Tyr Gln Tyr Met Ser Gly Phe Thr Ala Arg
        115                 120                 125

Trp Lys Tyr Tyr Phe Ile Trp Ser Ile Ser Glu Ala Ser Ile Ile Ile
    130                 135                 140

Ser Gly Leu Gly Phe Ser Gly Trp Thr Asp Ser Asp Pro Pro Lys Ala
145                 150                 155                 160

Leu Trp Asp Arg Ala Lys Asn Val Asp Val Leu Gly Val Glu Leu Ala
                165                 170                 175

Lys Ser Ser Val Gln Leu Pro Leu Val Trp Asn Ile Gln Val Ser Thr
            180                 185                 190

Trp Leu Lys His Tyr Val Tyr Glu Arg Leu Val Gln Lys Gly Lys Lys
        195                 200                 205

Pro Gly Phe Phe Gln Leu Leu Ala Thr Gln Thr Val Ser Ala Val Trp
    210                 215                 220

His Gly Leu Tyr Pro Gly Tyr Ile Ile Phe Phe
225                 230                 235
```

<210> SEQ ID NO 26
<211> LENGTH: 653
<212> TYPE: DNA
<213> ORGANISM: Sorghum

<400> SEQUENCE: 26

```
gcacgaggct ctcacggttt agtgagccct tatattatga atggggtttc tggcaccgac     60
tcttctatca gtacatgtca ggcttcactg ctcgttggaa atattacttt atatggtcaa    120
tttcagaagc ctcaattatc atatctggtc tgggctttac tggttggtca gaatcttctc    180
ccccgaaagc caaatgggat cgtgcgaaaa atgttgatgt attaggtgtt gaattagctg    240
```

```
gaagtgcagt tcaaattccc cttgtgtgga atattcaagt gagcacatgg ttacgatact    300
atgtctatga gaggctaatt cagaaaggaa agaaaccagg tttccttcag ttgttgggta    360
cacagacagt cagcgccatc tggcatggac tgtatcctgg atatatcata ttctttgttc    420
agtcagcatt gatgataaat ggttcacgag ttatatacag atggcagcaa gcagtgagca    480
gttcattcct ccgcggtatc ctggcttttc taaattttgc ttatacattg ctggtgctta    540
actactcctg catcgggttc ctggtactga gcttcaaaga aaccttggcg tcctaccaga    600
gcgtatatta tgttggcaca attgttccca ttgtgtttct cctgctgggc aat           653
```

<210> SEQ ID NO 27
<211> LENGTH: 217
<212> TYPE: PRT
<213> ORGANISM: Sorghum

<400> SEQUENCE: 27

```
Thr Arg Leu Ser Arg Phe Ser Glu Pro Leu Tyr Tyr Glu Trp Gly Phe
1               5                   10                  15

Trp His Arg Leu Phe Tyr Gln Tyr Met Ser Gly Phe Thr Ala Arg Trp
            20                  25                  30

Lys Tyr Tyr Phe Ile Trp Ser Ile Ser Glu Ala Ser Ile Ile Ile Ser
        35                  40                  45

Gly Leu Gly Phe Thr Gly Trp Ser Glu Ser Ser Pro Pro Lys Ala Lys
    50                  55                  60

Trp Asp Arg Ala Lys Asn Val Asp Val Leu Gly Val Glu Leu Ala Gly
65                  70                  75                  80

Ser Ala Val Gln Ile Pro Leu Val Trp Asn Ile Gln Val Ser Thr Trp
                85                  90                  95

Leu Arg Tyr Tyr Val Tyr Glu Arg Leu Ile Gln Lys Gly Lys Lys Pro
            100                 105                 110

Gly Phe Leu Gln Leu Leu Gly Thr Gln Thr Val Ser Ala Ile Trp His
        115                 120                 125

Gly Leu Tyr Pro Gly Tyr Ile Ile Phe Phe Val Gln Ser Ala Leu Met
    130                 135                 140

Ile Asn Gly Ser Arg Val Ile Tyr Arg Trp Gln Gln Ala Val Ser Ser
145                 150                 155                 160

Ser Phe Leu Arg Gly Ile Leu Ala Phe Leu Asn Phe Ala Tyr Thr Leu
                165                 170                 175

Leu Val Leu Asn Tyr Ser Cys Ile Gly Phe Leu Val Leu Ser Phe Lys
            180                 185                 190

Glu Thr Leu Ala Ser Tyr Gln Ser Val Tyr Tyr Val Gly Thr Ile Val
        195                 200                 205

Pro Ile Val Phe Leu Leu Leu Gly Asn
    210                 215
```

<210> SEQ ID NO 28
<211> LENGTH: 865
<212> TYPE: DNA
<213> ORGANISM: Sunflower

<400> SEQUENCE: 28

```
gaaaaccgca tacttaagtt gccatcttta atcgagtatg tgggatattg cttatgctgc    60
ggaagtcact ttgctggtcc ggtttacgaa atcaaagatt atttggattg gaccgaaaga   120
aaggggattt ggacaaagtc cgagaaaggc acaccatcac catttttgcc aacactacga   180
```

-continued

```
gcgattctcc aagcgggttt ctgtatgggt ttgtatttat atctatcgcc ttcgtatccg      240
ctttcaagat tcagtgagcc gatatatcaa gaatggggat ttgtgaaacg tctgaccgtc      300
caatacatgt cgggcttcac cgcgcgttgg aaatactatt tcatttggtc tatctcagaa      360
gcttctatca ttatttcggg cttcggtttc agtggctgga ctgattcttc tccaccaaaa      420
gcccgatggg accgtgcgaa aaacgttgac gttttgggtg ttgagtttgc aaagagttca      480
gttgagttac cactcgtgtg gaatatccaa gtcagcacat ggcttcgtca ctatgtttat      540
gacagacttg ttcaaaaggg aaagaagcct ggcttttttcc aattgttagc aacacagact      600
gttagcgctg tctggcatgg attatatcct gggtacttga tattctttgt tcaatctgct      660
ttgatgattt ccgggtcaag agccatttac agatggcagc aggcggttcc gccaaccgtt      720
aagaagtttt tgatgctcat gaactttgct tacacgcttc ttgttcttaa ctactcctgc      780
ataggtttta tggtattaag cctacacgaa acactggctg catacggaag tgtatactac      840
gttggaaaca tcattccagt ggcgt                                            865
```

<210> SEQ ID NO 29
<211> LENGTH: 288
<212> TYPE: PRT
<213> ORGANISM: Sunflower

<400> SEQUENCE: 29

```
Glu Asn Arg Ile Leu Lys Leu Pro Ser Leu Ile Glu Tyr Val Gly Tyr
1               5                   10                  15

Cys Leu Cys Cys Gly Ser His Phe Ala Gly Pro Val Tyr Glu Ile Lys
            20                  25                  30

Asp Tyr Leu Asp Trp Thr Glu Arg Lys Gly Ile Trp Thr Lys Ser Glu
        35                  40                  45

Lys Gly Thr Pro Ser Pro Phe Leu Pro Thr Leu Arg Ala Ile Leu Gln
    50                  55                  60

Ala Gly Phe Cys Met Gly Leu Tyr Leu Tyr Leu Ser Pro Ser Tyr Pro
65                  70                  75                  80

Leu Ser Arg Phe Ser Glu Pro Ile Tyr Gln Glu Trp Gly Phe Val Lys
                85                  90                  95

Arg Leu Thr Val Gln Tyr Met Ser Gly Phe Thr Ala Arg Trp Lys Tyr
            100                 105                 110

Tyr Phe Ile Trp Ser Ile Ser Glu Ala Ser Ile Ile Ser Gly Phe
        115                 120                 125

Gly Phe Ser Gly Trp Thr Asp Ser Ser Pro Pro Lys Ala Arg Trp Asp
    130                 135                 140

Arg Ala Lys Asn Val Asp Val Leu Gly Val Glu Phe Ala Lys Ser Ser
145                 150                 155                 160

Val Glu Leu Pro Leu Val Trp Asn Ile Gln Val Ser Thr Trp Leu Arg
                165                 170                 175

His Tyr Val Tyr Asp Arg Leu Val Gln Lys Gly Lys Lys Pro Gly Phe
            180                 185                 190

Phe Gln Leu Leu Ala Thr Gln Thr Val Ser Ala Val Trp His Gly Leu
        195                 200                 205

Tyr Pro Gly Tyr Leu Ile Phe Phe Val Gln Ser Ala Leu Met Ile Ser
    210                 215                 220

Gly Ser Arg Ala Ile Tyr Arg Trp Gln Gln Ala Val Pro Pro Thr Val
225                 230                 235                 240

Lys Lys Phe Leu Met Leu Met Asn Phe Ala Tyr Thr Leu Leu Val Leu
                245                 250                 255
```

Asn Tyr Ser Cys Ile Gly Phe Met Val Leu Ser Leu His Glu Thr Leu
            260                 265                 270

Ala Ala Tyr Gly Ser Val Tyr Tyr Val Gly Asn Ile Ile Pro Val Ala
        275                 280                 285

<210> SEQ ID NO 30
<211> LENGTH: 748
<212> TYPE: DNA
<213> ORGANISM: Tomato

<400> SEQUENCE: 30

```
ggtatggggt tgtatctcta tctggtgcct cagttcccac tttccaggtt cactgagtca      60
gtataccacg aatggggttt cttcaaacga ctgggttacc aatatatggc tggctttact     120
gcccggtgga aatattattt tatttggtca atctctgaag cttctataat catatctgga     180
ctgggtttca gtggttggac aaactcttct ccgccaaaac cacgtttggga ccgagcaaaa    240
aatgttgatg tattgggtgt tgagttagca aagagctcgg ttcagttacc actagtatgg     300
aacattcaag tcagcacatg gctgcggcat tatgtgtatg aaaggctcgt acagaaggga     360
aggaagcctg gtttcttcca gttgctggct acccaaactg tcagtgccgt ttggcatgga     420
ttatatcctg gatacatcat attctttgtt cagtccgctt tgatgattgc tggatcaaga     480
gtcatttaca gatggcagca agctacaaaa ggtactatgt ttgagaagat actgatagca     540
atgaattttg catacacact gctggttcta aactactccg ctgttggatt catggtatta    600
agtctgcatg aaactcttac tgcttatgga agtgtatact atattggaac aattgtacca     660
attcttctca tcctgcttag taaagtgatt aagcctccaa gacctgcgac gtctaaagct     720
aggaaagcag agtaaatcca agtcagtt                                        748
```

<210> SEQ ID NO 31
<211> LENGTH: 244
<212> TYPE: PRT
<213> ORGANISM: Tomato

<400> SEQUENCE: 31

Gly Met Gly Leu Tyr Leu Tyr Leu Val Pro Gln Phe Pro Leu Ser Arg
1               5                   10                  15

Phe Thr Glu Ser Val Tyr His Glu Trp Gly Phe Phe Lys Arg Leu Gly
            20                  25                  30

Tyr Gln Tyr Met Ala Gly Phe Thr Ala Arg Trp Lys Tyr Tyr Phe Ile
        35                  40                  45

Trp Ser Ile Ser Glu Ala Ser Ile Ile Ser Gly Leu Gly Phe Ser
    50                  55                  60

Gly Trp Thr Asn Ser Ser Pro Pro Lys Pro Arg Trp Asp Arg Ala Lys
65                  70                  75                  80

Asn Val Asp Val Leu Gly Val Glu Leu Ala Lys Ser Ser Val Gln Leu
                85                  90                  95

Pro Leu Val Trp Asn Ile Gln Val Ser Thr Trp Leu Arg His Tyr Val
            100                 105                 110

Tyr Glu Arg Leu Val Gln Lys Gly Arg Lys Pro Gly Phe Phe Gln Leu
        115                 120                 125

Leu Ala Thr Gln Thr Val Ser Ala Val Trp His Gly Leu Tyr Pro Gly
    130                 135                 140

Tyr Ile Ile Phe Phe Val Gln Ser Ala Leu Met Ile Ala Gly Ser Arg
145                 150                 155                 160

```
Val Ile Tyr Arg Trp Gln Gln Ala Thr Lys Gly Thr Met Phe Glu Lys
                165                 170                 175

Ile Leu Ile Ala Met Asn Phe Ala Tyr Thr Leu Leu Val Leu Asn Tyr
            180                 185                 190

Ser Ala Val Gly Phe Met Val Leu Ser Leu His Glu Thr Leu Thr Ala
        195                 200                 205

Tyr Gly Ser Val Tyr Ile Gly Thr Ile Val Pro Ile Leu Leu Ile
    210                 215                 220

Leu Leu Ser Lys Val Ile Lys Pro Pro Arg Pro Ala Thr Ser Lys Ala
225                 230                 235                 240

Arg Lys Ala Glu

<210> SEQ ID NO 32
<211> LENGTH: 609
<212> TYPE: DNA
<213> ORGANISM: Vaccinium corymbosum

<400> SEQUENCE: 32
ggggttgggt taccagtaca tggctggctt tacagcacgg tggaagtatt atttcatttg      60
gtcaatctca gaagcttcca tcatcatttc tggcctgggg ttcagtggtt ggacagattc     120
ttctccacca aaaccaaaat gggaccgtgc aaagaatgta gatattttgc gggttgagtt     180
tgcaaagact gcagctcaga ttccacttgc atggaacatt caagtcagca cctggctacg     240
ccattatgtt tatgagaggc tcgtgcagaa gggaaagaaa cctggtttct tcagttgtt     300 ggctacccag actgtcagtg ctgtttggca tggtttatat cctggataca tcatattctt     360
tgtgcagtca gcattgatga ttgctggttc aagagttatt tatagatggc agcaagctgt     420
tcctcctaaa atggatctgg tgaagaaagt attcgtactt ttaaactttg cttacacagt     480
tctggtgttg aactactcct ctgtcggttt catggtacta agcctacatg aaacaattgt     540
tgcatacggg agcgtgtatt cgttggaacc attgttccca tacttgtaat cctccttggt     600
tacgtaatt                                                             609

<210> SEQ ID NO 33
<211> LENGTH: 195
<212> TYPE: PRT
<213> ORGANISM: Vaccinium corymbosum

<400> SEQUENCE: 33

Gly Leu Gly Tyr Gln Tyr Met Ala Gly Phe Thr Ala Arg Trp Lys Tyr
1               5                   10                  15

Tyr Phe Ile Trp Ser Ile Ser Glu Ala Ser Ile Ile Ser Gly Leu
            20                  25                  30

Gly Phe Ser Gly Trp Thr Asp Ser Ser Pro Lys Pro Lys Trp Asp
        35                  40                  45

Arg Ala Lys Asn Val Asp Ile Leu Arg Val Glu Phe Ala Lys Thr Ala
    50                  55                  60

Ala Gln Ile Pro Leu Ala Trp Asn Ile Gln Val Ser Thr Trp Leu Arg
65                  70                  75                  80

His Tyr Val Tyr Glu Arg Leu Val Gln Lys Gly Lys Pro Gly Phe
                85                  90                  95

Phe Gln Leu Leu Ala Thr Gln Thr Val Ser Ala Val Trp His Gly Leu
            100                 105                 110

Tyr Pro Gly Tyr Ile Ile Phe Phe Val Gln Ser Ala Leu Met Ile Ala
        115                 120                 125
```

Gly Ser Arg Val Ile Tyr Arg Trp Gln Gln Ala Val Pro Pro Lys Met
        130                 135                 140

Asp Leu Val Lys Lys Val Phe Val Leu Leu Asn Phe Ala Tyr Thr Val
145                 150                 155                 160

Leu Val Leu Asn Tyr Ser Ser Val Gly Phe Met Val Leu Ser Leu His
                165                 170                 175

Glu Thr Ile Val Ala Tyr Gly Ser Val Tyr Ser Leu Glu Pro Leu Phe
                180                 185                 190

Pro Tyr Leu
        195

<210> SEQ ID NO 34
<211> LENGTH: 841
<212> TYPE: DNA
<213> ORGANISM: Wheat

<400> SEQUENCE: 34

```
cactttgctg gaccagtata tgagatgaaa gattatcttg aatggactga aaggaaagga      60
atatgggccg gctcaactcc ttcaccatta ttacctactc tgcgtgctct agttcaggct     120
ggaatatgca tggggttata tttgtatctg tcacctatgt ttccccattc ataatataga     180
ggttcactaa atcgtgaaag gggtttctgg caccggctct tctttcaata catgtcagga     240
tttactgctc gatggaaata ctactttata tggtcagtct cagaagctgc aattattata     300
tctggcctgg gtttcactgg ttggtctgat tcttctcccc aaaagccaa atgggaccgt      360
gctataaatg ttgatattct gggcgtcgag ctagctggaa gtgcagctca attgccactt     420
aagtggaata ttcaagtgag cacatggcta agatactatg tgtatgagag gttaattcag     480
aaagggaaga agcctggttt ccttcagttg ttgggtacac agacagtcag tgctatctgg     540
catggactgt atccaggata tatgtttttc tttgttcagt cagcgttgat gataaatggt     600
tcaaaagtta tatacagatg gcaacaagct gtgagcaatc caggcctccg cactatcctg     660
tctttactaa attgtgcata caccatgatg gtgcttaact actcatgcat tggcttccag     720
gtactgagct tccaggagac cttagcatcc tacaagagcg tgtattatgt cggcacaatc     780
gttcctattc tatgtgtctt gctgggctat gtcgtcaagc ccacgagacc tgtgaagccg     840
a                                                                    841
```

<210> SEQ ID NO 35
<211> LENGTH: 279
<212> TYPE: PRT
<213> ORGANISM: Wheat

<400> SEQUENCE: 35

His Phe Ala Gly Pro Val Tyr Glu Met Lys Asp Tyr Leu Glu Trp Thr
1               5                   10                  15

Glu Arg Lys Gly Ile Trp Ala Gly Ser Thr Pro Ser Pro Leu Leu Pro
            20                  25                  30

Thr Leu Arg Ala Leu Val Gln Ala Gly Ile Cys Met Gly Leu Tyr Leu
        35                  40                  45

Tyr Leu Ser Pro Met Phe Pro His Ser Tyr Arg Gly Ser Leu Asn Arg
    50                  55                  60

Glu Arg Gly Phe Trp His Arg Leu Phe Phe Gln Tyr Met Ser Gly Phe
65                  70                  75                  80

Thr Ala Arg Trp Lys Tyr Tyr Phe Ile Trp Ser Val Ser Glu Ala Ala
                85                  90                  95

```
Ile Ile Ile Ser Gly Leu Gly Phe Thr Gly Trp Ser Asp Ser Ser Pro
            100                 105                 110

Pro Lys Ala Lys Trp Asp Arg Ala Ile Asn Val Asp Ile Leu Gly Val
        115                 120                 125

Glu Leu Ala Gly Ser Ala Ala Gln Leu Pro Leu Lys Trp Asn Ile Gln
    130                 135                 140

Val Ser Thr Trp Leu Arg Tyr Tyr Val Tyr Glu Arg Leu Ile Gln Lys
145                 150                 155                 160

Gly Lys Lys Pro Gly Phe Leu Gln Leu Leu Gly Thr Gln Thr Val Ser
                165                 170                 175

Ala Ile Trp His Gly Leu Tyr Pro Gly Tyr Met Phe Phe Val Gln
                180                 185                 190

Ser Ala Leu Met Ile Asn Gly Ser Lys Val Ile Tyr Arg Trp Gln Gln
            195                 200                 205

Ala Val Ser Asn Pro Gly Leu Arg Thr Ile Leu Ser Leu Leu Asn Cys
        210                 215                 220

Ala Tyr Thr Met Met Val Leu Asn Tyr Ser Cys Ile Gly Phe Gln Val
225                 230                 235                 240

Leu Ser Phe Gln Glu Thr Leu Ala Ser Tyr Lys Ser Val Tyr Tyr Val
                245                 250                 255

Gly Thr Ile Val Pro Ile Leu Cys Val Leu Gly Tyr Val Val Lys
                260                 265                 270

Pro Thr Arg Pro Val Lys Pro
        275

<210> SEQ ID NO 36
<211> LENGTH: 462
<212> TYPE: PRT
<213> ORGANISM: Arabidopsis thaliana

<400> SEQUENCE: 36

Met Asp Met Ser Ser Met Ala Gly Ser Ile Gly Val Ser Val Ala Val
1               5                   10                  15

Leu Arg Phe Leu Leu Cys Phe Val Ala Thr Ile Pro Ser Phe Ala
            20                  25                  30

Cys Arg Ile Val Pro Ser Arg Leu Gly Lys His Leu Tyr Ala Ala Ala
        35                  40                  45

Ser Gly Ala Phe Leu Ser Tyr Leu Ser Phe Gly Phe Ser Ser Asn Leu
    50                  55                  60

His Phe Leu Val Pro Met Thr Ile Gly Tyr Ala Ser Met Ala Ile Tyr
65                  70                  75                  80

Arg Pro Lys Cys Gly Ile Ile Thr Phe Phe Leu Gly Phe Ala Tyr Leu
                85                  90                  95

Ile Gly Cys His Val Phe Tyr Met Ser Gly Asp Ala Trp Lys Glu Gly
            100                 105                 110

Gly Ile Asp Ser Thr Gly Ala Leu Met Val Leu Thr Leu Lys Val Ile
        115                 120                 125

Ser Cys Ser Met Asn Tyr Asn Asp Gly Met Leu Lys Glu Glu Gly Leu
    130                 135                 140

Arg Glu Ala Gln Lys Lys Asn Arg Leu Ile Gln Met Pro Ser Leu Ile
145                 150                 155                 160

Glu Tyr Phe Gly Tyr Cys Leu Cys Cys Gly Ser His Phe Ala Gly Pro
                165                 170                 175

Val Tyr Glu Met Lys Asp Tyr Leu Glu Trp Thr Glu Gly Lys Gly Ile
                180                 185                 190
```

```
Trp Asp Thr Thr Glu Lys Arg Lys Pro Ser Pro Tyr Gly Ala Thr
            195                 200                 205
Ile Arg Ala Ile Leu Gln Ala Ile Cys Met Ala Leu Tyr Leu Tyr
            210                 215                 220
Leu Val Pro Gln Tyr Pro Leu Thr Arg Phe Thr Glu Pro Val Tyr Gln
225                 230                 235                 240
Glu Trp Gly Phe Leu Arg Lys Phe Ser Tyr Gln Tyr Met Ala Gly Phe
                245                 250                 255
Thr Ala Arg Trp Lys Tyr Tyr Phe Ile Trp Ser Ile Ser Glu Ala Ser
                260                 265                 270
Ile Ile Ile Ser Gly Leu Gly Phe Ser Gly Trp Thr Asp Asp Ala Ser
            275                 280                 285
Pro Lys Pro Lys Trp Asp Arg Ala Lys Asn Val Asp Ile Leu Gly Val
            290                 295                 300
Glu Leu Ala Lys Ser Ala Val Gln Ile Pro Leu Val Trp Asn Ile Gln
305                 310                 315                 320
Val Ser Thr Trp Leu Arg His Tyr Val Tyr Glu Arg Leu Val Gln Asn
                325                 330                 335
Gly Lys Lys Ala Gly Phe Phe Gln Leu Leu Ala Thr Gln Thr Val Ser
                340                 345                 350
Ala Val Trp His Gly Leu Tyr Pro Gly Tyr Met Met Phe Phe Val Gln
            355                 360                 365
Ser Ala Leu Met Ile Ala Gly Ser Arg Val Ile Tyr Arg Trp Gln Gln
370                 375                 380
Ala Ile Ser Pro Lys Met Ala Met Leu Arg Asn Ile Met Val Phe Ile
385                 390                 395                 400
Asn Phe Leu Tyr Thr Val Leu Val Leu Asn Tyr Ser Ala Val Gly Phe
                405                 410                 415
Met Val Leu Ser Leu His Glu Thr Leu Thr Ala Tyr Gly Ser Val Tyr
            420                 425                 430
Tyr Ile Gly Thr Ile Ile Pro Val Gly Leu Ile Leu Ser Tyr Val
            435                 440                 445
Val Pro Ala Lys Pro Ser Arg Pro Lys Pro Arg Lys Glu Glu
450                 455                 460
```

<210> SEQ ID NO 37
<211> LENGTH: 465
<212> TYPE: PRT
<213> ORGANISM: Arabidopsis thaliana

<400> SEQUENCE: 37

```
Met Glu Leu Leu Asp Met Asn Ser Met Ala Ala Ser Ile Gly Val Ser
1               5                   10                  15
Val Ala Val Leu Arg Phe Leu Leu Cys Phe Val Ala Thr Ile Pro Ile
                20                  25                  30
Ser Phe Leu Trp Arg Phe Ile Pro Ser Arg Leu Gly Lys His Ile Tyr
            35                  40                  45
Ser Ala Ala Ser Gly Ala Phe Leu Ser Tyr Leu Ser Phe Gly Phe Ser
        50                  55                  60
Ser Asn Leu His Phe Leu Val Pro Met Thr Ile Gly Tyr Ala Ser Met
65                  70                  75                  80
Ala Ile Tyr Arg Pro Leu Ser Gly Phe Ile Thr Phe Leu Gly Phe
                85                  90                  95
Ala Tyr Leu Ile Gly Cys His Val Phe Tyr Met Ser Gly Asp Ala Trp
```

```
                        100                 105                 110
Lys Glu Gly Gly Ile Asp Ser Thr Gly Ala Leu Met Val Leu Thr Leu
            115                 120                 125

Lys Val Ile Ser Cys Ser Ile Asn Tyr Asn Asp Gly Met Leu Lys Glu
            130                 135                 140

Glu Gly Leu Arg Glu Ala Gln Lys Lys Asn Arg Leu Ile Gln Met Pro
145                 150                 155                 160

Ser Leu Ile Glu Tyr Phe Gly Tyr Cys Leu Cys Gly Ser His Phe
                165                 170                 175

Ala Gly Pro Val Phe Glu Met Lys Asp Tyr Leu Glu Trp Thr Glu Glu
            180                 185                 190

Lys Gly Ile Trp Ala Val Ser Glu Lys Gly Lys Arg Pro Ser Pro Tyr
            195                 200                 205

Gly Ala Met Ile Arg Ala Val Phe Gln Ala Ala Ile Cys Met Ala Leu
            210                 215                 220

Tyr Leu Tyr Leu Val Pro Gln Phe Pro Leu Thr Arg Phe Thr Glu Pro
225                 230                 235                 240

Val Tyr Gln Glu Trp Gly Phe Leu Lys Arg Phe Gly Tyr Gln Tyr Met
            245                 250                 255

Ala Gly Phe Thr Ala Arg Trp Lys Tyr Tyr Phe Ile Trp Ser Ile Ser
            260                 265                 270

Glu Ala Ser Ile Ile Ser Gly Leu Gly Phe Ser Gly Trp Thr Asp
            275                 280                 285

Glu Thr Gln Thr Lys Ala Lys Trp Asp Arg Ala Lys Asn Val Asp Ile
            290                 295                 300

Leu Gly Val Glu Leu Ala Lys Ser Ala Val Gln Ile Pro Leu Phe Trp
305                 310                 315                 320

Asn Ile Gln Val Ser Thr Trp Leu Arg His Tyr Val Tyr Glu Arg Ile
            325                 330                 335

Val Lys Pro Gly Lys Lys Ala Gly Phe Phe Gln Leu Leu Ala Thr Gln
            340                 345                 350

Thr Val Ser Ala Val Trp His Gly Leu Tyr Pro Gly Tyr Ile Ile Phe
            355                 360                 365

Phe Val Gln Ser Ala Leu Met Ile Asp Gly Ser Lys Ala Ile Tyr Arg
370                 375                 380

Trp Gln Gln Ala Ile Pro Pro Lys Met Ala Met Leu Arg Asn Val Leu
385                 390                 395                 400

Val Leu Ile Asn Phe Leu Tyr Thr Val Val Leu Asn Tyr Ser Ser
            405                 410                 415

Val Gly Phe Met Val Leu Ser Leu His Glu Thr Leu Val Ala Phe Lys
            420                 425                 430

Ser Val Tyr Tyr Ile Gly Thr Val Ile Pro Ile Ala Val Leu Leu Leu
            435                 440                 445

Ser Tyr Leu Val Pro Val Lys Pro Val Arg Pro Lys Thr Arg Lys Glu
            450                 455                 460

Glu
465

<210> SEQ ID NO 38
<211> LENGTH: 722
<212> TYPE: PRT
<213> ORGANISM: Drosophila melanogaster

<400> SEQUENCE: 38
```

```
Met Leu Glu Pro Pro Lys Phe Ile Glu Asn Asp Cys Tyr Asn Gly Ser
1               5                   10                  15

Arg Thr Phe Thr Trp Leu Ala Asp Met Val Gly Leu Ser Val Asp Leu
            20                  25                  30

Val Asn Phe Leu Ile Cys Gln Ile Ser Ala Leu Phe Leu Ala Ser Leu
            35                  40                  45

Phe Arg Ser Met Leu His Pro Ser Lys Val Ser Ser Lys Leu Arg His
50                  55                  60

Thr Phe Ala Leu Ser Ile Gly Leu Ala Phe Gly Tyr Phe Cys Phe Gly
65                  70                  75                  80

Gln Gln Ala Ile His Ile Ala Gly Leu Pro Ala Ile Cys Tyr Ile Val
                85                  90                  95

Ile Arg Thr Gln Asp Pro Arg Ile Val Gln Arg Ala Val Leu Leu Val
                100                 105                 110

Ala Met Ser Tyr Leu Leu Cys Val His Leu Met Arg Gln Leu Tyr Asp
            115                 120                 125

Tyr Gly Ser Tyr Ala Leu Asp Ile Thr Gly Pro Leu Met Ile Ile Thr
130                 135                 140

Gln Lys Val Thr Ser Leu Ala Phe Ser Ile His Asp Gly Phe Val Arg
145                 150                 155                 160

Gly Asp Glu Glu Leu Thr Lys Ala Gln Gln Tyr His Ala Ile Arg Lys
                165                 170                 175

Met Pro Ser Ala Leu Glu Tyr Phe Ser Tyr Val Trp His Phe Gln Ser
            180                 185                 190

Ile Leu Ala Gly Pro Leu Val Phe Tyr Lys Asp Tyr Ile Glu Phe Val
            195                 200                 205

Glu Gly Tyr Asn Leu Leu Ser Thr Pro Pro Gly Asn Gly Asn Leu Asp
210                 215                 220

Ser Ser Lys Arg Glu Val Val Leu Glu Pro Ser Pro Thr Lys Ala Val
225                 230                 235                 240

Ile Arg Lys Val Val Gly Ser Leu Val Cys Ala Phe Ile Phe Met Lys
                245                 250                 255

Phe Val Lys Ile Tyr Pro Val Lys Asp Met Lys Glu Asp Asp Phe Met
            260                 265                 270

Asn Asn Thr Ser Met Val Tyr Lys Tyr Trp Tyr Ala Met Met Ala Thr
            275                 280                 285

Thr Cys Ile Arg Phe Lys Tyr Tyr His Ala Trp Leu Leu Ala Asp Ala
290                 295                 300

Ile Cys Asn Asn Ser Gly Leu Gly Phe Thr Gly Tyr Asp Lys Asp Gly
305                 310                 315                 320

Asn Ser Lys Trp Asp Leu Ile Ser Asn Ile Asn Val Leu Ser Phe Glu
                325                 330                 335

Phe Ser Thr Asn Met Arg Asp Ala Ile Asn Asn Trp Asn Cys Gly Thr
            340                 345                 350

Asn Arg Trp Leu Arg Thr Leu Val Tyr Glu Arg Val Pro Gln Gln Tyr
            355                 360                 365

Gly Thr Leu Leu Thr Phe Ala Leu Ser Ala Val Trp His Gly Phe Tyr
370                 375                 380

Pro Gly Tyr Tyr Leu Thr Phe Ala Thr Gly Ala Val Val Thr Ala
385                 390                 395                 400

Ala Arg Thr Gly Arg Arg Leu Phe Arg His Arg Phe Gln Ser Thr Gln
                405                 410                 415

Val Thr Arg Met Phe Tyr Asp Ile Leu Thr Cys Leu Ile Thr Arg Val
```

-continued

```
                420                 425                 430
Val Leu Gly Tyr Ala Thr Phe Pro Phe Val Leu Glu Phe Met Gly
            435                 440                 445

Ser Ile Lys Leu Tyr Leu Arg Phe Tyr Leu Cys Leu His Ile Ile Ser
        450                 455                 460

Leu Val Thr Ile Phe Ile Leu Pro Lys Phe Ile Arg Gly Glu Arg Arg
465                 470                 475                 480

Leu Arg Thr Ser Asn Gly Asn Gly Asn Val Arg Leu Ser Gly Ser Gly
                485                 490                 495

Asn Thr Lys Asp Ala Val Thr Thr Ser Val Glu Ser Thr Ala Ala Leu
            500                 505                 510

Thr Ala Gly Asn Asp Leu Asn Glu Asp Lys Glu Glu Asp Lys His Ala
        515                 520                 525

Gln Cys Lys Val His Thr Pro Thr Gln Gln Pro Ala Ala Gly Pro
    530                 535                 540

His Lys Thr Thr Val Glu Gln Pro Thr Glu Pro Asn Asn Val Asn
545                 550                 555                 560

Leu Arg Ser Arg Pro Gln Gln Gln Gln Pro His Leu Glu Lys Lys Ala
                565                 570                 575

Met Pro Pro Thr Cys Ala Arg Asp Ala Val Ser Val Pro His Asp Gln
            580                 585                 590

Cys Glu Met Asp Gln Leu Ser Ser Lys Leu Lys Glu Lys Ile Glu Ala
        595                 600                 605

Glu Thr Lys Asn Ile Glu Glu Phe Ile Asp Lys Thr Val Thr Glu Thr
    610                 615                 620

Val Ser Gly Ile Val Glu Phe Lys Asn Asp Leu Met Arg Asp Ile Glu
625                 630                 635                 640

Phe Pro Lys Leu Lys Leu Pro Gly Ser Asn Gly Ala Ile Ser Leu Asp
                645                 650                 655

Ser Ser Asn Gly Gly Gly Leu Arg Lys Arg Asn Ile Ser Ser Val His
            660                 665                 670

Asp Asn Gly Thr Asp Pro Gly His Ala Thr Ala Asp Leu His Pro Pro
        675                 680                 685

Leu Glu Glu Asn Gly Ala Ala Phe Leu Lys Lys Glu Ile Glu Val Ile
    690                 695                 700

Asn Ala Val Val Gln Gln Ala Val Pro Ala Val Leu Ser Asn Gly His
705                 710                 715                 720

Ala Lys

<210> SEQ ID NO 39
<211> LENGTH: 497
<212> TYPE: PRT
<213> ORGANISM: Drosophila melanogaster

<400> SEQUENCE: 39

Met Ala Glu Phe Glu Glu Asp Leu Pro His Asn Gly Leu Met Asp Gly
1               5                   10                  15

Ile Ala Ser Gly Val Gly Val Pro Glu Ala Leu Arg Leu Leu Leu
            20                  25                  30

Thr Ile Leu Ala Gly Tyr Pro Val Ala Ala Leu Tyr Gln Lys Phe Ile
        35                  40                  45

Ser Val Ile Ala Asp Lys Thr Val His His Met Phe Phe Ala Gly Cys
    50                  55                  60

Gly Ala Gly Leu Cys Tyr Phe Asn Tyr Gly Leu Asp Thr Tyr His Ser
```

```
                65                  70                  75                  80
Leu Ile Ala Ile Leu Thr Thr Tyr Phe Leu Val Leu Leu Arg Lys
                85                  90                  95
Lys Thr Gln Ile Phe Leu Ala Ile Asn Phe Val Phe His Met Ser Tyr
            100                 105                 110
Leu Leu Leu Gly Tyr Phe Tyr Thr Ser Ser Asn Asp Tyr Asp Ile Leu
            115                 120                 125
Trp Thr Met Pro His Cys Ile Leu Val Leu Arg Met Ile Gly Tyr Gly
            130                 135                 140
Phe Asp Ile Thr Asp Gly Leu Lys Glu Glu Ser Glu Leu Ser Lys Asp
145                 150                 155                 160
Gln Lys Glu Thr Ala Leu Lys Lys Pro Pro Ser Leu Leu Glu Leu Leu
                165                 170                 175
Ala Phe Ser Tyr Phe Pro Ser Gly Phe Leu Val Gly Pro Gln Phe Pro
                180                 185                 190
Phe Arg Arg Tyr Lys Ala Phe Val Asp Gly Glu Phe Arg Gln His Glu
                195                 200                 205
Gly Asn Val Glu Ala Gly Val Arg Arg Phe Gly Ala Gly Ala Phe Tyr
            210                 215                 220
Leu Ile Val Cys Gln Val Gly Leu Arg Tyr Leu Pro Asp Ser Tyr Phe
225                 230                 235                 240
Leu Thr Pro Glu Phe Ala Gln Val Ser Phe Val Lys Arg Ile Tyr Leu
                245                 250                 255
Leu Gly Phe Trp Ala Lys Phe Ser Leu Tyr Lys Tyr Ile Ser Cys Trp
                260                 265                 270
Leu Leu Thr Glu Gly Ala Leu Ile Cys Ile Gly Leu Thr Tyr Lys Gly
                275                 280                 285
Glu Asp Lys Asn Gly Gln Pro Asp Trp Ser Gly Cys Ser Asn Val Lys
            290                 295                 300
Leu Lys Leu Leu Glu Thr Gly Asn Thr Met Glu His Tyr Val Gln Ser
305                 310                 315                 320
Phe Asn Val Asn Thr Asn Gln Trp Val Gly Gln Tyr Ile Tyr Lys Arg
                325                 330                 335
Leu Lys Phe Leu Asn Asn Arg Thr Ile Ser Tyr Gly Ala Ala Leu Gly
                340                 345                 350
Phe Leu Ala Val Trp His Gly Tyr His Ser Gly Tyr Tyr Met Thr Phe
                355                 360                 365
Leu Met Glu Tyr Met Val Val Ser Thr Glu Lys Gln Ile Thr Arg Phe
            370                 375                 380
Tyr Thr Lys Val Val Leu Pro Gln Trp Gly His Ile Leu Asn Asn Ser
385                 390                 395                 400
Asp Ile Tyr Lys Leu Leu Tyr Phe Ile Thr Leu Lys Ser Tyr Asn Val
                405                 410                 415
Val Tyr Met Gly Trp Cys Leu Thr Ala Phe Val Phe Leu Lys Tyr Glu
                420                 425                 430
Arg Trp Ile Val Val Tyr Gly Ala Val Ser Tyr Tyr Gly Phe Thr Phe
            435                 440                 445
Leu Val Leu Trp Ala Ala Phe Tyr His Thr Phe Asn His Phe Phe Arg
            450                 455                 460
Ser Ser Ser Arg Lys Leu Ala Gly Glu Asp Gln Lys Leu Gln Asp Ser
465                 470                 475                 480
Asn Thr Asp Lys Leu Val Glu Glu Lys Lys Pro Glu Asp Lys Lys Ser
                485                 490                 495
```

Glu

<210> SEQ ID NO 40
<211> LENGTH: 506
<212> TYPE: PRT
<213> ORGANISM: Homo sapiens

<400> SEQUENCE: 40

```
Met Lys Cys Cys Phe His His Ile Ile Pro Arg Val Asn Phe Val Val
1               5                   10                  15

Cys Gln Leu Phe Ala Leu Leu Ala Ala Ile Trp Phe Arg Thr Tyr Leu
            20                  25                  30

His Ser Ser Lys Thr Ser Ser Phe Ile Arg His Val Val Ala Thr Leu
        35                  40                  45

Leu Gly Leu Tyr Leu Ala Leu Phe Cys Phe Gly Trp Tyr Ala Leu His
    50                  55                  60

Phe Leu Val Gln Ser Gly Ile Ser Tyr Cys Ile Met Ile Ile Ile Gly
65                  70                  75                  80

Val Glu Asn Met His Asn Tyr Cys Phe Val Phe Ala Leu Gly Tyr Leu
                85                  90                  95

Thr Val Cys Gln Val Thr Arg Val Tyr Ile Phe Asp Tyr Gly Gln Tyr
            100                 105                 110

Ser Ala Asp Phe Ser Gly Pro Met Met Ile Thr Gln Lys Ile Thr
        115                 120                 125

Ser Leu Ala Cys Glu Ile His Asp Gly Met Phe Arg Lys Asp Glu Glu
    130                 135                 140

Leu Thr Ser Ser Gln Arg Asp Leu Ala Val Arg Arg Met Pro Ser Leu
145                 150                 155                 160

Leu Glu Tyr Leu Ser Tyr Asn Cys Asn Phe Met Gly Ile Leu Ala Gly
                165                 170                 175

Pro Leu Cys Ser Tyr Lys Asp Tyr Ile Thr Phe Ile Glu Gly Arg Ser
            180                 185                 190

Tyr His Ile Thr Gln Ser Gly Glu Asn Gly Lys Glu Glu Thr Gln Tyr
        195                 200                 205

Glu Arg Thr Glu Pro Ser Pro Asn Thr Ala Val Val Gln Lys Leu Leu
    210                 215                 220

Val Cys Gly Leu Ser Leu Leu Phe His Leu Thr Ile Cys Thr Thr Leu
225                 230                 235                 240

Pro Val Glu Tyr Asn Ile Asp Glu His Phe Gln Ala Thr Ala Ser Trp
                245                 250                 255

Pro Thr Lys Ile Ile Tyr Leu Tyr Ile Ser Leu Leu Ala Ala Arg Pro
            260                 265                 270

Lys Tyr Tyr Phe Ala Trp Thr Leu Ala Asp Ala Ile Asn Asn Ala Ala
        275                 280                 285

Gly Phe Gly Phe Arg Gly Tyr Asp Glu Asn Gly Ala Ala Arg Trp Asp
    290                 295                 300

Leu Ile Ser Asn Leu Arg Ile Gln Gln Ile Glu Met Ser Thr Ser Phe
305                 310                 315                 320

Lys Met Phe Leu Asp Asn Trp Asn Ile Gln Thr Ala Leu Trp Leu Lys
                325                 330                 335

Arg Val Cys Tyr Glu Arg Thr Ser Phe Ser Pro Thr Ile Gln Thr Phe
            340                 345                 350

Ile Leu Ser Ala Ile Trp His Gly Val Tyr Pro Gly Tyr Tyr Leu Thr
        355                 360                 365
```

```
Phe Leu Thr Gly Val Leu Met Thr Leu Ala Ala Arg Ala Met Arg Asn
        370                 375                 380

Asn Phe Arg His Tyr Phe Ile Glu Pro Ser Gln Leu Lys Leu Phe Tyr
385                 390                 395                 400

Asp Val Ile Thr Trp Ile Val Thr Gln Val Ala Ile Ser Tyr Thr Val
                405                 410                 415

Val Pro Phe Val Leu Leu Ser Ile Lys Pro Ser Leu Thr Phe Tyr Ser
            420                 425                 430

Ser Trp Tyr Tyr Cys Leu His Ile Leu Gly Ile Leu Val Leu Leu Leu
            435                 440                 445

Leu Pro Val Lys Lys Thr Gln Arg Arg Lys Asn Thr His Glu Asn Ile
        450                 455                 460

Gln Leu Ser Gln Ser Lys Lys Phe Asp Glu Gly Glu Asn Ser Leu Gly
465                 470                 475                 480

Gln Asn Ser Phe Ser Thr Thr Asn Asn Val Cys Asn Gln Asn Gln Glu
                485                 490                 495

Ile Ala Ser Arg His Ser Ser Leu Lys Gln
                500                 505

<210> SEQ ID NO 41
<211> LENGTH: 520
<212> TYPE: PRT
<213> ORGANISM: Homo sapiens

<400> SEQUENCE: 41

Met Ala Thr Thr Ser Thr Thr Gly Ser Thr Leu Leu Gln Pro Leu Ser
1               5                   10                  15

Asn Ala Val Gln Leu Pro Ile Asp Gln Val Asn Phe Val Val Cys Gln
            20                  25                  30

Leu Phe Ala Leu Leu Ala Ala Ile Trp Phe Arg Thr Tyr Leu His Ser
        35                  40                  45

Ser Lys Thr Ser Ser Phe Ile Arg His Val Val Ala Thr Leu Leu Gly
    50                  55                  60

Leu Tyr Leu Ala Leu Phe Cys Phe Gly Trp Tyr Ala Leu His Phe Leu
65                  70                  75                  80

Val Gln Ser Gly Ile Ser Tyr Cys Ile Met Ile Ile Gly Val Glu
            85                  90                  95

Asn Met His Asn Tyr Cys Phe Val Phe Ala Leu Gly Tyr Leu Thr Val
            100                 105                 110

Cys Gln Val Thr Arg Val Tyr Ile Phe Asp Tyr Gly Gln Tyr Ser Ala
        115                 120                 125

Asp Phe Ser Gly Pro Met Met Ile Ile Thr Gln Lys Ile Thr Ser Leu
    130                 135                 140

Ala Cys Glu Ile His Asp Gly Met Phe Arg Lys Asp Glu Glu Leu Thr
145                 150                 155                 160

Ser Ser Gln Arg Asp Leu Ala Val Arg Arg Met Pro Ser Leu Leu Glu
                165                 170                 175

Tyr Leu Ser Tyr Asn Cys Asn Phe Met Gly Ile Leu Ala Gly Pro Leu
            180                 185                 190

Cys Ser Tyr Lys Asp Tyr Ile Thr Phe Ile Glu Gly Arg Ser Tyr His
        195                 200                 205

Ile Thr Gln Ser Gly Glu Asn Gly Lys Glu Thr Gln Tyr Glu Arg
    210                 215                 220

Thr Glu Pro Ser Pro Asn Thr Ala Val Val Gln Lys Leu Leu Val Cys
```

-continued

```
                225                 230                 235                 240
Gly Leu Ser Leu Leu Phe His Leu Thr Ile Cys Thr Thr Leu Pro Val
                    245                 250                 255
Glu Tyr Asn Ile Asp Glu His Phe Gln Ala Thr Ala Ser Trp Pro Thr
                260                 265                 270
Lys Ile Ile Tyr Leu Tyr Ile Ser Leu Leu Ala Ala Arg Pro Lys Tyr
                275                 280                 285
Tyr Phe Ala Trp Thr Leu Ala Asp Ala Ile Asn Asn Ala Ala Gly Phe
            290                 295                 300
Gly Phe Arg Gly Tyr Asp Glu Asn Gly Ala Ala Arg Trp Asp Leu Ile
305                 310                 315                 320
Ser Asn Leu Arg Ile Gln Gln Ile Glu Met Ser Thr Ser Phe Lys Met
                325                 330                 335
Phe Leu Asp Asn Trp Asn Ile Gln Thr Ala Leu Trp Leu Lys Arg Val
                340                 345                 350
Cys Tyr Glu Arg Thr Ser Phe Ser Pro Thr Ile Gln Thr Phe Ile Leu
                355                 360                 365
Ser Ala Ile Trp His Gly Val Tyr Pro Gly Tyr Tyr Leu Thr Phe Leu
            370                 375                 380
Thr Gly Val Leu Met Thr Leu Ala Ala Arg Ala Met Arg Asn Asn Phe
385                 390                 395                 400
Arg His Tyr Phe Ile Glu Pro Ser Gln Leu Lys Leu Phe Tyr Asp Val
                    405                 410                 415
Ile Thr Trp Ile Val Thr Gln Val Ala Ile Ser Tyr Thr Val Val Pro
                420                 425                 430
Phe Val Leu Leu Ser Ile Lys Pro Ser Leu Thr Phe Tyr Ser Ser Trp
            435                 440                 445
Tyr Tyr Cys Leu His Ile Leu Gly Ile Leu Val Leu Leu Leu Leu Pro
        450                 455                 460
Val Lys Lys Thr Gln Arg Arg Lys Asn Thr His Glu Asn Ile Gln Leu
465                 470                 475                 480
Ser Gln Ser Arg Lys Phe Asp Glu Gly Glu Asn Ser Leu Gly Gln Asn
                485                 490                 495
Ser Phe Ser Thr Thr Asn Asn Val Cys Asn Gln Asn Gln Glu Ile Ala
                500                 505                 510
Ser Arg His Ser Ser Leu Lys Gln
            515                 520
```

<210> SEQ ID NO 42
<211> LENGTH: 492
<212> TYPE: PRT
<213> ORGANISM: Mus musculus

<400> SEQUENCE: 42

```
Met Ala Ala Arg Pro Pro Ala Ser Leu Ser Tyr Arg Thr Thr Gly Ser
1               5                   10                  15
Thr Cys Leu His Pro Leu Ser Gln Leu Leu Gly Ile Pro Leu Asp Gln
                20                  25                  30
Val Asn Phe Val Ala Cys Gln Leu Phe Ala Leu Ser Ala Ala Phe Trp
            35                  40                  45
Phe Arg Ile Tyr Leu His Pro Gly Lys Ala Ser Pro Glu Val Arg His
        50                  55                  60
Thr Leu Ala Thr Ile Leu Gly Ile Tyr Phe Val Val Phe Cys Phe Gly
65                  70                  75                  80
```

-continued

```
Trp Tyr Ala Val His Leu Phe Val Leu Val Leu Met Cys Tyr Gly Val
                 85                  90                  95

Met Val Ser Ala Ser Val Ser Asn Ile His Arg Tyr Ser Phe Phe Val
            100                 105                 110

Ala Met Gly Tyr Leu Thr Ile Cys His Ile Ser Arg Ile Tyr Ile Phe
            115                 120                 125

His Tyr Gly Ile Leu Thr Thr Asp Phe Ser Gly Pro Leu Met Ile Val
        130                 135                 140

Thr Gln Lys Ile Thr Thr Leu Ala Phe Gln Val His Asp Gly Leu Gly
145                 150                 155                 160

Arg Lys Ala Glu Asp Leu Ser Ala Glu Gln His Arg Leu Ala Val Lys
                165                 170                 175

Ala Lys Pro Ser Leu Leu Glu Tyr Leu Ser Tyr His Leu Asn Phe Met
            180                 185                 190

Ser Val Ile Ala Gly Pro Cys Asn Asn Phe Lys Asp Tyr Val Ala Phe
        195                 200                 205

Ile Glu Gly Arg His Ile His Met Lys Leu Leu Glu Val Asn Trp Thr
        210                 215                 220

Gln Arg Gly Phe Gln Ser Leu Pro Glu Pro Ser Pro Thr Gly Ala Val
225                 230                 235                 240

Ile Gln Lys Leu Cys Val Thr Leu Met Ser Leu Leu Leu Phe Leu Thr
                245                 250                 255

Leu Ser Lys Ser Phe Pro Val Thr Phe Leu Ile Asp Asp Trp Phe Val
            260                 265                 270

His Lys Ala Asn Phe Leu Ser Arg Leu Trp Tyr Leu Tyr Val Val Met
        275                 280                 285

Gln Ala Ala Lys Pro Lys Tyr Tyr Phe Ala Trp Thr Leu Ala Asp Ala
290                 295                 300

Val His Asn Ala Ala Gly Phe Gly Phe Asn Gly Met Asp Thr Asp Gly
305                 310                 315                 320

Lys Ser Arg Trp Asp Leu Leu Ser Asn Leu Asn Ile Trp Lys Ile Glu
                325                 330                 335

Thr Ala Thr Ser Phe Lys Met Tyr Leu Glu Asn Trp Asn Ile Gln Thr
            340                 345                 350

Ser Thr Trp Leu Lys Cys Val Cys Tyr Glu Arg Val Ser Trp Tyr Pro
        355                 360                 365

Thr Val Leu Thr Phe Leu Leu Ser Ala Leu Trp His Gly Val Tyr Pro
        370                 375                 380

Gly Tyr Tyr Phe Thr Phe Leu Thr Gly Val Pro Val Thr Leu Ala Ala
385                 390                 395                 400

Arg Ala Val Arg Asn Asn Tyr Arg His Phe Leu Ser Ser Lys Ala
                405                 410                 415

Arg Lys Ile Ala Tyr Asp Val Val Thr Trp Ala Val Thr Gln Leu Ala
            420                 425                 430

Val Ser Tyr Thr Ala Ala Pro Phe Val Met Leu Ala Val Glu Pro Thr
        435                 440                 445

Ile Ser Leu Tyr Lys Ser Val Phe Phe Leu His Ile Ile Cys Leu
        450                 455                 460

Leu Ile Ile Leu Phe Leu Pro Ile Lys Pro His Gln Pro Gln Arg Gln
465                 470                 475                 480

Ser Arg Ser Pro Asn Ser Val Lys Lys Ala Asp
            485                 490
```

<210> SEQ ID NO 43
<211> LENGTH: 519
<212> TYPE: PRT
<213> ORGANISM: Mus musculus

<400> SEQUENCE: 43

Met Ala Thr Thr Ser Thr Thr Gly Ser Thr Leu Leu Gln Pro Leu Ser
1               5                   10                  15

Asn Ala Val Gln Leu Pro Ile Asp Gln Val Asn Phe Val Val Cys Gln
            20                  25                  30

Leu Phe Ala Leu Leu Ala Ala Val Trp Phe Arg Thr Tyr Leu His Ser
        35                  40                  45

Ser Lys Thr Ser Ser Phe Ile Arg His Val Val Ala Thr Leu Leu Gly
    50                  55                  60

Leu Tyr Leu Ala Phe Phe Cys Phe Gly Trp Tyr Ala Leu His Phe Leu
65                  70                  75                  80

Val Gln Ser Gly Ile Ser Tyr Cys Ile Met Ile Ala Gly Val Glu
                85                  90                  95

Ser Met Gln Gln Cys Cys Phe Val Phe Ala Leu Gly Tyr Leu Ser Val
            100                 105                 110

Cys Gln Ile Thr Arg Val Tyr Ile Phe Asp Tyr Gly Gln Tyr Ser Ala
            115                 120                 125

Asp Phe Ser Gly Pro Met Met Ile Ile Thr Gln Lys Ile Thr Ser Leu
    130                 135                 140

Ala Tyr Glu Ile His Asp Gly Met Phe Arg Lys Asp Glu Glu Leu Thr
145                 150                 155                 160

Pro Ser Gln Arg Gly Leu Ala Val Arg Arg Met Pro Ser Leu Leu Glu
                165                 170                 175

Tyr Val Ser Tyr Thr Cys Asn Phe Met Gly Ile Leu Ala Gly Pro Leu
            180                 185                 190

Cys Ser Tyr Lys Asp Tyr Ile Ala Phe Ile Glu Gly Arg Ala Ser His
            195                 200                 205

Val Ala Gln Pro Ser Glu Asn Gly Lys Asp Glu Gln His Gly Lys Ala
    210                 215                 220

Asp Pro Ser Pro Asn Ala Ala Val Thr Glu Lys Leu Leu Val Cys Gly
225                 230                 235                 240

Leu Ser Leu Leu Phe His Leu Thr Ile Ser Asn Met Leu Pro Val Glu
                245                 250                 255

Tyr Asn Ile Asp Glu His Phe Gln Ala Thr Ala Ser Trp Pro Thr Lys
            260                 265                 270

Ala Thr Tyr Leu Tyr Val Ser Leu Leu Ala Ala Arg Pro Lys Tyr Tyr
            275                 280                 285

Phe Ala Trp Thr Leu Ala Asp Ala Ile Asn Asn Ala Gly Phe Gly
    290                 295                 300

Phe Arg Gly Tyr Asp Lys Asn Gly Val Ala Arg Trp Asp Leu Ile Ser
305                 310                 315                 320

Asn Leu Arg Ile Gln Gln Ile Glu Met Ser Thr Ser Phe Lys Met Phe
                325                 330                 335

Leu Asp Asn Trp Asn Ile Gln Thr Ala Leu Trp Leu Lys Arg Val Cys
            340                 345                 350

Tyr Glu Arg Ala Thr Phe Ser Pro Thr Ile Gln Thr Phe Phe Leu Ser
            355                 360                 365

Ala Ile Trp His Gly Val Tyr Pro Gly Tyr Tyr Leu Thr Phe Leu Thr
    370                 375                 380

```
Gly Val Leu Met Thr Leu Ala Ala Arg Ala Val Arg Asn Asn Phe Arg
385                 390                 395                 400

His Tyr Phe Leu Glu Pro Pro Gln Leu Lys Leu Phe Tyr Asp Leu Ile
                405                 410                 415

Thr Trp Val Ala Thr Gln Ile Thr Ile Ser Tyr Thr Val Pro Phe
                420                 425                 430

Val Leu Leu Ser Ile Lys Pro Ser Phe Thr Phe Tyr Ser Ser Trp Tyr
            435                 440                 445

Tyr Cys Leu His Val Cys Ser Ile Leu Val Leu Leu Leu Pro Val
        450                 455                 460

Lys Lys Ser Gln Arg Arg Thr Ser Thr Gln Glu Asn Val His Leu Ser
465                 470                 475                 480

Gln Ala Lys Lys Phe Asp Glu Arg Asp Asn Pro Leu Gly Gln Asn Ser
                485                 490                 495

Phe Ser Thr Met Asn Asn Val Cys Asn Gln Asn Arg Asp Thr Gly Ser
                500                 505                 510

Arg His Ser Ser Leu Thr Gln
        515
```

<210> SEQ ID NO 44
<211> LENGTH: 509
<212> TYPE: PRT
<213> ORGANISM: Schizosaccharomyces pombe

<400> SEQUENCE: 44

```
Met Ala Tyr Leu Ile Asp Ile Pro Phe Glu Tyr Phe Ser Ser Phe Leu
1               5                   10                  15

Gly Val His Pro Asp Gln Leu Lys Leu Leu Phe Cys Phe Leu Ser Ala
                20                  25                  30

Tyr Pro Phe Ala Gly Ile Leu Lys Arg Leu Pro Ser Ala Pro Trp Ile
            35                  40                  45

Arg Asn Leu Phe Ser Ile Ser Ile Gly Leu Phe Tyr Leu Ile Gly Val
50                  55                  60

His His Leu Tyr Asp Gly Val Leu Val Leu Leu Phe Asp Ala Leu Phe
65                  70                  75                  80

Thr Tyr Phe Val Ala Ala Phe Tyr Arg Ser Ser Arg Met Pro Trp Ile
                85                  90                  95

Ile Phe Ile Val Ile Leu Gly His Thr Phe Ser Ser His Val Ile Arg
                100                 105                 110

Tyr Ile Tyr Pro Ser Glu Asn Thr Asp Ile Thr Ala Ser Gln Met Val
            115                 120                 125

Leu Cys Met Lys Leu Thr Ala Phe Ala Trp Ser Val Tyr Asp Gly Arg
130                 135                 140

Leu Pro Ser Ser Glu Leu Ser Ser Tyr Gln Lys Asp Arg Ala Leu Arg
145                 150                 155                 160

Lys Ile Pro Asn Ile Leu Tyr Phe Leu Gly Tyr Val Phe Phe Pro
                165                 170                 175

Ser Leu Leu Val Gly Pro Ala Phe Asp Tyr Val Asp Tyr Glu Arg Phe
            180                 185                 190

Ile Thr Leu Ser Met Phe Lys Pro Leu Ala Asp Pro Tyr Glu Lys Gln
            195                 200                 205

Ile Thr Pro His Ser Leu Glu Pro Ala Leu Gly Arg Cys Trp Arg Gly
            210                 215                 220

Leu Leu Trp Leu Ile Leu Phe Ile Thr Gly Ser Ser Ile Tyr Pro Leu
225                 230                 235                 240
```

```
Lys Phe Leu Leu Thr Pro Lys Phe Ala Ser Ser Pro Ile Leu Leu Lys
                245                 250                 255

Tyr Gly Tyr Val Cys Ile Thr Ala Phe Val Ala Arg Met Lys Tyr Tyr
            260                 265                 270

Gly Ala Trp Glu Leu Ser Asp Gly Ala Cys Ile Leu Ser Gly Ile Gly
        275                 280                 285

Tyr Asn Gly Leu Asp Ser Ser Lys His Pro Arg Trp Asp Arg Val Lys
    290                 295                 300

Asn Ile Asp Pro Ile Lys Phe Glu Phe Ala Asp Asn Ile Lys Cys Ala
305                 310                 315                 320

Leu Glu Ala Trp Asn Met Asn Thr Asn Lys Trp Leu Arg Asn Tyr Val
                325                 330                 335

Tyr Leu Arg Val Ala Lys Lys Gly Lys Arg Pro Gly Phe Lys Ser Thr
            340                 345                 350

Leu Ser Thr Phe Thr Val Ser Ala Met Trp His Gly Val Ser Ala Gly
        355                 360                 365

Tyr Tyr Leu Thr Phe Val Ser Ala Ala Phe Ile Gln Thr Val Ala Lys
    370                 375                 380

Tyr Thr Arg Arg His Val Arg Pro Phe Phe Leu Lys Pro Asp Met Glu
385                 390                 395                 400

Thr Pro Gly Pro Phe Lys Arg Val Tyr Asp Val Ile Gly Met Val Ala
                405                 410                 415

Thr Asn Leu Ser Leu Ser Tyr Leu Ile Ile Ser Phe Leu Leu Leu Asn
            420                 425                 430

Leu Lys Glu Ser Ile His Val Trp Lys Glu Leu Tyr Phe Ile Val His
        435                 440                 445

Ile Tyr Ile Leu Ile Ala Leu Ala Val Phe Asn Ser Pro Ile Arg Ser
    450                 455                 460

Lys Leu Asp Asn Lys Ile Arg Ser Arg Val Asn Ser Tyr Lys Leu Lys
465                 470                 475                 480

Ser Tyr Glu Gln Ser Met Lys Ser Thr Ser Asp Thr Asp Met Leu Asn
                485                 490                 495

Met Ser Val Pro Lys Arg Glu Asp Phe Glu Asn Asp Glu
            500                 505

<210> SEQ ID NO 45
<211> LENGTH: 539
<212> TYPE: PRT
<213> ORGANISM: Aspergillus oryzae

<400> SEQUENCE: 45

Met Leu Pro Tyr Val Asp Leu Leu Lys Leu Ile Ala Ser Phe Leu Leu
1               5                   10                  15

Ser Tyr Pro Leu Ala Ala Leu Leu Lys Arg Ile Pro Asp Ala Gln Pro
                20                  25                  30

Trp Lys Lys Asn Ala Phe Ile Ile Ala Val Ser Leu Phe Tyr Leu Val
            35                  40                  45

Gly Leu Phe Asp Leu Trp Asp Gly Leu Arg Thr Leu Ala Tyr Ser Ala
        50                  55                  60

Ala Gly Ile Tyr Ala Ile Ala Tyr Tyr Ile Asp Gly Ser Leu Met Pro
65                  70                  75                  80

Trp Ile Gly Phe Ile Phe Leu Met Gly His Met Ser Ile Ser His Ile
                85                  90                  95

Tyr Arg Gln Ile Ile Asp Asp Ala His Val Thr Asp Ile Thr Gly Ala
```

-continued

```
            100                 105                 110
Gln Met Val Leu Val Met Lys Leu Ser Ser Phe Cys Trp Asn Val His
            115                 120                 125
Asp Gly Arg Leu Ser Gln Glu Gln Leu Ser Asp Pro Gln Lys Tyr Ala
    130                 135                 140
Ala Ile Lys Asp Phe Pro Gly Ile Leu Asp Tyr Leu Gly Tyr Val Leu
145                 150                 155                 160
Phe Phe Pro Ser Leu Phe Ala Gly Pro Ser Phe Glu Tyr Val Asp Tyr
                165                 170                 175
Arg Arg Trp Ile Asp Thr Thr Leu Phe Asp Val Pro Pro Gly Thr Asp
            180                 185                 190
Pro Ser Lys Val Pro Pro Thr Arg Lys Lys Arg Lys Ile Pro Arg Ser
        195                 200                 205
Gly Thr Pro Ala Ala Lys Lys Ala Leu Ala Gly Leu Gly Trp Ile Leu
    210                 215                 220
Ala Phe Leu Gln Leu Gly Ser Leu Tyr Asn Gln Glu Leu Val Leu Asp
225                 230                 235                 240
Glu Thr Phe Met Gln Tyr Ser Phe Val Gln Arg Val Trp Ile Leu His
                245                 250                 255
Met Leu Gly Phe Thr Ala Arg Leu Lys Tyr Tyr Gly Val Trp Tyr Leu
            260                 265                 270
Thr Glu Gly Ala Cys Val Leu Ser Gly Met Gly Tyr Asn Gly Phe Asp
        275                 280                 285
Pro Lys Ser Gly Lys Val Phe Trp Asn Arg Leu Glu Asn Val Asp Pro
    290                 295                 300
Trp Ser Leu Glu Thr Ala Gln Asn Ser His Gly Tyr Leu Gly Ser Trp
305                 310                 315                 320
Asn Lys Asn Thr Asn His Trp Leu Arg Asn Tyr Val Tyr Leu Arg Val
                325                 330                 335
Thr Pro Lys Gly Lys Pro Gly Phe Arg Ala Ser Leu Ala Thr Phe
            340                 345                 350
Val Thr Ser Ala Phe Trp His Gly Phe Tyr Pro Gly Tyr Tyr Leu Thr
        355                 360                 365
Phe Val Leu Gly Ser Phe Ile Gln Thr Val Ala Lys Asn Phe Arg Arg
    370                 375                 380
His Val Arg Pro Phe Phe Leu Thr Pro Asp Gly Ser Arg Pro Thr Ala
385                 390                 395                 400
Tyr Lys Lys Tyr Tyr Asp Ile Ala Ser Tyr Val Val Thr Gln Leu Thr
                405                 410                 415
Leu Ser Phe Ala Val Met Pro Phe Ile Phe Leu Ser Phe Gly Asp Ser
            420                 425                 430
Ile Lys Val Trp His Ser Val Tyr Phe Tyr Gly Ile Val Gly Asn Ile
        435                 440                 445
Val Ser Leu Ala Phe Phe Val Ser Pro Ala Arg Gly Leu Leu Leu Lys
    450                 455                 460
Lys Leu Lys Ala Arg Asn Lys Pro His Val Pro Arg Ala Val Ser Ser
465                 470                 475                 480
Glu Asn Ile Arg Gln Pro Thr Leu Gly Leu Pro Asn Asp Ala Ile Gln
                485                 490                 495
Glu Phe Asp Asp Ala Val Gln Glu Ile Arg Ala Glu Ile Glu Ser Arg
            500                 505                 510
Gln Arg Arg Gly Ser Leu Ala His Met Pro Ile Gly Asp Glu Leu Lys
        515                 520                 525
```

```
Ala Ala Val Glu Asp Lys Ile Gly Arg Gly His
    530                 535

<210> SEQ ID NO 46
<211> LENGTH: 17
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: X can be Val or Ile
<220> FEATURE:
<221> NAME/KEY: MISC_FEATURE
<222> LOCATION: (3)..(3)
<223> OTHER INFORMATION: X can be Leu or Ile
<220> FEATURE:
<221> NAME/KEY: MISC_FEATURE
<222> LOCATION: (4)..(5)
<223> OTHER INFORMATION: X can be any amino acid
<220> FEATURE:
<221> NAME/KEY: MISC_FEATURE
<222> LOCATION: (7)..(7)
<223> OTHER INFORMATION: X can be Leu, Ile or Val
<220> FEATURE:
<221> NAME/KEY: MISC_FEATURE
<222> LOCATION: (8)..(15)
<223> OTHER INFORMATION: X can be any amino acid

<400> SEQUENCE: 46

Met Xaa Xaa Xaa Xaa Lys Xaa Xaa Xaa Xaa Xaa Xaa Xaa Xaa Xaa Asp
1               5                   10                  15

Gly

<210> SEQ ID NO 47
<211> LENGTH: 24
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (6)..(7)
<223> OTHER INFORMATION: X can be any amino acid
<220> FEATURE:
<221> NAME/KEY: MISC_FEATURE
<222> LOCATION: (9)..(11)
<223> OTHER INFORMATION: X can be any amino acid
<220> FEATURE:
<221> NAME/KEY: MISC_FEATURE
<222> LOCATION: (12)..(12)
<223> OTHER INFORMATION: X can be Glu or Asp
<220> FEATURE:
<221> NAME/KEY: MISC_FEATURE
<222> LOCATION: (13)..(13)
<223> OTHER INFORMATION: X can be Ala or Gly
<220> FEATURE:
<221> NAME/KEY: MISC_FEATURE
<222> LOCATION: (14)..(18)
<223> OTHER INFORMATION: X can be any amino acid
<220> FEATURE:
<221> NAME/KEY: MISC_FEATURE
<222> LOCATION: (20)..(20)
<223> OTHER INFORMATION: X can be any amino acid
<220> FEATURE:
<221> NAME/KEY: MISC_FEATURE
<222> LOCATION: (22)..(22)
<223> OTHER INFORMATION: X can be Phe or Tyr
<220> FEATURE:
```

```
<221> NAME/KEY: MISC_FEATURE
<222> LOCATION: (23)..(23)
<223> OTHER INFORMATION: X can be any amino acid

<400> SEQUENCE: 47

Arg Xaa Lys Tyr Tyr Xaa Xaa Trp Xaa Xaa Xaa Xaa Xaa Xaa Xaa
1               5                   10                  15

Xaa Xaa Gly Xaa Gly Xaa Xaa Gly
            20

<210> SEQ ID NO 48
<211> LENGTH: 20
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(12)
<223> OTHER INFORMATION: X can be any amino acid
<220> FEATURE:
<221> NAME/KEY: MISC_FEATURE
<222> LOCATION: (15)..(16)
<223> OTHER INFORMATION: X can be any amino acid
<220> FEATURE:
<221> NAME/KEY: MISC_FEATURE
<222> LOCATION: (17)..(17)
<223> OTHER INFORMATION: X can be Thr or Val
<220> FEATURE:
<221> NAME/KEY: MISC_FEATURE
<222> LOCATION: (18)..(19)
<223> OTHER INFORMATION: X can be any amino acid

<400> SEQUENCE: 48

Glu Xaa Xaa Xaa Xaa Xaa Xaa Xaa Xaa Xaa Xaa Xaa Trp Asn Xaa Xaa
1               5                   10                  15

Xaa Xaa Xaa Trp
            20

<210> SEQ ID NO 49
<211> LENGTH: 15
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (7)..(8)
<223> OTHER INFORMATION: X can be any amino acid
<220> FEATURE:
<221> NAME/KEY: MISC_FEATURE
<222> LOCATION: (12)..(13)
<223> OTHER INFORMATION: X can be any amino acid
<220> FEATURE:
<221> NAME/KEY: MISC_FEATURE
<222> LOCATION: (14)..(14)
<223> OTHER INFORMATION: X can be Thr or Phe

<400> SEQUENCE: 49

Ser Ala Xaa Trp His Gly Xaa Xaa Pro Gly Tyr Xaa Xaa Xaa Phe
1               5                   10                  15

<210> SEQ ID NO 50
<211> LENGTH: 539
<212> TYPE: PRT
<213> ORGANISM: Aspergillus oryzae
```

<400> SEQUENCE: 50

```
Met Leu Pro Tyr Val Asp Leu Leu Lys Leu Ile Ala Ser Phe Leu Leu
1               5                   10                  15
Ser Tyr Pro Leu Ala Ala Leu Leu Lys Arg Ile Pro Asp Ala Gln Pro
            20                  25                  30
Trp Lys Lys Asn Ala Phe Ile Ile Ala Val Ser Leu Phe Tyr Leu Val
                35                  40                  45
Gly Leu Phe Asp Leu Trp Asp Gly Leu Arg Thr Leu Ala Tyr Ser Ala
50                  55                  60
Ala Gly Ile Tyr Ala Ile Ala Tyr Tyr Ile Asp Gly Ser Leu Met Pro
65                  70                  75                  80
Trp Ile Gly Phe Ile Phe Leu Met Gly His Met Ser Ile Ser His Ile
                85                  90                  95
Tyr Arg Gln Ile Ile Asp Asp Ala His Val Thr Asp Ile Thr Gly Ala
                100                 105                 110
Gln Met Val Leu Val Met Lys Leu Ser Ser Phe Cys Trp Asn Val His
            115                 120                 125
Asp Gly Arg Leu Ser Gln Glu Gln Leu Ser Asp Pro Gln Lys Tyr Ala
130                 135                 140
Ala Ile Lys Asp Phe Pro Gly Ile Leu Asp Tyr Leu Gly Tyr Val Leu
145                 150                 155                 160
Phe Phe Pro Ser Leu Phe Ala Gly Pro Ser Phe Glu Tyr Val Asp Tyr
                165                 170                 175
Arg Arg Trp Ile Asp Thr Thr Leu Phe Asp Val Pro Pro Gly Thr Asp
                180                 185                 190
Pro Ser Lys Val Pro Pro Thr Arg Lys Lys Arg Lys Ile Pro Arg Ser
            195                 200                 205
Gly Thr Pro Ala Ala Lys Lys Ala Leu Ala Gly Leu Gly Trp Ile Leu
210                 215                 220
Ala Phe Leu Gln Leu Gly Ser Leu Tyr Asn Gln Glu Leu Val Leu Asp
225                 230                 235                 240
Glu Thr Phe Met Gln Tyr Ser Phe Val Gln Arg Val Trp Ile Leu His
                245                 250                 255
Met Leu Gly Phe Thr Ala Arg Leu Lys Tyr Tyr Gly Val Trp Tyr Leu
                260                 265                 270
Thr Glu Gly Ala Cys Val Leu Ser Gly Met Gly Tyr Asn Gly Phe Asp
            275                 280                 285
Pro Lys Ser Gly Lys Val Phe Trp Asn Arg Leu Glu Asn Val Asp Pro
290                 295                 300
Trp Ser Leu Glu Thr Ala Gln Asn Ser His Gly Tyr Leu Gly Ser Trp
305                 310                 315                 320
Asn Lys Asn Thr Asn His Trp Leu Arg Asn Tyr Val Tyr Leu Arg Val
                325                 330                 335
Thr Pro Lys Gly Lys Pro Gly Phe Arg Ala Ser Leu Ala Thr Phe
                340                 345                 350
Val Thr Ser Ala Phe Trp His Gly Phe Tyr Pro Gly Tyr Tyr Leu Thr
            355                 360                 365
Phe Val Leu Gly Ser Phe Ile Gln Thr Val Ala Lys Asn Phe Arg Arg
        370                 375                 380
His Val Arg Pro Phe Phe Leu Thr Pro Asp Gly Ser Arg Pro Thr Ala
385                 390                 395                 400
Tyr Lys Lys Tyr Tyr Asp Ile Ala Ser Tyr Val Val Thr Gln Leu Thr
                405                 410                 415
```

```
Leu Ser Phe Ala Val Met Pro Phe Ile Phe Leu Ser Phe Gly Asp Ser
                420                 425                 430

Ile Lys Val Trp His Ser Val Tyr Phe Tyr Gly Ile Val Gly Asn Ile
            435                 440                 445

Val Ser Leu Ala Phe Phe Val Ser Pro Ala Arg Gly Leu Leu Leu Lys
        450                 455                 460

Lys Leu Lys Ala Arg Asn Lys Pro His Val Pro Arg Ala Val Ser Ser
465                 470                 475                 480

Glu Asn Ile Arg Gln Pro Thr Leu Gly Leu Pro Asn Asp Ala Ile Gln
                485                 490                 495

Glu Phe Asp Asp Ala Val Gln Glu Ile Arg Ala Glu Ile Glu Ser Arg
            500                 505                 510

Gln Arg Arg Gly Ser Leu Ala His Met Pro Ile Gly Asp Glu Leu Lys
        515                 520                 525

Ala Ala Val Glu Asp Lys Ile Gly Arg Gly His
530                 535

<210> SEQ ID NO 51
<211> LENGTH: 539
<212> TYPE: PRT
<213> ORGANISM: Schizosaccharomyces pombe

<400> SEQUENCE: 51

Met Leu Pro Tyr Val Asp Leu Leu Lys Leu Ile Ala Ser Phe Leu Leu
1               5                   10                  15

Ser Tyr Pro Leu Ala Ala Leu Leu Lys Arg Ile Pro Asp Ala Gln Pro
                20                  25                  30

Trp Lys Lys Asn Ala Phe Ile Ile Ala Val Ser Leu Phe Tyr Leu Val
            35                  40                  45

Gly Leu Phe Asp Leu Trp Asp Gly Leu Arg Thr Leu Ala Tyr Ser Ala
        50                  55                  60

Ala Gly Ile Tyr Ala Ile Ala Tyr Tyr Ile Asp Gly Ser Leu Met Pro
65                  70                  75                  80

Trp Ile Gly Phe Ile Phe Leu Met Gly His Met Ser Ile Ser His Ile
                85                  90                  95

Tyr Arg Gln Ile Ile Asp Asp Ala His Val Thr Asp Ile Thr Gly Ala
                100                 105                 110

Gln Met Val Leu Val Met Lys Leu Ser Ser Phe Cys Trp Asn Val His
            115                 120                 125

Asp Gly Arg Leu Ser Gln Glu Gln Leu Ser Asp Pro Gln Lys Tyr Ala
        130                 135                 140

Ala Ile Lys Asp Phe Pro Gly Ile Leu Asp Tyr Leu Gly Tyr Val Leu
145                 150                 155                 160

Phe Phe Pro Ser Leu Phe Ala Gly Pro Ser Phe Glu Tyr Val Asp Tyr
                165                 170                 175

Arg Arg Trp Ile Asp Thr Thr Leu Phe Asp Val Pro Gly Thr Asp
            180                 185                 190

Pro Ser Lys Val Pro Pro Thr Arg Lys Arg Lys Ile Pro Arg Ser
        195                 200                 205

Gly Thr Pro Ala Ala Lys Lys Ala Leu Ala Gly Leu Gly Trp Ile Leu
        210                 215                 220

Ala Phe Leu Gln Leu Gly Ser Leu Tyr Asn Gln Glu Leu Val Leu Asp
225                 230                 235                 240

Glu Thr Phe Met Gln Tyr Ser Phe Val Gln Arg Val Trp Ile Leu His
```

-continued

```
                245                 250                 255
Met Leu Gly Phe Thr Ala Arg Leu Lys Tyr Tyr Gly Val Trp Tyr Leu
            260                 265                 270

Thr Glu Gly Ala Cys Val Leu Ser Gly Met Gly Tyr Asn Gly Phe Asp
        275                 280                 285

Pro Lys Ser Gly Lys Val Phe Trp Asn Arg Leu Glu Asn Val Asp Pro
    290                 295                 300

Trp Ser Leu Glu Thr Ala Gln Asn Ser His Gly Tyr Leu Gly Ser Trp
305                 310                 315                 320

Asn Lys Asn Thr Asn His Trp Leu Arg Asn Tyr Val Tyr Leu Arg Val
            325                 330                 335

Thr Pro Lys Gly Lys Pro Gly Phe Arg Ala Ser Leu Ala Thr Phe
        340                 345                 350

Val Thr Ser Ala Phe Trp His Gly Phe Tyr Pro Gly Tyr Tyr Leu Thr
            355                 360                 365

Phe Val Leu Gly Ser Phe Ile Gln Thr Val Ala Lys Asn Phe Arg Arg
        370                 375                 380

His Val Arg Pro Phe Phe Leu Thr Pro Asp Gly Ser Arg Pro Thr Ala
385                 390                 395                 400

Tyr Lys Lys Tyr Tyr Asp Ile Ala Ser Tyr Val Val Thr Gln Leu Thr
            405                 410                 415

Leu Ser Phe Ala Val Met Pro Phe Ile Phe Leu Ser Phe Gly Asp Ser
        420                 425                 430

Ile Lys Val Trp His Ser Val Tyr Phe Tyr Gly Ile Val Gly Asn Ile
            435                 440                 445

Val Ser Leu Ala Phe Phe Val Ser Pro Ala Arg Gly Leu Leu Leu Lys
        450                 455                 460

Lys Leu Lys Ala Arg Asn Lys Pro His Val Pro Arg Ala Val Ser Ser
465                 470                 475                 480

Glu Asn Ile Arg Gln Pro Thr Leu Gly Leu Pro Asn Asp Ala Ile Gln
            485                 490                 495

Glu Phe Asp Asp Ala Val Gln Glu Ile Arg Ala Glu Ile Glu Ser Arg
        500                 505                 510

Gln Arg Arg Gly Ser Leu Ala His Met Pro Ile Gly Asp Glu Leu Lys
    515                 520                 525

Ala Ala Val Glu Asp Lys Ile Gly Arg Gly His
    530                 535
```

<210> SEQ ID NO 52
<211> LENGTH: 619
<212> TYPE: PRT
<213> ORGANISM: Saccharomyces cerevisiae

<400> SEQUENCE: 52

```
Met Tyr Asn Pro Val Asp Ala Val Leu Thr Lys Ile Ile Thr Asn Tyr
1               5                   10                  15

Gly Ile Asp Ser Phe Thr Leu Arg Tyr Ala Ile Cys Leu Leu Gly Ser
            20                  25                  30

Phe Pro Leu Asn Ala Ile Leu Lys Arg Ile Pro Glu Lys Arg Ile Gly
        35                  40                  45

Leu Lys Cys Cys Phe Ile Ile Ser Met Ser Met Phe Tyr Leu Phe Gly
    50                  55                  60

Val Leu Asn Leu Val Ser Gly Phe Arg Thr Leu Phe Ile Ser Thr Met
65                  70                  75                  80
```

-continued

```
Phe Thr Tyr Leu Ile Ser Arg Phe Tyr Arg Ser Lys Phe Met Pro His
                 85                  90                  95

Leu Asn Phe Met Phe Val Met Gly His Leu Ala Ile Asn His Ile His
            100                 105                 110

Ala Gln Phe Leu Asn Glu Gln Thr Gln Thr Thr Val Asp Ile Thr Ser
        115                 120                 125

Ser Gln Met Val Leu Ala Met Lys Leu Thr Ser Phe Ala Trp Ser Tyr
    130                 135                 140

Tyr Asp Gly Ser Cys Thr Ser Glu Ser Asp Phe Lys Asp Leu Thr Glu
145                 150                 155                 160

His Gln Lys Ser Arg Ala Val Arg Gly His Pro Pro Leu Leu Lys Phe
                165                 170                 175

Leu Ala Tyr Ala Phe Phe Tyr Ser Thr Leu Leu Thr Gly Pro Ser Phe
            180                 185                 190

Asp Tyr Ala Asp Phe Asp Ser Trp Leu Asn Cys Glu Met Phe Arg Asp
        195                 200                 205

Leu Pro Glu Ser Lys Lys Pro Met Arg Arg His His Pro Gly Glu Arg
    210                 215                 220

Arg Gln Ile Pro Lys Asn Gly Lys Leu Ala Leu Trp Lys Val Val Gln
225                 230                 235                 240

Gly Leu Ala Trp Met Ile Leu Ser Thr Leu Gly Met Lys His Phe Pro
                245                 250                 255

Val Lys Tyr Val Leu Asp Lys Asp Gly Phe Pro Thr Arg Ser Phe Ile
            260                 265                 270

Phe Arg Ile His Tyr Leu Phe Leu Leu Gly Phe Ile His Arg Phe Lys
        275                 280                 285

Tyr Tyr Ala Ala Trp Thr Ile Ser Glu Gly Ser Cys Ile Leu Cys Gly
    290                 295                 300

Leu Gly Tyr Asn Gly Tyr Asp Ser Lys Thr Gln Lys Ile Arg Trp Asp
305                 310                 315                 320

Arg Val Arg Asn Ile Asp Ile Trp Thr Val Glu Thr Ala Gln Asn Thr
                325                 330                 335

Arg Glu Met Leu Glu Ala Trp Asn Met Asn Thr Asn Lys Trp Leu Lys
            340                 345                 350

Tyr Ser Val Tyr Leu Arg Val Thr Lys Lys Gly Lys Lys Pro Gly Phe
        355                 360                 365

Arg Ser Thr Leu Phe Thr Phe Leu Thr Ser Ala Phe Trp His Gly Thr
    370                 375                 380

Arg Pro Gly Tyr Tyr Leu Thr Phe Ala Thr Gly Ala Leu Tyr Gln Thr
385                 390                 395                 400

Cys Gly Lys Ile Tyr Arg Arg Asn Phe Arg Pro Ile Phe Leu Arg Glu
                405                 410                 415

Asp Gly Val Thr Pro Leu Pro Ser Lys Lys Ile Tyr Asp Leu Val Gly
            420                 425                 430

Ile Tyr Ala Ile Lys Leu Ala Phe Gly Tyr Met Val Gln Pro Phe Ile
        435                 440                 445

Ile Leu Asp Leu Lys Pro Ser Leu Met Val Trp Gly Ser Val Tyr Phe
    450                 455                 460

Tyr Val His Ile Ile Val Ala Phe Ser Phe Leu Phe Arg Gly Pro
465                 470                 475                 480

Tyr Ala Lys Gln Val Thr Glu Phe Phe Lys Ser Lys Gln Pro Lys Glu
                485                 490                 495

Ile Phe Ile Arg Lys Gln Lys Lys Leu Glu Lys Asp Ile Ser Ala Ser
```

```
                    500                 505                 510
Ser Pro Asn Leu Gly Gly Ile Leu Lys Ala Lys Ile Glu His Glu Lys
            515                 520                 525

Gly Lys Thr Ala Glu Glu Glu Met Asn Leu Gly Ile Pro Pro Ile
        530                 535                 540

Glu Leu Glu Lys Trp Asp Asn Ala Lys Glu Asp Trp Glu Asp Phe Cys
545                 550                 555                 560

Lys Asp Tyr Lys Glu Trp Arg Asn Lys Asn Gly Leu Glu Ile Glu Glu
                565                 570                 575

Glu Asn Leu Ser Lys Ala Phe Glu Arg Phe Lys Gln Glu Phe Ser Asn
            580                 585                 590

Ala Ala Ser Gly Ser Gly Glu Arg Val Arg Lys Met Ser Phe Ser Gly
            595                 600                 605

Tyr Ser Pro Lys Pro Ile Ser Lys Lys Glu Glu
        610                 615
```

<210> SEQ ID NO 53
<211> LENGTH: 487
<212> TYPE: PRT
<213> ORGANISM: Thalassiosira pseudonana

<400> SEQUENCE: 53

```
Met Arg Leu Tyr Leu Gln Phe Asn Leu Ser Ile Asn Asp Tyr Cys His
1               5                   10                  15

Phe Phe Thr Val Pro Ser Phe Val Lys Glu Gly Val Glu Ser Leu Ser
            20                  25                  30

Ala Ser Thr Gly Gln Asp Val Glu Thr Leu Glu Tyr Leu Leu Gly Met
        35                  40                  45

Leu Ile Cys Tyr Pro Leu Gly Met Ile Met Leu Ala Leu Pro Tyr Gly
    50                  55                  60

Lys Val Lys His Leu Phe Ser Phe Ile Leu Gly Ala Phe Leu Leu Gln
65                  70                  75                  80

Phe Thr Ile Gly Ile Gln Trp Ile His His Leu Ile Ser Ser Met Ile
                85                  90                  95

Ala Tyr Val Met Phe Leu Val Leu Pro Ala Lys Phe Ala Lys Thr Ala
            100                 105                 110

Val Pro Val Phe Ala Met Ile Tyr Ile Thr Ala Gly His Leu His Arg
        115                 120                 125

Gln Tyr Ile Asn Tyr Leu Gly Trp Asp Met Asp Phe Thr Gly Pro Gln
    130                 135                 140

Met Val Leu Thr Met Lys Leu Tyr Met Leu Ala Tyr Asn Leu Ala Asp
145                 150                 155                 160

Gly Asp Leu Leu Lys Lys Gly Lys Glu Asp Arg Ala Ala Lys Lys Cys
                165                 170                 175

Ala Asp Val Ala Ile Ser Ser Val Pro Gly Ile Ile Glu Tyr Leu Gly
            180                 185                 190

Tyr Thr Phe Cys Phe Ala Ser Val Leu Ala Gly Pro Ala Phe Glu Tyr
        195                 200                 205

Lys Phe Tyr Ala Asp Ala Cys Asp Gly Ser Leu Leu Tyr Asp Lys Ser
    210                 215                 220

Gly Lys Pro Lys Gly Lys Ile Pro Ser Gln Val Trp Pro Thr Leu Arg
225                 230                 235                 240

Pro Leu Phe Gly Ser Leu Leu Cys Leu Gly Ile Phe Val Val Gly Thr
                245                 250                 255
```

```
Gly Met Tyr Pro Leu Leu Asp Pro Asn Asp Pro Gln Asn Ala Thr Pro
            260                 265                 270

Ile Pro Leu Thr Pro Glu Met Leu Ala Lys Pro Ala Tyr Ala Arg Tyr
            275                 280                 285

Ala Tyr Ser Trp Leu Ala Leu Phe Phe Ile Arg Phe Lys Tyr Tyr Phe
        290                 295                 300

Ala Trp Met Asn Ala Glu Gly Ala Ser Asn Ile Trp Tyr Ala Gly Phe
305                 310                 315                 320

Glu Gly Phe Asp Ala Ser Gly Asn Pro Lys Gly Trp Glu Val Ser Asn
                325                 330                 335

Asn Ile Asp Val Ile Gln Phe Glu Thr Ala Pro Asn Leu Lys Thr Leu
            340                 345                 350

Ser Ala Ala Trp Asn Lys Lys Thr Ala Asn Trp Leu Ala Lys Tyr Val
        355                 360                 365

Tyr Ile Arg Thr Gly Gly Ser Leu Phe Ala Thr Tyr Gly Met Ser Ala
    370                 375                 380

Phe Trp His Gly Phe Tyr Pro Gly Tyr Tyr Leu Phe Phe Met Ser Val
385                 390                 395                 400

Pro Met Met Ala Phe Cys Glu Arg Ile Gly Arg Lys Lys Leu Thr Pro
                405                 410                 415

Arg Phe Gly Asn Gly Lys Lys Trp Ser Pro Tyr Gly Ile Val Cys Ile
                420                 425                 430

Ile Ala Thr Ser Leu Met Thr Glu Tyr Met Ile Gln Pro Phe Gln Leu
            435                 440                 445

Leu Ala Phe Asp Trp Ala Trp Glu Asn Trp Ser Ser Tyr Tyr Phe Ala
        450                 455                 460

Gly His Ile Val Cys Val Val Phe Tyr Leu Val Val Ser Asn Met Pro
465                 470                 475                 480

Thr Pro Lys Thr Lys Glu Thr
                485

<210> SEQ ID NO 54
<211> LENGTH: 462
<212> TYPE: PRT
<213> ORGANISM: Arabidopsis thaliana

<400> SEQUENCE: 54

Met Asp Met Ser Ser Met Ala Gly Ser Ile Gly Val Ser Val Ala Val
1               5                   10                  15

Leu Arg Phe Leu Leu Cys Phe Val Ala Thr Ile Pro Val Ser Phe Ala
            20                  25                  30

Cys Arg Ile Val Pro Ser Arg Leu Gly Lys His Leu Tyr Ala Ala Ala
        35                  40                  45

Ser Gly Ala Phe Leu Ser Tyr Leu Ser Phe Gly Phe Ser Ser Asn Leu
    50                  55                  60

His Phe Leu Val Pro Met Thr Ile Gly Tyr Ala Ser Met Ala Ile Tyr
65                  70                  75                  80

Arg Pro Lys Cys Gly Ile Ile Thr Phe Phe Leu Gly Phe Ala Tyr Leu
                85                  90                  95

Ile Gly Cys His Val Phe Tyr Met Ser Gly Asp Ala Trp Lys Glu Gly
            100                 105                 110

Gly Ile Asp Ser Thr Gly Ala Leu Met Val Leu Thr Leu Lys Val Ile
        115                 120                 125

Ser Cys Ser Met Asn Tyr Asn Asp Gly Met Leu Lys Glu Glu Gly Leu
    130                 135                 140
```

```
Arg Glu Ala Gln Lys Lys Asn Arg Leu Ile Gln Met Pro Ser Leu Ile
145                 150                 155                 160

Glu Tyr Phe Gly Tyr Cys Leu Cys Gly Ser His Phe Ala Gly Pro
            165                 170                 175

Val Tyr Glu Met Lys Asp Tyr Leu Glu Trp Thr Glu Gly Lys Gly Ile
            180                 185                 190

Trp Asp Thr Thr Glu Lys Arg Lys Lys Pro Ser Pro Tyr Gly Ala Thr
            195                 200                 205

Ile Arg Ala Ile Leu Gln Ala Ala Ile Cys Met Ala Leu Tyr Leu Tyr
    210                 215                 220

Leu Val Pro Gln Tyr Pro Leu Thr Arg Phe Thr Glu Pro Val Tyr Gln
225                 230                 235                 240

Glu Trp Gly Phe Leu Arg Lys Phe Ser Tyr Gln Tyr Met Ala Gly Phe
                245                 250                 255

Thr Ala Arg Trp Lys Tyr Tyr Phe Ile Trp Ser Ile Ser Glu Ala Ser
            260                 265                 270

Ile Ile Ile Ser Gly Leu Gly Phe Ser Gly Trp Thr Asp Asp Ala Ser
    275                 280                 285

Pro Lys Pro Lys Trp Asp Arg Ala Lys Asn Val Asp Ile Leu Gly Val
290                 295                 300

Glu Leu Ala Lys Ser Ala Val Gln Ile Pro Leu Val Trp Asn Ile Gln
305                 310                 315                 320

Val Ser Thr Trp Leu Arg His Tyr Val Tyr Glu Arg Leu Val Gln Asn
            325                 330                 335

Gly Lys Lys Ala Gly Phe Phe Gln Leu Leu Ala Thr Gln Thr Val Ser
            340                 345                 350

Ala Val Trp His Gly Leu Tyr Pro Gly Tyr Met Met Phe Val Gln
            355                 360                 365

Ser Ala Leu Met Ile Ala Gly Ser Arg Val Ile Tyr Arg Trp Gln Gln
370                 375                 380

Ala Ile Ser Pro Lys Met Ala Met Leu Arg Asn Ile Met Val Phe Ile
385                 390                 395                 400

Asn Phe Leu Tyr Thr Val Leu Val Leu Asn Tyr Ser Ala Val Gly Phe
                405                 410                 415

Met Val Leu Ser Leu His Glu Thr Leu Thr Ala Tyr Gly Ser Val Tyr
            420                 425                 430

Tyr Ile Gly Thr Ile Ile Pro Val Gly Leu Ile Leu Ser Tyr Val
            435                 440                 445

Val Pro Ala Lys Pro Ser Arg Pro Lys Pro Arg Lys Glu Glu
    450                 455                 460

<210> SEQ ID NO 55
<211> LENGTH: 465
<212> TYPE: PRT
<213> ORGANISM: Arabidopsis thaliana

<400> SEQUENCE: 55

Met Glu Leu Leu Asp Met Asn Ser Met Ala Ala Ser Ile Gly Val Ser
1               5                   10                  15

Val Ala Val Leu Arg Phe Leu Leu Cys Phe Val Ala Thr Ile Pro Ile
            20                  25                  30

Ser Phe Leu Trp Arg Phe Ile Pro Ser Arg Leu Gly Lys His Ile Tyr
        35                  40                  45

Ser Ala Ala Ser Gly Ala Phe Leu Ser Tyr Leu Ser Phe Gly Phe Ser
```

-continued

```
                50                  55                  60
Ser Asn Leu His Phe Leu Val Pro Met Thr Ile Gly Tyr Ala Ser Met
 65                  70                  75                  80

Ala Ile Tyr Arg Pro Leu Ser Gly Phe Ile Thr Phe Leu Gly Phe
                     85                  90                  95

Ala Tyr Leu Ile Gly Cys His Val Phe Tyr Met Ser Gly Asp Ala Trp
                    100                 105                 110

Lys Glu Gly Gly Ile Asp Ser Thr Gly Ala Leu Met Val Leu Thr Leu
                    115                 120                 125

Lys Val Ile Ser Cys Ser Ile Asn Tyr Asn Asp Gly Met Leu Lys Glu
                    130                 135                 140

Glu Gly Leu Arg Glu Ala Gln Lys Lys Asn Arg Leu Ile Gln Met Pro
145                 150                 155                 160

Ser Leu Ile Glu Tyr Phe Gly Tyr Cys Leu Cys Cys Gly Ser His Phe
                    165                 170                 175

Ala Gly Pro Val Phe Glu Met Lys Asp Tyr Leu Glu Trp Thr Glu Glu
                    180                 185                 190

Lys Gly Ile Trp Ala Val Ser Glu Lys Gly Lys Arg Pro Ser Pro Tyr
                    195                 200                 205

Gly Ala Met Ile Arg Ala Val Phe Gln Ala Ala Ile Cys Met Ala Leu
                    210                 215                 220

Tyr Leu Tyr Leu Val Pro Gln Phe Pro Leu Thr Arg Phe Thr Glu Pro
225                 230                 235                 240

Val Tyr Gln Glu Trp Gly Phe Leu Lys Arg Phe Gly Tyr Gln Tyr Met
                    245                 250                 255

Ala Gly Phe Thr Ala Arg Trp Lys Tyr Tyr Phe Ile Trp Ser Ile Ser
                    260                 265                 270

Glu Ala Ser Ile Ile Ser Gly Leu Gly Phe Ser Gly Trp Thr Asp
                    275                 280                 285

Glu Thr Gln Thr Lys Ala Lys Trp Asp Arg Ala Lys Asn Val Asp Ile
                    290                 295                 300

Leu Gly Val Glu Leu Ala Lys Ser Ala Val Gln Ile Pro Leu Phe Trp
305                 310                 315                 320

Asn Ile Gln Val Ser Thr Trp Leu Arg His Tyr Val Tyr Glu Arg Ile
                    325                 330                 335

Val Lys Pro Gly Lys Lys Ala Gly Phe Phe Gln Leu Leu Ala Thr Gln
                    340                 345                 350

Thr Val Ser Ala Val Trp His Gly Leu Tyr Pro Gly Tyr Ile Ile Phe
                    355                 360                 365

Phe Val Gln Ser Ala Leu Met Ile Asp Gly Ser Lys Ala Ile Tyr Arg
                    370                 375                 380

Trp Gln Gln Ala Ile Pro Pro Lys Met Ala Met Leu Arg Asn Val Leu
385                 390                 395                 400

Val Leu Ile Asn Phe Leu Tyr Thr Val Val Leu Asn Tyr Ser Ser
                    405                 410                 415

Val Gly Phe Met Val Leu Ser Leu His Glu Thr Leu Val Ala Phe Lys
                    420                 425                 430

Ser Val Tyr Tyr Ile Gly Thr Val Ile Pro Ile Ala Val Leu Leu Leu
                    435                 440                 445

Ser Tyr Leu Val Pro Val Lys Pro Val Arg Pro Lys Thr Arg Lys Glu
                    450                 455                 460

Glu
465
```

<210> SEQ ID NO 56
<211> LENGTH: 459
<212> TYPE: PRT
<213> ORGANISM: Oryza sativa

<400> SEQUENCE: 56

```
Met Gly Leu Glu Met Glu Gly Met Ala Ala Ile Gly Val Ser Val
1               5                   10                  15

Pro Val Leu Arg Phe Leu Leu Cys Phe Ala Ala Thr Ile Pro Thr Gly
            20                  25                  30

Leu Met Trp Arg Ala Val Pro Gly Ala Ala Gly Arg His Leu Tyr Ala
        35                  40                  45

Gly Leu Thr Gly Ala Ala Leu Ser Tyr Leu Ser Phe Gly Ala Thr Ser
    50                  55                  60

Asn Leu Leu Phe Val Val Pro Met Ala Phe Gly Tyr Leu Ala Met Leu
65                  70                  75                  80

Leu Cys Arg Arg Leu Ala Gly Leu Val Thr Phe Leu Gly Ala Phe Gly
                85                  90                  95

Phe Leu Ile Ala Cys His Met Tyr Tyr Met Ser Gly Asp Ala Trp Lys
            100                 105                 110

Glu Gly Gly Ile Asp Ala Thr Gly Ala Leu Met Val Leu Thr Leu Lys
        115                 120                 125

Ile Ile Ser Cys Ala Ile Asn Tyr Ser Asp Gly Met Leu Lys Glu Glu
    130                 135                 140

Gly Leu Arg Asp Ala Gln Lys Lys Tyr Arg Leu Ala Lys Leu Pro Ser
145                 150                 155                 160

Leu Ile Glu Tyr Phe Gly Tyr Cys Leu Cys Cys Gly Ser His Phe Ala
                165                 170                 175

Gly Pro Val Tyr Glu Met Lys Asp Tyr Leu Glu Tyr Thr Glu Arg Lys
            180                 185                 190

Gly Leu Trp Ala Ser Pro Thr Pro Ser Pro Leu Leu Pro Thr Leu Arg
        195                 200                 205

Ala Leu Val Gln Ala Gly Ala Cys Met Gly Leu Tyr Leu Tyr Leu Ser
    210                 215                 220

Pro Gln Phe Pro Leu Ser Arg Phe Ser Glu Pro Leu Tyr Tyr Glu Trp
225                 230                 235                 240

Gly Phe Trp His Arg Leu Phe Tyr Gln Tyr Met Ser Gly Phe Thr Ala
                245                 250                 255

Arg Trp Lys Tyr Tyr Phe Ile Trp Ser Leu Ser Glu Ala Ala Ile Ile
            260                 265                 270

Ile Ser Gly Leu Gly Phe Ser Gly Trp Ser Asp Ser Ser Pro Pro Lys
        275                 280                 285

Ala Lys Trp Asp Arg Ala Lys Asn Val Asp Val Leu Gly Val Glu Leu
    290                 295                 300

Ala Thr Ser Ala Val Gln Leu Pro Leu Met Trp Asn Ile Gln Val Ser
305                 310                 315                 320

Thr Trp Leu Arg Tyr Tyr Val Tyr Glu Arg Leu Val Gln Lys Gly Lys
                325                 330                 335

Lys Pro Gly Phe Leu Gln Leu Leu Gly Thr Gln Thr Val Ser Ala Val
            340                 345                 350

Trp His Gly Leu Tyr Pro Gly Tyr Ile Ile Phe Phe Val Gln Ser Ala
        355                 360                 365

Leu Met Ile Asn Gly Ser Lys Val Ile Tyr Arg Trp Gln Gln Ala Val
```

```
                370               375               380
Ser Asn Pro Val Phe His Ala Ile Leu Val Phe Val Asn Phe Ser Tyr
385                 390                 395                 400

Thr Leu Met Val Leu Asn Tyr Ser Cys Ile Gly Phe Gln Val Leu Ser
                405                 410                 415

Phe Lys Glu Thr Leu Ala Ser Tyr Gln Ser Val Tyr Tyr Ile Gly Thr
                420                 425                 430

Ile Val Pro Ile Val Val Leu Gly Tyr Val Ile Lys Pro Ala
                435                 440                 445

Arg Pro Val Lys Pro Lys Ala Arg Lys Ala Glu
    450                 455

<210> SEQ ID NO 57
<211> LENGTH: 370
<212> TYPE: PRT
<213> ORGANISM: Rice

<400> SEQUENCE: 57

Met Tyr Tyr Met Ser Gly Asp Ala Trp Lys Glu Gly Gly Ile Asp Ala
1               5                   10                  15

Thr Gly Ala Leu Met Val Leu Thr Leu Lys Ile Ile Ser Cys Ala Ile
                20                  25                  30

Asn Tyr Ser Asp Gly Met Leu Lys Glu Gly Leu Arg Asp Ala Gln
                35                  40                  45

Lys Lys Tyr Arg Leu Ala Lys Leu Pro Ser Leu Ile Glu Tyr Phe Gly
    50                  55                  60

Tyr Cys Leu Cys Cys Gly Ser His Phe Ala Gly Pro Val Tyr Glu Met
65                  70                  75                  80

Lys Asp Tyr Leu Glu Tyr Thr Glu Arg Lys Gly Leu Trp Ala Ser Pro
                85                  90                  95

Thr Pro Ser Pro Leu Leu Pro Thr Leu Arg Ala Leu Val Gln Ala Gly
                100                 105                 110

Ala Cys Met Gly Leu Tyr Leu Tyr Leu Ser Pro Gln Phe Pro Leu Ser
                115                 120                 125

Arg Phe Ser Glu Pro Leu Tyr Tyr Glu Trp Gly Phe Trp His Arg Leu
                130                 135                 140

Phe Tyr Gln Tyr Met Ser Gly Phe Thr Ala Arg Trp Lys Tyr Tyr Phe
145                 150                 155                 160

Ile Trp Ser Leu Ser Glu Ala Ala Ile Ile Ser Gly Leu Gly Phe
                165                 170                 175

Ser Gly Trp Ser Asp Ser Ser Pro Pro Lys Ala Lys Trp Asp Arg Ala
                180                 185                 190

Lys Asn Val Asp Val Leu Gly Val Glu Leu Ala Thr Ser Ala Val Gln
                195                 200                 205

Leu Pro Leu Met Trp Asn Ile Gln Val Ser Thr Trp Leu Arg Tyr Tyr
                210                 215                 220

Val Tyr Glu Arg Leu Val Gln Lys Gly Lys Pro Gly Phe Leu Gln
225                 230                 235                 240

Leu Leu Gly Thr Gln Thr Val Ser Ala Val Trp His Gly Leu Tyr Pro
                245                 250                 255

Gly Tyr Ile Ile Phe Phe Val Gln Ser Ala Leu Met Ile Asn Gly Ser
                260                 265                 270

Lys Val Ile Tyr Arg Trp Gln Gln Ala Val Ser Asn Pro Val Phe His
                275                 280                 285
```

```
Ala Ile Leu Val Phe Val Asn Phe Ser Tyr Thr Leu Met Val Leu Asn
    290                 295                 300

Tyr Ser Cys Ile Gly Phe Gln Phe Val Phe Thr Met Leu Tyr Thr Leu
305                 310                 315                 320

Arg Phe Leu Gln Val Leu Ser Phe Lys Glu Thr Leu Ala Ser Tyr Gln
                325                 330                 335

Ser Val Tyr Tyr Ile Gly Thr Ile Val Pro Ile Val Val Leu Leu
                340                 345                 350

Gly Tyr Val Ile Lys Pro Ala Arg Pro Val Lys Pro Lys Ala Arg Lys
            355                 360                 365

Ala Glu
    370

<210> SEQ ID NO 58
<211> LENGTH: 722
<212> TYPE: PRT
<213> ORGANISM: Drosophila melanogaster

<400> SEQUENCE: 58

Met Leu Glu Pro Pro Lys Phe Ile Glu Asn Asp Cys Tyr Asn Gly Ser
1               5                   10                  15

Arg Thr Phe Thr Trp Leu Ala Asp Met Val Gly Leu Ser Val Asp Leu
            20                  25                  30

Val Asn Phe Leu Ile Cys Gln Ile Ser Ala Leu Phe Leu Ala Ser Leu
        35                  40                  45

Phe Arg Ser Met Leu His Pro Ser Lys Val Ser Ser Lys Leu Arg His
    50                  55                  60

Thr Phe Ala Leu Ser Ile Gly Leu Ala Phe Gly Tyr Phe Cys Phe Gly
65                  70                  75                  80

Gln Gln Ala Ile His Ile Ala Gly Leu Pro Ala Ile Cys Tyr Ile Val
                85                  90                  95

Ile Arg Thr Gln Asp Pro Arg Ile Val Gln Arg Ala Val Leu Leu Val
            100                 105                 110

Ala Met Ser Tyr Leu Leu Cys Val His Leu Met Arg Gln Leu Tyr Asp
        115                 120                 125

Tyr Gly Ser Tyr Ala Leu Asp Ile Thr Gly Pro Leu Met Ile Ile Thr
    130                 135                 140

Gln Lys Val Thr Ser Leu Ala Phe Ser Ile His Asp Gly Phe Val Arg
145                 150                 155                 160

Gly Asp Glu Glu Leu Thr Lys Ala Gln Gln Tyr His Ala Ile Arg Lys
                165                 170                 175

Met Pro Ser Ala Leu Glu Tyr Phe Ser Tyr Val Trp His Phe Gln Ser
            180                 185                 190

Ile Leu Ala Gly Pro Leu Val Phe Tyr Lys Asp Tyr Ile Glu Phe Val
        195                 200                 205

Glu Gly Tyr Asn Leu Leu Ser Thr Pro Pro Gly Asn Gly Asn Leu Asp
    210                 215                 220

Ser Ser Lys Arg Glu Val Val Leu Glu Pro Ser Pro Thr Lys Ala Val
225                 230                 235                 240

Ile Arg Lys Val Val Gly Ser Leu Val Cys Ala Phe Ile Phe Met Lys
                245                 250                 255

Phe Val Lys Ile Tyr Pro Val Lys Asp Met Lys Glu Asp Asp Phe Met
            260                 265                 270

Asn Asn Thr Ser Met Val Tyr Lys Tyr Trp Tyr Ala Met Met Ala Thr
        275                 280                 285
```

```
Thr Cys Ile Arg Phe Lys Tyr Tyr His Ala Trp Leu Leu Ala Asp Ala
290                 295                 300

Ile Cys Asn Asn Ser Gly Leu Gly Phe Thr Gly Tyr Asp Lys Asp Gly
305                 310                 315                 320

Asn Ser Lys Trp Asp Leu Ile Ser Asn Ile Asn Val Leu Ser Phe Glu
                325                 330                 335

Phe Ser Thr Asn Met Arg Asp Ala Ile Asn Asn Trp Asn Cys Gly Thr
            340                 345                 350

Asn Arg Trp Leu Arg Thr Leu Val Tyr Glu Arg Val Pro Gln Gln Tyr
        355                 360                 365

Gly Thr Leu Leu Thr Phe Ala Leu Ser Ala Val Trp His Gly Phe Tyr
    370                 375                 380

Pro Gly Tyr Tyr Leu Thr Phe Ala Thr Gly Ala Val Val Val Thr Ala
385                 390                 395                 400

Ala Arg Thr Gly Arg Arg Leu Phe Arg His Arg Phe Gln Ser Thr Gln
                405                 410                 415

Val Thr Arg Met Phe Tyr Asp Ile Leu Thr Cys Leu Ile Thr Arg Val
                420                 425                 430

Val Leu Gly Tyr Ala Thr Phe Pro Phe Val Leu Leu Glu Phe Met Gly
        435                 440                 445

Ser Ile Lys Leu Tyr Leu Arg Phe Tyr Leu Cys Leu His Ile Ile Ser
    450                 455                 460

Leu Val Thr Ile Phe Ile Leu Pro Lys Phe Ile Arg Gly Glu Arg Arg
465                 470                 475                 480

Leu Arg Thr Ser Asn Gly Asn Gly Asn Val Arg Leu Ser Gly Ser Gly
                485                 490                 495

Asn Thr Lys Asp Ala Val Thr Thr Ser Val Glu Ser Thr Ala Ala Leu
                500                 505                 510

Thr Ala Gly Asn Asp Leu Asn Glu Asp Lys Glu Glu Asp Lys His Ala
        515                 520                 525

Gln Cys Lys Val His Thr Pro Thr Gln Gln Pro Ala Ala Gly Pro
    530                 535                 540

His Lys Thr Thr Val Glu Gln Pro Thr Glu Gln Pro Asn Asn Val Asn
545                 550                 555                 560

Leu Arg Ser Arg Pro Gln Gln Gln Pro His Leu Glu Lys Lys Ala
                565                 570                 575

Met Pro Pro Thr Cys Ala Arg Asp Ala Val Ser Val Pro His Asp Gln
            580                 585                 590

Cys Glu Met Asp Gln Leu Ser Ser Lys Leu Lys Glu Lys Ile Glu Ala
        595                 600                 605

Glu Thr Lys Asn Ile Glu Glu Phe Ile Asp Lys Thr Val Thr Glu Thr
    610                 615                 620

Val Ser Gly Ile Val Glu Phe Lys Asn Asp Leu Met Arg Asp Ile Glu
625                 630                 635                 640

Phe Pro Lys Leu Lys Leu Pro Gly Ser Asn Gly Ala Ile Ser Leu Asp
                645                 650                 655

Ser Ser Asn Gly Gly Gly Leu Arg Lys Arg Asn Ile Ser Ser Val His
                660                 665                 670

Asp Asn Gly Thr Asp Pro Gly His Ala Thr Ala Asp Leu His Pro Pro
        675                 680                 685

Leu Glu Glu Asn Gly Ala Ala Phe Leu Lys Lys Glu Ile Glu Val Ile
    690                 695                 700
```

Asn Ala Val Val Gln Gln Ala Val Pro Ala Val Leu Ser Asn Gly His
705                 710                 715                 720

Ala Lys

<210> SEQ ID NO 59
<211> LENGTH: 471
<212> TYPE: PRT
<213> ORGANISM: Homo Sapiens

<400> SEQUENCE: 59

Lys Thr Ser Ser Phe Ile Arg His Val Ala Thr Leu Leu Gly Leu
1               5                   10                  15

Tyr Leu Ala Leu Phe Cys Phe Gly Trp Tyr Ala Leu His Phe Leu Val
                20                  25                  30

Gln Ser Gly Ile Ser Tyr Cys Ile Met Ile Ile Gly Val Glu Asn
                35                  40                  45

Met His Asn Tyr Cys Phe Val Phe Ala Leu Gly Tyr Leu Thr Val Cys
50                  55                  60

Gln Val Thr Arg Val Tyr Ile Phe Asp Tyr Gly Gln Tyr Ser Ala Asp
65                  70                  75                  80

Phe Ser Gly Pro Met Met Ile Ile Thr Gln Lys Ile Thr Ser Leu Ala
                85                  90                  95

Cys Glu Ile His Asp Gly Met Phe Arg Lys Asp Glu Leu Thr Ser
                100                 105                 110

Ser Gln Arg Asp Leu Ala Val Arg Arg Met Pro Ser Leu Leu Glu Tyr
                115                 120                 125

Leu Ser Tyr Asn Cys Asn Phe Met Gly Ile Leu Ala Gly Pro Leu Cys
130                 135                 140

Ser Tyr Lys Asp Tyr Ile Thr Phe Ile Glu Gly Arg Ser Tyr His Ile
145                 150                 155                 160

Thr Gln Ser Gly Glu Asn Gly Lys Glu Glu Thr Gln Tyr Glu Arg Thr
                165                 170                 175

Glu Pro Ser Pro Asn Thr Ala Val Val Gln Lys Leu Leu Val Cys Gly
                180                 185                 190

Leu Ser Leu Leu Phe His Leu Thr Ile Cys Thr Thr Leu Pro Val Glu
                195                 200                 205

Tyr Asn Ile Asp Glu His Phe Gln Ala Thr Ala Ser Trp Pro Thr Lys
                210                 215                 220

Ile Ile Tyr Leu Tyr Ile Ser Leu Leu Ala Ala Arg Pro Lys Tyr Tyr
225                 230                 235                 240

Phe Ala Trp Thr Leu Ala Asp Ala Ile Asn Asn Ala Ala Gly Phe Gly
                245                 250                 255

Phe Arg Gly Tyr Asp Glu Asn Gly Ala Ala Arg Trp Asp Leu Ile Ser
                260                 265                 270

Asn Leu Arg Ile Gln Gln Ile Glu Met Ser Thr Ser Phe Lys Met Phe
                275                 280                 285

Leu Asp Asn Trp Asn Ile Gln Thr Ala Leu Trp Leu Lys Arg Val Cys
                290                 295                 300

Tyr Glu Arg Thr Ser Phe Ser Pro Thr Ile Gln Thr Phe Ile Leu Ser
305                 310                 315                 320

Ala Ile Trp His Gly Val Tyr Pro Gly Tyr Tyr Leu Thr Phe Leu Thr
                325                 330                 335

Gly Val Leu Met Thr Leu Ala Arg Ala Met Arg Asn Asn Phe Arg
                340                 345                 350

```
His Tyr Phe Ile Glu Pro Ser Gln Leu Lys Leu Phe Tyr Asp Val Ile
            355                 360                 365

Thr Trp Ile Val Thr Gln Val Ala Ile Ser Tyr Thr Val Val Pro Phe
370                 375                 380

Val Leu Leu Ser Ile Lys Pro Ser Leu Thr Phe Tyr Ser Ser Trp Tyr
385                 390                 395                 400

Tyr Cys Leu His Ile Leu Gly Ile Leu Val Leu Leu Leu Pro Val
                405                 410                 415

Lys Lys Thr Gln Arg Lys Asn Thr His Glu Asn Ile Gln Leu Ser
                420                 425                 430

Gln Ser Lys Lys Phe Asp Glu Gly Glu Asn Ser Leu Gly Gln Asn Ser
                435                 440                 445

Phe Ser Thr Thr Asn Asn Val Cys Asn Gln Asn Gln Glu Ile Ala Ser
450                 455                 460

Arg His Ser Ser Leu Lys Gln
465                 470

<210> SEQ ID NO 60
<211> LENGTH: 471
<212> TYPE: PRT
<213> ORGANISM: Homo Sapiens

<400> SEQUENCE: 60

Lys Thr Ser Ser Phe Ile Arg His Val Val Ala Thr Leu Leu Gly Leu
1               5                   10                  15

Tyr Leu Ala Leu Phe Cys Phe Gly Trp Tyr Ala Leu His Phe Leu Val
                20                  25                  30

Gln Ser Gly Ile Ser Tyr Cys Ile Met Ile Ile Gly Val Glu Asn
            35                  40                  45

Met His Asn Tyr Cys Phe Val Phe Ala Leu Gly Tyr Leu Thr Val Cys
    50                  55                  60

Gln Val Thr Arg Val Tyr Ile Phe Asp Tyr Gln Tyr Ser Ala Asp
65                  70                  75                  80

Phe Ser Gly Pro Met Met Ile Leu Thr Gln Lys Ile Thr Ser Leu Ala
                85                  90                  95

Cys Glu Ile His Asp Gly Met Phe Arg Lys Asp Glu Glu Leu Thr Ser
            100                 105                 110

Ser Gln Arg Asp Leu Ala Val Arg Arg Met Pro Ser Leu Leu Glu Tyr
        115                 120                 125

Leu Ser Tyr Asn Cys Asn Phe Met Gly Ile Leu Ala Gly Pro Leu Cys
    130                 135                 140

Ser Tyr Lys Asp Tyr Ile Thr Phe Ile Glu Gly Arg Ser Tyr His Ile
145                 150                 155                 160

Thr Gln Ser Gly Glu Asn Gly Lys Glu Thr Gln Tyr Glu Arg Thr
                165                 170                 175

Glu Pro Ser Pro Asn Thr Ala Val Val Gln Lys Leu Leu Val Cys Gly
            180                 185                 190

Leu Ser Leu Leu Phe His Leu Thr Ile Cys Thr Thr Leu Pro Val Glu
        195                 200                 205

Tyr Asn Ile Asp Glu His Phe Gln Ala Thr Ala Ser Trp Pro Thr Lys
    210                 215                 220

Ile Ile Tyr Leu Tyr Ile Ser Leu Leu Ala Ala Arg Pro Lys Tyr Tyr
225                 230                 235                 240

Phe Ala Trp Thr Leu Ala Asp Ala Ile Asn Asn Ala Ala Gly Phe Gly
                245                 250                 255
```

```
Phe Arg Gly Tyr Asp Glu Asn Gly Ala Ala Arg Trp Asp Leu Ile Ser
            260                 265                 270

Asn Leu Arg Ile Gln Gln Ile Glu Met Ser Thr Ser Phe Lys Met Phe
            275                 280                 285

Leu Asp Asn Trp Asn Ile Gln Thr Ala Leu Trp Leu Lys Arg Val Cys
            290                 295                 300

Tyr Glu Arg Thr Ser Phe Ser Pro Thr Ile Gln Thr Phe Ile Leu Ser
305                 310                 315                 320

Ala Ile Trp His Gly Val Tyr Pro Gly Tyr Tyr Leu Thr Phe Leu Thr
                325                 330                 335

Gly Val Leu Met Thr Leu Ala Ala Arg Ala Met Arg Asn Asn Phe Arg
                340                 345                 350

His Tyr Phe Ile Glu Pro Ser Gln Leu Lys Leu Phe Tyr Asp Val Ile
                355                 360                 365

Thr Trp Ile Val Thr Gln Val Ala Ile Ser Tyr Thr Val Val Pro Phe
                370                 375                 380

Val Leu Leu Ser Ile Lys Pro Ser Leu Thr Phe Tyr Ser Ser Trp Tyr
385                 390                 395                 400

Tyr Cys Leu His Ile Leu Gly Ile Leu Val Leu Leu Leu Leu Pro Val
                405                 410                 415

Lys Lys Thr Gln Arg Arg Lys Asn Thr His Glu Asn Ile Gln Leu Ser
                420                 425                 430

Gln Ser Arg Lys Phe Asp Glu Gly Glu Asn Ser Leu Gly Gln Asn Ser
                435                 440                 445

Phe Ser Thr Thr Asn Asn Val Cys Asn Gln Asn Gln Glu Ile Ala Ser
            450                 455                 460

Arg His Ser Ser Leu Lys Gln
465                 470

<210> SEQ ID NO 61
<211> LENGTH: 470
<212> TYPE: PRT
<213> ORGANISM: Mus musculus

<400> SEQUENCE: 61

Lys Thr Ser Ser Phe Ile Arg His Val Val Ala Thr Leu Leu Gly Leu
1               5                   10                  15

Tyr Leu Ala Phe Phe Cys Phe Gly Trp Tyr Ala Leu His Phe Leu Val
                20                  25                  30

Gln Ser Gly Ile Ser Tyr Cys Ile Met Ile Ala Gly Val Glu Ser
            35                  40                  45

Met Gln Gln Cys Cys Phe Val Phe Ala Leu Gly Tyr Leu Ser Val Cys
            50                  55                  60

Gln Ile Thr Arg Val Tyr Ile Phe Asp Tyr Gly Gln Tyr Ser Ala Asp
65                  70                  75                  80

Phe Ser Gly Pro Met Met Ile Ile Thr Gln Lys Ile Thr Ser Leu Ala
                85                  90                  95

Tyr Glu Ile His Asp Gly Met Phe Arg Lys Asp Glu Leu Thr Pro
                100                 105                 110

Ser Gln Arg Gly Leu Ala Val Arg Arg Met Pro Ser Leu Leu Glu Tyr
            115                 120                 125

Val Ser Tyr Thr Cys Asn Phe Met Gly Ile Leu Ala Gly Pro Leu Cys
130                 135                 140

Ser Tyr Lys Asp Tyr Ile Ala Phe Ile Glu Gly Arg Ala Ser His Val
```

```
                145                 150                 155                 160
        Ala Gln Pro Ser Glu Asn Gly Lys Asp Glu Gln His Gly Lys Ala Asp
                        165                 170                 175

Pro Ser Pro Asn Ala Ala Val Thr Glu Lys Leu Leu Val Cys Gly Leu
                        180                 185                 190

Ser Leu Leu Phe His Leu Thr Ile Ser Asn Met Leu Pro Val Glu Tyr
                        195                 200                 205

Asn Ile Asp Glu His Phe Gln Ala Thr Ala Ser Trp Pro Thr Lys Ala
                        210                 215                 220

Thr Tyr Leu Tyr Val Ser Leu Leu Ala Ala Arg Pro Lys Tyr Tyr Phe
        225                 230                 235                 240

Ala Trp Thr Leu Ala Asp Ala Ile Asn Asn Ala Ala Gly Phe Gly Phe
                        245                 250                 255

Arg Gly Tyr Asp Lys Asn Gly Val Ala Arg Trp Asp Leu Ile Ser Asn
                        260                 265                 270

Leu Arg Ile Gln Gln Ile Glu Met Ser Thr Ser Phe Lys Met Phe Leu
                        275                 280                 285

Asp Asn Trp Asn Ile Gln Thr Ala Leu Trp Leu Lys Arg Val Cys Tyr
                        290                 295                 300

Glu Arg Ala Thr Phe Ser Pro Thr Ile Gln Thr Phe Leu Ser Ala
        305                 310                 315                 320

Ile Trp His Gly Val Tyr Pro Gly Tyr Tyr Leu Thr Phe Leu Thr Gly
                        325                 330                 335

Val Leu Met Thr Leu Ala Ala Arg Ala Val Arg Asn Asn Phe Arg His
                        340                 345                 350

Tyr Phe Leu Glu Pro Pro Gln Leu Lys Leu Phe Tyr Asp Leu Ile Thr
                        355                 360                 365

Trp Val Ala Thr Gln Ile Thr Ile Ser Tyr Thr Val Val Pro Phe Val
                        370                 375                 380

Leu Leu Ser Ile Lys Pro Ser Phe Thr Phe Tyr Ser Ser Trp Tyr Tyr
        385                 390                 395                 400

Cys Leu His Val Cys Ser Ile Leu Val Leu Leu Leu Pro Val Lys
                        405                 410                 415

Lys Ser Gln Arg Arg Thr Ser Thr Gln Glu Asn Val His Leu Ser Gln
                        420                 425                 430

Ala Lys Lys Phe Asp Glu Arg Asp Asn Pro Leu Gly Gln Asn Ser Phe
                        435                 440                 445

Ser Thr Met Asn Asn Val Cys Asn Gln Asn Arg Asp Thr Gly Ser Arg
                        450                 455                 460

His Ser Ser Leu Thr Gln
        465                 470

<210> SEQ ID NO 62
<211> LENGTH: 492
<212> TYPE: PRT
<213> ORGANISM: Mus musculus

<400> SEQUENCE: 62

Met Ala Ala Arg Pro Ala Ser Leu Ser Tyr Arg Thr Thr Gly Ser
        1               5                   10                  15

Thr Cys Leu His Pro Leu Ser Gln Leu Leu Gly Ile Pro Leu Asp Gln
                        20                  25                  30

Val Asn Phe Val Ala Cys Gln Leu Phe Ala Leu Ser Ala Ala Phe Trp
                        35                  40                  45
```

-continued

```
Phe Arg Ile Tyr Leu His Pro Gly Lys Ala Ser Pro Glu Val Arg His
 50                  55                  60

Thr Leu Ala Thr Ile Leu Gly Ile Tyr Phe Val Phe Cys Phe Gly
 65                  70                  75                  80

Trp Tyr Ala Val His Leu Phe Val Leu Val Leu Met Cys Tyr Gly Val
                 85                  90                  95

Met Val Ser Ala Ser Val Ser Asn Ile His Arg Tyr Ser Phe Phe Val
            100                 105                 110

Ala Met Gly Tyr Leu Thr Ile Cys His Ile Ser Arg Ile Tyr Ile Phe
        115                 120                 125

His Tyr Gly Ile Leu Thr Thr Asp Phe Ser Gly Pro Leu Met Ile Val
130                 135                 140

Thr Gln Lys Ile Thr Thr Leu Ala Phe Gln Val His Asp Gly Leu Gly
145                 150                 155                 160

Arg Lys Ala Glu Asp Leu Ser Ala Glu Gln His Arg Leu Ala Val Lys
                165                 170                 175

Ala Lys Pro Ser Leu Leu Glu Tyr Leu Ser Tyr His Leu Asn Phe Met
            180                 185                 190

Ser Val Ile Ala Gly Pro Cys Asn Asn Phe Lys Asp Tyr Val Ala Phe
        195                 200                 205

Ile Glu Gly Arg His Ile His Met Lys Leu Leu Glu Val Asn Trp Thr
210                 215                 220

Gln Arg Gly Phe Gln Ser Leu Pro Glu Pro Ser Pro Thr Gly Ala Val
225                 230                 235                 240

Ile Gln Lys Leu Cys Val Thr Leu Met Ser Leu Leu Leu Phe Leu Thr
                245                 250                 255

Leu Ser Lys Ser Phe Pro Val Thr Phe Leu Ile Asp Asp Trp Phe Val
            260                 265                 270

His Lys Ala Asn Phe Leu Ser Arg Leu Trp Tyr Leu Tyr Val Val Met
        275                 280                 285

Gln Ala Ala Lys Pro Lys Tyr Tyr Phe Ala Trp Thr Leu Ala Asp Ala
290                 295                 300

Val His Asn Ala Ala Gly Phe Gly Phe Asn Gly Met Asp Thr Asp Gly
305                 310                 315                 320

Lys Ser Arg Trp Asp Leu Leu Ser Asn Leu Asn Ile Trp Lys Ile Glu
                325                 330                 335

Thr Ala Thr Ser Phe Lys Met Tyr Leu Glu Asn Trp Asn Ile Gln Thr
            340                 345                 350

Ser Thr Trp Leu Lys Cys Val Cys Tyr Glu Arg Val Ser Trp Tyr Pro
        355                 360                 365

Thr Val Leu Thr Phe Leu Leu Ser Ala Leu Trp His Gly Val Tyr Pro
370                 375                 380

Gly Tyr Tyr Phe Thr Phe Leu Thr Gly Val Pro Val Thr Leu Ala Ala
385                 390                 395                 400

Arg Ala Val Arg Asn Asn Tyr Arg His His Phe Leu Ser Ser Lys Ala
                405                 410                 415

Arg Lys Ile Ala Tyr Asp Val Val Thr Trp Ala Val Thr Gln Leu Ala
            420                 425                 430

Val Ser Tyr Thr Ala Ala Pro Phe Val Met Leu Ala Val Glu Pro Thr
        435                 440                 445

Ile Ser Leu Tyr Lys Ser Val Phe Phe Leu His Ile Ile Cys Leu
450                 455                 460

Leu Ile Ile Leu Phe Leu Pro Ile Lys Pro His Gln Pro Gln Arg Gln
```

Ser Arg Ser Pro Asn Ser Val Lys Lys Ala Asp
465                 470                 475                 480
            485                 490

<210> SEQ ID NO 63
<211> LENGTH: 497
<212> TYPE: PRT
<213> ORGANISM: Drosophila melanogaster

<400> SEQUENCE: 63

Met Ala Glu Phe Glu Glu Asp Leu Pro His Asn Gly Leu Met Asp Gly
1               5                   10                  15

Ile Ala Ser Gly Val Gly Val Pro Val Glu Ala Leu Arg Leu Leu Leu
            20                  25                  30

Thr Ile Leu Ala Gly Tyr Pro Val Ala Leu Tyr Gln Lys Phe Ile
        35                  40                  45

Ser Val Ile Ala Asp Lys Thr Val His His Met Phe Phe Ala Gly Cys
50                  55                  60

Gly Ala Gly Leu Cys Tyr Phe Asn Tyr Gly Leu Asp Thr Tyr His Ser
65                  70                  75                  80

Leu Ile Ala Ile Leu Thr Thr Tyr Phe Leu Val Leu Leu Arg Lys
            85                  90                  95

Lys Thr Gln Ile Phe Leu Ala Ile Asn Phe Val Phe His Met Ser Tyr
            100                 105                 110

Leu Leu Leu Gly Tyr Phe Tyr Thr Ser Ser Asn Asp Tyr Asp Ile Leu
            115                 120                 125

Trp Thr Met Pro His Cys Ile Leu Val Leu Arg Met Ile Gly Tyr Gly
            130                 135                 140

Phe Asp Ile Thr Asp Gly Leu Lys Glu Glu Ser Glu Leu Ser Lys Asp
145                 150                 155                 160

Gln Lys Glu Thr Ala Leu Lys Lys Pro Pro Ser Leu Leu Glu Leu Leu
            165                 170                 175

Ala Phe Ser Tyr Phe Pro Ser Gly Phe Leu Val Gly Pro Gln Phe Pro
            180                 185                 190

Phe Arg Arg Tyr Lys Ala Phe Val Asp Gly Glu Phe Arg Gln His Glu
            195                 200                 205

Gly Asn Val Glu Ala Gly Val Arg Arg Phe Gly Ala Gly Ala Phe Tyr
            210                 215                 220

Leu Ile Val Cys Gln Val Gly Leu Arg Tyr Leu Pro Asp Ser Tyr Phe
225                 230                 235                 240

Leu Thr Pro Glu Phe Ala Gln Val Ser Phe Val Lys Arg Ile Tyr Leu
            245                 250                 255

Leu Gly Phe Trp Ala Lys Phe Ser Leu Tyr Lys Tyr Ile Ser Cys Trp
            260                 265                 270

Leu Leu Thr Glu Gly Ala Leu Ile Cys Ile Gly Leu Thr Tyr Lys Gly
            275                 280                 285

Glu Asp Lys Asn Gly Gln Pro Asp Trp Ser Gly Cys Ser Asn Val Lys
            290                 295                 300

Leu Lys Leu Leu Glu Thr Gly Asn Thr Met Glu His Tyr Val Gln Ser
305                 310                 315                 320

Phe Asn Val Asn Thr Asn Gln Trp Val Gly Gln Tyr Ile Tyr Lys Arg
            325                 330                 335

Leu Lys Phe Leu Asn Asn Arg Thr Ile Ser Tyr Gly Ala Ala Leu Gly
            340                 345                 350

Phe Leu Ala Val Trp His Gly Tyr His Ser Gly Tyr Tyr Met Thr Phe
            355                 360                 365

Leu Met Glu Tyr Met Val Val Ser Thr Glu Lys Gln Ile Thr Arg Phe
        370                 375                 380

Tyr Thr Lys Val Val Leu Pro Gln Trp Gly His Ile Leu Asn Asn Ser
385                 390                 395                 400

Asp Ile Tyr Lys Leu Leu Tyr Phe Ile Thr Leu Lys Ser Tyr Asn Val
                405                 410                 415

Val Tyr Met Gly Trp Cys Leu Thr Ala Phe Val Phe Leu Lys Tyr Glu
            420                 425                 430

Arg Trp Ile Val Val Tyr Gly Ala Val Ser Tyr Tyr Gly Phe Thr Phe
        435                 440                 445

Leu Val Leu Trp Ala Ala Phe Tyr His Thr Phe Asn His Phe Phe Arg
    450                 455                 460

Ser Ser Ser Arg Lys Leu Ala Gly Glu Asp Gln Lys Leu Gln Asp Ser
465                 470                 475                 480

Asn Thr Asp Lys Leu Val Glu Glu Lys Lys Pro Glu Asp Lys Lys Ser
                485                 490                 495

Glu

<210> SEQ ID NO 64
<211> LENGTH: 209
<212> TYPE: PRT
<213> ORGANISM: Apple

<400> SEQUENCE: 64

Arg Arg Pro Lys Phe Pro Leu Ser Arg Phe Thr Glu Pro Ile Tyr Gln
1               5                   10                  15

Glu Trp Gly Phe Trp Lys Arg Leu Phe Tyr Gln Tyr Met Ser Gly Phe
            20                  25                  30

Thr Ala Arg Trp Lys Tyr Tyr Phe Ile Trp Ser Ile Ser Glu Ala Ser
        35                  40                  45

Ile Ile Leu Ser Gly Leu Gly Phe Ser Gly Trp Thr Glu Ser Ser Pro
    50                  55                  60

Pro Lys Pro Arg Trp Asp Arg Ala Lys Asn Val Asp Ile Ile Gly Val
65                  70                  75                  80

Glu Phe Ala Lys Ser Ser Val Gln Leu Pro Leu Val Trp Asn Ile Gln
                85                  90                  95

Val Ser Thr Trp Leu Arg His Tyr Val Tyr Asp Arg Leu Val Lys Pro
            100                 105                 110

Gly Lys Lys Pro Gly Phe Phe Gln Leu Leu Ala Thr Gln Thr Val Ser
        115                 120                 125

Ala Val Trp His Gly Leu Tyr Pro Gly Tyr Ile Ile Phe Phe Val Gln
    130                 135                 140

Ser Ala Leu Met Ile Ala Gly Ser Arg Val Ile Tyr Arg Trp Gln Gln
145                 150                 155                 160

Ala Val Pro Pro Thr Met Asp Val Val Lys Lys Ile Leu Val Phe Ile
                165                 170                 175

Asn Phe Ala Tyr Thr Val Leu Val Leu Asn Tyr Ser Cys Val Gly Phe
            180                 185                 190

Ile Val Leu Ser Leu Arg Glu Thr Leu Ala Ser Tyr Gly Ser Val His
        195                 200                 205

Phe

```
<210> SEQ ID NO 65
<211> LENGTH: 203
<212> TYPE: PRT
<213> ORGANISM: Peach

<400> SEQUENCE: 65

Lys Tyr Tyr Phe Ile Trp Ser Ile Ser Glu Ala Ser Ile Ile Leu Ser
1               5                   10                  15

Gly Leu Gly Phe Thr Gly Trp Thr Glu Ser Ser Pro Pro Lys Pro Arg
            20                  25                  30

Trp Asp Arg Ala Lys Asn Val Asp Ile Leu Gly Val Glu Phe Ala Lys
        35                  40                  45

Ser Ser Val Gln Leu Pro Leu Val Trp Asn Ile Gln Val Ser Thr Trp
    50                  55                  60

Leu Arg His Tyr Val Tyr Glu Arg Leu Val Lys Pro Gly Lys Lys Ala
65                  70                  75                  80

Gly Phe Phe Gln Leu Leu Thr Thr Gln Thr Val Ser Ala Val Trp His
                85                  90                  95

Gly Leu Tyr Pro Gly Tyr Ile Ile Phe Phe Val Gln Ser Ala Leu Met
            100                 105                 110

Ile Ala Gly Ser Arg Val Ile Tyr Arg Trp Gln Gln Ala Val Pro Gln
        115                 120                 125

Asn Met Asp Ala Val Lys Asn Ile Leu Val Phe Ile Asn Phe Ala Tyr
    130                 135                 140

Thr Leu Leu Val Leu Asn Tyr Ser Cys Val Gly Phe Ile Val Leu Ser
145                 150                 155                 160

Leu Arg Glu Thr Leu Ala Ser Tyr Gly Ser Val His Phe Ile Gly Thr
                165                 170                 175

Ile Leu Pro Ile Ala Leu Ile Leu Ser Tyr Val Ile Lys Pro Pro
            180                 185                 190

Arg Pro Ala Arg Ser Lys Ala Arg Lys Glu Glu
        195                 200

<210> SEQ ID NO 66
<211> LENGTH: 135
<212> TYPE: PRT
<213> ORGANISM: Barley

<400> SEQUENCE: 66

Glu Ala Ala Ile Ile Ile Ser Gly Leu Gly Phe Thr Gly Trp Ser Asp
1               5                   10                  15

Ser Ser Pro Pro Lys Ala Lys Trp Asp Arg Ala Ile Asn Val Asp Ile
            20                  25                  30

Leu Gly Val Glu Leu Ala Gly Ser Ala Ala Gln Leu Pro Leu Lys Trp
        35                  40                  45

Asn Ile Gln Val Ser Thr Trp Leu Arg Tyr Tyr Val Tyr Glu Arg Leu
    50                  55                  60

Ile Gln Lys Gly Lys Lys Pro Gly Phe Leu Gln Leu Leu Gly Thr Gln
65                  70                  75                  80

Thr Val Ser Ala Ile Trp His Gly Leu Tyr Pro Gly Tyr Met Ile Phe
                85                  90                  95

Phe Val Gln Ser Ala Leu Met Ile Asn Gly Ser Lys Val Ile Tyr Arg
            100                 105                 110

Trp Gln Gln Ala Val Lys Gln Phe Arg Pro Pro His Tyr Pro Val Phe
        115                 120                 125

Thr Lys Leu Leu His Thr Pro
```

```
              130                 135

<210> SEQ ID NO 67
<211> LENGTH: 279
<212> TYPE: PRT
<213> ORGANISM: Wheat

<400> SEQUENCE: 67

His Phe Ala Gly Pro Val Tyr Glu Met Lys Asp Tyr Leu Glu Trp Thr
1               5                  10                  15

Glu Arg Lys Gly Ile Trp Ala Gly Ser Thr Pro Ser Pro Leu Leu Pro
            20                  25                  30

Thr Leu Arg Ala Leu Val Gln Ala Gly Ile Cys Met Gly Leu Tyr Leu
        35                  40                  45

Tyr Leu Ser Pro Met Phe Pro His Ser Tyr Arg Gly Ser Leu Asn Arg
    50                  55                  60

Glu Arg Gly Phe Trp His Arg Leu Phe Phe Gln Tyr Met Ser Gly Phe
65                  70                  75                  80

Thr Ala Arg Trp Lys Tyr Tyr Phe Ile Trp Ser Val Ser Glu Ala Ala
                85                  90                  95

Ile Ile Ile Ser Gly Leu Gly Phe Thr Gly Trp Ser Asp Ser Ser Pro
            100                 105                 110

Pro Lys Ala Lys Trp Asp Arg Ala Ile Asn Val Asp Ile Leu Gly Val
        115                 120                 125

Glu Leu Ala Gly Ser Ala Ala Gln Leu Pro Leu Lys Trp Asn Ile Gln
    130                 135                 140

Val Ser Thr Trp Leu Arg Tyr Val Tyr Glu Arg Leu Ile Gln Lys
145                 150                 155                 160

Gly Lys Lys Pro Gly Phe Leu Gln Leu Leu Gly Thr Gln Thr Val Ser
                165                 170                 175

Ala Ile Trp His Gly Leu Tyr Pro Gly Tyr Met Phe Phe Val Gln
            180                 185                 190

Ser Ala Leu Met Ile Asn Gly Ser Lys Val Ile Tyr Arg Trp Gln Gln
        195                 200                 205

Ala Val Ser Asn Pro Gly Leu Arg Thr Ile Leu Ser Leu Leu Asn Cys
    210                 215                 220

Ala Tyr Thr Met Met Val Leu Asn Tyr Ser Cys Ile Gly Phe Gln Val
225                 230                 235                 240

Leu Ser Phe Gln Glu Thr Leu Ala Ser Tyr Lys Ser Val Tyr Val
                245                 250                 255

Gly Thr Ile Val Pro Ile Leu Cys Val Leu Leu Gly Tyr Val Val Lys
            260                 265                 270

Pro Thr Arg Pro Val Lys Pro
        275

<210> SEQ ID NO 68
<211> LENGTH: 287
<212> TYPE: PRT
<213> ORGANISM: Maize
<220> FEATURE:
<221> NAME/KEY: MISC_FEATURE
<222> LOCATION: (242)..(242)
<223> OTHER INFORMATION: X can be any amino acid

<400> SEQUENCE: 68

Ile Ser Cys Leu Ile Asn Tyr Ser Asp Gly Ile Leu Lys Glu Glu Gly
1               5                  10                  15
```

```
Leu Arg Asp Ala Gln Ile Lys His Arg Leu Thr Lys Leu Pro Ser Leu
            20                  25                  30

Ile Glu Tyr Phe Gly Tyr Cys Leu Cys Cys Gly Ser His Phe Ala Gly
        35                  40                  45

Pro Val Tyr Glu Met Lys Asp Tyr Leu Glu Trp Thr Glu Arg Lys Gly
    50                  55                  60

Ile Trp Ala Ser Pro Thr Pro Ser Pro Leu Leu Pro Thr Leu Arg Ala
65                  70                  75                  80

Leu Val Gln Ala Gly Ile Cys Met Gly Leu Tyr Leu Tyr Leu Ser Pro
                85                  90                  95

Lys Phe Pro Leu Ser Arg Phe Ser Glu Pro Leu Tyr Tyr Glu Trp Gly
            100                 105                 110

Phe Trp His Arg Leu Phe Tyr Gln Tyr Met Ser Gly Phe Thr Ala Arg
        115                 120                 125

Trp Lys Tyr Tyr Phe Ile Trp Ser Ile Ser Glu Ala Ser Ile Ile Ile
    130                 135                 140

Ser Gly Leu Gly Phe Thr Gly Trp Ser Glu Ser Pro Pro Lys Ala
145                 150                 155                 160

Lys Trp Asp Arg Ala Lys Asn Val Asp Val Leu Gly Val Glu Leu Ala
                165                 170                 175

Gly Ser Ser Val Gln Leu Pro Leu Val Trp Asn Ile Gln Val Ser Thr
            180                 185                 190

Trp Leu Arg Tyr Tyr Val Tyr Glu Arg Leu Ile Gln Lys Gly Lys Lys
        195                 200                 205

Pro Gly Phe Leu Gln Leu Leu Gly Thr Gln Thr Val Ser Ala Ile Trp
    210                 215                 220

His Gly Leu Tyr Pro Gly Tyr Ile Ile Phe Phe Phe Ser Ser Ala Leu
225                 230                 235                 240

Met Xaa Asn Gly Ser Arg Val Ile Tyr Arg Trp Gln Gln Ala Ala Ser
                245                 250                 255

Ser Ser Phe Leu Ser Gly Ile Leu Ala Leu Leu Ile Leu Leu Tyr Ile
            260                 265                 270

Ala Gly Ala Tyr Tyr Ser Cys Ile Gly Val Gln Val Leu Ser Phe
        275                 280                 285

<210> SEQ ID NO 69
<211> LENGTH: 217
<212> TYPE: PRT
<213> ORGANISM: Sorghum

<400> SEQUENCE: 69

Thr Arg Leu Ser Arg Phe Ser Glu Pro Leu Tyr Tyr Glu Trp Gly Phe
1               5                   10                  15

Trp His Arg Leu Phe Tyr Gln Tyr Met Ser Gly Phe Thr Ala Arg Trp
            20                  25                  30

Lys Tyr Tyr Phe Ile Trp Ser Ile Ser Glu Ala Ser Ile Ile Ile Ser
        35                  40                  45

Gly Leu Gly Phe Thr Gly Trp Ser Glu Ser Ser Pro Lys Ala Lys
    50                  55                  60

Trp Asp Arg Ala Lys Asn Val Asp Val Leu Gly Val Glu Leu Ala Gly
65                  70                  75                  80

Ser Ala Val Gln Ile Pro Leu Val Trp Asn Ile Gln Val Ser Thr Trp
                85                  90                  95

Leu Arg Tyr Tyr Val Tyr Glu Arg Leu Ile Gln Lys Gly Lys Lys Pro
            100                 105                 110
```

```
Gly Phe Leu Gln Leu Leu Gly Thr Gln Thr Val Ser Ala Ile Trp His
            115                 120                 125

Gly Leu Tyr Pro Gly Tyr Ile Ile Phe Phe Val Gln Ser Ala Leu Met
            130                 135                 140

Ile Asn Gly Ser Arg Val Ile Tyr Arg Trp Gln Gln Ala Val Ser Ser
145                 150                 155                 160

Ser Phe Leu Arg Gly Ile Leu Ala Phe Leu Asn Phe Ala Tyr Thr Leu
            165                 170                 175

Leu Val Leu Asn Tyr Ser Cys Ile Gly Phe Leu Val Leu Ser Phe Lys
            180                 185                 190

Glu Thr Leu Ala Ser Tyr Gln Ser Val Tyr Tyr Val Gly Thr Ile Val
            195                 200                 205

Pro Ile Val Phe Leu Leu Gly Asn
            210                 215

<210> SEQ ID NO 70
<211> LENGTH: 459
<212> TYPE: PRT
<213> ORGANISM: Oryza sativa

<400> SEQUENCE: 70

Met Gly Leu Glu Met Glu Gly Met Ala Ala Ile Gly Val Ser Val
1               5                   10                  15

Pro Val Leu Arg Phe Leu Cys Phe Ala Ala Thr Ile Pro Thr Gly
            20                  25                  30

Leu Met Trp Arg Ala Val Pro Gly Ala Ala Gly Arg His Leu Tyr Ala
            35                  40                  45

Gly Leu Thr Gly Ala Ala Leu Ser Tyr Leu Ser Phe Gly Ala Thr Ser
            50                  55                  60

Asn Leu Leu Phe Val Val Pro Met Ala Phe Gly Tyr Leu Ala Met Leu
65                  70                  75                  80

Leu Cys Arg Arg Leu Ala Gly Leu Val Thr Phe Leu Gly Ala Phe Gly
            85                  90                  95

Phe Leu Ile Ala Cys His Met Tyr Tyr Met Ser Gly Asp Ala Trp Lys
            100                 105                 110

Glu Gly Gly Ile Asp Ala Thr Gly Ala Leu Met Val Leu Thr Leu Lys
            115                 120                 125

Ile Ile Ser Cys Ala Ile Asn Tyr Ser Asp Gly Met Leu Lys Glu Glu
            130                 135                 140

Gly Leu Arg Asp Ala Gln Lys Lys Tyr Arg Leu Ala Lys Leu Pro Ser
145                 150                 155                 160

Leu Ile Glu Tyr Phe Gly Tyr Cys Leu Cys Cys Gly Ser His Phe Ala
            165                 170                 175

Gly Pro Val Tyr Glu Met Lys Asp Tyr Leu Glu Tyr Thr Glu Arg Lys
            180                 185                 190

Gly Leu Trp Ala Ser Pro Thr Pro Ser Pro Leu Pro Thr Leu Arg
            195                 200                 205

Ala Leu Val Gln Ala Gly Ala Cys Met Gly Leu Leu Tyr Leu Ser
            210                 215                 220

Pro Gln Phe Pro Leu Ser Arg Phe Ser Glu Pro Leu Tyr Tyr Glu Trp
225                 230                 235                 240

Gly Phe Trp His Arg Leu Phe Tyr Gln Tyr Met Ser Gly Phe Thr Ala
            245                 250                 255

Arg Trp Lys Tyr Tyr Phe Ile Trp Ser Leu Ser Glu Ala Ala Ile Ile
```

```
                260                 265                 270
Ile Ser Gly Leu Gly Phe Ser Gly Trp Ser Asp Ser Pro Pro Lys
            275                 280                 285

Ala Lys Trp Asp Arg Ala Lys Asn Val Asp Val Leu Gly Val Glu Leu
        290                 295                 300

Ala Thr Ser Ala Val Gln Leu Pro Leu Met Trp Asn Ile Gln Val Ser
305                 310                 315                 320

Thr Trp Leu Arg Tyr Tyr Val Tyr Glu Arg Leu Val Gln Lys Gly Lys
                325                 330                 335

Lys Pro Gly Phe Leu Gln Leu Leu Gly Thr Gln Thr Val Ser Ala Val
            340                 345                 350

Trp His Gly Leu Tyr Pro Gly Tyr Ile Ile Phe Phe Val Gln Ser Ala
                355                 360                 365

Leu Met Ile Asn Gly Ser Lys Val Ile Tyr Arg Trp Gln Gln Ala Val
        370                 375                 380

Ser Asn Pro Val Phe His Ala Ile Leu Val Phe Val Asn Phe Ser Tyr
385                 390                 395                 400

Thr Leu Met Val Leu Asn Tyr Ser Cys Ile Gly Phe Gln Val Leu Ser
                405                 410                 415

Phe Lys Glu Thr Leu Ala Ser Tyr Gln Ser Val Tyr Tyr Ile Gly Thr
            420                 425                 430

Ile Val Pro Ile Val Val Leu Leu Gly Tyr Val Ile Lys Pro Ala
        435                 440                 445

Arg Pro Val Lys Pro Lys Ala Arg Lys Ala Glu
    450                 455

<210> SEQ ID NO 71
<211> LENGTH: 370
<212> TYPE: PRT
<213> ORGANISM: Rice

<400> SEQUENCE: 71

Met Tyr Tyr Met Ser Gly Asp Ala Trp Lys Glu Gly Gly Ile Asp Ala
1               5                   10                  15

Thr Gly Ala Leu Met Val Leu Thr Leu Lys Ile Ile Ser Cys Ala Ile
            20                  25                  30

Asn Tyr Ser Asp Gly Met Leu Lys Glu Glu Gly Leu Arg Asp Ala Gln
        35                  40                  45

Lys Lys Tyr Arg Leu Ala Lys Leu Pro Ser Leu Ile Glu Tyr Phe Gly
    50                  55                  60

Tyr Cys Leu Cys Cys Gly Ser His Phe Ala Gly Pro Val Tyr Glu Met
65                  70                  75                  80

Lys Asp Tyr Leu Glu Tyr Thr Glu Arg Lys Gly Leu Trp Ala Ser Pro
                85                  90                  95

Thr Pro Ser Pro Leu Leu Pro Thr Leu Arg Ala Leu Val Gln Ala Gly
            100                 105                 110

Ala Cys Met Gly Leu Tyr Leu Tyr Leu Ser Pro Gln Phe Pro Leu Ser
        115                 120                 125

Arg Phe Ser Glu Pro Leu Tyr Tyr Glu Trp Gly Phe Trp His Arg Leu
    130                 135                 140

Phe Tyr Gln Tyr Met Ser Gly Phe Thr Ala Arg Trp Lys Tyr Tyr Phe
145                 150                 155                 160

Ile Trp Ser Leu Ser Glu Ala Ala Ile Ile Ile Ser Gly Leu Gly Phe
                165                 170                 175
```

```
Ser Gly Trp Ser Asp Ser Ser Pro Lys Ala Lys Trp Asp Arg Ala
            180                 185                 190

Lys Asn Val Asp Val Leu Gly Val Glu Leu Ala Thr Ser Ala Val Gln
        195                 200                 205

Leu Pro Leu Met Trp Asn Ile Gln Val Ser Thr Trp Leu Arg Tyr Tyr
    210                 215                 220

Val Tyr Glu Arg Leu Val Gln Lys Gly Lys Pro Gly Phe Leu Gln
225                 230                 235                 240

Leu Leu Gly Thr Gln Thr Val Ser Ala Val Trp His Gly Leu Tyr Pro
                245                 250                 255

Gly Tyr Ile Ile Phe Phe Val Gln Ser Ala Leu Met Ile Asn Gly Ser
            260                 265                 270

Lys Val Ile Tyr Arg Trp Gln Gln Ala Val Ser Asn Pro Val Phe His
        275                 280                 285

Ala Ile Leu Val Phe Val Asn Phe Ser Tyr Thr Leu Met Val Leu Asn
    290                 295                 300

Tyr Ser Cys Ile Gly Phe Gln Phe Val Phe Thr Met Leu Tyr Thr Leu
305                 310                 315                 320

Arg Phe Leu Gln Val Leu Ser Phe Lys Glu Thr Leu Ala Ser Tyr Gln
                325                 330                 335

Ser Val Tyr Tyr Ile Gly Thr Ile Val Pro Ile Val Val Leu Leu
            340                 345                 350

Gly Tyr Val Ile Lys Pro Ala Arg Pro Val Lys Pro Lys Ala Arg Lys
        355                 360                 365

Ala Glu
    370

<210> SEQ ID NO 72
<211> LENGTH: 312
<212> TYPE: PRT
<213> ORGANISM: Grapevine

<400> SEQUENCE: 72

Ser Ser Asn Leu His Phe Leu Val Pro Met Leu Leu Gly Tyr Ala Ala
1               5                   10                  15

Met Leu Leu Cys Arg Arg Arg Cys Gly Val Ile Thr Phe Phe Leu Gly
            20                  25                  30

Phe Gly Tyr Leu Ile Gly Cys His Val Tyr Tyr Met Ser Gly Asp Ala
        35                  40                  45

Trp Lys Glu Gly Gly Ile Asp Ala Thr Gly Ala Leu Met Val Leu Thr
    50                  55                  60

Leu Lys Val Ile Ser Cys Ala Met Asn Tyr Asn Asp Gly Leu Leu Lys
65                  70                  75                  80

Glu Asp Gly Leu Arg Glu Ala Gln Lys Lys Asn Arg Leu Leu Lys Leu
                85                  90                  95

Pro Ser Leu Ile Glu Tyr Phe Gly Tyr Cys Leu Cys Cys Gly Ser His
            100                 105                 110

Phe Ala Gly Pro Val Tyr Glu Ile Lys Asp Tyr Leu Glu Trp Thr Glu
        115                 120                 125

Arg Lys Gly Ile Trp Ala Lys Ser Glu Lys Gly Pro Pro Ser Pro
    130                 135                 140

Tyr Gly Ala Thr Ile Arg Ala Leu Ile Gln Ala Ala Phe Cys Met Gly
145                 150                 155                 160

Leu Tyr Val Tyr Leu Val Pro His Phe Pro Leu Thr Ile Phe Thr Asp
                165                 170                 175
```

```
Pro Val Tyr Gln Glu Trp Gly Phe Trp Lys Arg Leu Gly Tyr Gln Tyr
            180                 185                 190

Met Cys Gly Phe Thr Ala Arg Trp Lys Tyr Tyr Phe Ile Trp Ser Ile
        195                 200                 205

Ser Glu Ala Ala Val Ile Ile Ser Gly Leu Gly Phe Ser Gly Trp Thr
    210                 215                 220

Glu Ser Ser Pro Pro Lys Pro Lys Trp Asp Arg Ala Lys Asn Val Asp
225                 230                 235                 240

Ile Leu Gly Val Glu Leu Ala Lys Ser Ala Val Thr Leu Pro Leu Val
                245                 250                 255

Trp Asn Ile Gln Val Ser Thr Trp Leu Arg Tyr Tyr Val Tyr Glu Arg
            260                 265                 270

Leu Ile Gln Asn Gly Lys Lys Pro Gly Phe Phe Gln Leu Leu Ala Thr
        275                 280                 285

Gln Thr Val Ser Ala Val Trp His Gly Leu Tyr Pro Gly Tyr Ile Ile
    290                 295                 300

Phe Phe Val Gln Ser Ala Leu Met
305                 310

<210> SEQ ID NO 73
<211> LENGTH: 195
<212> TYPE: PRT
<213> ORGANISM: Vaccinium corymbosum

<400> SEQUENCE: 73

Gly Leu Gly Tyr Gln Tyr Met Ala Gly Phe Thr Ala Arg Trp Lys Tyr
1               5                   10                  15

Tyr Phe Ile Trp Ser Ile Ser Glu Ala Ser Ile Ile Ser Gly Leu
            20                  25                  30

Gly Phe Ser Gly Trp Thr Asp Ser Ser Pro Pro Lys Pro Lys Trp Asp
        35                  40                  45

Arg Ala Lys Asn Val Asp Ile Leu Arg Val Glu Phe Ala Lys Thr Ala
    50                  55                  60

Ala Gln Ile Pro Leu Ala Trp Asn Ile Gln Val Ser Thr Trp Leu Arg
65                  70                  75                  80

His Tyr Val Tyr Glu Arg Leu Val Gln Lys Gly Lys Lys Pro Gly Phe
                85                  90                  95

Phe Gln Leu Leu Ala Thr Gln Thr Val Ser Ala Val Trp His Gly Leu
            100                 105                 110

Tyr Pro Gly Tyr Ile Ile Phe Phe Val Gln Ser Ala Leu Met Ile Ala
        115                 120                 125

Gly Ser Arg Val Ile Tyr Arg Trp Gln Gln Ala Val Pro Pro Lys Met
    130                 135                 140

Asp Leu Val Lys Lys Val Phe Val Leu Leu Asn Phe Ala Tyr Thr Val
145                 150                 155                 160

Leu Val Leu Asn Tyr Ser Ser Val Gly Phe Met Val Leu Ser Leu His
                165                 170                 175

Glu Thr Ile Val Ala Tyr Gly Ser Val Tyr Ser Leu Glu Pro Leu Phe
            180                 185                 190

Pro Tyr Leu
        195

<210> SEQ ID NO 74
<211> LENGTH: 462
<212> TYPE: PRT
```

<213> ORGANISM: Arabidopsis thaliana

<400> SEQUENCE: 74

```
Met Asp Met Ser Ser Met Ala Gly Ser Ile Gly Val Ser Val Ala Val
1               5                   10                  15

Leu Arg Phe Leu Leu Cys Phe Val Ala Thr Ile Pro Val Ser Phe Ala
            20                  25                  30

Cys Arg Ile Val Pro Ser Arg Leu Gly Lys His Leu Tyr Ala Ala Ala
        35                  40                  45

Ser Gly Ala Phe Leu Ser Tyr Leu Ser Phe Gly Phe Ser Ser Asn Leu
    50                  55                  60

His Phe Leu Val Pro Met Thr Ile Gly Tyr Ala Ser Met Ala Ile Tyr
65                  70                  75                  80

Arg Pro Lys Cys Gly Ile Ile Thr Phe Phe Leu Gly Phe Ala Tyr Leu
                85                  90                  95

Ile Gly Cys His Val Phe Tyr Met Ser Gly Asp Ala Trp Lys Glu Gly
            100                 105                 110

Gly Ile Asp Ser Thr Gly Ala Leu Met Val Leu Thr Leu Lys Val Ile
        115                 120                 125

Ser Cys Ser Met Asn Tyr Asn Asp Gly Met Leu Lys Glu Glu Gly Leu
    130                 135                 140

Arg Glu Ala Gln Lys Lys Asn Arg Leu Ile Gln Met Pro Ser Leu Ile
145                 150                 155                 160

Glu Tyr Phe Gly Tyr Cys Leu Cys Gly Ser His Phe Ala Gly Pro
                165                 170                 175

Val Tyr Glu Met Lys Asp Tyr Leu Glu Trp Thr Glu Gly Lys Gly Ile
            180                 185                 190

Trp Asp Thr Thr Glu Lys Arg Lys Pro Ser Pro Tyr Gly Ala Thr
        195                 200                 205

Ile Arg Ala Ile Leu Gln Ala Ala Ile Cys Met Ala Leu Tyr Leu Tyr
    210                 215                 220

Leu Val Pro Gln Tyr Pro Leu Thr Arg Phe Thr Glu Pro Val Tyr Gln
225                 230                 235                 240

Glu Trp Gly Phe Leu Arg Lys Phe Ser Tyr Gln Tyr Met Ala Gly Phe
                245                 250                 255

Thr Ala Arg Trp Lys Tyr Phe Ile Trp Ser Ile Ser Glu Ala Ser
            260                 265                 270

Ile Ile Ile Ser Gly Leu Gly Phe Ser Gly Trp Thr Asp Asp Ala Ser
        275                 280                 285

Pro Lys Pro Lys Trp Asp Arg Ala Lys Asn Val Asp Ile Leu Gly Val
    290                 295                 300

Glu Leu Ala Lys Ser Ala Val Gln Ile Pro Leu Val Trp Asn Ile Gln
305                 310                 315                 320

Val Ser Thr Trp Leu Arg His Tyr Val Tyr Glu Arg Leu Val Gln Asn
                325                 330                 335

Gly Lys Lys Ala Gly Phe Phe Gln Leu Leu Ala Thr Gln Thr Val Ser
            340                 345                 350

Ala Val Trp His Gly Leu Tyr Pro Gly Tyr Met Met Phe Phe Val Gln
        355                 360                 365

Ser Ala Leu Met Ile Ala Gly Ser Arg Val Ile Tyr Arg Trp Gln Gln
    370                 375                 380

Ala Ile Ser Pro Lys Met Ala Met Leu Arg Asn Ile Met Val Phe Ile
385                 390                 395                 400
```

```
Asn Phe Leu Tyr Thr Val Leu Leu Asn Tyr Ser Ala Val Gly Phe
            405                 410                 415

Met Val Leu Ser Leu His Glu Thr Leu Thr Ala Tyr Gly Ser Val Tyr
        420                 425                 430

Tyr Ile Gly Thr Ile Ile Pro Val Gly Leu Ile Leu Ser Tyr Val
            435                 440                 445

Val Pro Ala Lys Pro Ser Arg Pro Lys Pro Arg Lys Glu Glu
    450                 455                 460

<210> SEQ ID NO 75
<211> LENGTH: 465
<212> TYPE: PRT
<213> ORGANISM: Arabidopsis thaliana

<400> SEQUENCE: 75

Met Glu Leu Leu Asp Met Asn Ser Met Ala Ala Ser Ile Gly Val Ser
1               5                   10                  15

Val Ala Val Leu Arg Phe Leu Leu Cys Phe Val Ala Thr Ile Pro Ile
            20                  25                  30

Ser Phe Leu Trp Arg Phe Ile Pro Ser Arg Leu Gly Lys His Ile Tyr
        35                  40                  45

Ser Ala Ala Ser Gly Ala Phe Leu Ser Tyr Leu Ser Phe Gly Phe Ser
    50                  55                  60

Ser Asn Leu His Phe Leu Val Pro Met Thr Ile Gly Tyr Ala Ser Met
65                  70                  75                  80

Ala Ile Tyr Arg Pro Leu Ser Gly Phe Ile Thr Phe Phe Leu Gly Phe
                85                  90                  95

Ala Tyr Leu Ile Gly Cys His Val Phe Tyr Met Ser Gly Asp Ala Trp
            100                 105                 110

Lys Glu Gly Gly Ile Asp Ser Thr Gly Ala Leu Met Val Leu Thr Leu
        115                 120                 125

Lys Val Ile Ser Cys Ser Ile Asn Tyr Asn Asp Gly Met Leu Lys Glu
    130                 135                 140

Glu Gly Leu Arg Glu Ala Gln Lys Lys Asn Arg Leu Ile Gln Met Pro
145                 150                 155                 160

Ser Leu Ile Glu Tyr Phe Gly Tyr Cys Leu Cys Cys Gly Ser His Phe
                165                 170                 175

Ala Gly Pro Val Phe Glu Met Lys Asp Tyr Leu Glu Trp Thr Glu Glu
            180                 185                 190

Lys Gly Ile Trp Ala Val Ser Glu Lys Gly Lys Arg Pro Ser Pro Tyr
        195                 200                 205

Gly Ala Met Ile Arg Ala Val Phe Gln Ala Ala Ile Cys Met Ala Leu
    210                 215                 220

Tyr Leu Tyr Leu Val Pro Gln Phe Pro Leu Thr Arg Phe Thr Glu Pro
225                 230                 235                 240

Val Tyr Gln Glu Trp Gly Phe Leu Lys Arg Phe Gly Tyr Gln Tyr Met
                245                 250                 255

Ala Gly Phe Thr Ala Arg Trp Lys Tyr Tyr Phe Ile Trp Ser Ile Ser
            260                 265                 270

Glu Ala Ser Ile Ile Ile Ser Gly Leu Gly Phe Ser Gly Trp Thr Asp
        275                 280                 285

Glu Thr Gln Thr Lys Ala Lys Trp Asp Arg Ala Lys Asn Val Asp Ile
    290                 295                 300

Leu Gly Val Glu Leu Ala Lys Ser Ala Val Gln Ile Pro Leu Phe Trp
305                 310                 315                 320
```

```
Asn Ile Gln Val Ser Thr Trp Leu Arg His Tyr Val Tyr Glu Arg Ile
                325                 330                 335

Val Lys Pro Gly Lys Ala Gly Phe Phe Gln Leu Leu Ala Thr Gln
            340                 345                 350

Thr Val Ser Ala Val Trp His Gly Leu Tyr Pro Gly Tyr Ile Ile Phe
        355                 360                 365

Phe Val Gln Ser Ala Leu Met Ile Asp Gly Ser Lys Ala Ile Tyr Arg
    370                 375                 380

Trp Gln Gln Ala Ile Pro Pro Lys Met Ala Met Leu Arg Asn Val Leu
385                 390                 395                 400

Val Leu Ile Asn Phe Leu Tyr Thr Val Val Leu Asn Tyr Ser Ser
                405                 410                 415

Val Gly Phe Met Val Leu Ser Leu His Glu Thr Leu Val Ala Phe Lys
            420                 425                 430

Ser Val Tyr Tyr Ile Gly Thr Val Ile Pro Ile Ala Val Leu Leu Leu
        435                 440                 445

Ser Tyr Leu Val Pro Val Lys Pro Val Arg Pro Lys Thr Arg Lys Glu
    450                 455                 460

Glu
465

<210> SEQ ID NO 76
<211> LENGTH: 213
<212> TYPE: PRT
<213> ORGANISM: Capsicum annuum

<400> SEQUENCE: 76

His Glu Lys Arg Leu Gly Tyr Gln Tyr Met Ala Gly Phe Thr Ala Arg
1               5                   10                  15

Trp Lys Tyr Tyr Phe Ile Trp Ser Ile Ser Glu Ala Ala Ile Ile Ile
            20                  25                  30

Ser Gly Leu Gly Phe Ser Gly Trp Thr Asp Ser Ser Pro Pro Lys Pro
        35                  40                  45

Arg Trp Asp Arg Ala Lys Asn Val Asp Val Leu Gly Val Glu Leu Ala
    50                  55                  60

Lys Ser Ser Val Gln Leu Pro Ala Val Trp Asn Ile Gln Val Ser Thr
65                  70                  75                  80

Trp Leu Arg His Tyr Val Tyr Glu Arg Leu Ile Gln Lys Gly Arg Lys
                85                  90                  95

Pro Gly Phe Phe Gln Leu Leu Ala Thr Gln Thr Val Ser Ala Val Trp
            100                 105                 110

His Gly Leu Tyr Pro Gly Tyr Ile Ile Phe Phe Val Gln Ser Ala Leu
        115                 120                 125

Met Ile Ala Gly Ser Arg Val Leu Tyr Arg Trp Gln Gln Ala Ala Lys
    130                 135                 140

Gly Ser Met Phe Glu Lys Ile Leu Val Ala Met Asn Phe Ala Tyr Thr
145                 150                 155                 160

Leu Leu Val Leu Asn Tyr Ser Ala Val Gly Phe Met Val Leu Ser Leu
                165                 170                 175

His Glu Thr Leu Thr Ala Tyr Gly Ser Val Tyr Tyr Val Gly Thr Ile
            180                 185                 190

Ile Pro Ile Ala Leu Ile Leu Leu Ser Lys Val Ile Lys Pro Pro Arg
        195                 200                 205

Pro Cys Thr Ser Lys
```

<210> SEQ ID NO 77
<211> LENGTH: 244
<212> TYPE: PRT
<213> ORGANISM: Tomato

<400> SEQUENCE: 77

```
Gly Met Gly Leu Tyr Leu Tyr Leu Val Pro Gln Phe Pro Leu Ser Arg
1               5                   10                  15

Phe Thr Glu Ser Val Tyr His Glu Trp Gly Phe Lys Arg Leu Gly
            20                  25                  30

Tyr Gln Tyr Met Ala Gly Phe Thr Ala Arg Trp Lys Tyr Tyr Phe Ile
        35                  40                  45

Trp Ser Ile Ser Glu Ala Ser Ile Ile Ser Gly Leu Gly Phe Ser
    50                  55                  60

Gly Trp Thr Asn Ser Ser Pro Pro Lys Pro Arg Trp Asp Arg Ala Lys
65                  70                  75                  80

Asn Val Asp Val Leu Gly Val Glu Leu Ala Lys Ser Ser Val Gln Leu
                85                  90                  95

Pro Leu Val Trp Asn Ile Gln Val Ser Thr Trp Leu Arg His Tyr Val
            100                 105                 110

Tyr Glu Arg Leu Val Gln Lys Gly Arg Lys Pro Gly Phe Phe Gln Leu
        115                 120                 125

Leu Ala Thr Gln Thr Val Ser Ala Val Trp His Gly Leu Tyr Pro Gly
    130                 135                 140

Tyr Ile Ile Phe Phe Val Gln Ser Ala Leu Met Ile Ala Gly Ser Arg
145                 150                 155                 160

Val Ile Tyr Arg Trp Gln Gln Ala Thr Lys Gly Thr Met Phe Glu Lys
                165                 170                 175

Ile Leu Ile Ala Met Asn Phe Ala Tyr Thr Leu Leu Val Leu Asn Tyr
            180                 185                 190

Ser Ala Val Gly Phe Met Val Leu Ser Leu His Glu Thr Leu Thr Ala
        195                 200                 205

Tyr Gly Ser Val Tyr Tyr Ile Gly Thr Ile Val Pro Ile Leu Leu Ile
    210                 215                 220

Leu Leu Ser Lys Val Ile Lys Pro Pro Arg Pro Ala Thr Ser Lys Ala
225                 230                 235                 240

Arg Lys Ala Glu
```

<210> SEQ ID NO 78
<211> LENGTH: 235
<212> TYPE: PRT
<213> ORGANISM: Snapdragon

<400> SEQUENCE: 78

```
Ile Asn Tyr Asn Asp Gly Leu Leu Lys Lys Glu Asp Leu Arg Glu Pro
1               5                   10                  15

Gln Lys Lys Asn Arg Leu Leu Lys Met Pro Ser Leu Leu Glu Tyr Ile
            20                  25                  30

Gly Tyr Cys Leu Cys Cys Gly Ser His Phe Ala Gly Pro Val Tyr Glu
        35                  40                  45

Met Lys Asp Tyr Leu Glu Trp Thr Glu Arg Lys Gly Ile Trp Gln His
    50                  55                  60

Thr Thr Lys Gly Pro Lys Pro Ser Pro Tyr Trp Ala Thr Leu Arg Ala
65                  70                  75                  80
```

```
Ile Leu Gln Ala Ala Ile Cys Met Gly Leu Tyr Leu Tyr Leu Val Pro
                85                  90                  95

His Tyr Pro Leu Ser Arg Phe Thr Glu Pro Glu Tyr Gln Glu Tyr Gly
            100                 105                 110

Phe Trp Lys Arg Leu Ser Tyr Gln Tyr Met Ser Gly Phe Thr Ala Arg
        115                 120                 125

Trp Lys Tyr Tyr Phe Ile Trp Ser Ile Ser Glu Ala Ser Ile Ile Ile
130                 135                 140

Ser Gly Leu Gly Phe Ser Gly Trp Thr Asp Ser Asp Pro Pro Lys Ala
145                 150                 155                 160

Leu Trp Asp Arg Ala Lys Asn Val Asp Val Leu Gly Val Glu Leu Ala
                165                 170                 175

Lys Ser Ser Val Gln Leu Pro Leu Val Trp Asn Ile Gln Val Ser Thr
            180                 185                 190

Trp Leu Lys His Tyr Val Tyr Glu Arg Leu Val Gln Lys Gly Lys Lys
        195                 200                 205

Pro Gly Phe Phe Gln Leu Leu Ala Thr Gln Thr Val Ser Ala Val Trp
210                 215                 220

His Gly Leu Tyr Pro Gly Tyr Ile Ile Phe Phe
225                 230                 235

<210> SEQ ID NO 79
<211> LENGTH: 252
<212> TYPE: PRT
<213> ORGANISM: Castor Bean

<400> SEQUENCE: 79

Ile His Leu Tyr Leu Val Pro His Tyr Pro Leu Ser Arg Phe Thr Asp
1               5                   10                  15

Pro Val Tyr Gln Glu Trp Gly Phe Trp Lys Arg Leu Thr Tyr Gln Tyr
            20                  25                  30

Met Ser Gly Leu Thr Ala Arg Trp Lys Tyr Tyr Phe Ile Trp Ser Ile
        35                  40                  45

Ser Glu Ala Ser Ile Ile Ile Ser Gly Leu Gly Phe Ser Gly Trp Thr
50                  55                  60

Asp Thr Ser Pro Pro Lys Pro Gln Trp Asp Arg Ala Arg Asn Val Asp
65                  70                  75                  80

Ile Leu Gly Val Glu Phe Ala Lys Ser Ala Ala Glu Leu Pro Leu Val
                85                  90                  95

Trp Asn Ile Gln Val Ser Thr Trp Leu Arg His Tyr Val Tyr Asp Arg
            100                 105                 110

Leu Val Pro Lys Gly Lys Lys Ala Gly Phe Leu Gln Leu Leu Ala Thr
        115                 120                 125

Gln Thr Thr Ser Ala Val Trp His Gly Leu Tyr Pro Gly Tyr Ile Ile
130                 135                 140

Phe Phe Val Gln Ser Ala Leu Met Ile Ala Gly Ser Lys Val Ile Tyr
145                 150                 155                 160

Arg Trp Gln Gln Ala Ile Pro Ser Asn Lys Ala Leu Glu Lys Lys Ile
                165                 170                 175

Leu Val Phe Met Asn Phe Ala Tyr Thr Val Leu Val Leu Asn Tyr Ser
            180                 185                 190

Cys Val Gly Phe Met Val Leu Ser Leu His Glu Thr Ile Ala Ala Tyr
        195                 200                 205

Gly Ser Val Tyr Phe Ile Gly Thr Ile Val Pro Val Val Phe Phe Leu
```

```
                 210                 215                 220

Leu Gly Phe Ile Ile Lys Pro Ala Arg Pro Ser Arg Ser Lys His Gly
225                 230                 235                 240

Thr Met Ser Glu Val Glu Thr Val Phe Leu Leu Leu
                    245                 250
```

<210> SEQ ID NO 80
<211> LENGTH: 288
<212> TYPE: PRT
<213> ORGANISM: Sunflower

<400> SEQUENCE: 80

```
Glu Asn Arg Ile Leu Lys Leu Pro Ser Leu Ile Glu Tyr Val Gly Tyr
1               5                   10                  15

Cys Leu Cys Cys Gly Ser His Phe Ala Gly Pro Val Tyr Glu Ile Lys
                20                  25                  30

Asp Tyr Leu Asp Trp Thr Glu Arg Lys Gly Ile Trp Thr Lys Ser Glu
            35                  40                  45

Lys Gly Thr Pro Ser Pro Phe Leu Pro Thr Leu Arg Ala Ile Leu Gln
50                  55                  60

Ala Gly Phe Cys Met Gly Leu Tyr Leu Tyr Leu Ser Pro Ser Tyr Pro
65                  70                  75                  80

Leu Ser Arg Phe Ser Glu Pro Ile Tyr Gln Gly Trp Gly Phe Val Lys
                85                  90                  95

Arg Leu Thr Val Gln Tyr Met Ser Gly Phe Thr Ala Arg Trp Lys Tyr
            100                 105                 110

Tyr Phe Ile Trp Ser Ile Ser Glu Ala Ser Ile Ile Ser Gly Phe
            115                 120                 125

Gly Phe Ser Gly Trp Thr Asp Ser Ser Pro Pro Lys Ala Arg Trp Asp
130                 135                 140

Arg Ala Lys Asn Val Asp Val Leu Gly Val Glu Phe Ala Lys Ser Ser
145                 150                 155                 160

Val Glu Leu Pro Leu Val Trp Asn Ile Gln Val Ser Thr Trp Leu Arg
                165                 170                 175

His Tyr Val Tyr Asp Arg Leu Val Gln Lys Gly Lys Pro Gly Phe
            180                 185                 190

Phe Gln Leu Leu Ala Thr Gln Thr Val Ser Ala Val Trp His Gly Leu
            195                 200                 205

Tyr Pro Gly Tyr Leu Ile Phe Phe Val Gln Ser Ala Leu Met Ile Ser
210                 215                 220

Gly Ser Arg Ala Ile Tyr Arg Trp Gln Gln Ala Val Pro Pro Thr Val
225                 230                 235                 240

Lys Lys Phe Leu Met Leu Met Asn Phe Ala Tyr Thr Leu Leu Val Leu
                245                 250                 255

Asn Tyr Ser Cys Ile Gly Phe Met Val Leu Ser Leu His Glu Thr Leu
            260                 265                 270

Ala Ala Tyr Gly Ser Val Tyr Tyr Val Gly Asn Ile Ile Pro Val Ala
            275                 280                 285
```

<210> SEQ ID NO 81
<211> LENGTH: 14
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE

```
<222> LOCATION: (3)..(4)
<223> OTHER INFORMATION: X can be any amino acid
<220> FEATURE:
<221> NAME/KEY: MISC_FEATURE
<222> LOCATION: (6)..(6)
<223> OTHER INFORMATION: X can be Ile or Leu
<220> FEATURE:
<221> NAME/KEY: MISC_FEATURE
<222> LOCATION: (9)..(9)
<223> OTHER INFORMATION: X can be any amino acid
<220> FEATURE:
<221> NAME/KEY: MISC_FEATURE
<222> LOCATION: (12)..(12)
<223> OTHER INFORMATION: X can be Ser or Thr

<400> SEQUENCE: 81

Glu Ala Xaa Xaa Ile Xaa Ser Gly Xaa Gly Phe Xaa Gly Trp
1               5                   10

<210> SEQ ID NO 82
<211> LENGTH: 8
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (5)..(5)
<223> OTHER INFORMATION: X can be any amino acid

<400> SEQUENCE: 82

Trp Asp Arg Ala Xaa Asn Val Asp
1               5

<210> SEQ ID NO 83
<211> LENGTH: 14
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (10)..(11)
<223> OTHER INFORMATION: X can be any amino acid

<400> SEQUENCE: 83

Trp Asn Ile Gln Val Ser Thr Trp Leu Xaa Xaa Tyr Val Tyr
1               5                   10

<210> SEQ ID NO 84
<211> LENGTH: 22
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (7)..(7)
<223> OTHER INFORMATION: X can be any amino acid
<220> FEATURE:
<221> NAME/KEY: MISC_FEATURE
<222> LOCATION: (11)..(11)
<223> OTHER INFORMATION: X can be any amino acid
<220> FEATURE:
<221> NAME/KEY: MISC_FEATURE
<222> LOCATION: (14)..(14)
<223> OTHER INFORMATION: X can be any amino acid

<400> SEQUENCE: 84
```

```
Gly Phe Xaa Gln Leu Leu Xaa Thr Gln Thr Xaa Ser Ala Xaa Trp His
1               5                   10                  15

Gly Leu Tyr Pro Gly Tyr
                20

<210> SEQ ID NO 85
<211> LENGTH: 487
<212> TYPE: PRT
<213> ORGANISM: Homo Sapiens

<400> SEQUENCE: 85

Met Ala Ser Ser Ala Glu Gly Asp Glu Gly Thr Val Val Ala Leu Ala
1               5                   10                  15

Gly Val Leu Gln Ser Gly Phe Gln Glu Leu Ser Leu Asn Lys Leu Ala
                20                  25                  30

Thr Ser Leu Gly Ala Ser Glu Gln Ala Leu Arg Leu Ile Ile Ser Ile
            35                  40                  45

Phe Leu Gly Tyr Pro Phe Ala Leu Phe Tyr Arg His Tyr Leu Phe Tyr
    50                  55                  60

Lys Glu Thr Tyr Leu Ile His Leu Phe His Thr Phe Thr Gly Leu Ser
65                  70                  75                  80

Ile Ala Tyr Phe Asn Phe Gly Asn Gln Leu Tyr His Ser Leu Leu Cys
                85                  90                  95

Ile Val Leu Gln Phe Leu Ile Leu Arg Leu Met Gly Arg Thr Ile Thr
                100                 105                 110

Ala Val Leu Thr Thr Phe Cys Phe Gln Met Ala Tyr Leu Leu Ala Gly
            115                 120                 125

Tyr Tyr Tyr Thr Ala Thr Gly Asn Tyr Asp Ile Lys Trp Thr Met Pro
    130                 135                 140

His Cys Val Leu Thr Leu Lys Leu Ile Gly Leu Ala Val Asp Tyr Phe
145                 150                 155                 160

Asp Gly Gly Lys Asp Gln Asn Ser Leu Ser Ser Glu Gln Gln Lys Tyr
                165                 170                 175

Ala Ile Arg Gly Val Pro Ser Leu Leu Glu Val Ala Gly Phe Ser Tyr
                180                 185                 190

Phe Tyr Gly Ala Phe Leu Val Gly Pro Gln Phe Ser Met Asn His Tyr
            195                 200                 205

Met Lys Leu Val Gln Gly Glu Leu Ile Asp Ile Pro Gly Lys Ile Pro
    210                 215                 220

Asn Ser Ile Ile Pro Ala Leu Lys Arg Leu Ser Leu Gly Leu Phe Tyr
225                 230                 235                 240

Leu Val Gly Tyr Thr Leu Leu Ser Pro His Ile Thr Glu Asp Tyr Leu
                245                 250                 255

Leu Thr Glu Asp Tyr Asp Asn His Pro Phe Trp Phe Arg Cys Met Tyr
                260                 265                 270

Met Leu Ile Trp Gly Lys Phe Val Leu Tyr Lys Tyr Val Thr Cys Trp
            275                 280                 285

Leu Val Thr Glu Gly Val Cys Ile Leu Thr Gly Leu Gly Phe Asn Gly
    290                 295                 300

Phe Glu Glu Lys Gly Lys Ala Lys Trp Asp Ala Cys Ala Asn Met Lys
305                 310                 315                 320

Val Trp Leu Phe Glu Thr Asn Pro Arg Phe Thr Gly Thr Ile Ala Ser
                325                 330                 335

Phe Asn Ile Asn Thr Asn Ala Trp Val Ala Arg Tyr Ile Phe Lys Arg
```

```
                    340                 345                 350
Leu Lys Phe Leu Gly Asn Lys Glu Leu Ser Gln Gly Leu Ser Leu Leu
            355                 360                 365

Phe Leu Ala Leu Trp His Gly Leu His Ser Gly Tyr Leu Val Cys Phe
        370                 375                 380

Gln Met Glu Phe Leu Ile Val Ile Val Glu Arg Gln Ala Ala Arg Leu
385                 390                 395                 400

Ile Gln Glu Ser Pro Thr Leu Ser Lys Leu Ala Ala Ile Thr Val Leu
                405                 410                 415

Gln Pro Phe Tyr Tyr Leu Val Gln Gln Thr Ile His Trp Leu Phe Met
            420                 425                 430

Gly Tyr Ser Met Thr Ala Phe Cys Leu Phe Thr Trp Asp Lys Trp Leu
        435                 440                 445

Lys Val Tyr Lys Ser Ile Tyr Phe Leu Gly His Ile Phe Phe Leu Ser
    450                 455                 460

Leu Leu Phe Ile Leu Pro Tyr Ile His Lys Ala Met Val Pro Arg Lys
465                 470                 475                 480

Glu Lys Leu Lys Lys Met Glu
                485

<210> SEQ ID NO 86
<211> LENGTH: 495
<212> TYPE: PRT
<213> ORGANISM: Homo Sapiens

<400> SEQUENCE: 86

Met Ala Ala Glu Pro Gln Pro Ser Ser Leu Ser Tyr Arg Thr Thr Gly
1               5                   10                  15

Ser Thr Tyr Leu His Pro Leu Ser Glu Leu Leu Gly Ile Pro Leu Asp
            20                  25                  30

Gln Val Asn Phe Val Val Cys Gln Leu Val Ala Leu Phe Ala Ala Phe
        35                  40                  45

Trp Phe Arg Ile Tyr Leu Arg Pro Gly Thr Thr Ser Ser Asp Val Arg
    50                  55                  60

His Ala Val Ala Thr Ile Phe Gly Ile Tyr Phe Val Ile Phe Cys Phe
65                  70                  75                  80

Gly Trp Tyr Ser Val His Leu Phe Val Leu Val Leu Met Cys Tyr Ala
                85                  90                  95

Ile Met Val Thr Ala Ser Val Ser Asn Ile His Arg Tyr Ser Phe Phe
            100                 105                 110

Val Ala Met Gly Tyr Leu Thr Ile Cys His Ile Ser Arg Ile Tyr Ile
        115                 120                 125

Phe His Tyr Gly Ile Leu Thr Thr Asp Phe Ser Gly Pro Leu Met Ile
    130                 135                 140

Val Thr Gln Lys Ile Thr Thr Leu Ala Phe Gln Val His Asp Gly Leu
145                 150                 155                 160

Gly Arg Arg Ala Glu Asp Leu Ser Ala Glu Gln His Arg Leu Ala Ile
                165                 170                 175

Lys Val Lys Pro Ser Phe Leu Glu Tyr Leu Ser Tyr Leu Leu Asn Phe
            180                 185                 190

Met Ser Val Ile Ala Gly Pro Cys Asn Asn Phe Lys Asp Tyr Ile Ala
        195                 200                 205

Phe Ile Glu Gly Lys His Ile His Met Lys Leu Leu Glu Val Asn Trp
    210                 215                 220
```

```
Lys Arg Lys Gly Phe His Ser Leu Pro Glu Pro Ser Pro Thr Gly Ala
225                 230                 235                 240

Val Ile His Lys Leu Gly Ile Thr Leu Val Ser Leu Leu Leu Phe Leu
            245                 250                 255

Thr Leu Thr Lys Thr Phe Pro Val Thr Cys Leu Val Asp Asp Trp Phe
            260                 265                 270

Val His Lys Ala Ser Phe Pro Ala Arg Leu Cys Tyr Leu Tyr Val Val
            275                 280                 285

Met Gln Ala Ser Lys Pro Lys Tyr Tyr Phe Ala Trp Thr Leu Ala Asp
    290                 295                 300

Ala Val Asn Asn Ala Ala Gly Phe Gly Phe Ser Gly Val Asp Lys Asn
305                 310                 315                 320

Gly Asn Phe Cys Trp Asp Leu Leu Ser Asn Leu Asn Ile Trp Lys Ile
                325                 330                 335

Glu Thr Ala Thr Ser Phe Lys Met Tyr Leu Glu Asn Trp Asn Ile Gln
            340                 345                 350

Thr Ala Thr Trp Leu Lys Cys Val Cys Tyr Gln Arg Val Pro Trp Tyr
        355                 360                 365

Pro Thr Val Leu Thr Phe Ile Leu Ser Ala Leu Trp His Gly Val Tyr
    370                 375                 380

Pro Gly Tyr Tyr Phe Thr Phe Leu Thr Gly Ile Leu Val Thr Leu Ala
385                 390                 395                 400

Ala Arg Ala Val Arg Asn Asn Tyr Arg His Tyr Phe Leu Ser Ser Arg
                405                 410                 415

Ala Leu Lys Ala Val Tyr Asp Ala Gly Thr Trp Ala Val Thr Gln Leu
            420                 425                 430

Ala Val Ser Tyr Thr Val Ala Pro Phe Val Met Leu Ala Val Glu Pro
        435                 440                 445

Thr Ile Ser Leu Tyr Lys Ser Met Tyr Phe Tyr Leu His Ile Ile Ser
    450                 455                 460

Leu Leu Ile Ile Leu Phe Leu Pro Met Lys Pro Gln Ala His Thr Gln
465                 470                 475                 480

Arg Arg Pro Gln Thr Leu Asn Ser Ile Asn Lys Arg Lys Thr Asp
                485                 490                 495

<210> SEQ ID NO 87
<211> LENGTH: 810
<212> TYPE: PRT
<213> ORGANISM: Homo Sapiens

<400> SEQUENCE: 87

Met Val Met Met Met Met Lys Val Leu Leu Leu Met Lys Gln
1               5                   10                  15

Arg Gly Ala Gly Leu Pro Ala Pro Ala Gly Val Glu Pro Arg Pro Ser
                20                  25                  30

Ser His His Pro Lys Ala Arg Val Arg Leu Gln Gly Asp Glu Ser Val
            35                  40                  45

Arg Pro Arg Gly Cys Ser Gln Leu Trp Ala Phe Thr Arg His Ser Pro
50                  55                  60

Arg Gln Arg Gly Phe Ser Ala Arg Ser Leu Phe Trp Phe Val Val Leu
65                  70                  75                  80

Pro Ala Pro Thr Phe Val Pro Asn Phe Pro Trp Arg Trp Leu Gly Gly
                85                  90                  95

Val Pro His Ile Val Pro Pro Ala Ala Thr Pro Gly Pro Phe Val Val
            100                 105                 110
```

```
Cys Arg Leu Ser Gln Arg Gly Val Gly Gly Arg Asp Ile Pro Gly Arg
            115                 120                 125

Arg Asn Arg Gly Val Arg Gly Lys Asp Ala Leu Pro Cys Ser His Pro
        130                 135                 140

Arg Ser Ala Pro His Asp Ala Gly Gln Pro Phe Ser Gly Asp Ala Arg
145                 150                 155                 160

His Pro Arg Ala Glu Arg Glu Val Gly Arg Ala Leu Leu Pro Ala Thr
                165                 170                 175

Ala Pro Gly Glu Gly Gly Arg Met Gly Val Arg Val Cys Met Arg Ser
            180                 185                 190

Leu Pro Phe Ala Ala Ala Leu Gly Ser Gly Arg Val Pro Glu
        195                 200                 205

Gln Pro Pro Val Arg Met Asp Arg Val Val Glu Arg Val Arg Lys Ala
    210                 215                 220

Ala Leu Trp Gly Ala Trp Arg Gly Ala Ala Cys Pro Ala Arg Ala Ser
225                 230                 235                 240

Glu Arg Pro Pro Glu Arg Leu Met His Gly Ser Gly Asp Gly Leu Leu
                245                 250                 255

Gly Phe Ser Phe Val Arg Ala Ser Leu Thr Val Phe Gly Glu Glu Ala
            260                 265                 270

Gly Pro Ser Phe Leu Leu Ala Val Leu Cys Ala Val Val Trp Gly Gly
        275                 280                 285

Arg Gly Glu Asp Val Val Ser Asp Val Gln Ala Cys Pro Ala Glu Gln
    290                 295                 300

Gly Phe Leu Leu Ala Glu Pro Ser Val Phe Gly Val Asn Phe Val Val
305                 310                 315                 320

Cys Gln Leu Phe Ala Leu Leu Ala Ala Ile Trp Phe Arg Thr Tyr Leu
                325                 330                 335

His Ser Ser Lys Thr Ser Ser Phe Ile Arg His Val Val Ala Thr Leu
            340                 345                 350

Leu Gly Leu Tyr Leu Ala Leu Phe Cys Phe Gly Trp Tyr Ala Leu His
        355                 360                 365

Phe Leu Val Gln Ser Gly Ile Ser Tyr Cys Ile Met Ile Ile Ile Gly
    370                 375                 380

Val Glu Asn Met His Asn Tyr Cys Phe Val Phe Ala Leu Gly Tyr Leu
385                 390                 395                 400

Thr Val Cys Gln Val Thr Arg Val Tyr Ile Phe Asp Tyr Gly Gln Tyr
                405                 410                 415

Ser Ala Asp Phe Ser Gly Pro Met Met Ile Ile Thr Gln Lys Ile Thr
            420                 425                 430

Ser Leu Ala Cys Glu Ile His Asp Gly Met Phe Arg Lys Asp Glu Glu
        435                 440                 445

Leu Thr Ser Ser Gln Arg Asp Leu Ala Val Arg Arg Met Pro Ser Leu
    450                 455                 460

Leu Glu Tyr Leu Ser Tyr Asn Cys Asn Phe Met Gly Ile Leu Ala Gly
465                 470                 475                 480

Pro Leu Cys Ser Tyr Lys Asp Tyr Ile Thr Phe Ile Glu Gly Arg Ser
                485                 490                 495

Tyr His Ile Thr Gln Ser Gly Glu Asn Gly Lys Glu Thr Gln Tyr
            500                 505                 510

Glu Arg Thr Glu Pro Ser Pro Asn Thr Ala Val Val Gln Lys Leu Leu
        515                 520                 525
```

```
Val Cys Gly Leu Ser Leu Leu Phe His Leu Thr Ile Cys Thr Thr Leu
    530                 535                 540

Pro Val Glu Tyr Asn Ile Asp Glu His Phe Gln Ala Thr Ala Ser Trp
545                 550                 555                 560

Pro Thr Lys Ile Ile Tyr Leu Tyr Ile Ser Leu Leu Ala Ala Arg Pro
                565                 570                 575

Lys Tyr Tyr Phe Ala Trp Thr Leu Ala Asp Ala Ile Asn Asn Ala Ala
                580                 585                 590

Gly Phe Gly Phe Arg Gly Tyr Asp Glu Asn Gly Ala Ala Arg Trp Asp
                595                 600                 605

Leu Ile Ser Asn Leu Arg Ile Gln Gln Ile Glu Met Ser Thr Ser Phe
    610                 615                 620

Lys Met Phe Leu Asp Asn Trp Asn Ile Gln Thr Ala Leu Trp Leu Lys
625                 630                 635                 640

Arg Val Cys Tyr Glu Arg Thr Ser Phe Ser Pro Thr Ile Gln Thr Phe
                645                 650                 655

Ile Leu Ser Ala Ile Trp His Gly Val Tyr Pro Gly Tyr Tyr Leu Thr
                660                 665                 670

Phe Leu Thr Gly Val Leu Met Thr Leu Ala Ala Arg Ala Met Arg Asn
            675                 680                 685

Asn Phe Arg His Tyr Phe Ile Glu Pro Ser Gln Leu Lys Leu Phe Tyr
        690                 695                 700

Asp Val Ile Thr Trp Ile Val Thr Gln Val Ala Ile Ser Tyr Thr Val
705                 710                 715                 720

Val Pro Phe Val Leu Leu Ser Ile Lys Pro Ser Leu Thr Phe Tyr Ser
                725                 730                 735

Ser Trp Tyr Tyr Cys Leu His Ile Leu Gly Ile Leu Val Leu Leu Leu
                740                 745                 750

Leu Pro Val Lys Lys Thr Gln Arg Arg Lys Asn Thr His Glu Asn Ile
            755                 760                 765

Gln Leu Ser Gln Ser Lys Lys Phe Asp Glu Gly Glu Asn Ser Leu Gly
    770                 775                 780

Gln Asn Ser Phe Ser Thr Thr Asn Asn Val Cys Asn Gln Asn Gln Glu
785                 790                 795                 800

Ile Ala Ser Arg His Ser Ser Leu Lys Gln
                805                 810

<210> SEQ ID NO 88
<211> LENGTH: 463
<212> TYPE: PRT
<213> ORGANISM: Homo Sapiens

<400> SEQUENCE: 88

Met Val Asn Phe Val Cys Gln Leu Val Ala Leu Phe Ala Ala Phe
1               5                   10                  15

Trp Phe Arg Ile Tyr Leu Arg Pro Gly Thr Thr Ser Ser Asp Val Arg
                20                  25                  30

His Ala Val Ala Thr Ile Phe Gly Ile Tyr Phe Val Ile Phe Cys Phe
            35                  40                  45

Gly Trp Tyr Ser Val His Leu Phe Val Leu Val Leu Met Cys Tyr Ala
        50                  55                  60

Ile Met Val Thr Ala Ser Val Ser Asn Ile His Arg Tyr Ser Phe Phe
65                  70                  75                  80

Val Ala Met Gly Tyr Leu Thr Ile Cys His Ile Ser Arg Ile Tyr Ile
                85                  90                  95
```

```
Phe His Tyr Gly Ile Leu Thr Thr Asp Phe Ser Gly Pro Leu Met Ile
                100                 105                 110

Val Thr Gln Lys Ile Thr Thr Leu Ala Phe Gln Val His Asp Gly Leu
            115                 120                 125

Gly Arg Arg Ala Glu Asp Leu Ser Ala Glu Gln His Arg Leu Ala Ile
        130                 135                 140

Lys Val Lys Pro Ser Phe Leu Glu Tyr Leu Ser Tyr Leu Leu Asn Phe
145                 150                 155                 160

Met Ser Val Ile Ala Gly Pro Cys Asn Asn Phe Lys Asp Tyr Ile Ala
                165                 170                 175

Phe Ile Glu Gly Lys His Ile His Met Lys Leu Leu Glu Val Asn Trp
            180                 185                 190

Lys Arg Lys Gly Phe His Ser Leu Pro Glu Pro Ser Pro Thr Gly Ala
        195                 200                 205

Val Ile His Lys Leu Gly Ile Thr Leu Val Ser Leu Leu Leu Phe Leu
    210                 215                 220

Thr Leu Thr Lys Thr Phe Pro Val Thr Cys Leu Val Asp Asp Trp Phe
225                 230                 235                 240

Val His Lys Ala Ser Phe Pro Ala Arg Leu Cys Tyr Leu Tyr Val Val
                245                 250                 255

Met Gln Ala Ser Lys Pro Lys Tyr Tyr Phe Ala Trp Thr Leu Ala Asp
            260                 265                 270

Ala Val Asn Asn Ala Ala Gly Phe Gly Phe Ser Gly Val Asp Lys Asn
        275                 280                 285

Gly Asn Phe Cys Trp Asp Leu Leu Ser Asn Leu Asn Ile Trp Lys Ile
    290                 295                 300

Glu Thr Ala Thr Ser Phe Lys Met Tyr Leu Glu Asn Trp Asn Ile Gln
305                 310                 315                 320

Thr Ala Thr Trp Leu Lys Cys Val Cys Tyr Gln Arg Val Pro Trp Tyr
                325                 330                 335

Pro Thr Val Leu Thr Phe Ile Leu Ser Ala Leu Trp His Gly Val Tyr
            340                 345                 350

Pro Gly Tyr Tyr Phe Thr Phe Leu Thr Gly Ile Leu Val Thr Leu Ala
        355                 360                 365

Ala Arg Ala Val Arg Asn Asn Tyr Arg His Tyr Phe Leu Ser Ser Arg
    370                 375                 380

Ala Leu Lys Ala Val Tyr Asp Ala Gly Thr Trp Ala Val Thr Gln Leu
385                 390                 395                 400

Ala Val Ser Tyr Thr Val Ala Pro Phe Val Met Leu Ala Val Glu Pro
                405                 410                 415

Thr Ile Ser Leu Tyr Lys Ser Met Tyr Phe Tyr Leu His Ile Ile Ser
            420                 425                 430

Leu Leu Ile Ile Leu Phe Leu Pro Met Lys Pro Gln Ala His Thr Gln
        435                 440                 445

Arg Arg Pro Gln Thr Leu Asn Ser Ile Asn Lys Arg Lys Thr Asp
    450                 455                 460
```

<210> SEQ ID NO 89
<211> LENGTH: 24
<212> TYPE: DNA
<213> ORGANISM: Thalassiosira pseudonana

<400> SEQUENCE: 89
ggtatgctca tctgctaccc cctc        24

```
<210> SEQ ID NO 90
<211> LENGTH: 26
<212> TYPE: DNA
<213> ORGANISM: Thalassiosira pseudonana

<400> SEQUENCE: 90
ttaagtctcc ttcgtctttg gtgtag                                          26
```

What is claimed is:

1. A method for identifying a lyso-phosphatidylcholine acyltransferase, the method comprising:

screening a peptide for SEQ ID NO:49;
wherein Xaa at position 3 of SEQ ID NO: 49 is selected from the group consisting of phenylalanine, methionine, valine, and isoleucine;
wherein Xaa at position 7 of SEQ ID NO: 49 is selected from the group consisting of phenylalanine, valine, threonine, and leucine;
wherein Xaa at position 8 of SEQ ID NO: 49 is selected from the group consisting of tyrosine, serine, and arginine;
wherein Xaa at position 12 of SEQ ID NO: 49 is selected from the group consisting of tyrosine, methionine, and isoleucine;
wherein Xaa at position 13 of SEQ ID NO: 49 is selected from the group consisting of leucine, methionine, isoleucine, and phenylalanine; and
wherein Xaa at position 14 of SEQ ID NO: 49 is selected from the group consisting of threonine and phenylalanine; and
testing said screened peptide comprising SEQ ID NO:49 for lyso-phosphatidylcholine acyltransferase function, so as to identify the lyso-phosphatidylcholine acyltransferase.

2. The method according to claim 1, further comprising screening the peptide for SEQ ID NO: 46;

wherein Xaa at position 2 of SEQ ID NO: 46 is selected from the group consisting of valine and isoleucine;
wherein Xaa at position 3 of SEQ ID NO: 46 is selected from the group consisting of leucine, isoleucine, and valine;
wherein Xaa at position 4 of SEQ ID NO: 46 is selected from the group consisting of valine, cysteine, alanine, and threonine;
wherein Xaa at position 5 of SEQ ID NO: 46 is selected from the group consisting of methionine, leucine, and glutamine;
wherein Xaa at position 7 of SEQ ID NO: 46 is selected from the group consisting of leucine, valine, isoleucine, and methionine;
wherein Xaa at position 8 of SEQ ID NO: 46 is selected from the group consisting of serine, threonine, tyrosine, and isoleucine;
wherein Xaa at position 9 of SEQ ID NO: 46 is selected from the group consisting of serine, threonine, alanine, methionine, and glycine;
wherein Xaa at position 10 of SEQ ID NO: 46 is selected from the group consisting of phenylalanine, leucine, cysteine, and tyrosine;
wherein Xaa at position 11 of SEQ ID NO: 46 is selected from the group consisting of cysteine, alanine, glycine, and serine;
wherein Xaa at position 12 of SEQ ID NO: 46 is selected from the group consisting of tryptophan, tyrosine, methionine, isoleucine, phenylalanine and cysteine;
wherein Xaa at position 13 of SEQ ID NO: 46 is selected from the group consisting of asparagine, serine, glutamic acid, glutamine, and aspartic acid;
wherein Xaa at position 14 of SEQ ID NO: 46 is selected from the group consisting of valine, tyrosine, leucine, and isoleucine; and
wherein Xaa at position 15 of SEQ ID NO: 46 is selected from the group consisting of histidine, tyrosine, alanine, asparagine, serine, and threonine.

3. The method according to claim 1, further comprising screening the peptide for SEQ ID NO: 47;

wherein Xaa at position 2 of SEQ ID NO: 47 is selected from the group consisting of leucine, methionine, phenylalanine, tryptophan, proline, and tyrosine;
wherein Xaa at position 6 of SEQ ID NO: 47 is selected from the group consisting of glycine, alanine, phenylalanine, histidine, and serine;
wherein Xaa at position 7 of SEQ ID NO: 47 is selected from the group consisting of valine, alanine, isoleucine, and cysteine;
wherein Xaa at position 9 of SEQ ID NO: 47 is selected from the group consisting of tyrosine, glutamic acid, threonine, methionine, serine, and leucine;
wherein Xaa at position 10 of SEQ ID NO: 47 is selected from the group consisting of leucine, isoleucine, and asparagine;
wherein Xaa at position 11 of SEQ ID NO: 47 is selected from the group consisting of threonine, serine, and alanine;
wherein Xaa at position 12 of SEQ ID NO: 47 is selected from the group consisting of glutamic acid and aspartic acid;
wherein Xaa at position 13 of SEQ ID NO: 47 is selected from the group consisting of glycine and alanine;
wherein Xaa at position 14 of SEQ ID NO: 47 is selected from the group consisting of alanine, serine, isoleucine, and valine;
wherein Xaa at position 15 of SEQ ID NO: 47 is selected from the group consisting of cysteine, serine, isoleucine, asparagine, histidine, and leucine;
wherein Xaa at position 16 of SEQ ID NO: 47 is selected from the group consisting of valine, isoleucine, and asparagine;
wherein Xaa at position 17 of SEQ ID NO: 47 is selected from the group consisting of leucine, isoleucine, asparagine, alanine, and cysteine;

wherein Xaa at position 18 of SEQ ID NO: 47 is selected from the group consisting of serine, cysteine, tryptophan, alanine, and isoleucine;

wherein Xaa at position 20 of SEQ ID NO: 47 is selected from the group consisting of methionine, isoleucine, leucine, alanine, and phenylalanine;

wherein Xaa at position 22 of SEQ ID NO: 47 is selected from the group consisting of tyrosine, and phenylalanine; and wherein Xaa at position 23 of SEQ ID NO: 47 is selected from the group consisting of asparagine, glutamic acid, serine, threonine, arginine, and lysine.

4. The method according to claim 1, further comprising screening the peptide for SEQ ID NO: 48;

wherein Xaa at position 2 of SEQ ID NO: 48 is selected from the group consisting of threonine, phenylalanine, leucine, and methionine;

wherein Xaa at position 3 of SEQ ID NO: 48 is selected from the group consisting of alanine and serine;

wherein Xaa at position 4 of SEQ ID NO: 48 is selected from the group consisting of glutamine, aspartic acid, proline, lysine, and threonine;

wherein Xaa at position 5 of SEQ ID NO: 48 is selected from the group consisting of asparagine and serine;

wherein Xaa at position 6 of SEQ ID NO: 48 is selected from the group consisting of serine, isoleucine, threonine, leucine, alanine, methionine, and phenylalanine;

wherein Xaa at position 7 of SEQ ID NO: 48 is selected from the group consisting of histidine, lysine, arginine, and valine;

wherein Xaa at position 8 of SEQ ID NO: 48 is selected from the group consisting of glycine, cysteine, glutamic acid, threonine, glutamine, aspartic acid, and methionine;

wherein Xaa at position 9 of SEQ ID NO: 48 is selected from the group consisting of tyrosine, alanine, methionine, leucine, isoleucine, and phenylalanine;

wherein Xaa at position 10 of SEQ ID NO: 48 is selected from the group consisting of leucine, serine, proline, and isoleucine;

wherein Xaa at position 11 of SEQ ID NO: 48 is selected from the group consisting of glycine, glutamic acid, alanine, leucine, asparagine, and aspartic acid;

wherein Xaa at position 12 of SEQ ID NO: 48 is selected from the group consisting of serine, alanine, valine, phenylalanine, methionine, and asparagine;

wherein Xaa at position 15 of SEQ ID NO: 48 is selected from the group consisting of lysine, methionine, isoleucine, and cysteine;

wherein Xaa at position 16 of SEQ ID NO: 48 is selected from the group consisting of asparagine, lysine, glutamine, and glycine;

wherein Xaa at position 17 of SEQ ID NO: 48 is selected from the group consisting of threonine and valine;

wherein Xaa at position 18 of SEQ ID NO: 48 is selected from the group consisting of asparagine, alanine, and serine; and wherein Xaa at position 19 of SEQ ID NO: 48 is selected from the group consisting of histidine, lysine, asparagine, threonine, arginine, and leucine.

5. The method according to claim 1, further comprising screening the peptide for SEQ ID NO: 46 and SEQ ID NO: 47.

6. The method according to claim 1, further comprising screening the peptide for SEQ ID NO: 47 and SEQ ID NO: 48.

7. The method according to claim 1, further comprising screening the peptide for SEQ ID NO: 46 and SEQ ID NO: 48.

8. The method according to claim 1, further comprising screening the peptide for SEQ ID NO: 46, SEQ ID NO: 47, and SEQ ID NO: 48.

9. The method according to claim 2, wherein lyso-phosphatidylcholine acyltransferase function may be determined by an assay comprising:

interacting the screened peptide with $^{14}$C-labelled lyso-phosphatidylcholine as an acceptor and different unlabeled acyl-CoA as an acyl donor to determine if acylation of lyso-phosphatidylcholine to form phosphatidylcholine is catalyzed by the screened peptide, so as to identify the screened peptide as a lyso-phosphatidylcholine acyltransferase.

10. The method according to claim 3, wherein lyso-phosphatidylcholine acyltransferase function may be determined by an assay comprising:

interacting the screened peptide with $^{14}$C-labelled lyso-phosphatidylcholine as an acceptor and different unlabeled acyl-CoA as an acyl donor to determine if acylation of lyso-phosphatidylcholine to form phosphatidylcholine is catalyzed by the screened peptide, so as to identify the screened peptide as a lyso-phosphatidylcholine acyltransferase.

11. The method according to claim 4, wherein lyso-phosphatidylcholine acyltransferase function may be determined by an assay comprising:

interacting the screened peptide with $^{14}$C-labelled lyso-phosphatidylcholine as an acceptor and different unlabeled acyl-CoA as an acyl donor to determine if acylation of lyso-phosphatidylcholine to form phosphatidylcholine is catalyzed by the screened peptide, so as to identify the screened peptide as a lyso-phosphatidylcholine acyltransferase.

12. A method for identifying a lyso-phosphatidylcholine acyltransferase, the method comprising:

screening a peptide for SEQ ID NO:49, wherein Xaa at position 3 of SEQ ID NO: 49 is selected from the group consisting of phenylalanine, methionine, valine, and isoleucine;

wherein Xaa at position 7 of SEQ ID NO: 49 is selected from the group consisting of phenylalanine, valine, threonine, and leucine;

wherein Xaa at position 8 of SEQ ID NO: 49 is selected from the group consisting of tyrosine, serine, and arginine;

wherein Xaa at position 12 of SEQ ID NO: 49 is selected from the group consisting of tyrosine, methionine, and isoleucine;

wherein Xaa at position 13 of SEQ ID NO: 49 is selected from the group consisting of leucine, methionine, isoleucine, and phenylalanine;

wherein Xaa at position 14 of SEQ ID NO: 49 is selected from the group consisting of threonine and phenylalanine; and testing a screened peptide comprising SEQ ID NO:49 for lyso-phosphatidylcholine acyltransferase function, wherein said lyso-phosphatidylcholine acyltransferase function may be determined by an assay comprising:

interacting the screened peptide comprising SEQ ID NO:49 with $^{14}$C-labelled lyso-phosphatidylcholine as an acceptor and different unlabeled acyl-CoA as an acyl donor to determine if acylation of lyso-phosphatidylcholine to form phosphatidylcholine is catalyzed by the screened peptide comprising SEQ ID NO:49, so as to identify the screened peptide as a lyso-phosphatidylcholine acyltransferase.

* * * * *